US012297258B2

(12) United States Patent
Pizzuto et al.

(10) Patent No.: US 12,297,258 B2
(45) Date of Patent: May 13, 2025

(54) **ANTIBODIES AGAINST *CAMPYLOBACTER* SPECIES**

(71) Applicants: HUMABS BIOMED SA, Bellinzona (CH); INSTITUTE FOR RESEARCH IN BIOMEDICINE, Bellinzona (CH)

(72) Inventors: Matteo Samuele Pizzuto, Bellinzona (CH); Fabio Benigni, Bellinzona (CH); Davide Corti, Bellinzona (CH); Fabio Grassi, Bellinzona (CH); Lisa Perruzza, Bellinzona (CH)

(73) Assignees: Humabs BioMed SA, Bellinzona (CH); Institute for Research in Biomedicine, Bellinzona (CH)

( * ) Notice: Subject to any disclaimer, the term of this patent is extended or adjusted under 35 U.S.C. 154(b) by 1018 days.

(21) Appl. No.: 17/260,966

(22) PCT Filed: Jul. 16, 2019

(86) PCT No.: PCT/US2019/042070
§ 371 (c)(1),
(2) Date: Jan. 15, 2021

(87) PCT Pub. No.: WO2020/018584
PCT Pub. Date: Jan. 23, 2020

(65) Prior Publication Data

US 2021/0284718 A1 Sep. 16, 2021

Related U.S. Application Data

(60) Provisional application No. 62/699,573, filed on Jul. 17, 2018.

(51) Int. Cl.
*C07K 16/12* (2006.01)
*A61K 39/00* (2006.01)
*A61P 31/04* (2006.01)

(52) U.S. Cl.
CPC ............ *C07K 16/121* (2013.01); *A61P 31/04* (2018.01); *A61K 2039/505* (2013.01); *A61K 2039/542* (2013.01); *C07K 2317/52* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

2015/0307597 A1 10/2015 Arbabi Ghahroudi et al.
2016/0039944 A1 2/2016 Gakuen

FOREIGN PATENT DOCUMENTS

JP 2015-535224 A 12/2015
WO 2014-142084 A1 9/2014

OTHER PUBLICATIONS

Yeh et al (J Medical Microbiol., 63:602-609, 2014).*
Yeh et al. "Characterization and Antigenicity of Recombinant Campylobacter Jejuni Flagellar Capping Protein FliD." Journal of Medical Microbiology, vol. 63, No. 4, Jan. 2014, pp. 602-609. https://doi.org/10.1099/jmm.0.060095-0.
Chintoan-Uta et al. "Evaluation of flagellum-related proteins FliD and FspA as subunit vaccines against Campylobacter jejuni colonisation in chickens." Vaccine, vol. 34, No. 15, Feb. 2016, pp. 1739-1743. https://doi.org/10.1016/j.vaccine.2016.02.052.
Mulvey et al. "Therapeutic Potential of Egg Yolk Antibodies for Treating Clostridium Difficile Infection." Journal of Medical Microbiology, vol. 60, No. 8, Apr. 2011, pp. 1181-1187. https://doi.org/10.1099/jmm.0.029835-0.
Riazi et al. "Pentavalent Single-Domain Antibodies Reduce Campylobacter Jejuni Motility and Colonization in Chickens." PLoS One, vol. 8, No. 12, Dec. 2013, p. e83928. https://doi.org/10.1371/journal.pone.0083928.
Ghose et al. "Immunogenicity and Protective Efficacy of Recombinant Clostridium Difficile Flagellar Protein FliC." Emerging Microbes & Infections, vol. 5, No. 1, Jan. 2016, pp. 1-10. https://doi.org/10.1038/emi.2016.8.
Yeh et al. "Reactions of Chicken Sera to Recombinant Campylobacter Jejuni Flagellar Proteins." Archives of Microbiology, vol. 197, No. 2, Nov. 2014, pp. 353-358. https://doi.org/10.1007/s00203-014-1062-3.
Giuntini et al. "Identification and Characterization of Human Monoclonal Antibodies for Immunoprophylaxis Against Enterotoxigenic Escherichia Coli Infection." Infection and Immunity, vol. 86, No. 8, Jun. 2018, https://doi.org/10.1128/ ial. 00355-18.
International Search Report, mailed Feb. 26, 2020, for International Application No. PCT/US2019/042070, 20 pages.
International Preliminary Search Report on Patentability, mailed Jan. 19, 2021, for International Application No. PCT/US2019/042070, 11 pages.
Ueki et al., "Protection Against Campylobacter Jejuni Infection in Suckling Mice by Anti-Flagellar Antibody," Microbiology and Immunology 31, No. 12 (May 1987): 1161-71, https://doi.org/10.1111/j.1348-0421.1987.tb01350.x.

(Continued)

*Primary Examiner* — Brian Gangle
(74) *Attorney, Agent, or Firm* — Fox Rothschild LLP

(57) ABSTRACT

The instant disclosure provides antibodies and antigen-binding fragments thereof that are specific for *Campylobacter* and, in certain embodiments, are capable of neutralizing a *Campylobacter* infection in a subject. In certain embodiments, the antibody or antigen binding fragment comprises an IgA antibody, such as, for example, a secretory IgA antibody. Also provided are pharmaceutical compositions comprising a disclosed antibody or antigen-binding fragment. Methods of using the antibodies, antigen-binding fragments, and compositions to treat or prevent a *Campylobacter* infection in a subject are also provided. In certain embodiments, recombinant secretory IgA antibodies of the instant disclosure are administered orally to a subject having or at risk of developing a *Campylobacter* infection.

38 Claims, 77 Drawing Sheets

Specification includes a Sequence Listing.

(56) References Cited

OTHER PUBLICATIONS

Strid et al., "Antibody Responses to Campylobacter Infections Determined by an Enzyme-Linked Immunosorbent Assay: 2-Year Follow-Up Study of 210 Patients," Clinical and Diagnostic Laboratory Immunology 8, No. 2 (Mar. 2001): 314-19, https://doi.org/10.1128/cdli.8.2.314-319.2001.

Pizzuto et al., "Prophylactic activity of orally administered Human SigA Monoclonal Antibodies against Campylobacter species," Poster, Mucosal Immunology Course & Symposium, Oxford, UK, Jul. 17, 2018.

* cited by examiner

CAA1

HGN194

No mAb

```
                                    20                  40
                                     |                   |
Consensus        MAFGSLSSLGFGSGVLTQDTIDKLKEAEQKARIDPYTKKI
YP_002343979.1   ........................................
WP_038400380.1   ........................................
EAQ73028.1       ........................................
WP_010790846.1   ........................................
WP_004316510.1   ......A.................................
WP_004306838.1   ........................................
WP_002935293.1   ........................................
WP_002928464.1   ........................................
WP_002924910.1   ........................................
WP_002921586.1   ........................................
WP_002908989.1   ........................................
WP_002901368.1   ........................................
WP_002892358.1   ........................................
WP_002874097.1   ........................................
WP_002873395.1   ........................................
EFV08769.1       ........................................
EFV10698.1       ........................................
EAQ94619.1       ........................................
EAQ60315.1       ........................................
EAQ58732.1       ........................................
EAQ57731.1       ........................................
CDH62398.1       ........................................
ADN90737.1       ........................................
APA80830.1       ........................................
AOW96893.1       ........................................
AON66729.1       ........................................
AON65179.1       ........................................
AOH51565.1       ........................................
```

FIG. 12

```
                   60                  80
                   |                   |
EENTTKQKDLTEIKTKLLSFQTAVSSLADATVFAKRKVVGSISDN 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
............................................. 85
```

FIG. 12 (Continued)

```
      140                 160
       |                   |
ADLTFFSNGKEYTVTVDKNTTYRDLADKINEASGGEI 170
..................................... 170
T.................................... 170
T......................E............. 170
..................................... 170
.................R................... 170
..................................... 170
..................................... 170
..................................... 170
..................................... 170
T.................................... 170
..................................... 170
T.................................... 170
T.................................... 170
..................................... 170
..................................... 170
..................................... 170
T.................................... 170
T.................................... 170
T.................S.................. 170
..................................... 170
..................................... 170
..................................... 170
T.................................... 170
T.................................... 170
T.................S.................. 170
..................................... 170
T.................................... 170
..................................... 170
```

FIG. 12
(Continued)

| | 260 … 280 |
|---|---|
| Consensus | T A Q N A E F T L D G I K M F R S S N T V T D L G V G M T L T L N K T G E I N F |
| YP_002343979.1 | ........................................ |
| WP_038400380.1 | ........................................ |
| EAQ73028.1 | ........................................ |
| WP_010790846.1 | ........................................ |
| WP_004316510.1 | ........................................ |
| WP_004306838.1 | ........................................ |
| WP_002935293.1 | ........................................ |
| WP_002928464.1 | ........................................ |
| WP_002924910.1 | ........................................ |
| WP_002921586.1 | ........................................ |
| WP_002908989.1 | ........................................ |
| WP_002901368.1 | ........................................ |
| WP_002892358.1 | ........................................ |
| WP_002874097.1 | ........................................ |
| WP_002873395.1 | ........................................ |
| EFV08769.1 | ........................................ |
| EFV10698.1 | ........................................ |
| EAQ94619.1 | ........................................ |
| EAQ60315.1 | ........................................ |
| EAQ58732.1 | ........................................ |
| EAQ57731.1 | ........................................ |
| CDH62398.1 | ........................................ |
| ADN90737.1 | ........................................ |
| APA80830.1 | ........................................ |
| AOW96893.1 | ........................................ |
| AON66729.1 | ........................................ |
| AON65179.1 | ........................................ |
| AOH51565.1 | ........................................ |

*FIG. 12 (Continued)*

```
300                 320                 340
 |                   |                   |
DVQQDFEGVTKAMQDLVDAYNDLVTNLNAATDYNSETGTKGTLQG 339
............................................. 339
............................................. 339
............................................. 339
............................................. 339
............................................. 339
............................................. 339
............................................. 339
............................................. 339
............................................. 339
............................................. 339
............................................. 339
............................................. 339
............................................. 340
............................................. 339
............................................. 339
............................................. 339
............................................. 340
............................................. 340
............................................. 340
............................................. 339
............................................. 339
............................................. 339
............................................. 340
............................................. 340
............................................. 340
.....................................-....... 339
............................................. 340
............................................. 339
```

FIG. 12 (Continued)

```
                                                   360                                   380
                                                    |                                     |
Consensus        I S E V N S I R S S I L A D L F D S Q V V D G T T E D A N G N K V N T K V M L S M Q D
YP_002343979.1   . . . . . . . . . . . . . . . . . . . . . . . . . . . . . . . . . . . . . . . . . . .
WP_038400380.1   . . . . . . . . . . . . . . . . . . . . . . . . . . . . . . . . . . . . . . . . . . .
EAQ73028.1       . . . . . . . . . . . . . . . . . . . . . . . . . . . . . . . . . . . . . . . . . . .
WP_010790846.1   . . . . . . . . . . . . . . . . . . . . . . . . . . . . . . . . . . . . . . . . . . .
WP_004316510.1   . . . . . . . . . . . . . . . . . . . . . . . . . . . . . . . . . . . . . . . . . . .
WP_004306838.1   . . . . . . . . . . . . . . . . . . . . . . . . . . . . . . . . . . . . . . . . . . .
WP_002935293.1   . . . . . . . . . . . . . . . . . . . . . . . . . . . . . . . . . . . . . . . . . . .
WP_002928464.1   . . . . . . . . . . . . . . . . . . . . . . . . . . . . . . . . . . . . . . . . . . .
WP_002924910.1   . . . . . . . . . . . . . . . . . . . . . . . . . . . . . . . . . . . . . . . . . . .
WP_002921586.1   . . . . . . . . . . . . . . . . . . . . . . . . . . . . . . . . . . . . . . . . . . .
WP_002908989.1   . . . . . . . . . . . . . . . . . . . . . . . . . . . . . . . . . . . . . . . . . . .
WP_002901368.1   . . . . . . . . . . . . . . . . . . . . . . . . . . . . . . . . . . . . . . . . . . .
WP_002892358.1   . . . . . . . . . . . . . . . . . . . . . . . . . . . . . . . . . . . . . . . . . . .
WP_002874097.1   . . . . . . . . . . . . . . . . . . . . . . . . . . . . . . . . . . . . . . . . . . .
WP_002873395.1   . . . . . . . . . . . . . . . . . . . . . . . . . . . . . . . . . . . . . . . . . . .
EFV08769.1       . . . . . . . . . . . . . . . . . . . . . . . . . . . . . . . . . . . . . . . . . . .
EFV10698.1       . . . . . . . . . . . . . . . . . . . . . . . . . . . . . . . . . . . . . . . . . . .
EAQ94619.1       . . . . . . . . . . . . . . . . . . . . . . . . . . . . . . . . . . . . . . . . . . .
EAQ60315.1       . . . . . . . . . . . . . . . . . . . . . . . . . . . . . . . . . . . . . . . . . . .
EAQ58732.1       . . . . . . . . . . . . . . . . . . . . . . . . . . . . . . . . . . . . . . . . . . .
EAQ57731.1       . . . . . . . . . . . . . . . . . . . . . . . . . . . . . . . . . . . . . . . . . . .
CDH62398.1       . . . . . . . . . . . . . . . . . . . . . . . . . . . . . . . . . . . . . . . . . . .
ADN90737.1       . . . . . . . . . . . . . . . . . . . . . . . . . . . . . . . . . . . . . . . . . . .
APA80830.1       . . . . . . . . . . . . . . . . . . . . . . . . . . . . . . . . . . . . . . . . . . .
AOW96893.1       . . . . . . . . . . . . . . . . . . . . . . . . . . . . . . . . . . . . . . . . . . .
AON66729.1       . . . . . . . . . . . . . . . . . . . . . . . . . . . . . . . . . . . . . . . . . . .
AON65179.1       . . . . . . . . . . . . . . . . . . . . . . . . . . . . . . . . . . . . . . . . . . .
AOH51565.1       . . . . . . . . . . . . . . . . . . . . . . . . . . . . . . . . . . . . . . . . . . .
```

FIG. 12 (Continued)

```
                400                 420
                 |                   |
FGLSLNDAGTLSFDSSKFEQKVKEDPDSTESFFSNITKYEDI 424
.......................................... 424
.......................................... 424
.......................................... 424
...........N................A............. 424
.......................................... 424
...................K........A............. 424
.......................................... 424
...........N................A............. 424
.......................................... 424
.......................................... 424
.......................................... 424
.......................................... 424
.......................................... 425
.......................................... 424
.......................................... 424
.......................................... 424
.......................................... 425
.......................................... 425
.......................................... 425
...........N................A............. 424
.......................................... 424
.......................................... 424
.......................................... 425
.......................................... 425
.......................................... 425
.......................................... 424
.......................................... 425
.......................................... 424
```

FIG. 12
(Continued)

```
                                  440                 460
                                   |                   |
Consensus        NHTGEVIKTGSLSKYLNSNGGNTNGLEFKPGDFTIVFNNQTYDL
YP_002343979.1   ............................................
WP_038400380.1   ..........................A.................
EAQ73028.1       ........Q...NQ..D.S.TGNK..D.................
WP_010790846.1   .....I....................D.................
WP_004316510.1   ............................................
WP_004306838.1   .....................SA...D.................
WP_002935293.1   ...............................Y............
WP_002928464.1   .....I....................D.................
WP_002924910.1   ............................................
WP_002921586.1   ........Q...NQ..D.S.TGNK..D.................
WP_002908989.1   ........Q...NQ..D.S.TGNK..D.................
WP_002901368.1   ........Q...NQ..D.S.TGNK..D.................
WP_002892358.1   ........Q...NQ..D.S.TGNK..D.................
WP_002874097.1   ............................................
WP_002873395.1   ............................................
EFV08769.1       ............................................
EFV10698.1       ........Q...NQ..D.S.TGNK..D.................
EAQ94619.1       ............................................
EAQ60315.1       ........Q...NQ..D.S.TGNK.......G............
EAQ58732.1       .....I....N...............D.................
EAQ57731.1       ............................................
CDH62398.1       ............................................
ADN90737.1       ........Q...NQ..D.S.TGNK..D.................
APA80830.1       ............................................
AOW96893.1       ........Q...NQ..D.S.TGNK.......G............
AON66729.1       ............................................
AON65179.1       ..........................A.................
AOH51565.1       .......N.........P..-----.D.................
```

FIG. 12 (Continued)

```
          480                 500
          |                   |
SKNSDGTNFKLTGKTEEELLQNLANHINSKGIEGLKVKVES 509
......................................... 509
......................................... 509
......................................... 509
......................................... 509
......I.................................. 509
......................................... 509
......................................... 509
......................................... 509
......................................... 509
......................................... 509
......................................... 509
......................................... 509
......................................... 510
......................................... 509
......................................... 509
......................................... 509
......................................... 510
......................................... 510
......................................... 510
......................................... 509
......................................... 509
......................................... 509
......................................... 510
......................................... 510
......................................... 510
......................................... 509
......................................... 510
......................................... 504
```

FIG. 12 (Continued)

```
                        520                 540
                         |                   |
Consensus       YNQNNVTGFRLNFSGDGSSDFSIKGDANILKELGLSDVNITSKP
YP_002343979.1  ............................................
WP_038400380.1  ..........................GS................
EAQ73028.1      .D..G.K..K...............N.T................
WP_010790846.1  .D....K..K.................S.......P........
WP_004316510.1  ............................................
WP_004306838.1  .D....K..K..............................S...
WP_002935293.1  ............................................
WP_002928464.1  .D....K..K.................S................
WP_002924910.1  ............................................
WP_002921586.1  .D..G.K..K...............N.T.Q..............
WP_002908989.1  .........K...............N.S................
WP_002901368.1  ............................................
WP_002892358.1  .D..G.K..K...............N.T.Q..............
WP_002874097.1  ............................................
WP_002873395.1  ............................................
EFV08769.1      ............................................
EFV10698.1      .D..G.K..K...............N.T.Q..............
EAQ94619.1      ............................................
EAQ60315.1      .D..G.K..K..................................
EAQ58732.1      .D....K..K.................S............I...
EAQ57731.1      ............................................
CDH62398.1      ............................................
ADN90737.1      .D..G.K..K...............N.T.Q..............
APA80830.1      ............................................
AOW96893.1      .D..G.K..K.K................................
AON66729.1      ............................................
AON65179.1      ..........................GS................
AOH51565.1      .........................N.T................
```

```
          560                                   580
           |                                     |
I E G K G I F S K L K A T L Q E M T G K D G S I T K Y D E S L T N D I K S L N T S 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . N . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 595
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 595
. . . . . . . . . . . . . . . . . . . . . . . . . . . . . . . . . . . . . . . . . 595
. . . . . . . . . . . . . . . . . . . . . . . . . . . . . . . . . . . . . . . . . 595
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 594
. . . . . . . . . . . . . . . . . . . . . . . . . . . . . . . . . . . . . . . . . 595
. . . . . . . . . . . . . . . . . . . . . . . . . . . . . . . . . . . . . . . . . 595
. . . . . . . . . . . . . . . . . . . . . . . . . . . . . . . . . . . . . . . . . 595
. . . . . . . . . . . . . . . . . . . . . . . . . . . . . . . . . . . . . . . . . 594
. . . . . . . . . . . . . . . . . . . . . . . . . . . . . . . . . . . . . . . . . 595
. . . . . . . . . . . . . . . . . . . . . . . . . . . . . . . . . . . . . . . . . 589
```

```
                     600                 620
                       |                   |
      Consensus  K D S T Q A M I D T R Y D T M A N Q W L Q Y E S I L
 YP_002343979.1  . . . . . . . . . . . . . . . . . . . . . . . . . .
 WP_038400380.1  . . . . . . . . . . . . . . . . . . . . . . . . . .
    EAQ73028.1   . . . . . . . . . . . . . . . . . . . . . . . . . .
 WP_010790846.1  . . . . . . . . . . . . . . . . . . . . . . . . . .
 WP_004316510.1  . . . . . . . . . . . . . . . . . . . . . . . . . .
 WP_004306838.1  . . . . . V . . . . . . . . . . . . . . . . . . . .
 WP_002935293.1  . . . . . . . . . . . . . . . . . . . . . . . . . .
 WP_002928464.1  . . . . . . . . . . . . . . . . . . . . . . . . . .
 WP_002924910.1  . . . . . . . . . . . . . . . . . . . . . . . . . .
 WP_002921586.1  . . . . . . . . . . . . . . . . . . . . . . . . . .
 WP_002908989.1  . . . . . . . . . . . . . . . . . . . . . . . . . .
 WP_002901368.1  . . . . . . . . . . . . . . . . . . . . . . . . . .
 WP_002892358.1  . . . . . . . . . . . . . . . . . . . . . . . . . .
 WP_002874097.1  . . . . . . . . . . . . . . . . . . . . . . . . . .
 WP_002873395.1  . . . . . . . . . . . . . . . . . . . . . . . . . .
     EFV08769.1  . . . . . . . . . . . . . . . . . . . . . . . . . .
     EFV10698.1  . . . . . . . . . . . . . . . . . . . . . . . . . .
     EAQ94619.1  . . . . . . . . . . . . . . . . . . . . . . . . . .
     EAQ60315.1  . . . . . . . . . . . . . . . . . . . . . . . . . .
     EAQ58732.1  . . . . . . . . . . . . . . . . . . . . . . . . . .
     EAQ57731.1  . . . . . . . . . . . . . . . . . . . . . . . . . .
     CDH62398.1  . . . . . . . . . . . . . . . . . . . . . . . . . .
     ADN90737.1  . . . . . . . . . . . . . . . . . . . . . . . . . .
     APA80830.1  . . . . . . . . . . . . . . . . . . . . . . . . . .
     AOW96893.1  . . . . . . . . . . . . . . . . . . . . . . . . . .
     AON66729.1  . . . . . . . . . . . . . . . . . . . . . . . . . .
     AON65179.1  . . . . . . . . . . . . . . . . . . . . . . . . . .
     AOH51565.1  . . . . . . . . . . . . . . . . . . . . . . . . . .
```

FIG. 12
(Continued)

```
                                640
                                 |
NKLNQQLNTVTNMINAANNSNN 642
...................... 642
...................... 642
...................... 642
...................... 642
.......S.............. 642
...................... 642
...................... 642
...................... 642
...................... 642
...................... 642
...................... 642
...................... 642
...................... 643
...................... 642
...................... 642
...................... 642
...................... 643
...................... 643
...................... 643
...................... 642
...................... 642
...................... 642
...................... 643
...................... 643
...................... 643
...................... 642
...................... 643
...................... 637
```

FIG. 12 (Continued)

SEQUENCE LISTING

```
<160> NUMBER OF SEQ ID NOS: 95

<210> SEQ ID NO 1
<211> LENGTH: 385
<212> TYPE: DNA
<213> ORGANISM: Artificial Sequence
<220> FEATURE:
<223> OTHER INFORMATION: Synthetic sequence - CAA1
      (VH, codon optimized for IgA2m2)

<400> SEQUENCE: 1

gaagcacagc tggtggagag cggcggcggc ctgatccagc caggcggctc tctgagactg     60

agctgtgagg cctctggctt cagcctgagc tcccacgaga tgaactgggt gagacaggca    120

cctggcaagg gactggagtg gctgagctac atctccacct ctggcatcac aatctactat    180

gcagactccg tgcggggccg gttcaccatc agcagggata cagccaagaa ctccctgtac    240

ctgcagatga attctctgag ggccgaggac accgccctgt atcactgtgc ccgcgatctg    300

ggcggctact gctctggcgg cctgtgctat cctcgcggcg ccctggacct gtggggacag    360

ggaaccacag tgaccgtgtc tagcg                                          385


<210> SEQ ID NO 2
<211> LENGTH: 128
<212> TYPE: PRT
<213> ORGANISM: Artificial Sequence
```

<220> FEATURE:
<223> OTHER INFORMATION: Synthetic sequence - CAA1 (VH)

<400> SEQUENCE: 2

```
Glu Ala Gln Leu Val Glu Ser Gly Gly Gly Leu Ile Gln Pro Gly Gly
1               5                   10                  15

Ser Leu Arg Leu Ser Cys Glu Ala Ser Gly Phe Ser Leu Ser Ser His
            20                  25                  30

Glu Met Asn Trp Val Arg Gln Ala Pro Gly Lys Gly Leu Glu Trp Leu
        35                  40                  45

Ser Tyr Ile Ser Thr Ser Gly Ile Thr Ile Tyr Tyr Ala Asp Ser Val
    50                  55                  60

Arg Gly Arg Phe Thr Ile Ser Arg Asp Thr Ala Lys Asn Ser Leu Tyr
65                  70                  75                  80

Leu Gln Met Asn Ser Leu Arg Ala Glu Asp Thr Ala Leu Tyr His Cys
                85                  90                  95

Ala Arg Asp Leu Gly Gly Tyr Cys Ser Gly Gly Leu Cys Tyr Pro Arg
            100                 105                 110

Gly Ala Leu Asp Leu Trp Gly Gln Gly Thr Thr Val Thr Val Ser Ser
        115                 120                 125
```

<210> SEQ ID NO 3
<211> LENGTH: 322
<212> TYPE: DNA
<213> ORGANISM: Artificial Sequence
<220> FEATURE:
<223> OTHER INFORMATION: Synthetic sequence - CAA1 (VK, codon optimized)

<400> SEQUENCE: 3

```
gacatcctga tgacacagtc tcctagctcc ctgtctgcct ctgtgggcga tagggtgacc      60

atcacatgcc gcgcctccca gacaatccgg acctacgtga actggtatca gcagaagccc     120

ggcgagacac ctaggctgct gatctacgca gcaaccatcc tgcagcgggg cgtgccatcc     180

agattctccg gctctggcag cggcacagac tttaccctga caatcacctc tctgcagccc     240

gaggatttcg gcacctacta ttgtcagcag aattataaga cattcctgac ctttggccag     300

ggcacccggc tggagatcaa gc                                              322
```

<210> SEQ ID NO 4
<211> LENGTH: 107
<212> TYPE: PRT
<213> ORGANISM: Artificial Sequence
<220> FEATURE:
<223> OTHER INFORMATION: Synthetic sequence - CAA1 (VK)

<400> SEQUENCE: 4

```
Asp Ile Leu Met Thr Gln Ser Pro Ser Ser Leu Ser Ala Ser Val Gly
1               5                   10                  15

Asp Arg Val Thr Ile Thr Cys Arg Ala Ser Gln Thr Ile Arg Thr Tyr
            20                  25                  30

Val Asn Trp Tyr Gln Gln Lys Pro Gly Glu Thr Pro Arg Leu Leu Ile
        35                  40                  45

Tyr Ala Ala Thr Ile Leu Gln Arg Gly Val Pro Ser Arg Phe Ser Gly
    50                  55                  60

Ser Gly Ser Gly Thr Asp Phe Thr Leu Thr Ile Thr Ser Leu Gln Pro
65                  70                  75                  80

Glu Asp Phe Gly Thr Tyr Tyr Cys Gln Gln Asn Tyr Lys Thr Phe Leu
                85                  90                  95
```

Thr Phe Gly Gln Gly Thr Arg Leu Glu Ile Lys
100 105

<210> SEQ ID NO 5
<211> LENGTH: 385
<212> TYPE: DNA
<213> ORGANISM: Artificial Sequence
<220> FEATURE:
<223> OTHER INFORMATION: Synthetic sequence - CAA1 (VH, native)

<400> SEQUENCE: 5
gaggcgcagc tggtggagtc tgggggaggc ctgatacagc ctggagggtc cctgagactc 60
tcctgtgaag cctctggctt ctccctcagt tctcatgaaa tgaattgggt ccgccaggct 120
ccagggaagg ggctggagtg gctttcatat attagtacta gtggtattac aatatattac 180
gcggactctg tgaggggccg attcaccatc tccagagaca ccgccaagaa ctcactgtat 240
ctgcaaatga acagcctgag agccgaggac acggctcttt atcactgtgc gagagatctt 300
ggcggttatt gtagtggtgg tttgtgctac ccgaggggtg ccttggatct ctggggccaa 360
gggacaacgg tcaccgtctc gtcag 385

<210> SEQ ID NO 6
<211> LENGTH: 322
<212> TYPE: DNA
<213> ORGANISM: Artificial Sequence
<220> FEATURE:
<223> OTHER INFORMATION: Synthetic sequence - CAA1 (VK, native)

<400> SEQUENCE: 6
gacatcctga tgacccagtc tccatcctcc ctgtctgcat ctgtcggaga cagagtcacc 60
atcacttgcc gggcaagtca gaccattcgc acctatgtaa attggtatca gcagaagcca 120
ggggaaaccc caagactcct tatctatgct gcaaccattt tgcagagagg ggtcccatca 180
aggttcagtg gcagtggatc tgggacagat ttcactctca ccattaccag tctgcaacct 240
gaagattttg gaacttacta ctgtcaacag aactacaaaa cctttctcac cttcggccaa 300
gggacacgac tggagattaa ag 322

<210> SEQ ID NO 7
<211> LENGTH: 576
<212> TYPE: DNA
<213> ORGANISM: Artificial Sequence
<220> FEATURE:
<223> OTHER INFORMATION: Synthetic sequence - CAA1 (VH, codon optimized
for IgA1 backbone)

<400> SEQUENCE: 7
gaagcacagc tggtggagag cggcggcggc ctgatccagc caggcggctc tctgagactg 60
agctgtgagg catctggctt cagcctgagc tcccacgaga tgaactgggt gagacaggca 120
cctggcaagg gcctggagtg gctgagctac atctccacct ctggcatcac aatctactat 180
gcagactccg tgcggggccg gttcaccatc agcagggata cagccaagaa ctccctgtac 240
ctgcagatga attctctgag ggccgaggac accgccctgt atcactgtgc ccgcgatctg 300
ggcggctact gcagcggcgg cctgtgctat cctcgcggcg ccctggacct gtggggacag 360
ggaaccacag tgaccgtgtc tagcgcctcc ccaacatctc ccaaggtgtt ccccctgagc 420
ctgtgctcca cacagcctga tggcaacgtg gtcatcgcct gtctggtgca gggcttcttt 480
cctcaggagc cactgtctgt gacatggtct gagtctggac agggagtgac agcacggaat 540
tttccccctt cccaggacgc ctctggcgat ctgtat 576

<210> SEQ ID NO 8
<211> LENGTH: 384
<212> TYPE: DNA
<213> ORGANISM: Artificial Sequence
<220> FEATURE:
<223> OTHER INFORMATION: Synthetic sequence - CAA1 (VH codon optimized for IgG1 backbone)

<400> SEQUENCE: 8
gaggcccagc tggtggaaag cggcggcggc ctgattcagc ccggcggctc tctgagactg 60
agctgtgagg catctggctt ctccctgagc tcccacgaga tgaactgggt gagacaggca 120
cctggcaagg gcctggagtg gctgtcctac atctccacct ctggcatcac aatctactat 180
gccgactctg tgcggggccg gttcaccatc tccagggata cagccaagaa ctctctgtac 240
ctgcagatga atagcctgag ggccgaggac accgccctgt atcactgtgc acgcgatctg 300
ggcggctact gcagcggcgg cctgtgctat ccaagaggcg ccctggacct gtggggacag 360
ggaaccacag tgacagtgtc tagc 384

<210> SEQ ID NO 9
<211> LENGTH: 8
<212> TYPE: PRT
<213> ORGANISM: Artificial Sequence
<220> FEATURE:
<223> OTHER INFORMATION: Synthetic sequence - CAA1 (HCDR1)

<400> SEQUENCE: 9

Gly Phe Ser Leu Ser Ser His Glu
1               5

<210> SEQ ID NO 10
<211> LENGTH: 8
<212> TYPE: PRT
<213> ORGANISM: Artificial Sequence
<220> FEATURE:
<223> OTHER INFORMATION: Synthetic sequence - CAA1 (HCDR2)

<400> SEQUENCE: 10

Ile Ser Thr Ser Gly Ile Thr Ile
1               5

<210> SEQ ID NO 11
<211> LENGTH: 21
<212> TYPE: PRT
<213> ORGANISM: Artificial Sequence
<220> FEATURE:
<223> OTHER INFORMATION: Synthetic sequence - CAA1 (HCDR3)

<400> SEQUENCE: 11

Ala Arg Asp Leu Gly Gly Tyr Cys Ser Gly Gly Leu Cys Tyr Pro Arg
1               5                   10                  15

Gly Ala Leu Asp Leu
            20

<210> SEQ ID NO 12
<211> LENGTH: 6
<212> TYPE: PRT
<213> ORGANISM: Artificial Sequence
<220> FEATURE:
<223> OTHER INFORMATION: Synthetic sequence - CAA1 (LCDR1)

<400> SEQUENCE: 12

Gln Thr Ile Arg Thr Tyr 1 5

<210> SEQ ID NO 13
<211> LENGTH: 3
<212> TYPE: PRT
<213> ORGANISM: Artificial Sequence
<220> FEATURE:
<223> OTHER INFORMATION: Synthetic sequence - CAA1 (LCDR2)

<400> SEQUENCE: 13

Ala Ala Thr
1

<210> SEQ ID NO 14
<211> LENGTH: 9
<212> TYPE: PRT
<213> ORGANISM: Artificial Sequence
<220> FEATURE:
<223> OTHER INFORMATION: Synthetic sequence - CAA1 (LCDR3)

<400> SEQUENCE: 14

Gln Gln Asn Tyr Lys Thr Phe Leu Thr
1 5

<210> SEQ ID NO 15
<211> LENGTH: 24
<212> TYPE: DNA
<213> ORGANISM: Artificial Sequence
<220> FEATURE:
<223> OTHER INFORMATION: Synthetic sequence - CAA1 (HCDR1; native)

<400> SEQUENCE: 15
ggcttctccc tcagttctca tgaa 24

<210> SEQ ID NO 16
<211> LENGTH: 24
<212> TYPE: DNA
<213> ORGANISM: Artificial Sequence
<220> FEATURE:
<223> OTHER INFORMATION: Synthetic sequence - CAA1 (HCDR2; native)

<400> SEQUENCE: 16
attagtacta gtggtattac aata 24

<210> SEQ ID NO 17
<211> LENGTH: 63
<212> TYPE: DNA
<213> ORGANISM: Artificial Sequence
<220> FEATURE:
<223> OTHER INFORMATION: Synthetic sequence - CAA1 (HCDR3; native)

<400> SEQUENCE: 17
gcgagagatc ttggcggtta ttgtagtggt ggtttgtgct acccgagggg tgccttggat 60
ctc 63

<210> SEQ ID NO 18
<211> LENGTH: 18
<212> TYPE: DNA
<213> ORGANISM: Artificial Sequence
<220> FEATURE:
<223> OTHER INFORMATION: Synthetic sequence - CAA1 (LCDR1; native)

<400> SEQUENCE: 18
cagaccattc gcacctat 18

<210> SEQ ID NO 19
<211> LENGTH: 9
<212> TYPE: DNA
<213> ORGANISM: Artificial Sequence
<220> FEATURE:
<223> OTHER INFORMATION: Synthetic sequence - CAA1 (LCDR1; native)

<400> SEQUENCE: 19 gctgcaacc 9

<210> SEQ ID NO 20
<211> LENGTH: 27
<212> TYPE: DNA
<213> ORGANISM: Artificial Sequence
<220> FEATURE:
<223> OTHER INFORMATION: Synthetic sequence - CAA1 (LCDR3; native)

<400> SEQUENCE: 20
caacagaact acaaaacctt tctcacc 27

<210> SEQ ID NO 21
<211> LENGTH: 355
<212> TYPE: DNA
<213> ORGANISM: Artificial Sequence
<220> FEATURE:
<223> OTHER INFORMATION: Synthetic sequence - CCG4 (VH, native)

<400> SEQUENCE: 21
gaagtgcagc tggtggagtc tgggggaggc ttggtacagc ctggcaggtc cctgagactc 60
tcctgcgcag cctctggaat cacctttgat gaatatgcca tgtactgggt ccggcaagct 120
ccagggaagg gcctggagtg ggtctcaggt attagttgga acagtgctaa tataggctat 180
gcggactctg tgaagggccg attcaccatc tccagagaca acgccaagaa gtccctctat 240
ctgcaaatga atagtctgag agctgaagac acggccttgt attactgttc aggtataact 300
gggactacgg ggatacagta ctggggccag ggaaccctgg tcaccgtctc ctcag 355

<210> SEQ ID NO 22
<211> LENGTH: 118
<212> TYPE: PRT
<213> ORGANISM: Artificial Sequence
<220> FEATURE:
<223> OTHER INFORMATION: Synthetic sequence - CCG4 (VH)

<400> SEQUENCE: 22

```
Glu Val Gln Leu Val Glu Ser Gly Gly Gly Leu Val Gln Pro Gly Arg
1               5                   10                  15

Ser Leu Arg Leu Ser Cys Ala Ala Ser Gly Ile Thr Phe Asp Glu Tyr
            20                  25                  30

Ala Met Tyr Trp Val Arg Gln Ala Pro Gly Lys Gly Leu Glu Trp Val
        35                  40                  45

Ser Gly Ile Ser Trp Asn Ser Ala Asn Ile Gly Tyr Ala Asp Ser Val
    50                  55                  60

Lys Gly Arg Phe Thr Ile Ser Arg Asp Asn Ala Lys Lys Ser Leu Tyr
65                  70                  75                  80

Leu Gln Met Asn Ser Leu Arg Ala Glu Asp Thr Ala Leu Tyr Tyr Cys
                85                  90                  95

Ser Gly Ile Thr Gly Thr Thr Gly Ile Gln Tyr Trp Gly Gln Gly Thr
            100                 105                 110

Leu Val Thr Val Ser Ser
        115
```

<210> SEQ ID NO 23
<211> LENGTH: 322
<212> TYPE: DNA
<213> ORGANISM: Artificial Sequence
<220> FEATURE:
<223> OTHER INFORMATION: Synthetic sequence - CCG4 (VL, native)

<400> SEQUENCE: 23
tcctatgagc tgacacagcc atcctcagtg tcagtgtctc cgggacagac agccaggatc 60
acctgctcag gagatgtatt ggcaaataca tatgctcggt ggttccagca gaagccaggc 120
caggcccctg tactggtgat ttataaagac agtgagcggc cctcagggat ccctgagcga 180
ttctccggct ccagctcagg gaccacagtc accttgatca tcaggggggc ccaggttgag 240
gatgaggctg actattactg ttactctgcg gctgacaaca atcggagggt gttcggcgga 300
gggaccaagc tgaccgtcct ag 322

<210> SEQ ID NO 24
<211> LENGTH: 107
<212> TYPE: PRT
<213> ORGANISM: Artificial Sequence
<220> FEATURE:
<223> OTHER INFORMATION: Synthetic sequence - CCG4 (VL)

<400> SEQUENCE: 24

Ser Tyr Glu Leu Thr Gln Pro Ser Ser Val Ser Val Ser Pro Gly Gln
1 5 10 15

Thr Ala Arg Ile Thr Cys Ser Gly Asp Val Leu Ala Asn Thr Tyr Ala
20 25 30

Arg Trp Phe Gln Gln Lys Pro Gly Gln Ala Pro Val Leu Val Ile Tyr
35 40 45

Lys Asp Ser Glu Arg Pro Ser Gly Ile Pro Glu Arg Phe Ser Gly Ser
50 55 60

Ser Ser Gly Thr Thr Val Thr Leu Ile Ile Arg Gly Ala Gln Val Glu
65 70 75 80

Asp Glu Ala Asp Tyr Tyr Cys Tyr Ser Ala Ala Asp Asn Asn Arg Arg
85 90 95

Val Phe Gly Gly Gly Thr Lys Leu Thr Val Leu
100 105

<210> SEQ ID NO 25
<211> LENGTH: 8
<212> TYPE: PRT
<213> ORGANISM: Artificial Sequence
<220> FEATURE:
<223> OTHER INFORMATION: Synthetic sequence - CCG4 (HCDR1)

<400> SEQUENCE: 25

Gly Ile Thr Phe Asp Glu Tyr Ala
1 5

<210> SEQ ID NO 26
<211> LENGTH: 8
<212> TYPE: PRT
<213> ORGANISM: Artificial Sequence
<220> FEATURE:
<223> OTHER INFORMATION: Synthetic sequence - CCG4 (HCDR2)

<400> SEQUENCE: 26

Ile Ser Trp Asn Ser Ala Asn Ile
1 5

-continued

<210> SEQ ID NO 27
<211> LENGTH: 11
<212> TYPE: PRT
<213> ORGANISM: Artificial Sequence
<220> FEATURE:
<223> OTHER INFORMATION: Synthetic sequence - CCG4 (HCDR3)

<400> SEQUENCE: 27

Ser Gly Ile Thr Gly Thr Thr Gly Ile Gln Tyr
1 5 10

<210> SEQ ID NO 28
<211> LENGTH: 6
<212> TYPE: PRT
<213> ORGANISM: Artificial Sequence
<220> FEATURE:
<223> OTHER INFORMATION: Synthetic sequence - CCG4 (LCDR1)

<400> SEQUENCE: 28

Val Leu Ala Asn Thr Tyr
1 5

<210> SEQ ID NO 29
<211> LENGTH: 3
<212> TYPE: PRT
<213> ORGANISM: Artificial Sequence
<220> FEATURE:
<223> OTHER INFORMATION: Synthetic sequence - CCG4 (LCDR2)

<400> SEQUENCE: 29

Lys Asp Ser
1

<210> SEQ ID NO 30
<211> LENGTH: 10
<212> TYPE: PRT
<213> ORGANISM: Artificial Sequence
<220> FEATURE:
<223> OTHER INFORMATION: Synthetic sequence - CCG4 (LCDR3)

<400> SEQUENCE: 30

Tyr Ser Ala Ala Asp Asn Asn Arg Arg Val
1 5 10

<210> SEQ ID NO 31
<211> LENGTH: 24
<212> TYPE: DNA
<213> ORGANISM: Artificial Sequence
<220> FEATURE:
<223> OTHER INFORMATION: Synthetic sequence - CCG4 (HCDR1; native)

<400> SEQUENCE: 31
ggaatcacct ttgatgaata tgcc 24

<210> SEQ ID NO 32
<211> LENGTH: 24
<212> TYPE: DNA
<213> ORGANISM: Artificial Sequence
<220> FEATURE:
<223> OTHER INFORMATION: Synthetic sequence - CCG4 (HCDR2; native)

<400> SEQUENCE: 32
attagttgga acagtgctaa tata 24

<210> SEQ ID NO 33
<211> LENGTH: 33

<212> TYPE: DNA
<213> ORGANISM: Artificial Sequence
<220> FEATURE:
<223> OTHER INFORMATION: Synthetic sequence - CCG4 (HCDR3; native)

<400> SEQUENCE: 33
tcaggtataa ctgggactac ggggatacag tac 33

<210> SEQ ID NO 34
<211> LENGTH: 18
<212> TYPE: DNA
<213> ORGANISM: Artificial Sequence
<220> FEATURE:
<223> OTHER INFORMATION: Synthetic sequence - CCG4 (LCDR1; native)

<400> SEQUENCE: 34
gtattggcaa atacatat 18

<210> SEQ ID NO 35
<211> LENGTH: 9
<212> TYPE: DNA
<213> ORGANISM: Artificial Sequence
<220> FEATURE:
<223> OTHER INFORMATION: Synthetic sequence - CCG4 (LCDR2; native)

<400> SEQUENCE: 35 aaagacagt 9

<210> SEQ ID NO 36
<211> LENGTH: 30
<212> TYPE: DNA
<213> ORGANISM: Artificial Sequence
<220> FEATURE:
<223> OTHER INFORMATION: Synthetic sequence - CCG4 (LCDR2; native)

<400> SEQUENCE: 36
tactctgcgg ctgacaacaa tcggagggtg 30

<210> SEQ ID NO 37
<211> LENGTH: 549
<212> TYPE: DNA
<213> ORGANISM: Artificial Sequence
<220> FEATURE:
<223> OTHER INFORMATION: Synthetic sequence - CCG4 (VH, codon optimized
for IgA2M2 backbone)

<400> SEQUENCE: 37
gaggtgcagc tggtggaaag cggcggcggc ctggtgcagc caggccggtc tctgagactg 60
tcttgtgcag catctggaat caccttcgac gagtatgcaa tgtattgggt gcggcaggca 120
ccaggcaagg gactggagtg ggtgtccggc atctcttgga acagcgccaa tatcggctac 180
gccgactccg tgaagggcag gtttacaatc tcccgcgata acgccaagaa gtctctgtat 240
ctgcagatga atagcctgag ggccgaggat accgccctgt actattgctc tggcatcaca 300
ggcaccacag gcatccagta ctggggccag ggcaccctgg tgacagtgag ctccgcctcc 360
ccaacctctc ccaaggtgtt ccccctgagc ctggactcca cacctcagga tggcaacgtg 420
gtggtggcct gtctggtgca gggcttcttt cctcaggagc cactgagcgt gacctggtct 480
gagagcggcc agaacgtgac agcccggaat tttccccctt ctcaggacgc cagcggcgat 540
ctgtatacc 549

<210> SEQ ID NO 38
<211> LENGTH: 354

<212> TYPE: DNA
<213> ORGANISM: Artificial Sequence
<220> FEATURE:
<223> OTHER INFORMATION: Synthetic sequence - CCG4 (VH, codon optimized for IgG1 backbone)

<400> SEQUENCE: 38
gaggtgcagc tggtggaaag cggcggcggc ctggtgcagc ctggccggag cctgagactg 60
tcttgtgcag catctggaat caccttcgac gagtacgcca tgtattgggt gcggcaggca 120
cctggcaagg gcctggagtg ggtgtctggc atcagctgga actccgccaa tatcggctac 180
gccgactctg tgaagggcag gtttacaatc tctcgcgata acgccaagaa gagcctgtat 240
ctgcagatga attccctgag ggccgaggat accgccctgt actattgtag cggcatcaca 300
ggcaccacag gcatccagta ctggggccag ggcaccctgg tgacagtgag ctcc 354

<210> SEQ ID NO 39
<211> LENGTH: 321
<212> TYPE: DNA
<213> ORGANISM: Artificial Sequence
<220> FEATURE:
<223> OTHER INFORMATION: Synthetic sequence - CCG4 (VL, codon optimized)

<400> SEQUENCE: 39
agctacgagc tgacccagcc tagctccgtg tctgtgagcc ctggacagac agcaagaatc 60
acatgctctg gcgacgtgct ggccaacaca tacgccaggt ggtttcagca gaagcctgga 120
caggcccccg tgctggtcat ctacaaggat tccgagaggc catctggcat tcctgagcgg 180
ttcagcggct ctagctccgg caccacagtg accctgatca ttagaggcgc ccaggtggag 240
gatgaggcag attactattg ttatagcgcc gccgacaaca atcggagagt gttcggcggc 300
ggaaccaagc tgacagtgct g 321

<210> SEQ ID NO 40
<211> LENGTH: 353
<212> TYPE: PRT
<213> ORGANISM: Artificial Sequence
<220> FEATURE:
<223> OTHER INFORMATION: Synthetic sequence - IgA1 - heavy chain constant region

<400> SEQUENCE: 40

Ala Ser Pro Thr Ser Pro Lys Val Phe Pro Leu Ser Leu Cys Ser Thr
1 5 10 15

Gln Pro Asp Gly Asn Val Val Ile Ala Cys Leu Val Gln Gly Phe Phe
20 25 30

Pro Gln Glu Pro Leu Ser Val Thr Trp Ser Glu Ser Gly Gln Gly Val
35 40 45

Thr Ala Arg Asn Phe Pro Pro Ser Gln Asp Ala Ser Gly Asp Leu Tyr
50 55 60

Thr Thr Ser Ser Gln Leu Thr Leu Pro Ala Thr Gln Cys Leu Ala Gly
65 70 75 80

Lys Ser Val Thr Cys His Val Lys His Tyr Thr Asn Pro Ser Gln Asp
85 90 95

Val Thr Val Pro Cys Pro Val Pro Ser Thr Pro Pro Thr Pro Ser Pro
100 105 110

Ser Thr Pro Pro Thr Pro Ser Pro Ser Cys Cys His Pro Arg Leu Ser
115 120 125

Leu His Arg Pro Ala Leu Glu Asp Leu Leu Leu Gly Ser Glu Ala Asn
130 135 140

-continued

Leu Thr Cys Thr Leu Thr Gly Leu Arg Asp Ala Ser Gly Val Thr Phe
145 150 155 160

Thr Trp Thr Pro Ser Ser Gly Lys Ser Ala Val Gln Gly Pro Pro Glu
165 170 175

Arg Asp Leu Cys Gly Cys Tyr Ser Val Ser Ser Val Leu Pro Gly Cys
180 185 190

Ala Glu Pro Trp Asn His Gly Lys Thr Phe Thr Cys Thr Ala Ala Tyr
195 200 205

Pro Glu Ser Lys Thr Pro Leu Thr Ala Thr Leu Ser Lys Ser Gly Asn
210 215 220

Thr Phe Arg Pro Glu Val His Leu Leu Pro Pro Pro Ser Glu Glu Leu
225 230 235 240

Ala Leu Asn Glu Leu Val Thr Leu Thr Cys Leu Ala Arg Gly Phe Ser
245 250 255

Pro Lys Asp Val Leu Val Arg Trp Leu Gln Gly Ser Gln Glu Leu Pro
260 265 270

Arg Glu Lys Tyr Leu Thr Trp Ala Ser Arg Gln Glu Pro Ser Gln Gly
275 280 285

Thr Thr Thr Phe Ala Val Thr Ser Ile Leu Arg Val Ala Ala Glu Asp
290 295 300

Trp Lys Lys Gly Asp Thr Phe Ser Cys Met Val Gly His Glu Ala Leu
305 310 315 320

Pro Leu Ala Phe Thr Gln Lys Thr Ile Asp Arg Leu Ala Gly Lys Pro
325 330 335

Thr His Val Asn Val Ser Val Val Met Ala Glu Val Asp Gly Thr Cys
340 345 350

Tyr

<210> SEQ ID NO 41
<211> LENGTH: 340
<212> TYPE: PRT
<213> ORGANISM: Artificial Sequence
<220> FEATURE:
<223> OTHER INFORMATION: Synthetic sequence - IgA2(m1) - heavy chain constant region

<400> SEQUENCE: 41

Ala Ser Pro Thr Ser Pro Lys Val Phe Pro Leu Ser Leu Asp Ser Thr
1 5 10 15

Pro Gln Asp Gly Asn Val Val Val Ala Cys Leu Val Gln Gly Phe Phe
20 25 30

Pro Gln Glu Pro Leu Ser Val Thr Trp Ser Glu Ser Gly Gln Asn Val
35 40 45

Thr Ala Arg Asn Phe Pro Pro Ser Gln Asp Ala Ser Gly Asp Leu Tyr
50 55 60

Thr Thr Ser Ser Gln Leu Thr Leu Pro Ala Thr Gln Cys Pro Asp Gly
65 70 75 80

Lys Ser Val Thr Cys His Val Lys His Tyr Thr Asn Pro Ser Gln Asp
85 90 95

Val Thr Val Pro Cys Pro Val Pro Pro Pro Pro Pro Cys Cys His Pro
100 105 110

Arg Leu Ser Leu His Arg Pro Ala Leu Glu Asp Leu Leu Leu Gly Ser
115 120 125

Glu Ala Asn Leu Thr Cys Thr Leu Thr Gly Leu Arg Asp Ala Ser Gly
130 135 140

```
Ala Thr Phe Thr Trp Thr Pro Ser Ser Gly Lys Ser Ala Val Gln Gly
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Phe Ala Val Thr Ser Ile Leu Arg Val Ala
        275                 280                 285

Ala Glu Asp Trp Lys Lys Gly Asp Thr Phe Ser Cys Met Val Gly His
    290                 295                 300

Glu Ala Leu Pro Leu Ala Phe Thr Gln Lys Thr Ile Asp Arg Leu Ala
305                 310                 315                 320

Gly Lys Pro Thr His Val Asn Val Ser Val Val Met Ala Glu Val Asp
                325                 330                 335

Gly Thr Cys Tyr
            340


<210> SEQ ID NO 42
<211> LENGTH: 340
<212> TYPE: PRT
<213> ORGANISM: Artificial Sequence
<220> FEATURE:
<223> OTHER INFORMATION: Synthetic sequence - IgA2(m2) - heavy chain
      constant region

<400> SEQUENCE: 42

Ala Ser Pro Thr Ser Pro Lys Val Phe Pro Leu Ser Leu Asp Ser Thr
1               5                   10                  15

Pro Gln Asp Gly Asn Val Val Val Ala Cys Leu Val Gln Gly Phe Phe
            20                  25                  30

Pro Gln Glu Pro Leu Ser Val Thr Trp Ser Glu Ser Gly Gln Asn Val
        35                  40                  45

Thr Ala Arg Asn Phe Pro Pro Ser Gln Asp Ala Ser Gly Asp Leu Tyr
    50                  55                  60

Thr Thr Ser Ser Gln Leu Thr Leu Pro Ala Thr Gln Cys Pro Asp Gly
65                  70                  75                  80

Lys Ser Val Thr Cys His Val Lys His Tyr Thr Asn Ser Ser Gln Asp
                85                  90                  95

Val Thr Val Pro Cys Arg Val Pro Pro Pro Pro Pro Cys Cys His Pro
            100                 105                 110

Arg Leu Ser Leu His Arg Pro Ala Leu Glu Asp Leu Leu Leu Gly Ser
        115                 120                 125

Glu Ala Asn Leu Thr Cys Thr Leu Thr Gly Leu Arg Asp Ala Ser Gly
    130                 135                 140

Ala Thr Phe Thr Trp Thr Pro Ser Ser Gly Lys Ser Ala Val Gln Gly
```

-continued

```
145                 150                 155                 160

Pro Pro Glu Arg Asp Leu Cys Gly Cys Tyr Ser Val Ser Ser Val Leu
                165                 170                 175

Pro Gly Cys Ala Gln Pro Trp Asn His Gly Glu Thr Phe Thr Cys Thr
            180                 185                 190

Ala Ala His Pro Glu Leu Lys Thr Pro Leu Thr Ala Asn Ile Thr Lys
        195                 200                 205

Ser Gly Asn Thr Phe Arg Pro Glu Val His Leu Leu Pro Pro Pro Ser
    210                 215                 220

Glu Glu Leu Ala Leu Asn Glu Leu Val Thr Leu Thr Cys Leu Ala Arg
225                 230                 235                 240

Gly Phe Ser Pro Lys Asp Val Leu Val Arg Trp Leu Gln Gly Ser Gln
                245                 250                 255

Glu Leu Pro Arg Glu Lys Tyr Leu Thr Trp Ala Ser Arg Gln Glu Pro
            260                 265                 270

Ser Gln Gly Thr Thr Thr Tyr Ala Val Thr Ser Ile Leu Arg Val Ala
        275                 280                 285

Ala Glu Asp Trp Lys Lys Gly Glu Thr Phe Ser Cys Met Val Gly His
    290                 295                 300

Glu Ala Leu Pro Leu Ala Phe Thr Gln Lys Thr Ile Asp Arg Met Ala
305                 310                 315                 320

Gly Lys Pro Thr His Ile Asn Val Ser Val Val Met Ala Glu Ala Asp
                325                 330                 335

Gly Thr Cys Tyr
            340


<210> SEQ ID NO 43
<211> LENGTH: 642
<212> TYPE: PRT
<213> ORGANISM: Artificial Sequence
<220> FEATURE:
<223> OTHER INFORMATION: Synthetic sequence - Campylobacter jejuni
      subsp. jejuni serotype O:23/36 (strain 81-176) Flagellar
      hook-associated protein 2 (Uniprot A0A0H3PIU8)

<400> SEQUENCE: 43

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Glu Leu Ala Asp
145                 150                 155                 160
```

-continued

```
Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Ser Glu Ala Glu Thr Ile Phe Lys Asn
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Gly Val Lys Gly Phe Lys Leu Asn Phe Ser Gly Asp Gly Ser Ser
        515                 520                 525

Asp Phe Ser Ile Lys Gly Asn Ala Thr Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575
```

-continued

```
Ile Thr Lys Tyr Asp Glu Ser Leu Thr Asn Asn Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 44
<211> LENGTH: 642
<212> TYPE: PRT
<213> ORGANISM: Artificial Sequence
<220> FEATURE:
<223> OTHER INFORMATION: Synthetic sequence - Campylobacter jejuni
      subsp. jejuni serotype O:2 (strain ATCC 700819 / NCTC
      11168) (Uniprot Q9PHW6)

<400> SEQUENCE: 44

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Ile Asn Ala Glu Lys Ile Phe Asp Asp
    210                 215                 220

Leu Gly Trp Gly Leu Asp Val Ser Ala Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285
```

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn

<210> SEQ ID NO 45
<211> LENGTH: 642
<212> TYPE: PRT
<213> ORGANISM: Artificial Sequence
<220> FEATURE:
<223> OTHER INFORMATION: Synthetic sequence - flagellar hook-associated
      protein 2 [Campylobacter jejuni subsp. jejuni NCTC
      11168 = ATCC 700819] NCBI Reference Sequence:
      YP_002343979.1

-continued

<400> SEQUENCE: 45

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Lys Gly Leu Ala Asn Asp Gly Gly Phe Val Asn Ala
115 120 125

Gln Leu Asn Gly Thr Ala Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn
165 170 175

Thr Gly Glu Lys Gly Thr Pro Tyr Arg Leu Thr Leu Thr Ser Lys Glu
180 185 190

Thr Gly Glu Asp Ser Ala Ile Ser Phe Tyr Ala Gly Lys Lys Asp Ser
195 200 205

Asn Gly Lys Tyr Gln Lys Asp Ile Asn Ala Glu Lys Ile Phe Asp Asp
210 215 220

Leu Gly Trp Gly Leu Asp Val Ser Ala Ser Ile Asp Pro Asp Lys Asp
225 230 235 240

Lys Lys Gly Tyr Gly Ile Lys Asp Ala Ser Leu His Ile Gln Thr Ala
245 250 255

Gln Asn Ala Glu Phe Thr Leu Asp Gly Ile Lys Met Phe Arg Ser Ser
260 265 270

Asn Thr Val Thr Asp Leu Gly Val Gly Met Thr Leu Thr Leu Asn Lys
275 280 285

Thr Gly Glu Ile Asn Phe Asp Val Gln Gln Asp Phe Glu Gly Val Thr
290 295 300

Lys Ala Met Gln Asp Leu Val Asp Ala Tyr Asn Asp Leu Val Thr Asn
305 310 315 320

Leu Asn Ala Ala Thr Asp Tyr Asn Ser Glu Thr Gly Thr Lys Gly Thr
325 330 335

Leu Gln Gly Ile Ser Glu Val Asn Ser Ile Arg Ser Ser Ile Leu Ala
340 345 350

Asp Leu Phe Asp Ser Gln Val Val Asp Gly Thr Thr Glu Asp Ala Asn
355 360 365

Gly Asn Lys Val Asn Thr Lys Val Met Leu Ser Met Gln Asp Phe Gly
370 375 380

Leu Ser Leu Asn Asp Ala Gly Thr Leu Ser Phe Asp Ser Ser Lys Phe
385 390 395 400

Glu Gln Lys Val Lys Glu Asp Pro Asp Ser Thr Glu Ser Phe Phe Ser

```
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 46
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_038400380.1

<400> SEQUENCE: 46

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110
```

-continued

```
Val Tyr Gln Ser Gln Gly Leu Ala Asn Asp Ser Gly Phe Ile Asn Ala
        115                 120                 125

Asn Leu Ala Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Leu Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Ala Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Gly Ser Ile Leu Lys Glu Leu Gly Leu
```

```
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 47
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_038400380.1

<400> SEQUENCE: 47

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Glu Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Ser Glu Ala Glu Thr Ile Phe Lys Asn
    210                 215                 220

Leu Gly Trp Glu Leu Asp Thr Thr Ser Ser Ile Asp Pro Ala Lys Asp
225                 230                 235                 240
```

-continued

```
Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Gly Val Lys Gly Phe Lys Leu Asn Phe Ser Gly Asp Gly Ser Ser
        515                 520                 525

Asp Phe Ser Ile Lys Gly Asn Ala Thr Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asn Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 48

<211> LENGTH: 642
<212> TYPE: PRT
<213> ORGANISM: Artificial Sequence
<220> FEATURE:
<223> OTHER INFORMATION: Synthetic sequence - flagellar filament capping protein FliD [Campylobacter jejuni] NCBI Reference Sequence: WP_010790846.1

<400> SEQUENCE: 48

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Ala Ser Ala Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365
```

-continued

Gly Asn Lys Val Asn Thr Lys Val Met Leu Ser Met Gln Asp Phe Gly
370 375 380

Leu Ser Leu Asn Asp Ala Gly Thr Leu Asn Phe Asp Ser Ser Lys Phe
385 390 395 400

Glu Gln Lys Val Lys Glu Asp Pro Asp Ser Ala Glu Ser Phe Phe Ser
405 410 415

Asn Ile Thr Lys Tyr Glu Asp Ile Asn His Thr Gly Glu Ile Ile Lys
420 425 430

Thr Gly Ser Leu Ser Lys Tyr Leu Asn Ser Asn Gly Gly Asn Thr Asn
435 440 445

Gly Leu Asp Phe Lys Pro Gly Asp Phe Thr Ile Val Phe Asn Asn Gln
450 455 460

Thr Tyr Asp Leu Ser Lys Asn Ser Asp Gly Thr Asn Phe Lys Leu Thr
465 470 475 480

Gly Lys Thr Glu Glu Glu Leu Leu Gln Asn Leu Ala Asn His Ile Asn
485 490 495

Ser Lys Gly Ile Glu Gly Leu Lys Val Lys Val Glu Ser Tyr Asp Gln
500 505 510

Asn Asn Val Lys Gly Phe Lys Leu Asn Phe Ser Gly Asp Gly Ser Ser
515 520 525

Asp Phe Ser Ile Lys Gly Asp Ala Ser Ile Leu Lys Glu Leu Gly Leu
530 535 540

Pro Asp Val Asn Ile Thr Ser Lys Pro Ile Glu Gly Lys Gly Ile Phe
545 550 555 560

Ser Lys Leu Lys Ala Thr Leu Gln Glu Met Thr Gly Lys Asp Gly Ser
565 570 575

Ile Thr Lys Tyr Asp Glu Ser Leu Thr Asn Asp Ile Lys Ser Leu Asn
580 585 590

Thr Ser Lys Asp Ser Thr Gln Ala Met Ile Asp Thr Arg Tyr Asp Thr
595 600 605

Met Ala Asn Gln Trp Leu Gln Tyr Glu Ser Ile Leu Asn Lys Leu Asn
610 615 620

Gln Gln Leu Asn Thr Val Thr Asn Met Ile Asn Ala Ala Asn Asn Ser
625 630 635 640

Asn Asn

<210> SEQ ID NO 49
<211> LENGTH: 642
<212> TYPE: PRT
<213> ORGANISM: Artificial Sequence
<220> FEATURE:
<223> OTHER INFORMATION: Synthetic sequence - MULTISPECIES: flagellar
filament capping protein FliD [Campylobacter]
NCBI Reference Sequence: WP_004316510.1

<400> SEQUENCE: 49

Met Ala Phe Gly Ser Leu Ala Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

-continued

```
Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Asn Leu Asn Gly Thr Ala Asp Leu Thr Phe Phe Ser Asn Gly Lys Glu
    130                 135                 140

Tyr Thr Val Thr Val Asp Arg Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Asn Gly Ala Tyr Lys Asn Asp Pro Asn Ala Glu Thr Ile Phe Lys Asn
    210                 215                 220

Leu Gly Trp Glu Leu Asp Ala Thr Ser Ser Ile Asp Leu Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Ile Asn Phe Lys Leu Thr
465                 470                 475                 480

Gly Lys Thr Glu Glu Glu Leu Leu Gln Asn Leu Ala Asn His Ile Asn
                485                 490                 495
```

-continued

```
Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Ser Thr Val Thr Asn Met Ile Asn Ala Ala Asn Asn Ser
625                 630                 635                 640

Asn Asn


<210> SEQ ID NO 50
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_004306838.1

<400> SEQUENCE: 50

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205
```

-continued

```
Gln Gly Gln Tyr Lys Ser Asp Leu Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Lys Lys Val Lys Glu Asp Pro Asp Ser Ala Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Ser Ala Asn
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Asn Val Lys Gly Phe Lys Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Ser Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Val Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620
```

-continued

Gln Gln Leu Asn Thr Val Thr Asn Met Ile Asn Ala Ala Asn Asn Ser
625 630 635 640

Asn Asn

<210> SEQ ID NO 51
<211> LENGTH: 642
<212> TYPE: PRT
<213> ORGANISM: Artificial Sequence
<220> FEATURE:
<223> OTHER INFORMATION: Synthetic sequence - flagellar filament capping protein FliD [Campylobacter jejuni] NCBI Reference Sequence: WP_002935293.1

<400> SEQUENCE: 51

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Lys Gly Leu Ala Asn Asp Ser Gly Phe Val Asn Ala
115 120 125

Gln Leu Asn Gly Thr Ala Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn
165 170 175

Thr Gly Glu Lys Gly Thr Pro Tyr Arg Leu Thr Leu Thr Ser Lys Glu
180 185 190

Thr Gly Glu Asp Ser Ala Ile Ser Phe Tyr Ala Gly Lys Lys Asp Ser
195 200 205

Asn Gly Lys Tyr Gln Lys Asp Thr Asn Ala Glu Lys Ile Phe Asp Asp
210 215 220

Leu Gly Trp Glu Leu Asp Val Ser Ala Ser Ile Asp Pro Asp Lys Asp
225 230 235 240

Lys Lys Gly Tyr Gly Ile Lys Asp Ala Ser Leu His Ile Gln Thr Ala
245 250 255

Gln Asn Ala Glu Phe Thr Leu Asp Gly Ile Lys Met Phe Arg Ser Ser
260 265 270

Asn Thr Val Thr Asp Leu Gly Val Gly Met Thr Leu Thr Leu Asn Lys
275 280 285

Thr Gly Glu Ile Asn Phe Asp Val Gln Gln Asp Phe Glu Gly Val Thr
290 295 300

Lys Ala Met Gln Asp Leu Val Asp Ala Tyr Asn Asp Leu Val Thr Asn
305 310 315 320

Leu Asn Ala Ala Thr Asp Tyr Asn Ser Glu Thr Gly Thr Lys Gly Thr
325 330 335

```
Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Tyr Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 52
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_002928464.1

<400> SEQUENCE: 52

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
```

-continued

```
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Ala Ser Ala Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Asn Phe Asp Ser Ser Lys Phe
385                 390                 395                 400

Glu Gln Lys Val Lys Glu Asp Pro Asp Ser Ala Glu Ser Phe Phe Ser
                405                 410                 415

Asn Ile Thr Lys Tyr Glu Asp Ile Asn His Thr Gly Glu Ile Ile Lys
            420                 425                 430

Thr Gly Ser Leu Ser Lys Tyr Leu Asn Ser Asn Gly Gly Asn Thr Asn
        435                 440                 445

Gly Leu Asp Phe Lys Pro Gly Asp Phe Thr Ile Val Phe Asn Asn Gln
    450                 455                 460
```

Thr Tyr Asp Leu Ser Lys Asn Ser Asp Gly Thr Asn Phe Lys Leu Thr
465 470 475 480

Gly Lys Thr Glu Glu Glu Leu Leu Gln Asn Leu Ala Asn His Ile Asn
485 490 495

Ser Lys Gly Ile Glu Gly Leu Lys Val Lys Val Glu Ser Tyr Asp Gln
500 505 510

Asn Asn Val Lys Gly Phe Lys Leu Asn Phe Ser Gly Asp Gly Ser Ser
515 520 525

Asp Phe Ser Ile Lys Gly Asp Ala Ser Ile Leu Lys Glu Leu Gly Leu
530 535 540

Ser Asp Val Asn Ile Thr Ser Lys Pro Ile Glu Gly Lys Gly Ile Phe
545 550 555 560

Ser Lys Leu Lys Ala Thr Leu Gln Glu Met Thr Gly Lys Asp Gly Ser
565 570 575

Ile Thr Lys Tyr Asp Glu Ser Leu Thr Asn Asp Ile Lys Ser Leu Asn
580 585 590

Thr Ser Lys Asp Ser Thr Gln Ala Met Ile Asp Thr Arg Tyr Asp Thr
595 600 605

Met Ala Asn Gln Trp Leu Gln Tyr Glu Ser Ile Leu Asn Lys Leu Asn
610 615 620

Gln Gln Leu Asn Thr Val Thr Asn Met Ile Asn Ala Ala Asn Asn Ser
625 630 635 640

Asn Asn

<210> SEQ ID NO 53
<211> LENGTH: 642
<212> TYPE: PRT
<213> ORGANISM: Artificial Sequence
<220> FEATURE:
<223> OTHER INFORMATION: Synthetic sequence - flagellar filament capping protein FliD [Campylobacter jejuni] NCBI Reference Sequence: WP_002924910.1

<400> SEQUENCE: 53

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Gln Gly Leu Ala Asn Asp Gly Gly Phe Val Asn Ala
115 120 125

Lys Leu Asn Gly Thr Ala Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn

-continued

```
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Val
        195                 200                 205

Gln Gly Gln Tyr Lys Ser Asp Ser Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590
```

```
Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 54
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_002921586.1

<400> SEQUENCE: 54

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Asp Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Ser Glu Ala Glu Thr Ile Phe Lys Asn
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
```

```
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Gly Val Lys Gly Phe Lys Leu Asn Phe Ser Gly Asp Gly Ser Ser
        515                 520                 525

Asp Phe Ser Ile Lys Gly Asn Ala Thr Ile Leu Gln Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 55
<211> LENGTH: 642
<212> TYPE: PRT
<213> ORGANISM: Artificial Sequence
<220> FEATURE:
<223> OTHER INFORMATION: Synthetic sequence - flagellar filament capping protein FliD [Campylobacter jejuni] NCBI Reference Sequence: WP_002908989.1

<400> SEQUENCE: 55

-continued

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
```

```
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Lys Leu Asn Phe Ser Gly Asp Gly Ser Ser
        515                 520                 525

Asp Phe Ser Ile Lys Gly Asn Ala Ser Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 56
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_002901368.1

<400> SEQUENCE: 56

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125
```

-continued

```
Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Leu Glu Ala Lys Thr Ile Phe Lys Asn
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
```

```
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 57
<211> LENGTH: 643
<212> TYPE: PRT
<213> ORGANISM: Artificial Sequence
<220> FEATURE:
<223> OTHER INFORMATION: Synthetic sequence - MULTISPECIES: flagellar
      filament capping protein FliD [Campylobacter] NCBI
      Reference Sequence: WP_002892358.1

<400> SEQUENCE: 57

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Ala Tyr Lys Asn Asp Pro Asn Ala Glu Thr Ile Phe Lys Asn
    210                 215                 220

Leu Gly Trp Glu Leu Asp Thr Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255
```

```
Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Gln Gly Ser Leu Asn Gln Tyr Leu Asp Ser Ser Gly Thr Gly Asn
        435                 440                 445

Lys Gly Leu Asp Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Asn Phe Ser Gly Asp Gly Ser
        515                 520                 525

Ser Asp Phe Ser Ile Lys Gly Asn Ala Thr Ile Leu Gln Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn
```

<210> SEQ ID NO 58
<211> LENGTH: 642
<212> TYPE: PRT
<213> ORGANISM: Artificial Sequence

```
<220> FEATURE:
<223> OTHER INFORMATION: Synthetic sequence - flagellar filament capping
      protein FliD [Campylobacter jejuni] NCBI Reference
      Sequence: WP_002874097.1

<400> SEQUENCE: 58

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Lys Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Ser Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Ser Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380
```

-continued

```
Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 59
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter jejuni] NCBI Reference
      Sequence: WP_002873395.1

<400> SEQUENCE: 59

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95
```

-continued

```
Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510
```

```
Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 60
<211> LENGTH: 642
<212> TYPE: PRT
<213> ORGANISM: Artificial Sequence
<220> FEATURE:
<223> OTHER INFORMATION: Synthetic sequence - flagellar hook-associated
      protein FliD [Campylobacter jejuni subsp. jejuni
      305] GenBank: EFV08769.1

<400> SEQUENCE: 60

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Ile Asn Ala Glu Lys Ile Phe Asp Asp
    210                 215                 220
```

-continued

```
Leu Gly Trp Gly Leu Asp Val Ser Ala Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640
```

Asn Asn

<210> SEQ ID NO 61
<211> LENGTH: 643
<212> TYPE: PRT
<213> ORGANISM: Artificial Sequence
<220> FEATURE:
<223> OTHER INFORMATION: Synthetic sequence - flagellar hook-associated protein FliD [Campylobacter jejuni subsp. jejuni 327] GenBank: EFV10698.1

<400> SEQUENCE: 61

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Lys Gly Leu Ala Asn Asp Ser Gly Phe Val Asn Ala
115 120 125

Asn Leu Thr Gly Thr Thr Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn
165 170 175

Thr Gly Glu Lys Gly Thr Pro Tyr Arg Leu Thr Leu Thr Ser Lys Glu
180 185 190

Thr Gly Glu Asp Ser Ala Ile Ser Phe Tyr Ala Gly Lys Lys Asp Ala
195 200 205

Gln Gly Gln Tyr Gln Ser Asp Pro Glu Ala Glu Asn Ile Phe Ser Asn
210 215 220

Leu Gly Trp Glu Leu Asp Lys Thr Thr Gln Thr Ile Asp Pro Ala Lys
225 230 235 240

Asp Lys Lys Gly Tyr Gly Ile Lys Asp Ala Ser Leu His Ile Gln Thr
245 250 255

Ala Gln Asn Ala Glu Phe Thr Leu Asp Gly Ile Lys Met Phe Arg Ser
260 265 270

Ser Asn Thr Val Thr Asp Leu Gly Val Gly Met Thr Leu Thr Leu Asn
275 280 285

Lys Thr Gly Glu Ile Asn Phe Asp Val Gln Gln Asp Phe Glu Gly Val
290 295 300

Thr Lys Ala Met Gln Asp Leu Val Asp Ala Tyr Asn Asp Leu Val Thr
305 310 315 320

Asn Leu Asn Ala Ala Thr Asp Tyr Asn Ser Glu Thr Gly Thr Lys Gly
325 330 335

Thr Leu Gln Gly Ile Ser Glu Val Asn Ser Ile Arg Ser Ser Ile Leu
340 345 350

```
Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Gln Gly Ser Leu Asn Gln Tyr Leu Asp Ser Ser Gly Thr Gly Asn
        435                 440                 445

Lys Gly Leu Asp Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Asn Phe Ser Gly Asp Gly Ser
        515                 520                 525

Ser Asp Phe Ser Ile Lys Gly Asn Ala Thr Ile Leu Gln Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn


<210> SEQ ID NO 62
<211> LENGTH: 643
<212> TYPE: PRT
<213> ORGANISM: Artificial Sequence
<220> FEATURE:
<223> OTHER INFORMATION: Synthetic sequence - flagellar hook-associated
      protein FliD [Campylobacter jejuni subsp. jejuni
      84-25]

<400> SEQUENCE: 62

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
```

```
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Ser Gly Phe Ile Asn Ala
        115                 120                 125

Asn Leu Ala Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Gln Ser Asp Pro Glu Ala Glu Lys Ile Phe Ser Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Thr Gly Ser Leu Ser Lys Tyr Leu Asn Ser Asn Gly Gly Asn Thr
        435                 440                 445

Asn Gly Leu Glu Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480
```

-continued

```
Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asn
            500                 505                 510

Gln Asn Asn Val Thr Gly Phe Arg Leu Asn Phe Ser Gly Asp Gly Ser
        515                 520                 525

Ser Asp Phe Ser Ile Lys Gly Asp Ala Asn Ile Leu Lys Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn


<210> SEQ ID NO 63
<211> LENGTH: 643
<212> TYPE: PRT
<213> ORGANISM: Artificial Sequence
<220> FEATURE:
<223> OTHER INFORMATION: Synthetic sequence -  flagellar hook-associated
      protein FliD [Campylobacter jejuni subsp. jejuni
      HB93-13]
      GenBank: EAQ60315.1

<400> SEQUENCE: 63

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Ser Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175
```

-continued

```
Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Ser Glu Ala Glu Lys Ile Phe Ser Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Gln Gly Ser Leu Asn Gln Tyr Leu Asp Ser Ser Gly Thr Gly Asn
        435                 440                 445

Lys Gly Leu Glu Phe Lys Pro Gly Gly Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Asn Phe Ser Gly Asp Gly Ser
        515                 520                 525

Ser Asp Phe Ser Ile Lys Gly Asp Ala Asn Ile Leu Lys Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
```

595 600 605

Thr Met Ala Asn Gln Trp Leu Gln Tyr Glu Ser Ile Leu Asn Lys Leu
610 615 620

Asn Gln Gln Leu Asn Thr Val Thr Asn Met Ile Asn Ala Ala Asn Asn
625 630 635 640

Ser Asn Asn

<210> SEQ ID NO 64
<211> LENGTH: 642
<212> TYPE: PRT
<213> ORGANISM: Artificial Sequence
<220> FEATURE:
<223> OTHER INFORMATION: Synthetic sequence - flagellar hook-associated protein FliD [Campylobacter jejuni subsp. jejuni 260.94] GenBank: EAQ58732.1

<400> SEQUENCE: 64

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Lys Gly Leu Ala Asn Asp Gly Gly Phe Val Asn Ala
115 120 125

Gln Leu Asn Gly Thr Ala Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn
165 170 175

Thr Gly Glu Lys Gly Thr Pro Tyr Arg Leu Thr Leu Thr Ser Lys Glu
180 185 190

Thr Gly Glu Asp Ser Ala Ile Ser Phe Tyr Ala Gly Lys Lys Asp Ser
195 200 205

Asn Gly Lys Tyr Gln Lys Asp Thr Asn Ala Glu Lys Ile Phe Asp Asp
210 215 220

Leu Gly Trp Gly Leu Asp Ala Ser Ala Ser Ile Asp Pro Ala Lys Asp
225 230 235 240

Lys Lys Gly Tyr Gly Ile Lys Asp Ala Ser Leu His Ile Gln Thr Ala
245 250 255

Gln Asn Ala Glu Phe Thr Leu Asp Gly Ile Lys Met Phe Arg Ser Ser
260 265 270

Asn Thr Val Thr Asp Leu Gly Val Gly Met Thr Leu Thr Leu Asn Lys
275 280 285

Thr Gly Glu Ile Asn Phe Asp Val Gln Gln Asp Phe Glu Gly Val Thr
290 295 300

Lys Ala Met Gln Asp Leu Val Asp Ala Tyr Asn Asp Leu Val Thr Asn
305 310 315 320

Leu Asn Ala Ala Thr Asp Tyr Asn Ser Glu Thr Gly Thr Lys Gly Thr
325 330 335

Leu Gln Gly Ile Ser Glu Val Asn Ser Ile Arg Ser Ser Ile Leu Ala
340 345 350

Asp Leu Phe Asp Ser Gln Val Val Asp Gly Thr Thr Glu Asp Ala Asn
355 360 365

Gly Asn Lys Val Asn Thr Lys Val Met Leu Ser Met Gln Asp Phe Gly
370 375 380

Leu Ser Leu Asn Asp Ala Gly Thr Leu Asn Phe Asp Ser Ser Lys Phe
385 390 395 400

Glu Gln Lys Val Lys Glu Asp Pro Asp Ser Ala Glu Ser Phe Phe Ser
405 410 415

Asn Ile Thr Lys Tyr Glu Asp Ile Asn His Thr Gly Glu Ile Ile Lys
420 425 430

Thr Gly Asn Leu Ser Lys Tyr Leu Asn Ser Asn Gly Gly Asn Thr Asn
435 440 445

Gly Leu Asp Phe Lys Pro Gly Asp Phe Thr Ile Val Phe Asn Asn Gln
450 455 460

Thr Tyr Asp Leu Ser Lys Asn Ser Asp Gly Thr Asn Phe Lys Leu Thr
465 470 475 480

Gly Lys Thr Glu Glu Glu Leu Leu Gln Asn Leu Ala Asn His Ile Asn
485 490 495

Ser Lys Gly Ile Glu Gly Leu Lys Val Lys Val Glu Ser Tyr Asp Gln
500 505 510

Asn Asn Val Lys Gly Phe Lys Leu Asn Phe Ser Gly Asp Gly Ser Ser
515 520 525

Asp Phe Ser Ile Lys Gly Asp Ala Ser Ile Leu Lys Glu Leu Gly Leu
530 535 540

Ser Asp Val Asn Ile Ile Ser Lys Pro Ile Glu Gly Lys Gly Ile Phe
545 550 555 560

Ser Lys Leu Lys Ala Thr Leu Gln Glu Met Thr Gly Lys Asp Gly Ser
565 570 575

Ile Thr Lys Tyr Asp Glu Ser Leu Thr Asn Asp Ile Lys Ser Leu Asn
580 585 590

Thr Ser Lys Asp Ser Thr Gln Ala Met Ile Asp Thr Arg Tyr Asp Thr
595 600 605

Met Ala Asn Gln Trp Leu Gln Tyr Glu Ser Ile Leu Asn Lys Leu Asn
610 615 620

Gln Gln Leu Asn Thr Val Thr Asn Met Ile Asn Ala Ala Asn Asn Ser
625 630 635 640

Asn Asn

<210> SEQ ID NO 65
<211> LENGTH: 642
<212> TYPE: PRT
<213> ORGANISM: Artificial Sequence
<220> FEATURE:
<223> OTHER INFORMATION: Synthetic sequence - flagellar hook-associated protein FliD [Campylobacter jejuni subsp. jejuni CF93-6]
GenBank: EAQ57731.1

<400> SEQUENCE: 65

-continued

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Ile Asn Ala Glu Lys Ile Phe Asp Asp
    210                 215                 220

Leu Gly Trp Gly Leu Asp Val Ser Ala Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
```

-continued

```
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 66
<211> LENGTH: 642
<212> TYPE: PRT
<213> ORGANISM: Artificial Sequence
<220> FEATURE:
<223> OTHER INFORMATION: Synthetic sequence -  Flagellar hook-associated
      protein FliD [Campylobacter jejuni 4031] GenBank:
      CDH62398.1

<400> SEQUENCE: 66

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125
```

-continued

```
Lys Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Ser Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
```

-continued

```
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 67
<211> LENGTH: 643
<212> TYPE: PRT
<213> ORGANISM: Artificial Sequence
<220> FEATURE:
<223> OTHER INFORMATION: Synthetic sequence - Flagellar hook-associated
      protein 2 [Campylobacter jejuni subsp. jejuni M1]
      GenBank: ADN90737.1

<400> SEQUENCE: 67

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Val Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Gln Ser Asp Pro Glu Ala Glu Asn Ile Phe Ser Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255
```

-continued

```
Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Gln Gly Ser Leu Asn Gln Tyr Leu Asp Ser Ser Gly Thr Gly Asn
        435                 440                 445

Lys Gly Leu Asp Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Asn Phe Ser Gly Asp Gly Ser
        515                 520                 525

Ser Asp Phe Ser Ile Lys Gly Asn Ala Thr Ile Leu Gln Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn
```

<210> SEQ ID NO 68
<211> LENGTH: 643
<212> TYPE: PRT
<213> ORGANISM: Artificial Sequence

```
<220> FEATURE:
<223> OTHER INFORMATION: Synthetic sequence - flagellar filament cap
      protein FliD [Campylobacter jejuni subsp. jejuni
      str. RM3420]
      GenBank: AOW96893.1

<400> SEQUENCE: 68

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Ser Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Ser Glu Ala Glu Lys Ile Phe Ser Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380
```

```
Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Gln Gly Ser Leu Asn Gln Tyr Leu Asp Ser Ser Gly Thr Gly Asn
        435                 440                 445

Lys Gly Leu Glu Phe Lys Pro Gly Gly Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Lys Phe Ser Gly Asp Gly Ser
        515                 520                 525

Ser Asp Phe Ser Ile Lys Gly Asp Ala Asn Ile Leu Lys Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn


<210> SEQ ID NO 69
<211> LENGTH: 642
<212> TYPE: PRT
<213> ORGANISM: Artificial Sequence
<220> FEATURE:
<223> OTHER INFORMATION: Synthetic sequence - flagellar filament cap
      protein FliD [Campylobacter jejuni subsp. jejuni]
      GenBank: AON66729.1

<400> SEQUENCE: 69

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
```

```
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Lys Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Pro Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Ile Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510
```

```
Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 70
<211> LENGTH: 643
<212> TYPE: PRT
<213> ORGANISM: Artificial Sequence
<220> FEATURE:
<223> OTHER INFORMATION: Synthetic sequence - flagellar filament cap
      protein FliD [Campylobacter jejuni subsp. jejuni]
      GenBank: AON65179.1

<400> SEQUENCE: 70

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Ser Gly Phe Ile Asn Ala
        115                 120                 125

Asn Leu Ala Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Gln Ser Asp Pro Glu Ala Glu Lys Ile Phe Ser Asn
```

-continued

```
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Thr Gly Ser Leu Ser Lys Tyr Leu Asn Ser Asn Gly Gly Asn Thr
        435                 440                 445

Asn Gly Leu Ala Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asn
            500                 505                 510

Gln Asn Asn Val Thr Gly Phe Arg Leu Asn Phe Ser Gly Asp Gly Ser
        515                 520                 525

Ser Asp Phe Ser Ile Lys Gly Asp Gly Ser Ile Leu Lys Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640
```

Ser Asn Asn

<210> SEQ ID NO 71
<211> LENGTH: 637
<212> TYPE: PRT
<213> ORGANISM: Artificial Sequence
<220> FEATURE:
<223> OTHER INFORMATION: Synthetic sequence - flagellar filament cap protein [Campylobacter jejuni subsp. jejuni] GenBank: AOH51565.1

<400> SEQUENCE: 71

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala 340 345 350

Asp Leu Phe Asp Ser Gln Val Val Asp Gly Thr Thr Glu Asp Ala Asn
355 360 365

Gly Asn Lys Val Asn Thr Lys Val Met Leu Ser Met Gln Asp Phe Gly
370 375 380

Leu Ser Leu Asn Asp Ala Gly Thr Leu Ser Phe Asp Ser Ser Lys Phe
385 390 395 400

Glu Gln Lys Val Lys Glu Asp Pro Asp Ser Thr Glu Ser Phe Phe Ser
405 410 415

Asn Ile Thr Lys Tyr Glu Asp Ile Asn His Thr Gly Glu Val Ile Asn
420 425 430

Thr Gly Ser Leu Ser Lys Tyr Leu Asn Pro Asn Gly Leu Asp Phe Lys
435 440 445

Pro Gly Asp Phe Thr Ile Val Phe Asn Asn Gln Thr Tyr Asp Leu Ser
450 455 460

Lys Asn Ser Asp Gly Thr Asn Phe Lys Leu Thr Gly Lys Thr Glu Glu
465 470 475 480

Glu Leu Leu Gln Asn Leu Ala Asn His Ile Asn Ser Lys Gly Ile Glu
485 490 495

Gly Leu Lys Val Lys Val Glu Ser Tyr Asn Gln Asn Asn Val Thr Gly
500 505 510

Phe Arg Leu Asn Phe Ser Gly Asp Gly Ser Ser Asp Phe Ser Ile Lys
515 520 525

Gly Asn Ala Thr Ile Leu Lys Glu Leu Gly Leu Ser Asp Val Asn Ile
530 535 540

Thr Ser Lys Pro Ile Glu Gly Lys Gly Ile Phe Ser Lys Leu Lys Ala
545 550 555 560

Thr Leu Gln Glu Met Thr Gly Lys Asp Gly Ser Ile Thr Lys Tyr Asp
565 570 575

Glu Ser Leu Thr Asn Asp Ile Lys Ser Leu Asn Thr Ser Lys Asp Ser
580 585 590

Thr Gln Ala Met Ile Asp Thr Arg Tyr Asp Thr Met Ala Asn Gln Trp
595 600 605

Leu Gln Tyr Glu Ser Ile Leu Asn Lys Leu Asn Gln Gln Leu Asn Thr
610 615 620

Val Thr Asn Met Ile Asn Ala Ala Asn Asn Ser Asn Asn
625 630 635

<210> SEQ ID NO 72
<211> LENGTH: 642
<212> TYPE: PRT
<213> ORGANISM: Artificial Sequence
<220> FEATURE:
<223> OTHER INFORMATION: Synthetic sequence - flagellar filament cap protein FliD [Campylobacter jejuni subsp. jejuni] GenBank: ALF93210.1

<400> SEQUENCE: 72

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

-continued

```
Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Ala Ser Ala Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Asn Phe Asp Ser Ser Lys Phe
385                 390                 395                 400

Glu Gln Lys Val Lys Glu Asp Pro Asp Ser Ala Glu Ser Phe Phe Ser
                405                 410                 415

Asn Ile Thr Lys Tyr Glu Asp Ile Asn His Thr Gly Glu Ile Ile Lys
            420                 425                 430

Thr Gly Asn Leu Ser Lys Tyr Leu Asn Ser Asn Gly Gly Asn Thr Asn
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480
```

-continued

```
Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Asn Val Lys Gly Phe Lys Leu Asn Phe Ser Gly Asp Gly Ser Ser
        515                 520                 525

Asp Phe Ser Ile Lys Gly Asp Ala Ser Ile Leu Lys Glu Leu Gly Leu
    530                 535                 540

Ser Asp Val Asn Ile Ile Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 73
<211> LENGTH: 642
<212> TYPE: PRT
<213> ORGANISM: Artificial Sequence
<220> FEATURE:
<223> OTHER INFORMATION: Synthetic sequence - Flagellar hook-associated protein 2 [Campylobacter jejuni subsp. jejuni] GenBank: AJP35034.1

<400> SEQUENCE: 73

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190
```

-continued

```
Thr Gly Glu Asp Ser Ala Ile Ser Phe Tyr Ala Gly Lys Lys Asp Ala
        195                 200                 205

Gln Gly Gln Tyr Glu Ser Asp Ser Glu Ala Glu Lys Ile Phe Lys Ser
    210                 215                 220

Leu Gly Trp Glu Leu Asp Thr Thr Ser Ser Ile Asn Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Gln Pro Gly Asn Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Gly Val Lys Gly Phe Arg Leu Asn Phe Ser Gly Asp Gly Ser Ser
        515                 520                 525

Asp Phe Ser Ile Lys Gly Asp Ala Asn Ile Leu Lys Asp Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605
```

-continued

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn

<210> SEQ ID NO 74
<211> LENGTH: 637
<212> TYPE: PRT
<213> ORGANISM: Artificial Sequence
<220> FEATURE:
<223> OTHER INFORMATION: Synthetic sequence - flagellar filament cap
      protein [Campylobacter jejuni subsp. jejuni]
      GenBank: AOH51565.1

<400> SEQUENCE: 74

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

-continued

```
Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Asn
            420                 425                 430

Thr Gly Ser Leu Ser Lys Tyr Leu Asn Pro Asn Gly Leu Asp Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525

Gly Asn Ala Thr Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635
```

<210> SEQ ID NO 75
<211> LENGTH: 642
<212> TYPE: PRT
<213> ORGANISM: Artificial Sequence
<220> FEATURE:
<223> OTHER INFORMATION: Synthetic sequence - flagellar capping protein [Campylobacter jejuni subsp. jejuni CG8421] GenBank: AHY39787.1

<400> SEQUENCE: 75

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30
```

-continued

```
Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Ser Gly Phe Ile Asn Ala
        115                 120                 125

Asn Leu Ala Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Leu Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Ala Phe Lys Pro Gly Asp Phe Thr Ile Val Phe Asn Asn Gln
```

```
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Gly Ser Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 76
<211> LENGTH: 642
<212> TYPE: PRT
<213> ORGANISM: Artificial Sequence
<220> FEATURE:
<223> OTHER INFORMATION: Synthetic sequence - flagellar cap protein FliD
      [Campylobacter jejuni 32488] GenBank: AGQ95247.1

<400> SEQUENCE: 76

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Gln Gly Leu Ala Asn Asp Gly Gly Phe Val Asn Ala
        115                 120                 125

Lys Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
```

-continued

```
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Val
        195                 200                 205

Gln Gly Gln Tyr Lys Ser Asp Ser Glu Ala Glu Lys Ile Phe Lys Ser
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590
```

```
Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 77
<211> LENGTH: 642
<212> TYPE: PRT
<213> ORGANISM: Artificial Sequence
<220> FEATURE:
<223> OTHER INFORMATION: Synthetic sequence - flagellar capping protein
      [Campylobacter jejuni subsp. jejuni IA3902]
      GenBank: ADC28162.1

<400> SEQUENCE: 77

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Ile Asn Ala Glu Lys Ile Phe Asp Asp
    210                 215                 220

Leu Gly Trp Gly Leu Asp Val Ser Ala Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
```

```
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 78
<211> LENGTH: 643
<212> TYPE: PRT
<213> ORGANISM: Artificial Sequence
<220> FEATURE:
<223> OTHER INFORMATION: Synthetic sequence - flagellar hook-associated
      protein FliD [Campylobacter jejuni subsp. jejuni
      81116] GenBank: ABV52108.1

<400> SEQUENCE: 78
```

-continued

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Val Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Gln Ser Asp Pro Glu Ala Glu Asn Ile Phe Ser Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
```

```
            420                 425                 430

Lys Gln Gly Ser Leu Asn Gln Tyr Leu Asp Ser Ser Gly Thr Gly Asn
        435                 440                 445

Lys Gly Leu Asp Phe Lys Pro Gly Asp Phe Thr Ile Val Phe Asn Asn
    450                 455                 460

Gln Thr Tyr Asp Leu Ser Lys Asn Ser Asp Gly Thr Asn Phe Lys Leu
465                 470                 475                 480

Thr Gly Lys Thr Glu Glu Glu Leu Leu Gln Asn Leu Ala Asn His Ile
                485                 490                 495

Asn Ser Lys Gly Ile Glu Gly Leu Lys Val Lys Val Glu Ser Tyr Asp
            500                 505                 510

Gln Asn Gly Val Lys Gly Phe Lys Leu Asn Phe Ser Gly Asp Gly Ser
        515                 520                 525

Ser Asp Phe Ser Ile Lys Gly Asn Ala Thr Ile Leu Gln Glu Leu Gly
    530                 535                 540

Leu Ser Asp Val Asn Ile Thr Ser Lys Pro Ile Glu Gly Lys Gly Ile
545                 550                 555                 560

Phe Ser Lys Leu Lys Ala Thr Leu Gln Glu Met Thr Gly Lys Asp Gly
                565                 570                 575

Ser Ile Thr Lys Tyr Asp Glu Ser Leu Thr Asn Asp Ile Lys Ser Leu
            580                 585                 590

Asn Thr Ser Lys Asp Ser Thr Gln Ala Met Ile Asp Thr Arg Tyr Asp
        595                 600                 605

Thr Met Ala Asn Gln Trp Leu Gln Tyr Glu Ser Ile Leu Asn Lys Leu
    610                 615                 620

Asn Gln Gln Leu Asn Thr Val Thr Asn Met Ile Asn Ala Ala Asn Asn
625                 630                 635                 640

Ser Asn Asn


<210> SEQ ID NO 79
<211> LENGTH: 636
<212> TYPE: PRT
<213> ORGANISM: Artificial Sequence
<220> FEATURE:
<223> OTHER INFORMATION: Synthetic sequence - flagellar hook-associated
      protein FliD [Campylobacter jejuni RM1221]
      GenBank: AAW35835.1

<400> SEQUENCE: 79

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125
```

-continued

```
Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ala
        195                 200                 205

Gln Gly Gln Tyr Lys Ser Asp Ser Glu Ala Glu Glu Ile Phe Lys Ser
    210                 215                 220

Leu Gly Trp Glu Leu Asp Thr Ala Ser Ser Ile Asp Pro Ala Lys Asp
225                 230                 235                 240

Lys Lys Gly Tyr Gly Ile Lys Asp Pro Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Thr Asn Gly Leu Glu Phe Lys Pro
        435                 440                 445

Gly Asp Phe Thr Ile Val Phe Asn Asn Gln Thr Tyr Asp Leu Ser Lys
    450                 455                 460

Asn Ser Asp Gly Thr Asn Phe Lys Leu Thr Gly Lys Thr Glu Glu Glu
465                 470                 475                 480

Leu Leu Gln Asn Leu Ala Asn His Ile Asn Ser Lys Gly Ile Glu Gly
                485                 490                 495

Leu Lys Val Lys Val Glu Ser Tyr Asn Gln Asn Asn Val Thr Gly Phe
            500                 505                 510

Arg Leu Asn Phe Ser Gly Asp Gly Ser Ser Asp Phe Ser Ile Lys Gly
        515                 520                 525

Asn Ala Ser Ile Leu Lys Glu Leu Gly Leu Ser Asp Val Asn Ile Thr
    530                 535                 540

Ser Lys Pro Ile Glu Gly Lys Gly Ile Phe Ser Lys Leu Lys Ala Thr
```

-continued

```
545                 550                 555                 560

Leu Gln Glu Met Thr Gly Lys Asp Gly Ser Ile Thr Lys Tyr Asp Glu
                565                 570                 575

Ser Leu Thr Asn Asp Ile Lys Ser Leu Asn Thr Ser Lys Asp Ser Thr
            580                 585                 590

Gln Ala Met Ile Asp Thr Arg Tyr Asp Thr Met Ala Asn Gln Trp Leu
        595                 600                 605

Gln Tyr Glu Ser Ile Leu Asn Lys Leu Asn Gln Gln Leu Asn Thr Val
    610                 615                 620

Thr Asn Met Ile Asn Ala Ala Asn Asn Ser Asn Asn
625                 630                 635


<210> SEQ ID NO 80
<211> LENGTH: 642
<212> TYPE: PRT
<213> ORGANISM: Artificial Sequence
<220> FEATURE:
<223> OTHER INFORMATION: Synthetic sequence - flagellar cap protein FliD
      [Campylobacter coli RM5611] GenBank: AHK75426.1

<400> SEQUENCE: 80

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270
```

```
Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asn Ala Ser Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 81
<211> LENGTH: 637
<212> TYPE: PRT
<213> ORGANISM: Artificial Sequence
<220> FEATURE:
<223> OTHER INFORMATION: Synthetic sequence - flagellar cap protein FliD
      [Campylobacter coli RM4661] GenBank: AHK76446.1

-continued

<400> SEQUENCE: 81

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asn Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Asn Met Asn Ile Asn Val Thr Gln Leu Ala Gln Lys Asp
            100                 105                 110

Val Tyr Gln Ser Lys Gly Leu Ala Asn Asp Ser Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Ala Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Ser Gly Lys Tyr Thr Ser Asp Ser Asn Ala Glu Thr Ile Phe Lys Asn
    210                 215                 220

Leu Gly Trp Glu Leu Asp Thr Thr Ser Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Val Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser

```
                405                 410                 415

Asn Ile Thr Lys Tyr Glu Asp Ile Asn His Thr Gly Glu Val Ile Asn
            420                 425                 430

Thr Gly Ser Leu Ser Lys Tyr Leu Asn Pro Asn Gly Leu Asp Phe Lys
        435                 440                 445

Gln Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Gly Val Lys Gly
            500                 505                 510

Phe Lys Leu Asn Phe Ser Gly Asp Gly Ser Ser Asp Phe Ser Ile Lys
        515                 520                 525

Gly Asn Ala Ser Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Ser Asn
625                 630                 635


<210> SEQ ID NO 82
<211> LENGTH: 642
<212> TYPE: PRT
<213> ORGANISM: Artificial Sequence
<220> FEATURE:
<223> OTHER INFORMATION: Synthetic sequence - Flagellar hook-associated
      protein FliD [Campylobacter coli 15-537360]
      GenBank: AGZ21001.1

<400> SEQUENCE: 82

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125
```

-continued

```
Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Asn Ile Leu Lys Glu Leu Gly Leu
    530                 535                 540
```

-continued

Ser Asp Val Asn Ile Thr Ser Lys Pro Ile Glu Gly Lys Gly Ile Phe
545 550 555 560

Ser Lys Leu Lys Ala Thr Leu Gln Glu Met Thr Gly Lys Asp Gly Ser
565 570 575

Ile Thr Lys Tyr Asp Glu Ser Leu Thr Asn Asp Ile Lys Ser Leu Asn
580 585 590

Thr Ser Lys Asp Ser Thr Gln Ala Met Ile Asp Thr Arg Tyr Asp Thr
595 600 605

Met Ala Asn Gln Trp Leu Gln Tyr Glu Ser Ile Leu Asn Lys Leu Asn
610 615 620

Gln Gln Leu Asn Thr Val Thr Asn Met Ile Asn Ala Ala Asn Asn Ser
625 630 635 640

Asn Asn

<210> SEQ ID NO 83
<211> LENGTH: 637
<212> TYPE: PRT
<213> ORGANISM: Artificial Sequence
<220> FEATURE:
<223> OTHER INFORMATION: Synthetic sequence - flagellar filament capping protein FliD [Campylobacter coli] NCBI Reference Sequence: WP_004284951.1

<400> SEQUENCE: 83

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp
100 105 110

Val Tyr Gln Ser Lys Gly Leu Val Asn Asp Gly Gly Phe Val Asn Ala
115 120 125

Gln Leu Asn Gly Thr Ala Asp Leu Thr Phe Phe Ser Asn Gly Lys Glu
130 135 140

Tyr Thr Val Thr Val Asp Lys Asn Thr Thr Tyr Arg Asp Leu Ala Asp
145 150 155 160

Lys Ile Asn Glu Ala Ser Gly Gly Glu Ile Val Ala Lys Ile Val Asn
165 170 175

Thr Gly Glu Lys Gly Thr Pro Tyr Arg Leu Thr Leu Thr Ser Lys Glu
180 185 190

Thr Gly Glu Asp Ser Ala Ile Ser Phe Tyr Ala Gly Lys Lys Asp Ser
195 200 205

Asn Gly Lys Tyr Gln Lys Asp Thr Asn Ala Glu Lys Ile Phe Asp Asp
210 215 220

Leu Gly Trp Gly Leu Asp Val Ser Ala Ser Ile Asp Pro Ala Lys Asp
225 230 235 240

Lys Lys Gly Tyr Gly Ile Lys Asp Thr Ser Leu His Ile Gln Thr Ala
245 250 255

```
Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asn Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Leu Glu Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525

Gly Asn Ala Ser Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635
```

<210> SEQ ID NO 84
<211> LENGTH: 637
<212> TYPE: PRT
<213> ORGANISM: Artificial Sequence
<220> FEATURE:

<223> OTHER INFORMATION: Synthetic sequence - Flagellar hook-associated protein 2 [Campylobacter coli] GenBank: AJW57994.1

<400> SEQUENCE: 84

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asn Ser Ser Lys Phe
385                 390                 395                 400
```

```
Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Leu Glu Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525

Gly Asn Ala Ser Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635


<210> SEQ ID NO 85
<211> LENGTH: 638
<212> TYPE: PRT
<213> ORGANISM: Artificial Sequence
<220> FEATURE:
<223> OTHER INFORMATION: Synthetic sequence - Flagellar hook-associated
      protein 2 [Campylobacter coli] GenBank: ALV00075.1

<400> SEQUENCE: 85

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
```

```
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Ser Glu Ala Glu Thr Ile Phe Lys Asn
    210                 215                 220

Leu Gly Trp Glu Leu Asp Lys Thr Thr Gln Thr Ile Asp Pro Ala Lys
225                 230                 235                 240

Asp Lys Lys Gly Tyr Gly Ile Lys Asp Ala Ser Leu His Ile Gln Thr
                245                 250                 255

Ala Gln Asn Ala Glu Phe Thr Leu Asp Gly Ile Lys Met Phe Arg Ser
            260                 265                 270

Ser Asn Thr Val Thr Asp Leu Gly Val Gly Met Thr Leu Thr Leu Asn
        275                 280                 285

Lys Thr Gly Glu Ile Asn Phe Asp Val Gln Gln Asp Phe Glu Gly Val
    290                 295                 300

Thr Lys Ala Met Gln Asp Leu Val Asp Ala Tyr Asn Asp Leu Val Thr
305                 310                 315                 320

Asn Leu Asn Ala Ala Thr Asp Tyr Asn Ser Glu Thr Gly Thr Lys Gly
                325                 330                 335

Thr Leu Gln Gly Ile Ser Glu Val Asn Ser Ile Arg Ser Ser Ile Leu
            340                 345                 350

Ala Asp Leu Phe Asp Ser Gln Val Val Asp Gly Thr Thr Glu Asp Ala
        355                 360                 365

Asn Gly Asn Lys Val Asn Thr Lys Val Met Leu Ser Met Gln Asp Phe
    370                 375                 380

Gly Leu Ser Leu Asn Asp Ala Gly Thr Leu Ser Phe Asp Ser Ser Lys
385                 390                 395                 400

Phe Glu Gln Lys Val Lys Glu Asp Pro Asp Ser Thr Glu Ser Phe Phe
                405                 410                 415

Ser Asn Ile Thr Lys Tyr Glu Asp Ile Asn His Thr Gly Glu Val Ile
            420                 425                 430

Lys Thr Gly Ser Leu Ser Lys Tyr Leu Asn Ser Asn Gly Leu Glu Phe
        435                 440                 445

Lys Pro Gly Asp Phe Thr Ile Val Phe Asn Asn Gln Thr Tyr Asp Leu
    450                 455                 460

Ser Lys Asn Ser Asp Gly Thr Asn Phe Lys Leu Thr Gly Lys Thr Glu
465                 470                 475                 480

Glu Glu Leu Leu Gln Asn Leu Ala Asn His Ile Asn Ser Lys Gly Ile
                485                 490                 495

Glu Gly Leu Lys Val Lys Val Glu Ser Tyr Asn Gln Asn Asn Val Thr
            500                 505                 510

Gly Phe Arg Leu Asn Phe Ser Gly Asp Gly Ser Ser Asp Phe Ser Ile
        515                 520                 525

Lys Gly Asn Ala Ser Ile Leu Lys Glu Leu Gly Leu Ser Asp Val Asn
    530                 535                 540
```

```
Ile Thr Ser Lys Pro Ile Glu Gly Lys Gly Ile Phe Ser Lys Leu Lys
545                 550                 555                 560

Ala Thr Leu Gln Glu Met Thr Gly Lys Asp Gly Ser Ile Thr Lys Tyr
                565                 570                 575

Asp Glu Ser Leu Thr Asn Asp Ile Lys Ser Leu Asn Thr Ser Lys Asp
            580                 585                 590

Ser Thr Gln Ala Met Ile Asp Thr Arg Tyr Asp Thr Met Ala Asn Gln
        595                 600                 605

Trp Leu Gln Tyr Glu Ser Ile Leu Asn Lys Leu Asn Gln Gln Leu Asn
    610                 615                 620

Thr Val Thr Asn Met Ile Asn Ala Ala Asn Asn Ser Asn Asn
625                 630                 635


<210> SEQ ID NO 86
<211> LENGTH: 642
<212> TYPE: PRT
<213> ORGANISM: Artificial Sequence
<220> FEATURE:
<223> OTHER INFORMATION: Synthetic sequence - Flagellar hook-associated
      protein FliD [Campylobacter coli IPSID-1]
      GenBank: CDL88777.1

<400> SEQUENCE: 86

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Thr Ser Asp Ser Glu Ala Glu Thr Ile Phe Lys Asn
    210                 215                 220

Leu Gly Trp Glu Leu Asp Thr Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255
```

```
Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Gln Gly Ser Leu Asn Gln Tyr Leu Asp Ser Ser Gly Thr Gly Asn Lys
        435                 440                 445

Gly Leu Asp Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asp Gln
            500                 505                 510

Asn Gly Val Lys Gly Phe Lys Leu Asn Phe Ser Gly Asp Gly Ser Ser
        515                 520                 525

Asp Phe Ser Ile Lys Gly Asn Ala Thr Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 87
<211> LENGTH: 637
<212> TYPE: PRT
<213> ORGANISM: Artificial Sequence
<220> FEATURE:
<223> OTHER INFORMATION: Synthetic sequence - flagellar hook-associated
protein 2 (fliD), putative [Campylobacter coli
RM2228] GenBank: EAL57379.1

<400> SEQUENCE: 87

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380
```

Leu Ser Leu Asn Asp Ala Gly Thr Leu Ser Phe Asn Ser Ser Lys Phe
385 390 395 400

Glu Gln Lys Val Lys Glu Asp Pro Asp Ser Thr Glu Ser Phe Phe Ser
405 410 415

Asn Ile Thr Lys Tyr Glu Asp Ile Asn His Thr Gly Glu Val Ile Lys
420 425 430

Thr Gly Ser Leu Ser Lys Tyr Leu Asn Ser Asn Gly Leu Glu Phe Lys
435 440 445

Pro Gly Asp Phe Thr Ile Val Phe Asn Asn Gln Thr Tyr Asp Leu Ser
450 455 460

Lys Asn Ser Asp Gly Thr Asn Phe Lys Leu Thr Gly Lys Thr Glu Glu
465 470 475 480

Glu Leu Leu Gln Asn Leu Ala Asn His Ile Asn Ser Lys Gly Ile Glu
485 490 495

Gly Leu Lys Val Lys Val Glu Ser Tyr Asn Gln Asn Asn Val Thr Gly
500 505 510

Phe Arg Leu Asn Phe Ser Gly Asp Gly Ser Ser Asp Phe Ser Ile Lys
515 520 525

Gly Asn Ala Ser Ile Leu Lys Glu Leu Gly Leu Ser Asp Val Asn Ile
530 535 540

Thr Ser Lys Pro Ile Glu Gly Lys Gly Ile Phe Ser Lys Leu Lys Ala
545 550 555 560

Thr Leu Gln Glu Met Thr Gly Lys Asp Gly Ser Ile Thr Lys Tyr Asp
565 570 575

Glu Ser Leu Thr Asn Asp Ile Lys Ser Leu Asn Thr Ser Lys Asp Ser
580 585 590

Thr Gln Ala Met Ile Asp Thr Arg Tyr Asp Thr Met Ala Asn Gln Trp
595 600 605

Leu Gln Tyr Glu Ser Ile Leu Asn Lys Leu Asn Gln Gln Leu Asn Thr
610 615 620

Val Thr Asn Met Ile Asn Ala Ala Asn Asn Ser Asn Asn
625 630 635

<210> SEQ ID NO 88
<211> LENGTH: 637
<212> TYPE: PRT
<213> ORGANISM: Artificial Sequence
<220> FEATURE:
<223> OTHER INFORMATION: Synthetic sequence - flagellar filament capping protein FliD [Campylobacter coli] NCBI Reference Sequence: WP_002842748.1

<400> SEQUENCE: 88

Met Ala Phe Gly Ser Leu Ser Ser Leu Gly Phe Gly Ser Gly Val Leu
1 5 10 15

Thr Gln Asp Thr Ile Asp Lys Leu Lys Glu Ala Glu Gln Lys Ala Arg
20 25 30

Ile Asp Pro Tyr Thr Lys Lys Ile Glu Glu Asn Thr Thr Lys Gln Lys
35 40 45

Asp Leu Thr Glu Ile Lys Thr Lys Leu Leu Ser Phe Gln Thr Ala Val
50 55 60

Ser Ser Leu Ala Asp Ala Thr Val Phe Ala Lys Arg Lys Val Val Gly
65 70 75 80

Ser Ile Ser Asp Asn Pro Pro Ala Ser Leu Thr Val Asn Ser Gly Val
85 90 95

Ala Leu Gln Ser Met Asn Ile Asn Val Thr Gln Leu Ala Gln Lys Asp

-continued

```
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Leu Glu Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525
```

```
Gly Asn Ala Ser Ile Leu Lys Glu Leu Gly Leu Ser Asp Val Asn Ile
    530                 535                 540

Ser Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635


<210> SEQ ID NO 89
<211> LENGTH: 637
<212> TYPE: PRT
<213> ORGANISM: Artificial Sequence
<220> FEATURE:
<223> OTHER INFORMATION: Synthetic sequence - flagellar filament capping
      protein FliD [Campylobacter coli] NCBI Reference
      Sequence: WP_002833936.1

<400> SEQUENCE: 89

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240
```

-continued

```
Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asn Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Leu Glu Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525

Gly Asn Ala Ser Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635
```

<210> SEQ ID NO 90
<211> LENGTH: 637
<212> TYPE: PRT

<213> ORGANISM: Artificial Sequence
<220> FEATURE:
<223> OTHER INFORMATION: Synthetic sequence - flagellar hook-associated
      protein 2 [Campylobacter coli JV20] GenBank:
      EFM36457.1

<400> SEQUENCE: 90

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Val Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Lys Tyr Gln Lys Asp Thr Asn Ala Glu Lys Ile Phe Asp Asp
    210                 215                 220

Leu Gly Trp Gly Leu Asp Val Ser Ala Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380
```

```
Leu Ser Leu Asn Asp Ala Gly Thr Leu Ser Phe Asn Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Leu Glu Phe Lys
        435                 440                 445

Pro Gly Asp Phe Thr Ile Val Phe Asn Asn Gln Thr Tyr Asp Leu Ser
    450                 455                 460

Lys Asn Ser Asp Gly Thr Asn Phe Lys Leu Thr Gly Lys Thr Glu Glu
465                 470                 475                 480

Glu Leu Leu Gln Asn Leu Ala Asn His Ile Asn Ser Lys Gly Ile Glu
                485                 490                 495

Gly Leu Lys Val Lys Val Glu Ser Tyr Asn Gln Asn Asn Val Thr Gly
            500                 505                 510

Phe Arg Leu Asn Phe Ser Gly Asp Gly Ser Ser Asp Phe Ser Ile Lys
        515                 520                 525

Gly Asn Ala Ser Ile Leu Lys Glu Leu Gly Leu Ser Asp Val Asn Ile
    530                 535                 540

Thr Ser Lys Pro Ile Glu Gly Lys Gly Ile Phe Ser Lys Leu Lys Ala
545                 550                 555                 560

Thr Leu Gln Glu Met Thr Gly Lys Asp Gly Ser Ile Thr Lys Tyr Asp
                565                 570                 575

Glu Ser Leu Thr Asn Asp Ile Lys Ser Leu Asn Thr Ser Lys Asp Ser
            580                 585                 590

Thr Gln Ala Met Ile Asp Thr Arg Tyr Asp Thr Met Ala Asn Gln Trp
        595                 600                 605

Leu Gln Tyr Glu Ser Ile Leu Asn Lys Leu Asn Gln Gln Leu Asn Thr
    610                 615                 620

Val Thr Asn Met Ile Asn Ala Ala Asn Asn Ser Asn Asn
625                 630                 635


<210> SEQ ID NO 91
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter coli] NCBI Reference
      Sequence: WP_002832776.1

<400> SEQUENCE: 91

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95
```

```
Ala Leu Gln Ser Met Asn Ile Asn Val Thr Gln Leu Ala Gln Lys Asp
            100                 105                 110

Val Tyr Gln Ser Lys Gly Leu Ala Asn Asp Gly Gly Phe Val Asn Ala
        115                 120                 125

Gln Leu Asn Gly Thr Ala Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Gly Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Asn Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
```

```
        515                 520                 525

Asp Phe Ser Ile Lys Gly Asp Ala Asn Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 92
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter coli] NCBI Reference
      Sequence: WP_002825071.1

<400> SEQUENCE: 92

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asn Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Ser Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Ser Gly Lys Tyr Thr Ser Asp Ser Asn Ala Glu Thr Ile Phe Lys Asn
    210                 215                 220
```

-continued

```
Leu Gly Trp Glu Leu Asp Thr Thr Ser Ser Ile Asp Pro Asp Lys Asp
225                 230                 235                 240

Lys Lys Gly Tyr Gly Ile Lys Asp Ala Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Val Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Asn
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asn Ala Ser Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

<210> SEQ ID NO 93
<211> LENGTH: 642
<212> TYPE: PRT
<213> ORGANISM: Artificial Sequence
<220> FEATURE:
<223> OTHER INFORMATION: Synthetic sequence - flagellar filament capping
protein FliD [Campylobacter coli] NCBI Reference
Sequence: WP_002804771.1

<400> SEQUENCE: 93

```
Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Ile Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350
```

-continued

```
Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asn Ala Ser Ile Leu Lys Glu Leu Gly Leu
    530                 535                 540

Ser Asp Val Asn Ile Thr Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 94
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter coli] NCBI Reference
      Sequence: WP_002793506.1

<400> SEQUENCE: 94

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60
```

-continued

```
Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Val Asn Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190

Thr Gly Glu Asp Ser Ala Ile Ser Phe Tyr Ala Gly Lys Lys Asp Ser
        195                 200                 205

Asn Gly Gln Tyr Gln Ser Asp Ser Glu Ala Glu Asn Ile Phe Ser Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480
```

```
Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Ser Ile Leu Lys Glu Leu Gly Leu
    530                 535                 540

Ser Asp Val Asn Ile Ser Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605

Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn


<210> SEQ ID NO 95
<211> LENGTH: 642
<212> TYPE: PRT
<213> ORGANISM: Artificial Sequence
<220> FEATURE:
<223> OTHER INFORMATION: Synthetic sequence - flagellar filament capping
      protein FliD [Campylobacter coli] NCBI Reference
      Sequence: WP_002791831.1

<400> SEQUENCE: 95

Met Ala Phe Gly Ser Leu Ser Ser Leu Gly Phe Gly Ser Gly Val Leu
1               5                   10                  15

Thr Gln Asp Thr Ile Asp Lys Leu Lys Glu Ala Glu Gln Lys Ala Arg
            20                  25                  30

Ile Asp Pro Tyr Thr Lys Lys Ile Glu Glu Asn Thr Thr Lys Gln Lys
        35                  40                  45

Asp Leu Thr Glu Ile Lys Thr Lys Leu Leu Ser Phe Gln Thr Ala Val
    50                  55                  60

Ser Ser Leu Ala Asp Ala Thr Val Phe Ala Lys Arg Lys Val Val Gly
65                  70                  75                  80

Ser Ile Ser Asp Asn Pro Pro Ala Ser Leu Thr Val Asn Ser Gly Val
                85                  90                  95

Ala Leu Gln Ser Met Asn Ile Asn Val Thr Gln Leu Ala Gln Lys Asp
            100                 105                 110

Val Tyr Gln Ser Lys Gly Leu Ala Asn Asp Ser Gly Phe Val Ser Ala
        115                 120                 125

Asn Leu Thr Gly Thr Thr Asp Leu Thr Phe Phe Ser Asn Gly Lys Glu
    130                 135                 140

Tyr Thr Val Thr Val Asp Lys Asn Thr Thr Tyr Arg Asp Leu Ala Asp
145                 150                 155                 160

Lys Ile Asn Glu Ala Ser Gly Gly Glu Ile Val Ala Lys Ile Val Asn
                165                 170                 175

Thr Gly Glu Lys Gly Thr Pro Tyr Arg Leu Thr Leu Thr Ser Lys Glu
            180                 185                 190
```

-continued

```
Thr Gly Glu Asp Ser Ala Ile Ser Phe Tyr Ala Gly Lys Lys Asp Ser
        195                 200                 205

Ser Gly Lys Tyr Thr Ser Asp Ser Asn Ala Glu Thr Ile Phe Lys Asn
    210                 215                 220

Leu Gly Trp Glu Leu Asp Lys Thr Ser Ser Ile Asp Pro Ala Lys Asp
225                 230                 235                 240

Lys Lys Gly Tyr Gly Ile Lys Asp Thr Ser Leu His Ile Gln Thr Ala
                245                 250                 255

Gln Asn Ala Glu Phe Thr Leu Asp Gly Ile Lys Met Phe Arg Ser Ser
            260                 265                 270

Asn Thr Val Thr Asp Leu Gly Val Gly Met Thr Leu Thr Leu Asn Lys
        275                 280                 285

Thr Gly Glu Ile Asn Phe Asp Val Gln Gln Asp Phe Glu Gly Val Thr
    290                 295                 300

Lys Ala Met Gln Asp Leu Val Asp Ala Tyr Asn Asp Leu Val Thr Asn
305                 310                 315                 320

Leu Asn Ala Ala Thr Asp Tyr Asn Ser Glu Thr Gly Thr Lys Gly Thr
                325                 330                 335

Leu Gln Gly Ile Ser Glu Val Asn Ser Ile Arg Ser Ser Ile Leu Ala
            340                 345                 350

Asp Leu Phe Asp Ser Gln Val Val Asp Gly Thr Thr Glu Asp Ala Asn
        355                 360                 365

Gly Asn Lys Val Asn Thr Lys Val Met Leu Ser Met Gln Asp Phe Gly
    370                 375                 380

Leu Ser Leu Asn Asp Ala Gly Thr Leu Ser Phe Asp Ser Ser Lys Phe
385                 390                 395                 400

Glu Gln Lys Val Lys Glu Asp Pro Asp Ser Thr Glu Ser Phe Phe Ser
                405                 410                 415

Asn Ile Thr Lys Tyr Glu Asp Ile Asn His Thr Gly Glu Val Ile Lys
            420                 425                 430

Thr Gly Ser Leu Ser Lys Tyr Leu Asn Ser Asn Gly Gly Asn Thr Asn
        435                 440                 445

Gly Leu Glu Phe Lys Pro Gly Asp Phe Thr Ile Val Phe Asn Asn Gln
    450                 455                 460

Thr Tyr Asp Leu Ser Lys Asn Ser Asp Gly Thr Asn Phe Lys Leu Thr
465                 470                 475                 480

Gly Lys Thr Glu Glu Glu Leu Leu Gln Asn Leu Ala Asn His Ile Asn
                485                 490                 495

Ser Lys Gly Ile Glu Gly Leu Lys Val Lys Val Glu Ser Tyr Asn Gln
            500                 505                 510

Asn Asn Val Thr Gly Phe Arg Leu Asn Phe Ser Gly Asp Gly Ser Ser
        515                 520                 525

Asp Phe Ser Ile Lys Gly Asp Ala Ser Ile Leu Lys Glu Leu Gly Leu
    530                 535                 540

Ser Asp Val Asn Ile Ser Ser Lys Pro Ile Glu Gly Lys Gly Ile Phe
545                 550                 555                 560

Ser Lys Leu Lys Ala Thr Leu Gln Glu Met Thr Gly Lys Asp Gly Ser
                565                 570                 575

Ile Thr Lys Tyr Asp Glu Ser Leu Thr Asn Asp Ile Lys Ser Leu Asn
            580                 585                 590

Thr Ser Lys Asp Ser Thr Gln Ala Met Ile Asp Thr Arg Tyr Asp Thr
        595                 600                 605
```

-continued

```
Met Ala Asn Gln Trp Leu Gln Tyr Glu Ser Ile Leu Asn Lys Leu Asn
    610                 615                 620

Gln Gln Leu Asn Thr Val Thr Asn Met Ile Asn Ala Ala Asn Asn Ser
625                 630                 635                 640

Asn Asn
```

ANTIBODIES AGAINST *CAMPYLOBACTER* SPECIES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 470082_406USPC_SEQUENCE_LISTING.txt. The text file is 304 KB, was created on Jan. 15, 2021, and is being submitted electronically via EFS-Web.

BACKGROUND

*Campylobacter* is the most common cause of bacterial gastroenteritis worldwide and has recently been added to the World Health Organization (WHO) list of antibiotic resistant bacteria that pose a potential global threat to human health (see, e.g., “WHO publishes list of bacteria for which new antibiotics are urgently needed”, World Health Organization news release, Feb. 27 2017; who.int/en/news-room/detail/27-02-2017-who-publishes-list-of-bacteria-for-which-new-antibiotics-are-urgently-needed). *Campylobacter* species (*C. jejuni* and *C. coli*) are a significant cause of traveler's diarrhea in developed countries and a major cause of life-threatening acute watery diarrhea in children under the age of 2 in developing countries. Currently, there are no vaccines approved to prevent Campylobacteriosis. Rehydration is the main form of therapy, and although antibiotics have been shown to be beneficial in severe infections, they are often not recommended to avoid the rapid development of resistance.

Accordingly, new therapies for preventing or treating *Campylobacter* infections are needed.

21-day-old C57BL/6 mice were orally administered, via gavage, 200 μg of CAA1 as rSIgA2 or rIgG1. (A) Quantification of the bacterial load (CFU) in the stools of the animals at 24 h, 48 h and 72 h post-infection. (B) Representative dot plot and relative quantification of polymorphonucleated cells infiltrated in the caecum gated as $Gr1^+$ $CD11b^+$. (C) Quantification of Lipocalin-2 (LCN) in the stools, and (D) statistical analysis of histopathological score in the caecum at 72 h post infection in the different treatment conditions. Dots represent individual mice and results are shown as ±SEM. Mann-Whitney test (A-D) was used. *p<0.05, **p<0.01. One representative experiment out of at least two is shown.

Figure 12:
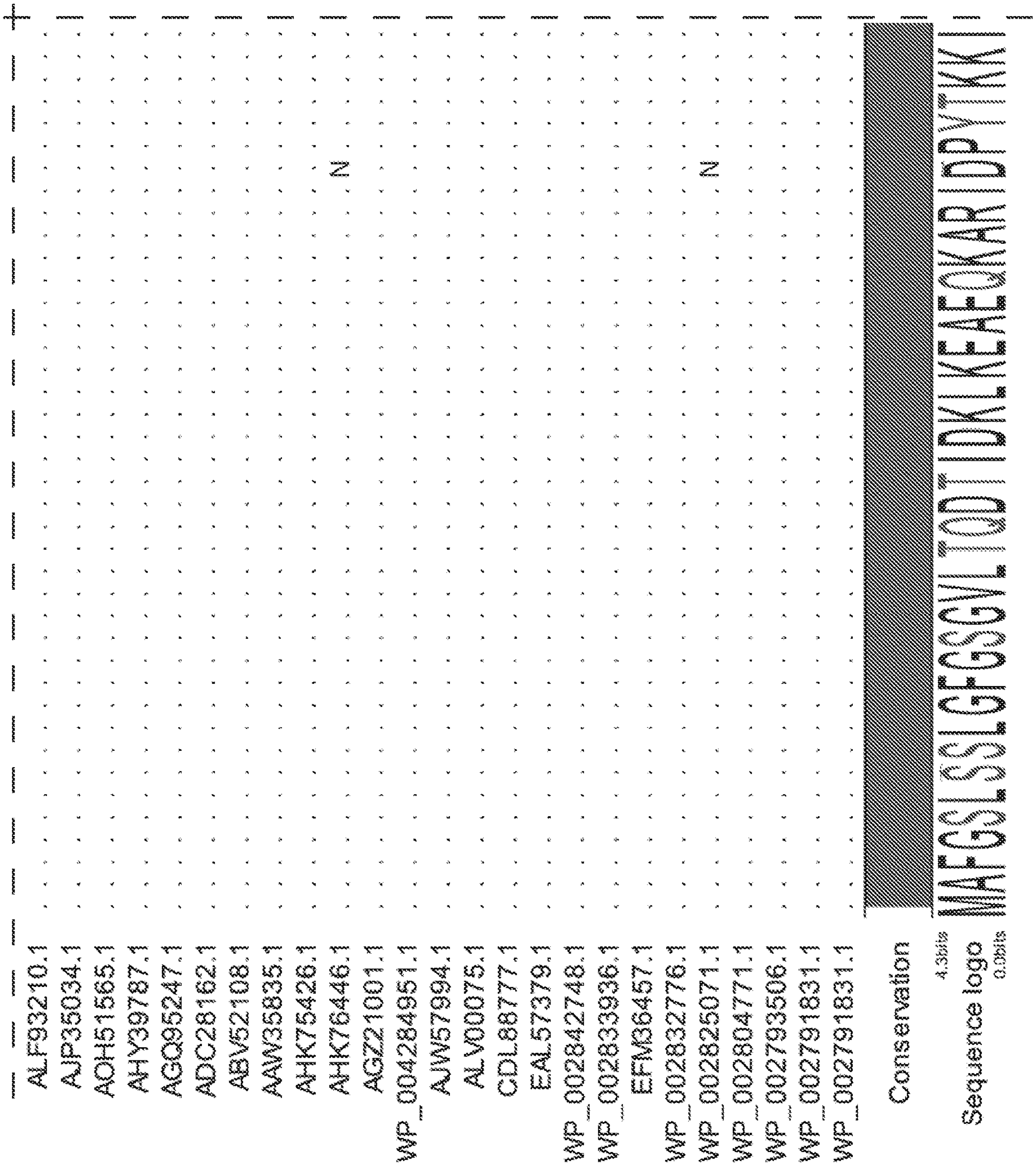
Figure 12:
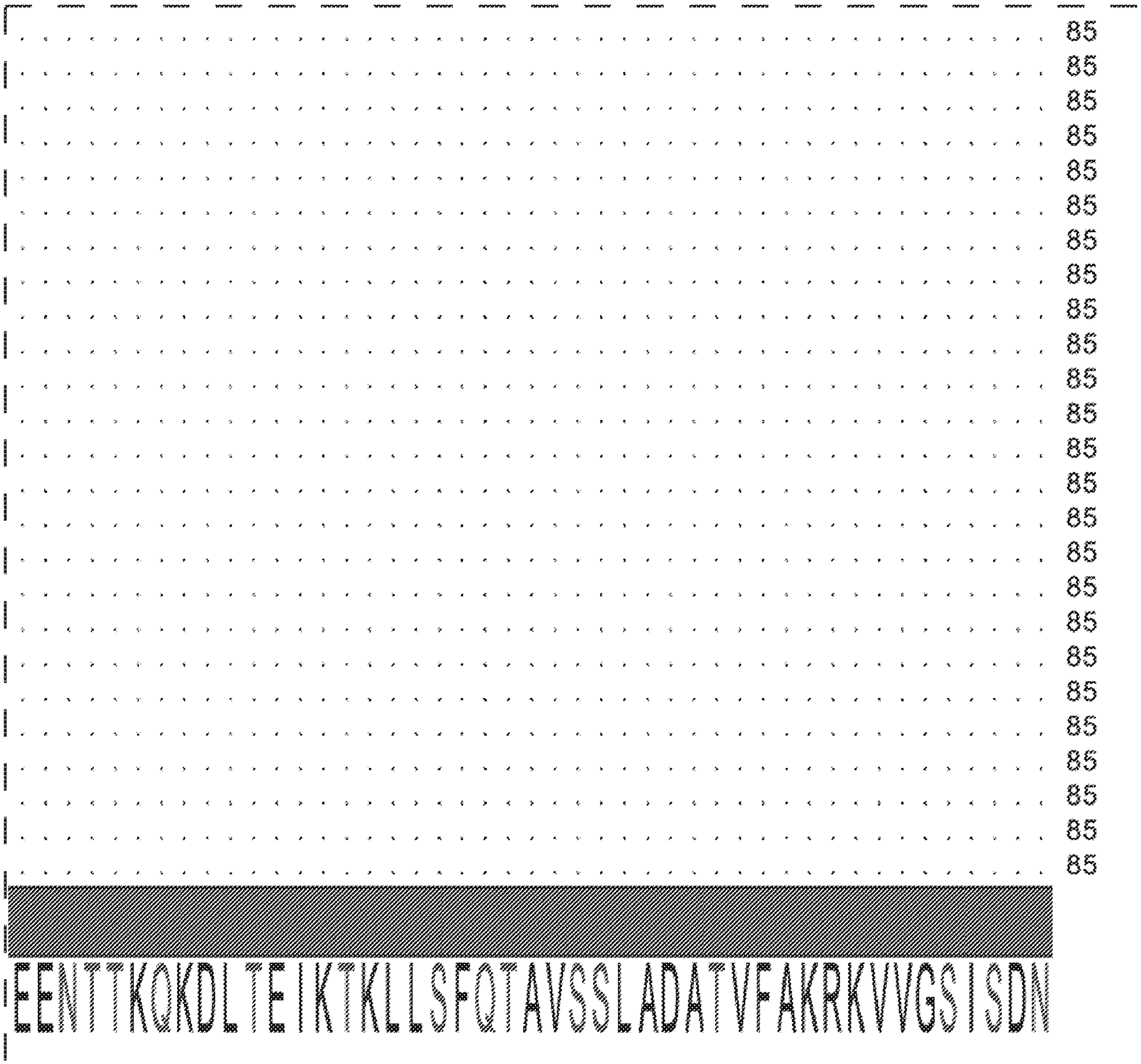
Figure 12:
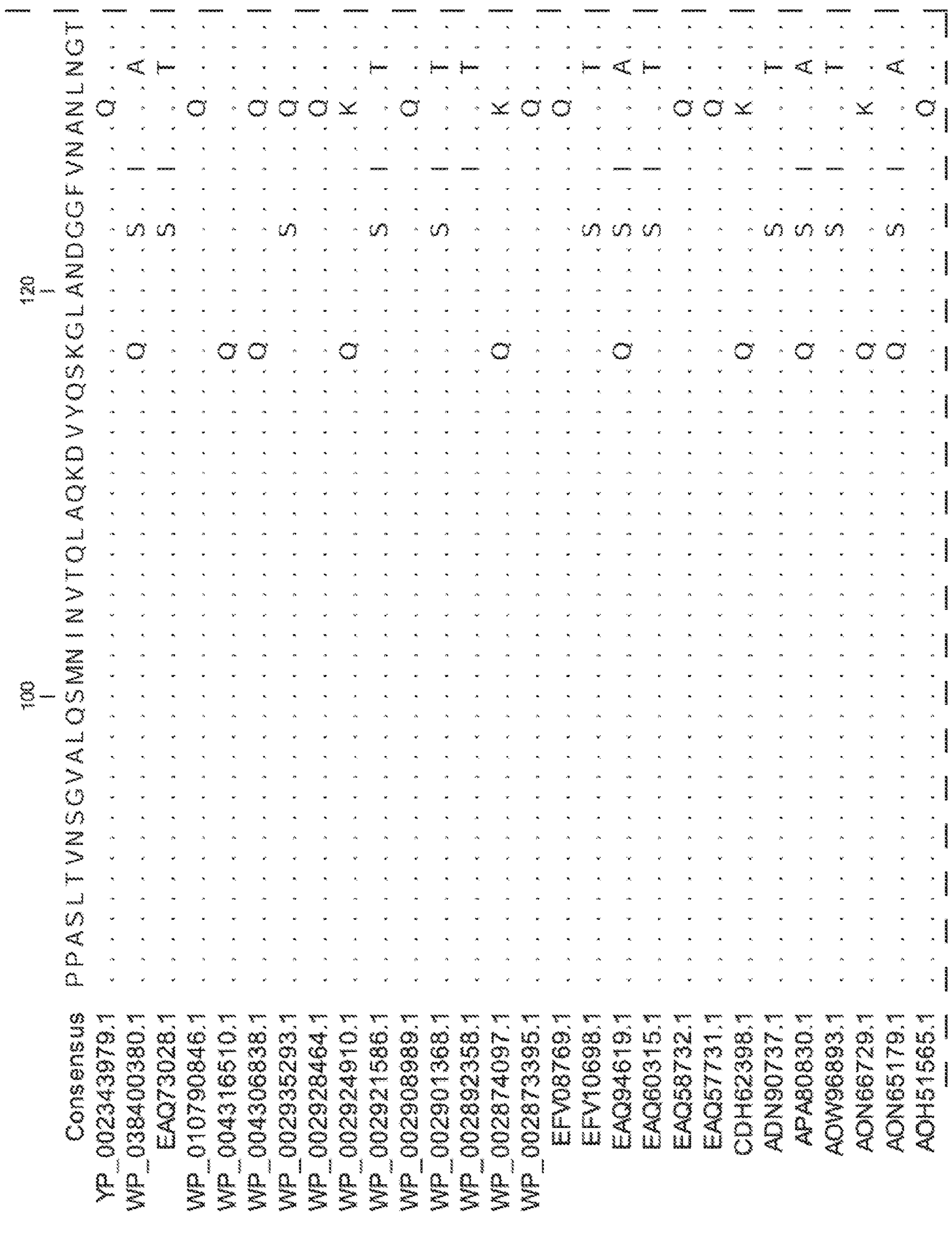
Figure 12:
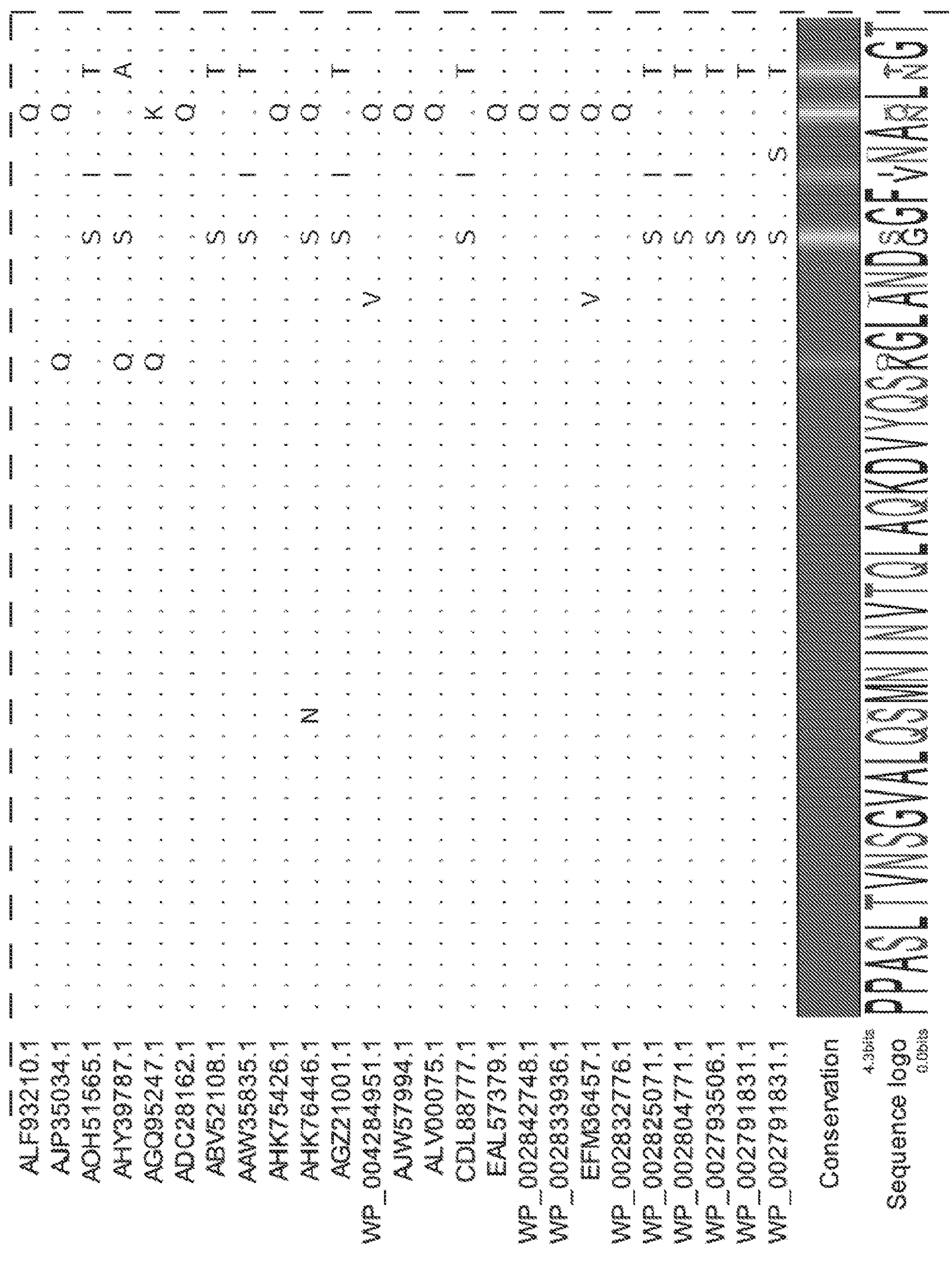
Figure 12:
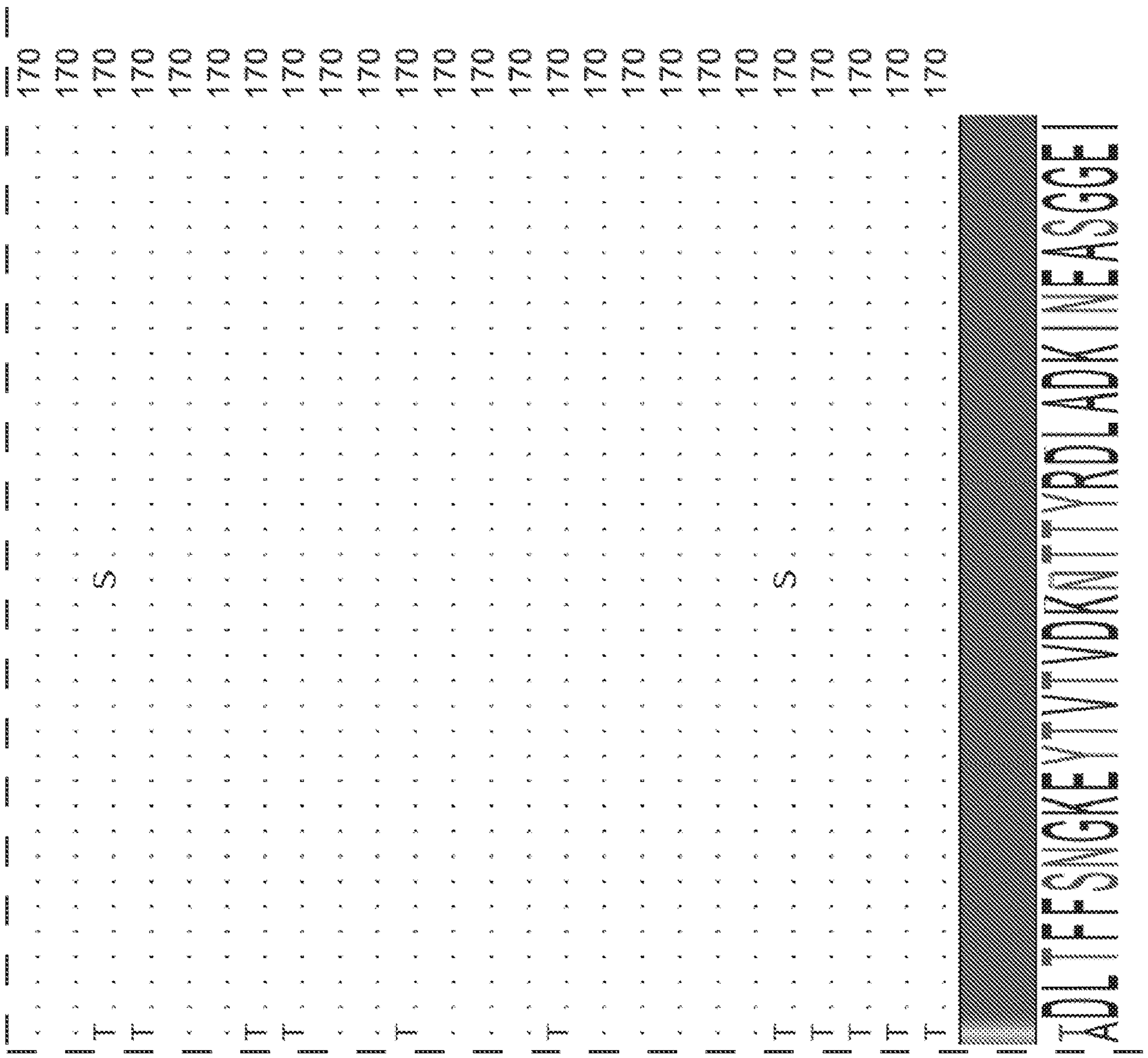
Figure 12:
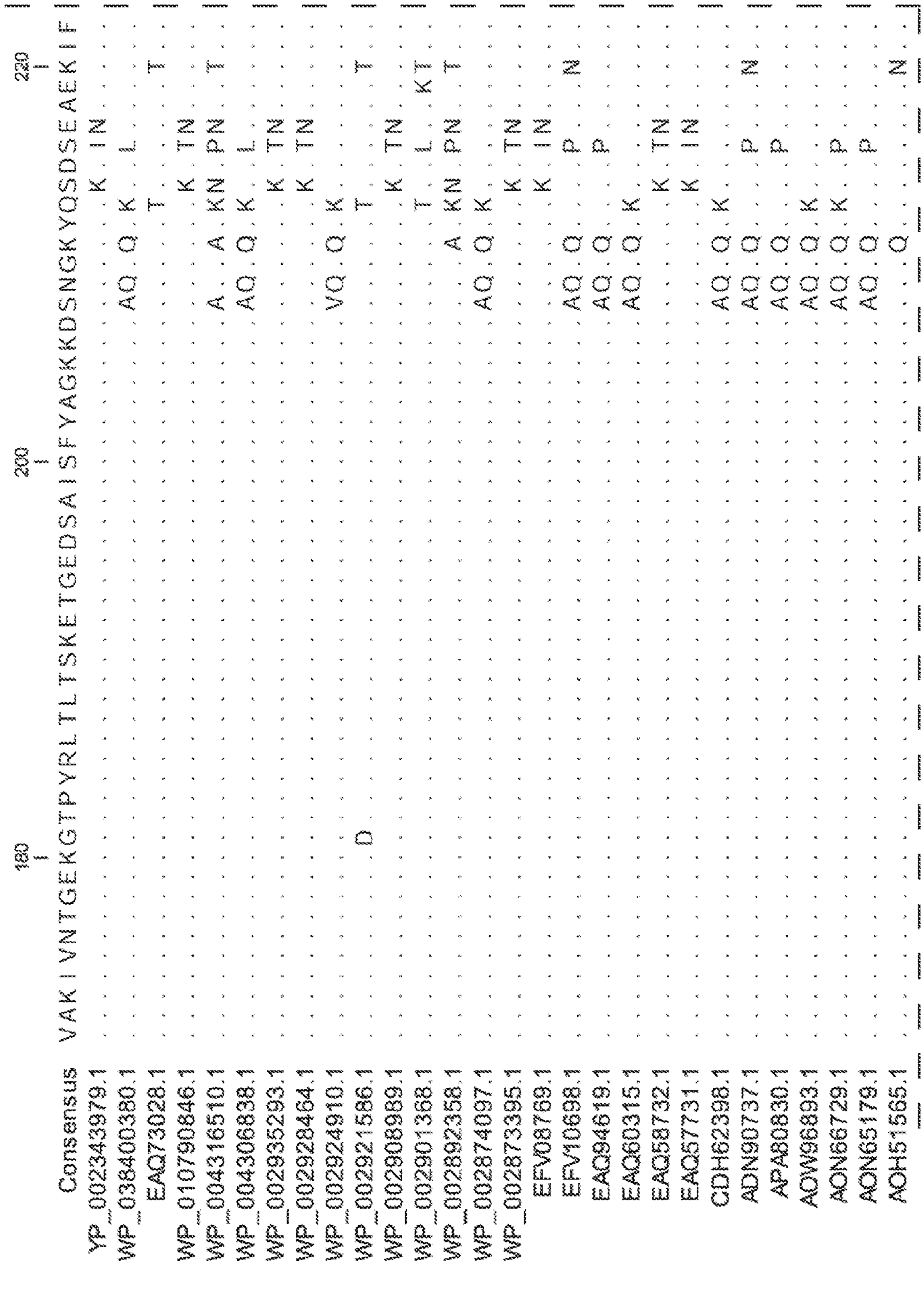
Figure 12:
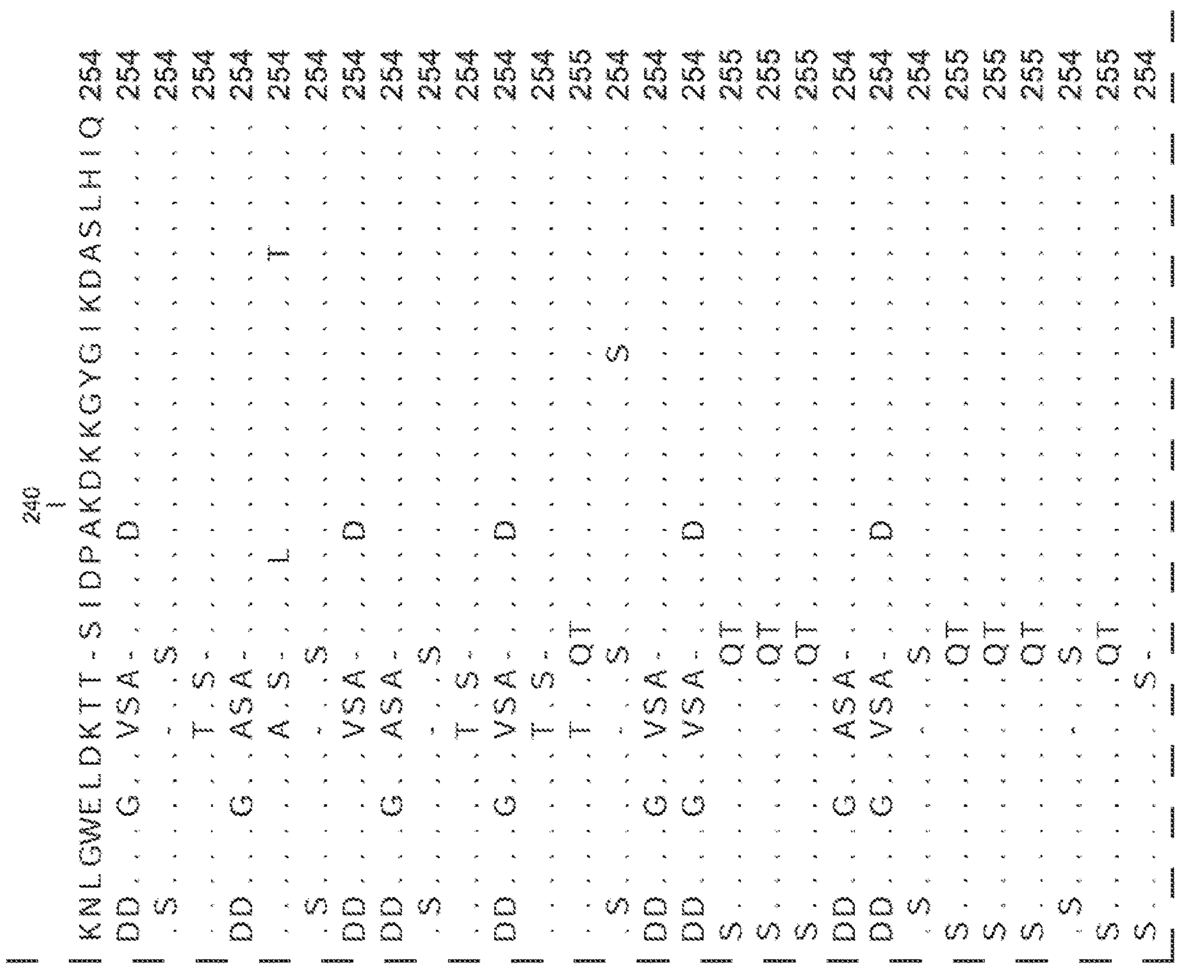
Figure 12:
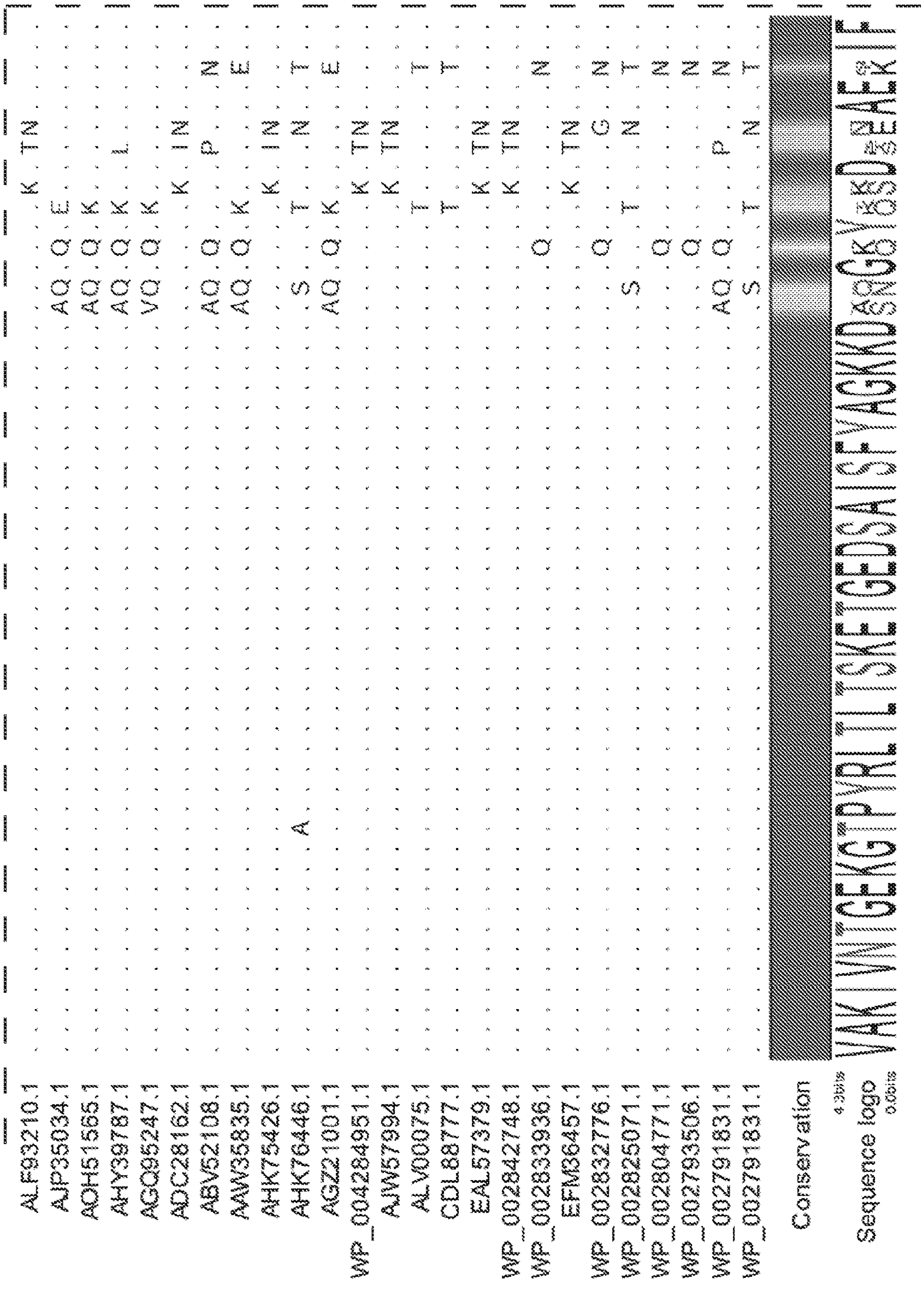
Figure 12:
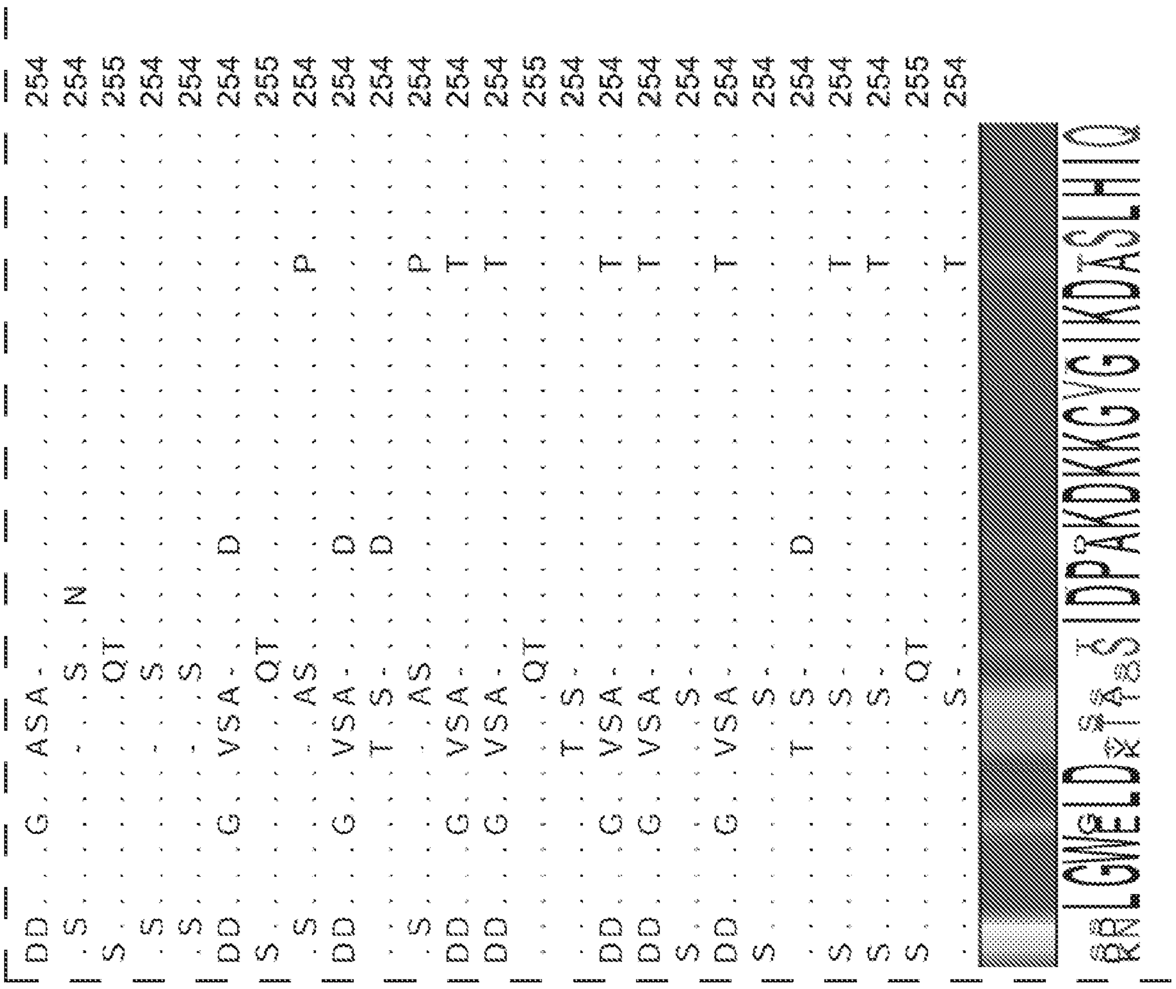
Figure 12:
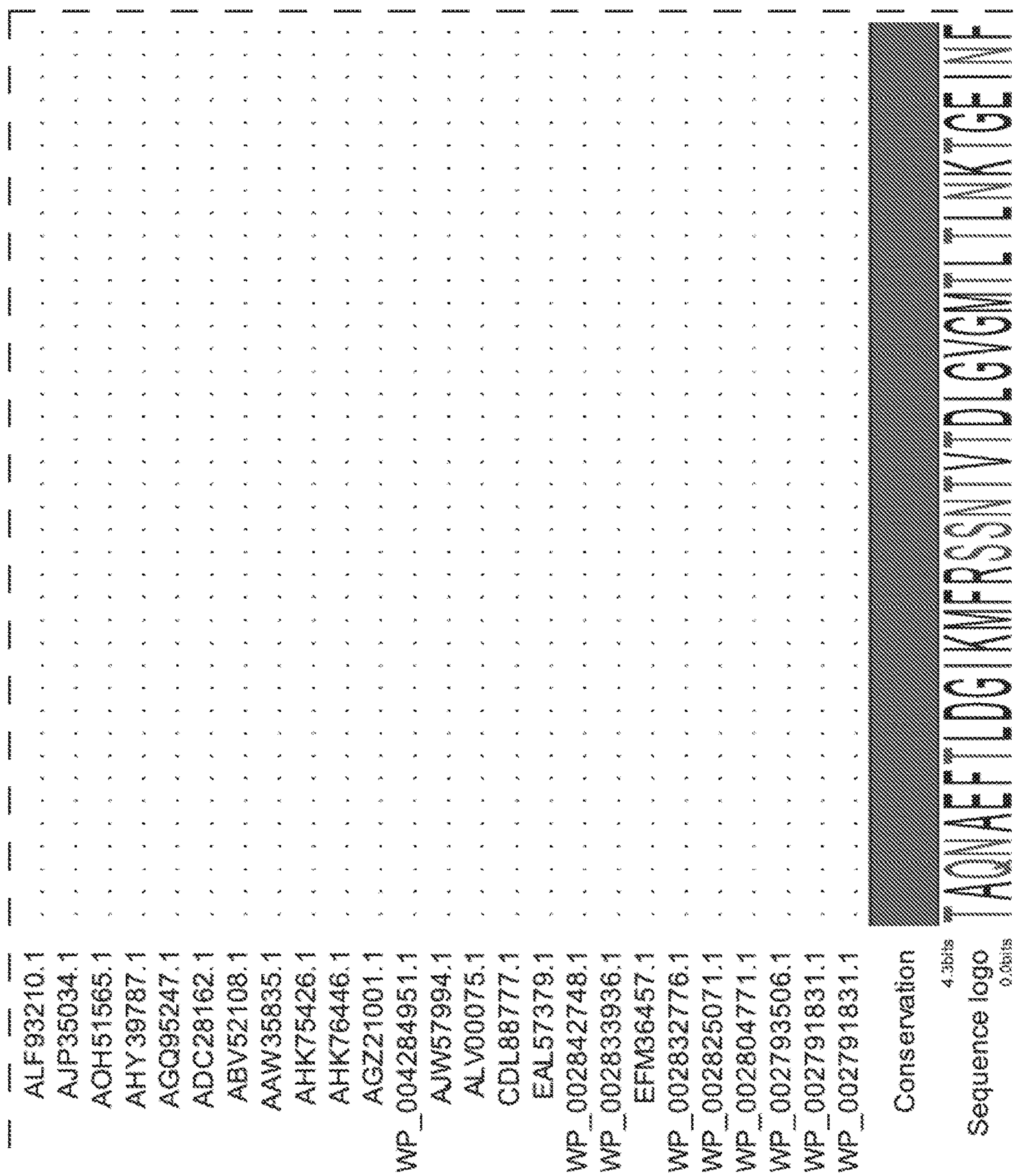
Figure 12:
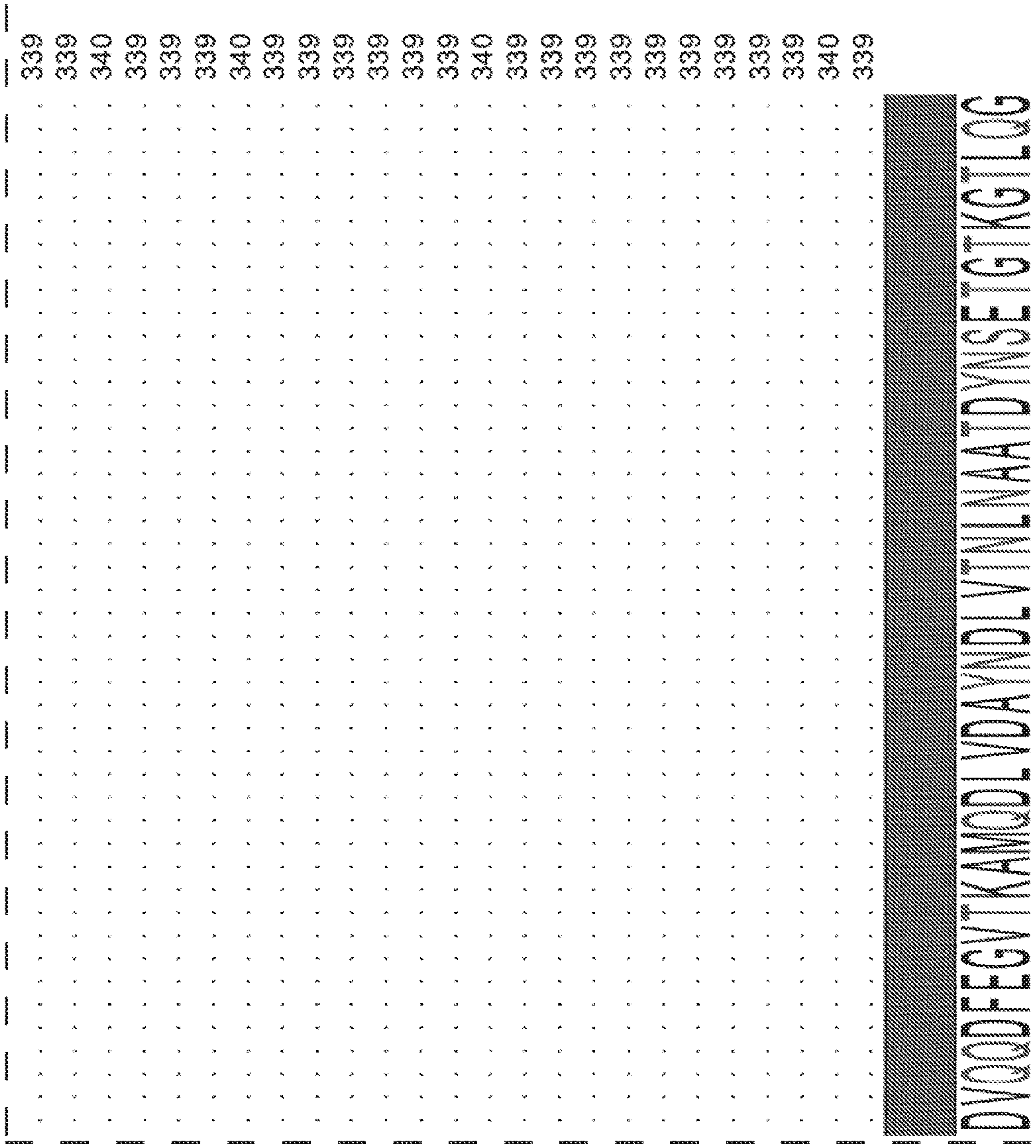
Figure 12:
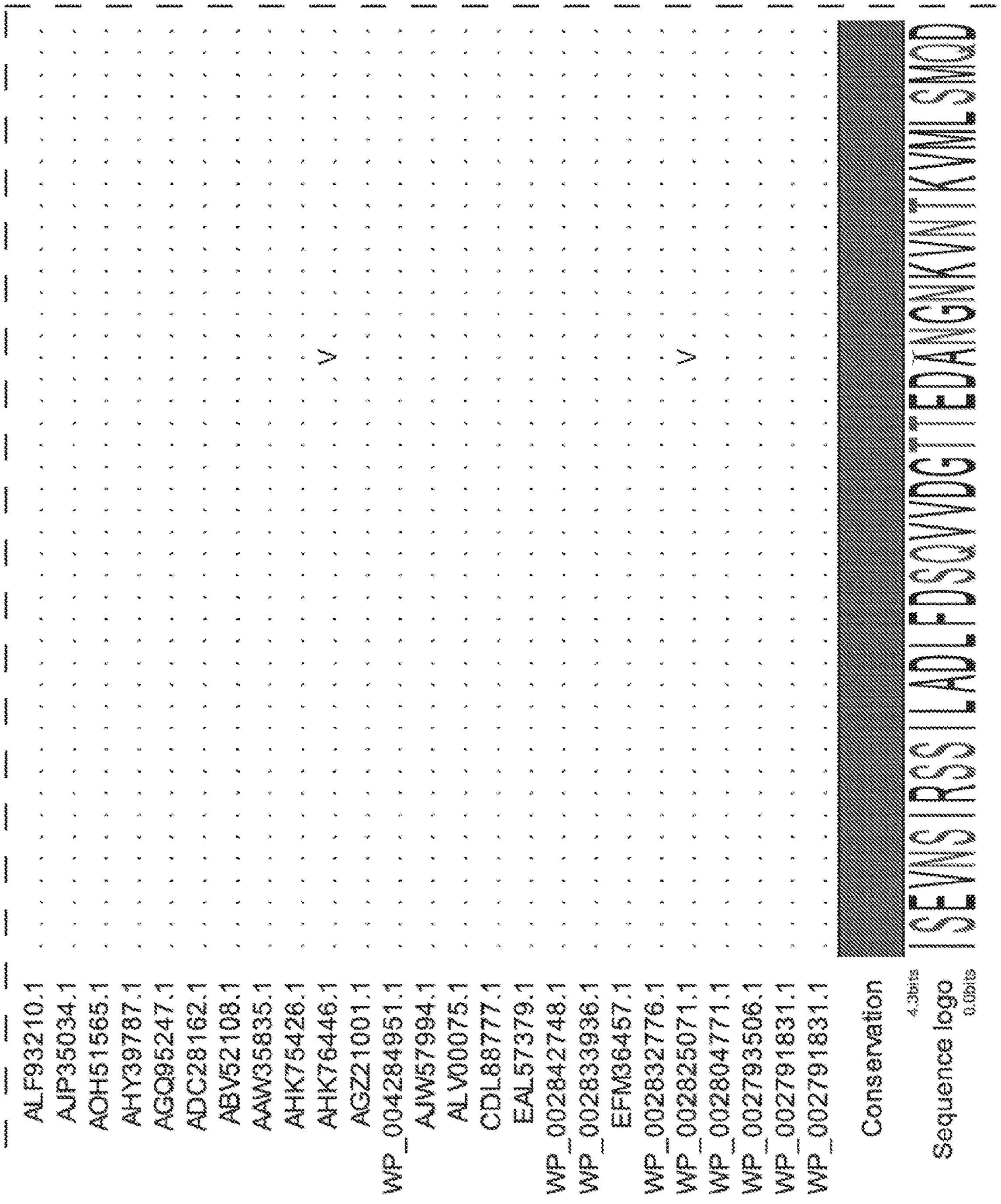
Figure 12:
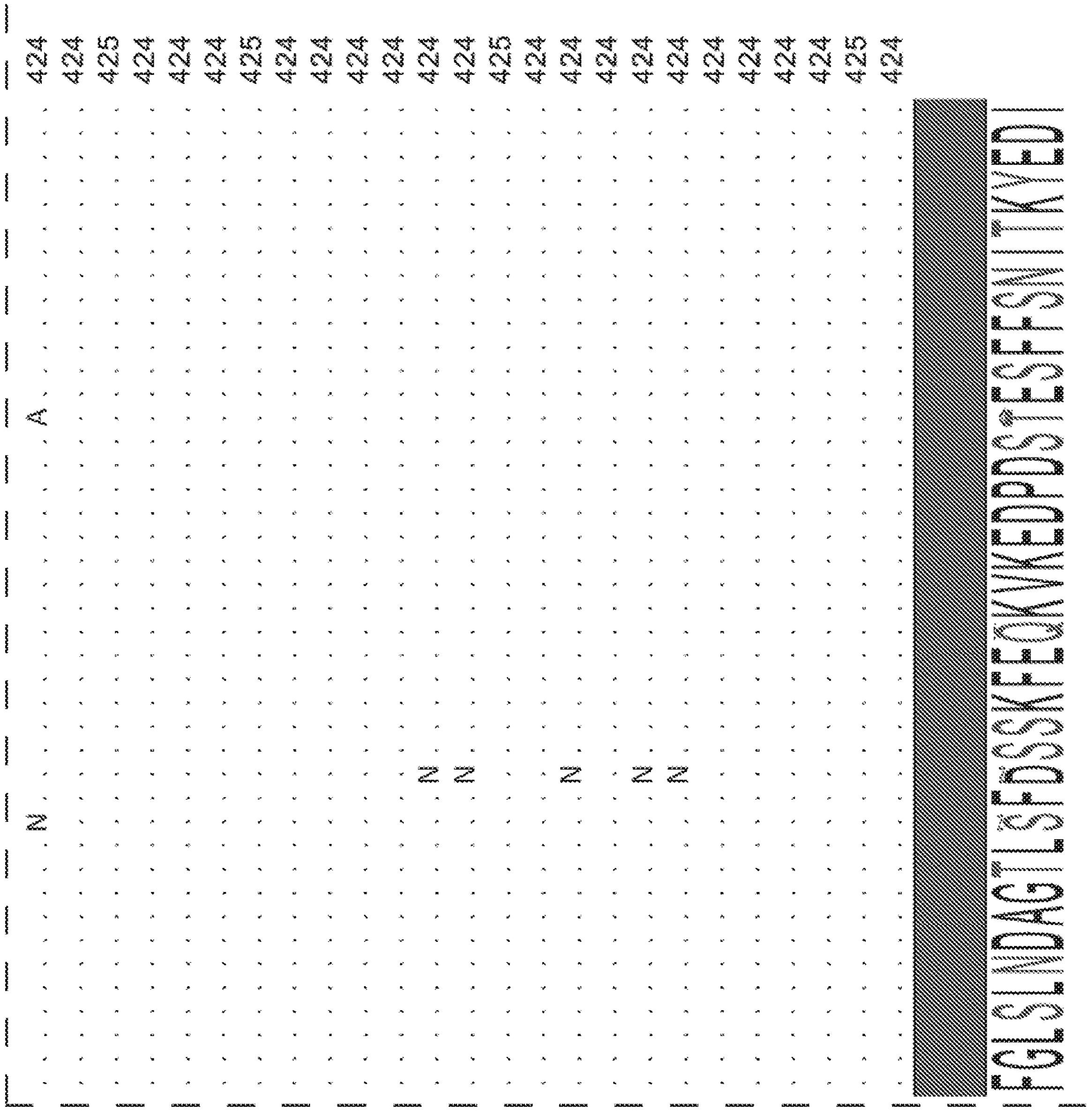
Figure 12:
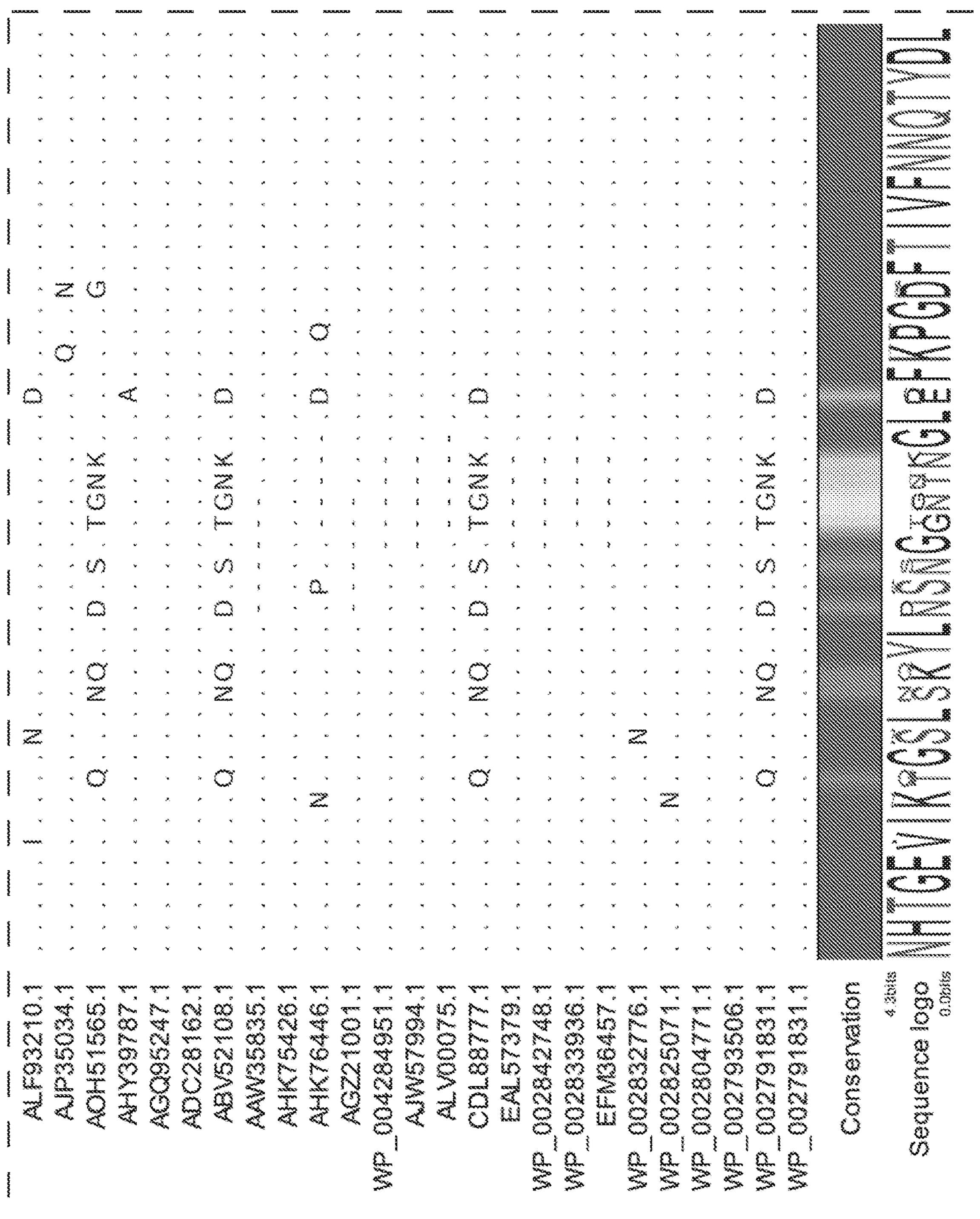
Figure 12:
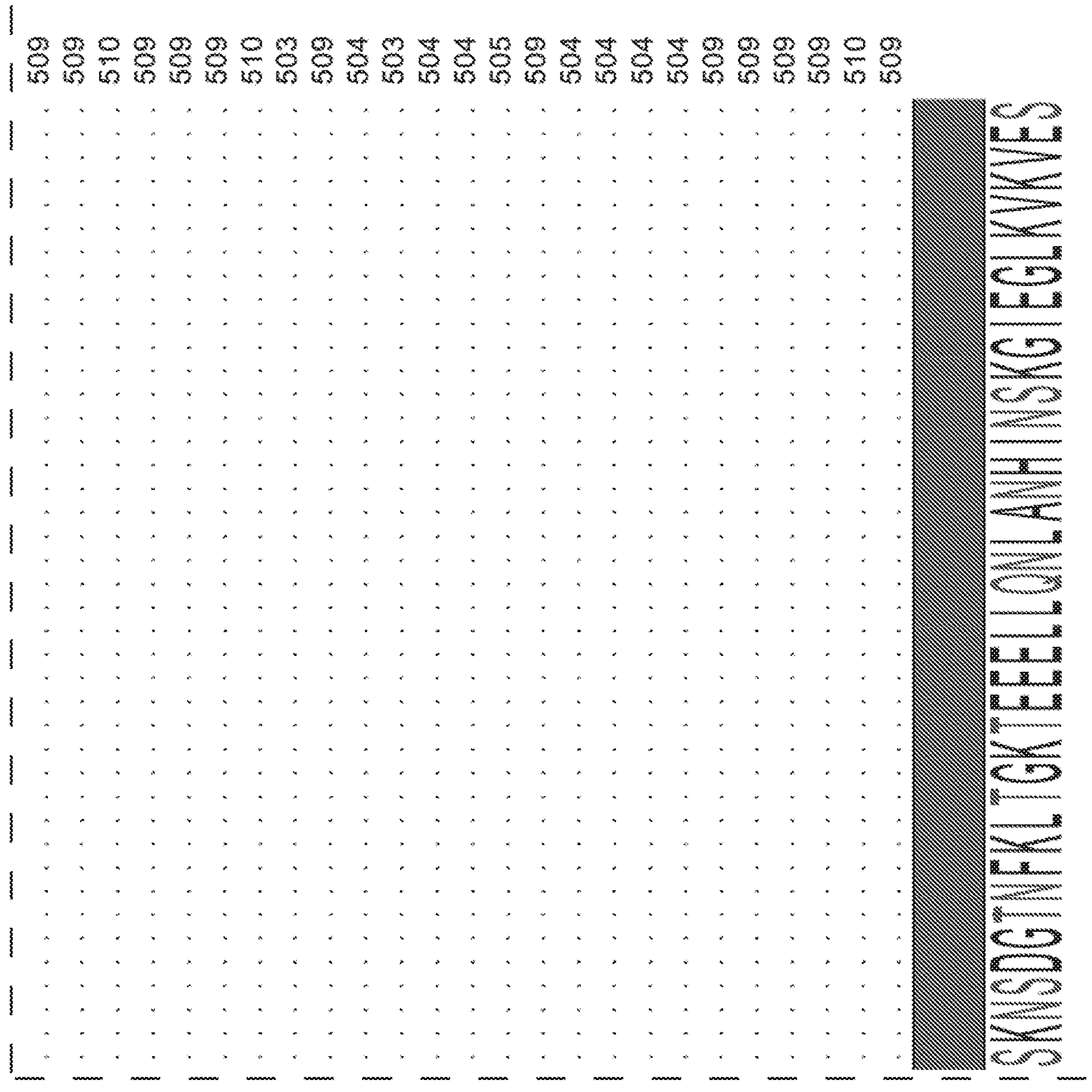
Figure 12:
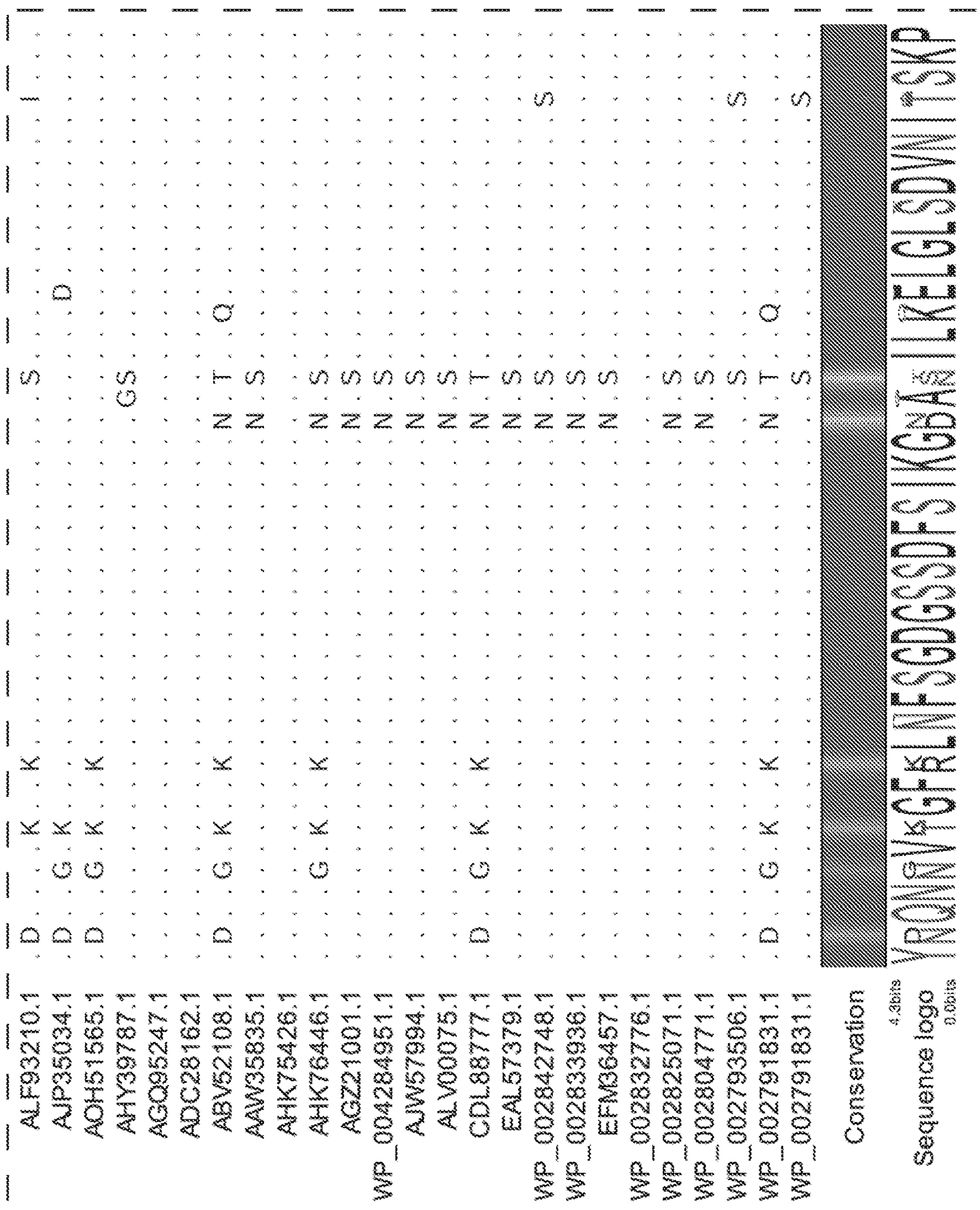
Figure 12:
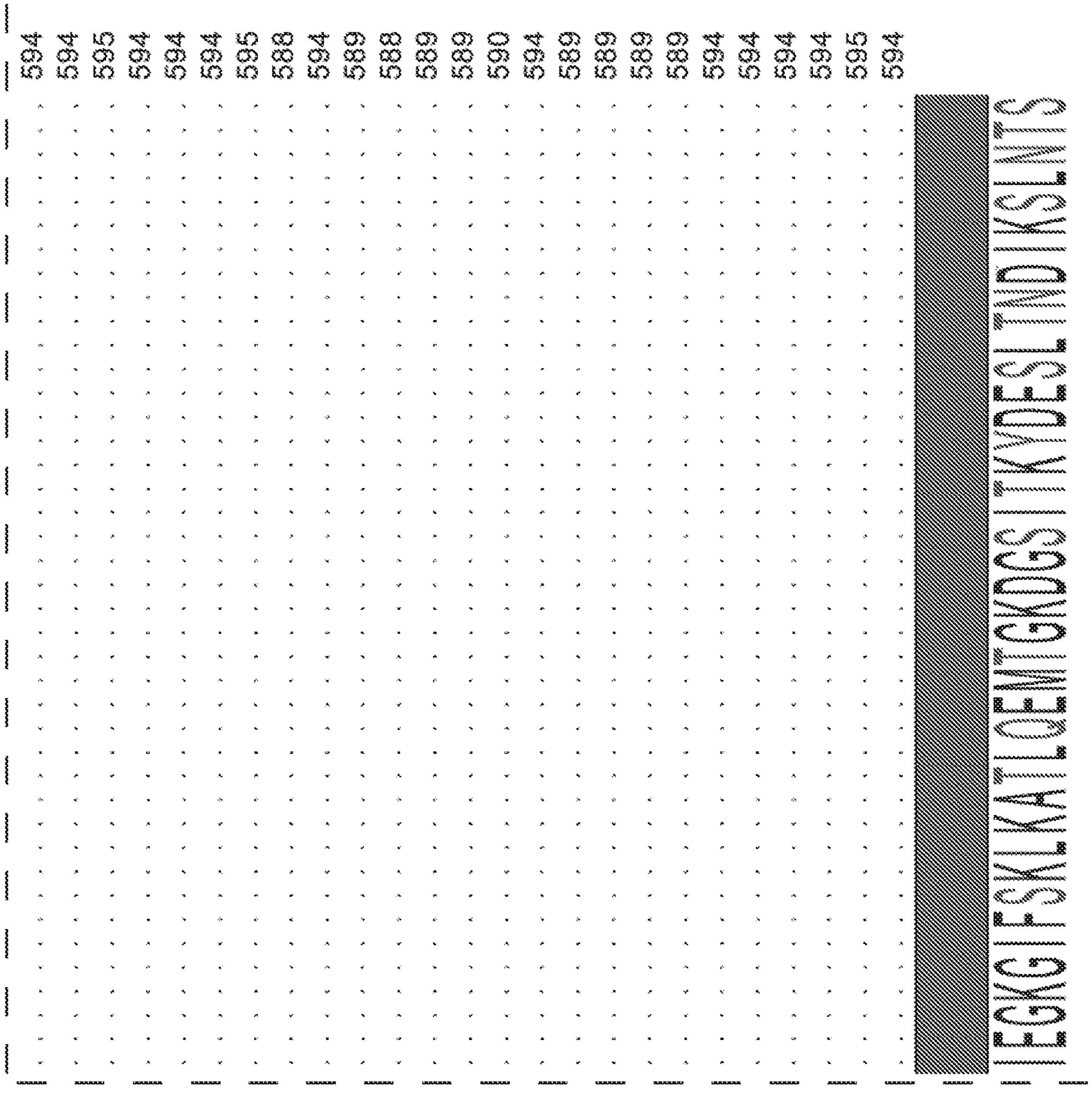
Figure 12:
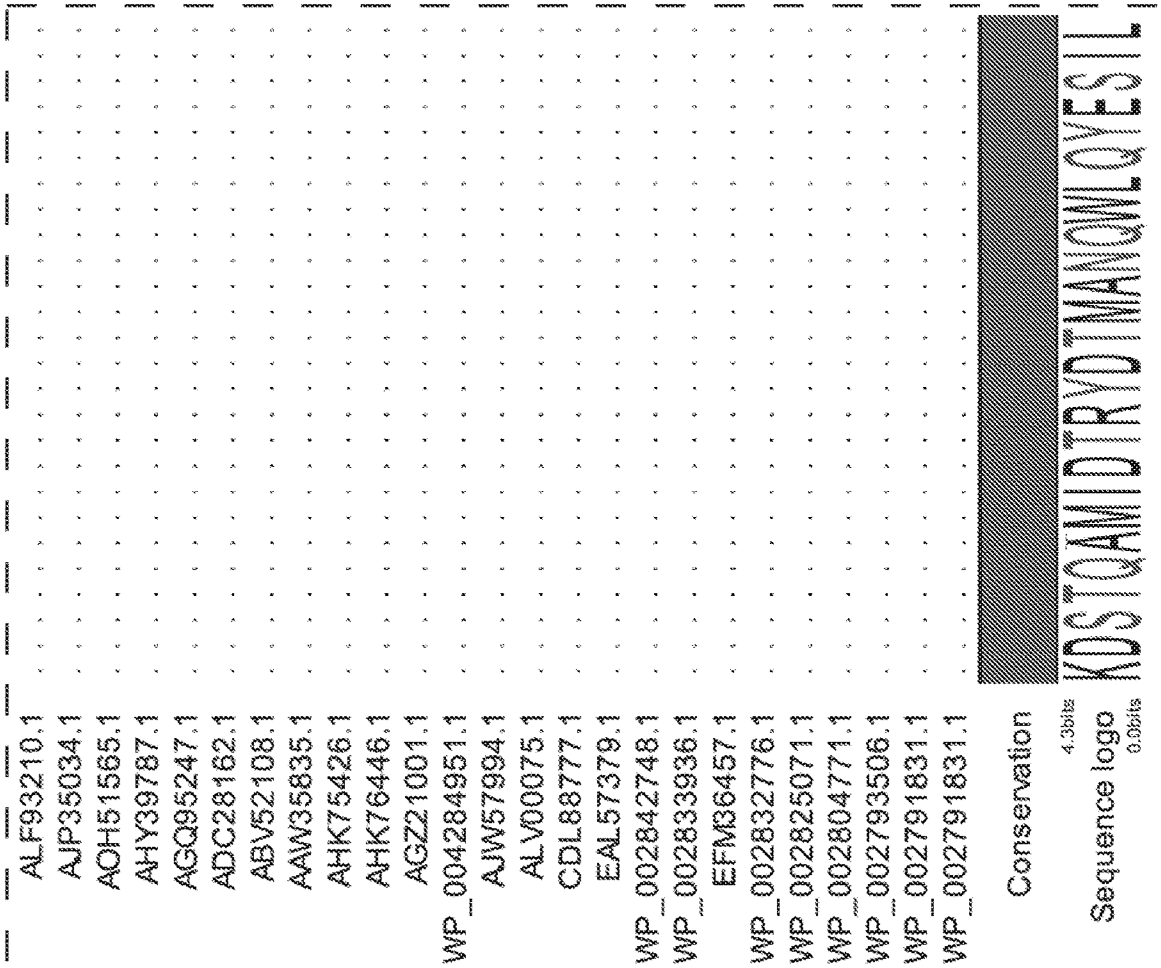
Figure 12:
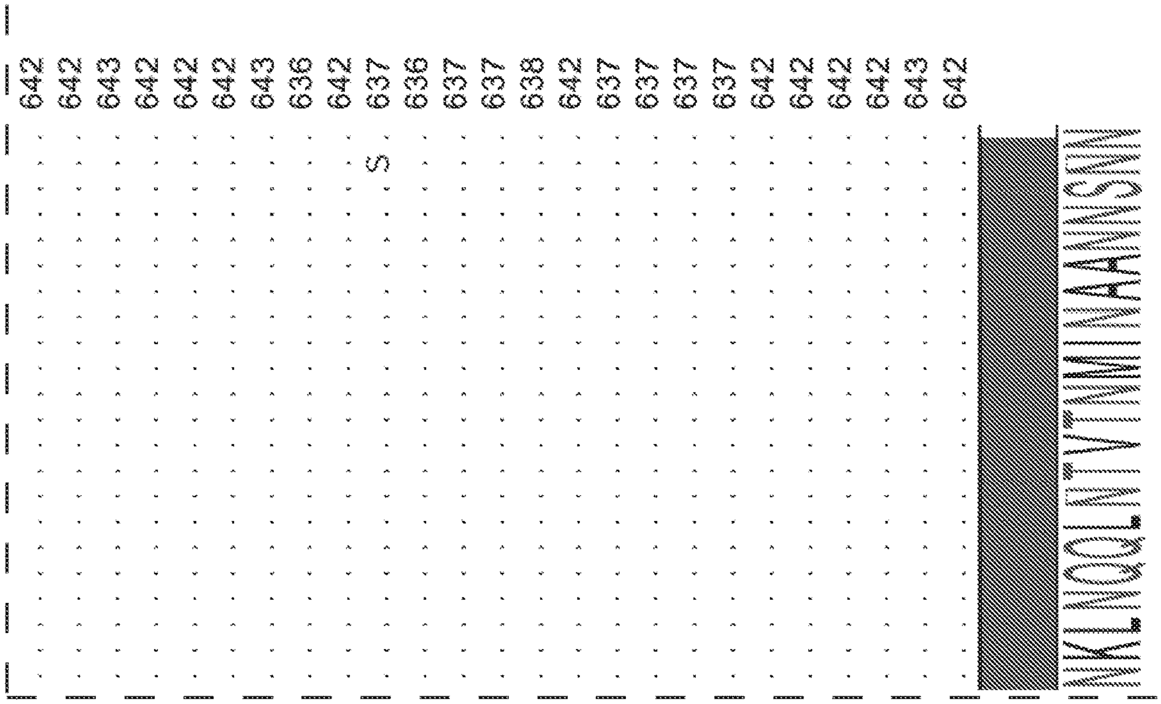

FIG. 12 shows analysis of FliD amino acid sequence conservation. FliD amino acid sequences from *C. jejuni* and *C. coli* isolates were retrieved from GenBank and analyzed using CLC Main Workbench software (Qiagen). The height of each letter in the sequence logo represents the level of conservation of that amino acid at the specific site. The consensus sequence for FliD is shown at top.

Figure 13:
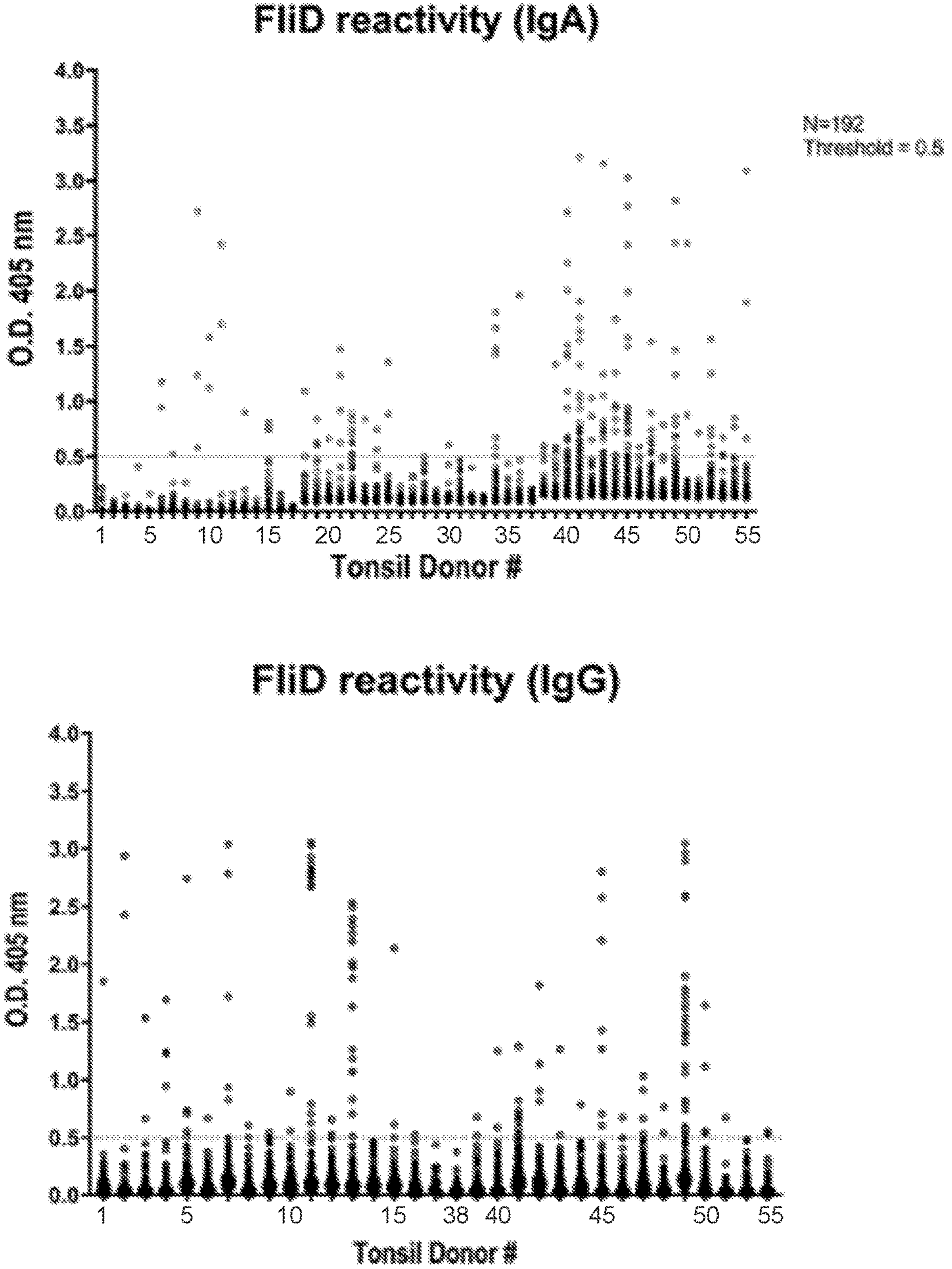

FIG. 13 shows frequency of FliD-reactive $IgA^+$ and $IgG^+$ memory B cells from different tonsillar samples. Analysis of reactivity against FliD antigen of the $IgA^+$ (upper panel) and $IgG^+$ (lower panel) memory B cell repertoire for different tonsillar samples is shown.

Figure 14A:
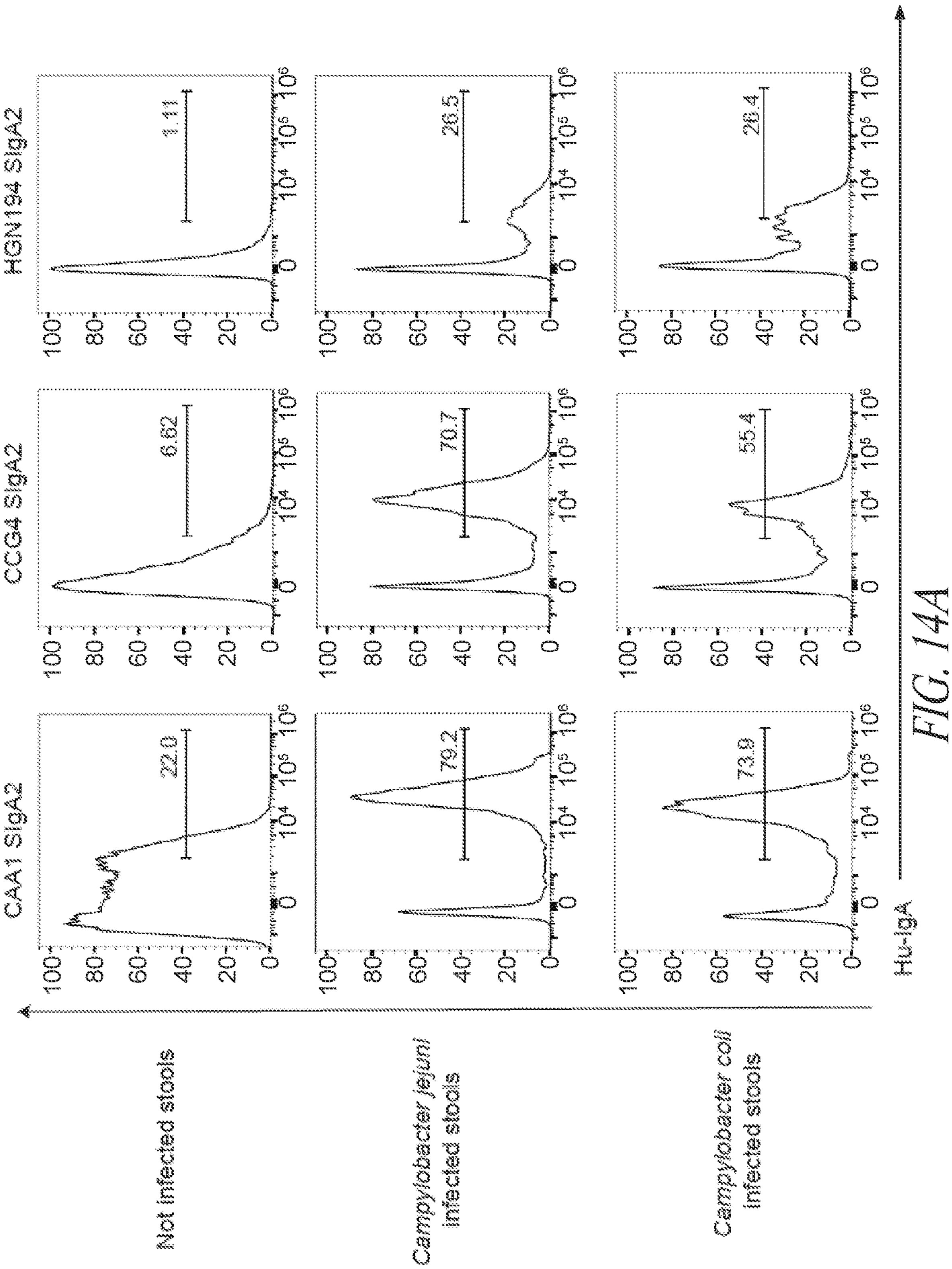
Figure 14B:
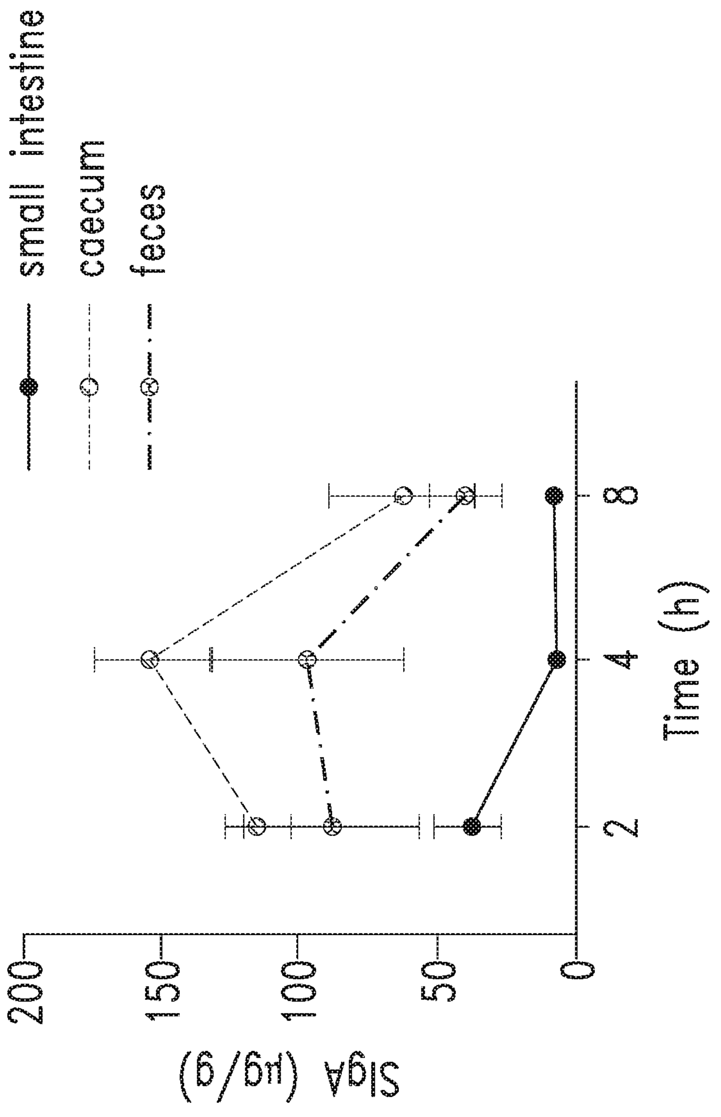
Figure 14C:
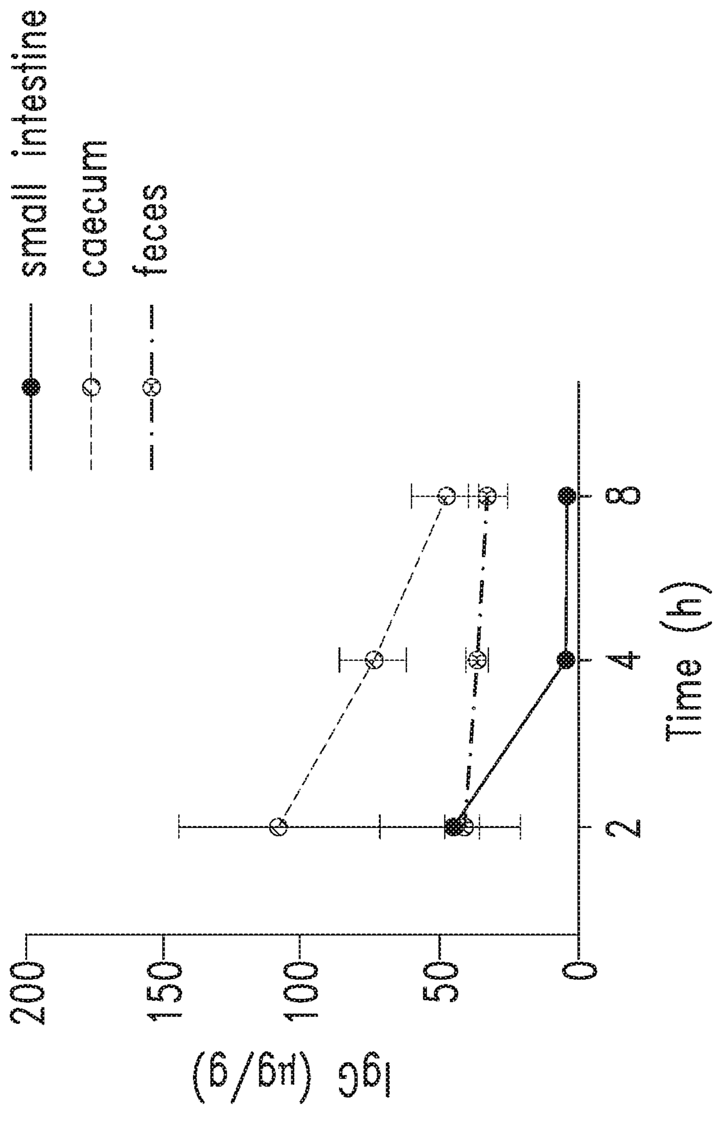

FIGS. 14A-14C show cross-reactivity of FliD-reactive mAbs with the murine microbiota and persistence in caecum of C57BL/6 just weaned mice. (A) Representative histograms of the specific binding of the indicated mAbs against fecal microbiota of mice mock infected or infected with *C. jejuni* or *C. coli*. One representative experiment out of three is shown. (B-C) Pharmacokinetics evaluation by ELISA of HGN194 (B) rSIgA and (C) rIgG antibody at the indicated time points in the different mouse intestinal sub-compartments. One representative experiment out of at two is shown.

FIGS. 15A-15D provide further data showing prophylactic activity of CAA1 rSIgA at different *C. jejuni* infection doses. (A-B) Quantification of the fecal bacterial load (CFU) in 21-day-old C57BL/6 mice administered via gavage with 200 μg of CAA1 rSIgA2 as measured at 24, 72 and 120 h post-infection with $10^7$ or $10^9$ CFU of *C. jejuni*. (C-D) Quantification of fecal lipocalin-2 (LCN) in 21-day-old C57BL/6 mice administered via gavage with 200 μg of CAA1 rSIgA2 as measured at 120 h post-infection with $10^7$ or $10^9$ CFU of *C. jejuni*. Dots represent individual mice and results are shown as ±SEM. Mann-Whitney test (A-D) was used. *p<0.05, **p<0.01. One representative experiment out of at least two is shown.

FIGS. 16A-16D show that IgA isotype switch affects Igase sensitivity, but not FliD affinity or specificity. (A) Denaturing non-reducing gel of CAA1 rSIgA1 and rSIgA2 incubated over-night (18 hours) with PBS or with rIgA protease (IgAse Pro-Pro-Y-Pro) from *Neisseria gonorrhoeae*. (1: SIgA1+PBS; 2: SIgA2+PBS; 3: SIgA1+Igase; 4: SIgA2+Igase). (B) Binding of rSIgA1 and rSIgA2 CAA1 to FliD, as measured by ELISA. Serial dilutions of the mAbs were incubated for 1 h at RT with FliD pre-coated 96 well ELISA plates. Detection was performed using a biotinylated anti-human SC antibody followed by incubation with Streptavidin-AP. (C) Representative histograms of the in vitro specific binding of the indicated mAbs against pure culture of *C. jejuni* and *C. coli*. One representative experiment out of three is shown. (D) Representative histograms of CAA1 rSIgA1 and rSIgA2 binding to the fecal microbiota of not infected C57BL/6 just-weaned mice.

FIGS. 17A-17D show that conversion to IgG format reduces oral CCG4 prophylactic activity against *C. jejuni* infection. (A-D) 2 h prior to infection with $10^8$ CFU of *C. jejuni,* 21-day-old C57BL/6 mice were orally administered via gavage with 200 μg of CCg4 as rSIgA2 or rIgG1. (A) Quantification of the bacterial load (CFU) in the stools of the animals at 24 and 72 h post-infection. (B) Representative dot plot and relative quantification of polymorphonucleated cells infiltrated in the caecum at 72 h post-infection. (C) Quantification of Lipocalin-2 (LCN) in the stools, and (D) statistical analysis of histopathological score in the caecum at 72 h post infection in the different treatment conditions. Dots represent individual mice and results are shown as ±SEM. Mann-Whitney test (A-D) was used. *p<0.05, **p<0.01. One representative experiment out of two is shown.

DETAILED DESCRIPTION

Provided herein are antibodies and antigen-binding fragments specific for *Campylobacter*, compositions comprising the same, and methods of using the antibodies and compositions to treat (e.g., reduce, delay, eliminate, or prevent) a *Campylobacter* infection in a subject. In some embodiments, an antibody of the present disclosure comprises an IgA molecule, such as a dimeric IgA molecule. In certain embodiments, an IgA antibody of the present disclosure is provided in a secretory form (SIgA), as described herein. Administration of antibodies and antigen-binding fragments of the present disclosure, e.g., via oral delivery of a presently disclosed SIgA, can treat infection by *Campylobacter*, such as *Campylobacter* species associated with severe neonatal gastroenteritis.

By way of background, *Campylobacter* is an established cause of diarrhea worldwide and has recently been added to the WHO list of bacteria whose antibiotic resistance might pose a global threat to human health (World Health Organization (WHO), 2017). *Campylobacter*'s epidemiology differs between high-income countries, where the encounter with the bacteria is sporadic, and low- and middle-income countries, in which the infection is almost universal in early childhood, and is a major cause of life-threatening acute watery diarrhea in infants (Riddle and Guerry, *Vaccine,* 34:2903-2906 (2016)).

Considered as a leading zoonosis, *Campylobacter* infection is mainly associated with the consumption of contaminated undercooked animal meat (poultry being the primary bacteria reservoir), water or unpasteurized milk (Kaakoush et al., *Clin. Microbiol. Rev.,* 28:687-720 (2015)). *Campylobacter jejuni* and *C. coli* are major causes of *Campylobacter* enteritis in humans (Man, *Nat. Rev. Gastroenterol. Hepatol.,* 8:669-685 (2011)).

Campylobacteriosis typically results in an acute, gastrointestinal illness characterized by watery or bloody diarrhea, fever, weight loss, and cramps that last on average 6 days Kaakoush et al., *Clin. Microbiol. Rev.,* 28:687-720 (2015); World Health Organization (WHO) (2013)). Severe dehydration associated with *Campylobacter* enteritis represents a significant cause of death among newborns and children, particularly in developing countries (Platts-Mills et al., *Lancet Glob. Health.,* 3:e564-75 (2015)). Furthermore, *C. jejuni* infection has been consistently linked with the onset of autoimmune conditions such as Guillain-Barré Syndrome (GB S) (Islam et al., *PLoS One,* 7: e43976 (2012); Yuki et al., *Proc. Natl. Acad. Sci. U.S.A.,* 101:11404-11409 (2004)) and Inflammatory Bowel Disease (IBD) (Gradel et al., Gastroenterology, 137:495-501 (2009)).

Flagellum-mediated motility is thought to be important for *Campylobacter*'s virulence and pathogenicity, as shown in both experimental animal models and in human healthy volunteer studies (Black et al., *J. Infect. Dis.,* 157:472-479 (1988); Morooka et al., *J. Gen. Microbiol.,* 131:1973-1980 (1985)). But, flagellin (FlaA), the major constituent of the flagellum, does not present a high level of conservation even within the same *C. jejuni* species, and its heavy glycosylation pattern varies greatly depending on the strain and growth phase (Parkhill et al., *Nature,* 403:665-668 (2000); Thibault et al., *J. Biol. Chem.,* 276:34862-34870 (2001)). A recombinant non-glycosylated form of *C. jejuni* flagellin was shown to be poorly immunogenic in clinical trials (Riddle and Guerry, *Vaccine,* 34:2903-2906 (2016)), making FlaA a challenging target for therapy. Moreover, the possibility to use *C. jejuni* in a vaccine has been limited by the risk of GBS development associated with ganglioside mimicry of bacterial lipo-oligosaccharide (LOS) (Riddle and Guerry, *Vaccine,* 34:2903-2906 (2016)).

Due to these shortcomings, there are currently no vaccines approved by a global regulatory authority to prevent *Campylobacter* infection. Rehydration is the main form of therapy, and while antibiotics have been shown to be beneficial in severe infections, they are often not recommended due to the rapid development of antibiotic resistance. Even in the case of recovery from the infection, the continuous exposure of infants in low-income countries to intestinal pathogens, including *Campylobacter*, has been linked to environmental enteropathy (EE)/environmental enteric dysfunction (EED), a subclinical chronic inflammation of the small intestine associated with malabsorption of nutrients, growth faltering, impaired cognitive development, changes in microbiota, and reduced responsiveness to oral vaccination (Watanabe and Petri, *EBioMedicine,* 10:25-32 (2016)).

The present disclosure provides antibodies and antigen-binding fragments that bind to the *Campylobacter* flagellar-capping protein FliD. Antibodies according to the present disclosure advantageously limit motility of *Campylobacter* and, in an animal model of *Campylobacter* infection described in this disclosure, are capable of boosting *Campylobacter* clearance infection, significantly reducing the levels of inflammation markers associated with epithelial damage and polymorphonuclear (PMN) cells infiltration.

Also provided herein are compositions that comprise a *Campylobacter* FliD-specific antibody or antigen-binding fragment of the present disclosure, polynucleotides that encode the antibody or antigen-binding fragment, vectors that contain the polynucleotide, and host cells that express the antibody or antigen-binding fragment, and/or comprise or contain a polynucleotide or vector of the present disclosure. Methods and uses are also provided for treating a *Campylobacter* infection and/or for reducing an associated symptom.

Also provided are non-human animal models for studying *Campylobacter* infection.

Prior to setting forth this disclosure in more detail, it may be helpful to an understanding thereof to provide definitions of certain terms to be used herein. Additional definitions are set forth throughout this disclosure.

In the present description, any concentration range, percentage range, ratio range, or integer range is to be understood to include the value of any integer within the recited range and, when appropriate, fractions thereof (such as one tenth and one hundredth of an integer), unless otherwise indicated. Also, any number range recited herein relating to any physical feature, such as polymer subunits, size or thickness, are to be understood to include any integer within the recited range, unless otherwise indicated. As used herein, the term "about" means±20% of the indicated range, value, or structure, unless otherwise indicated. It should be understood that the terms "a" and "an" as used herein refer to "one or more" of the enumerated components. The use of the alternative (e.g., "or") should be understood to mean either one, both, or any combination thereof of the alternatives. As used herein, the terms "include," "have," and "comprise" are used synonymously, which terms and variants thereof are intended to be construed as non-limiting.

"Optional" or "optionally" means that the subsequently described element, component, event, or circumstance may or may not occur, and that the description includes instances in which the element, component, event, or circumstance occurs and instances in which they do not.

In addition, it should be understood that the individual constructs, or groups of constructs, derived from the various combinations of the structures and subunits described herein, are disclosed by the present application to the same extent as if each construct or group of constructs was set forth individually. Thus, selection of particular structures or particular subunits is within the scope of the present disclosure.

The term "consisting essentially of" is not equivalent to "comprising" and refers to the specified materials or steps of a claim, or to those that do not materially affect the basic characteristics of a claimed subject matter. For example, a protein domain, region, or module (e.g., a binding domain, hinge region, or linker) or a protein (which may have one or more domains, regions, or modules) "consists essentially of" a particular amino acid sequence when the amino acid sequence of a domain, region, module, or protein includes extensions, deletions, mutations, or a combination thereof (e.g., amino acids at the amino- or carboxy-terminus or between domains) that, in combination, contribute to at most 20% (e.g., at most 15%, 10%, 8%, 6%, 5%, 4%, 3%, 2% or 1%) of the length of a domain, region, module, or protein and do not substantially affect (i.e., do not reduce the activity by more than 50%, such as no more than 40%, 30%, 25%, 20%, 15%, 10%, 5%, or 1%) the activity of the domain(s), region(s), module(s), or protein (e.g., the target binding affinity of a binding protein).

As used herein, "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refer to compounds that have the same basic chemical structure as a naturally occurring amino acid, i.e., an α-carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refer to chemical compounds that have a structure that is different from the general chemical structure of an amino acid, but that functions in a manner similar to a naturally occurring amino acid.

As used herein, "mutation" refers to a change in the sequence of a nucleic acid molecule or polypeptide molecule as compared to a reference or wild-type nucleic acid molecule or polypeptide molecule, respectively. A mutation can result in several different types of change in sequence, including substitution, insertion or deletion of nucleotide(s) or amino acid(s).

A "conservative substitution" refers to amino acid substitutions that do not significantly affect or alter binding characteristics of a particular protein. Generally, conservative substitutions are ones in which a substituted amino acid residue is replaced with an amino acid residue having a similar side chain. Conservative substitutions include a substitution found in one of the following groups: Group 1: Alanine (Ala or A), Glycine (Gly or G), Serine (Ser or S), Threonine (Thr or T); Group 2: Aspartic acid (Asp or D), Glutamic acid (Glu or Z); Group 3: Asparagine (Asn or N), Glutamine (Gln or Q); Group 4: Arginine (Arg or R), Lysine (Lys or K), Histidine (His or H); Group 5: Isoleucine (Ile or I), Leucine (Leu or L), Methionine (Met or M), Valine (Val or V); and Group 6: Phenylalanine (Phe or F), Tyrosine (Tyr or Y), Tryptophan (Trp or W). Additionally or alternatively, amino acids can be grouped into conservative substitution groups by similar function, chemical structure, or composition (e.g., acidic, basic, aliphatic, aromatic, or sulfur-containing). For example, an aliphatic grouping may include, for purposes of substitution, Gly, Ala, Val, Leu, and Ile. Other conservative substitutions groups include: sulfur-containing: Met and Cysteine (Cys or C); acidic: Asp, Glu, Asn, and Gln; small aliphatic, nonpolar or slightly polar residues: Ala, Ser, Thr, Pro, and Gly; polar, negatively charged residues and their amides: Asp, Asn, Glu, and Gln; polar, positively charged residues: His, Arg, and Lys; large aliphatic, nonpolar residues: Met, Leu, Ile, Val, and Cys; and large aromatic residues: Phe, Tyr, and Trp. Additional information can be found in Creighton (1984) Proteins, W.H. Freeman and Company.

As used herein, "protein" or "polypeptide" refers to a polymer of amino acid residues. Proteins apply to naturally occurring amino acid polymers, as well as to amino acid polymers in which one or more amino acid residue is an artificial chemical mimetic of a corresponding naturally occurring amino acid and non-naturally occurring amino acid polymers. Variants of proteins, peptides, and polypeptides of this disclosure are also contemplated. In certain embodiments, variant proteins, peptides, and polypeptides comprise or consist of an amino acid sequence that is at least 70%, 75%, 80%, 85%, 90%, 91%, 92%, 93%, 94%, 95%, 96%, 97%, 98%, 99%, or 99.9% identical to an amino acid sequence of a defined or reference amino acid sequence as described herein.

"Nucleic acid molecule" or "polynucleotide" or "polynucleic acid" refers to a polymeric compound including covalently linked nucleotides, which can be made up of natural subunits (e.g., purine or pyrimidine bases) or non-natural subunits (e.g., morpholine ring). Purine bases include adenine, guanine, hypoxanthine, and xanthine, and pyrimidine bases include uracil, thymine, and cytosine. Nucleic acid molecules include polyribonucleic acid (RNA), which includes mRNA, microRNA, siRNA, viral genomic RNA, and synthetic RNA, and polydeoxyribonucleic acid (DNA), which includes cDNA, genomic DNA, and synthetic DNA, either of which may be single or double stranded. If single-stranded, the nucleic acid molecule may be the coding strand or non-coding (anti-sense) strand. A nucleic acid molecule encoding an amino acid sequence includes all nucleotide sequences that encode the same amino acid sequence. Some versions of the nucleotide sequences may also include intron(s) to the extent that the intron(s) would be removed through co- or post-transcriptional mechanisms. In other words, different nucleotide sequences may encode the same amino acid sequence as the result of the redundancy or degeneracy of the genetic code, or by splicing.

Variants of nucleic acid molecules of this disclosure are also contemplated. Variant nucleic acid molecules are at least 70%, 75%, 80%, 85%, 90%, and are preferably 95%, 96%, 97%, 98%, 99%, or 99.9% identical a nucleic acid molecule of a defined or reference polynucleotide as described herein, or that hybridize to a polynucleotide under stringent hybridization conditions of 0.015M sodium chloride, 0.0015M sodium citrate at about 65-68° C. or 0.015M sodium chloride, 0.0015M sodium citrate, and 50% formamide at about 42° C. Nucleic acid molecule variants retain the capacity to encode a binding domain thereof having a functionality described herein, such as binding a target molecule.

"Percent sequence identity" refers to a relationship between two or more sequences, as determined by comparing the sequences. Preferred methods to determine sequence identity are designed to give the best match between the sequences being compared. For example, the sequences are aligned for optimal comparison purposes (e.g., gaps can be introduced in one or both of a first and a second amino acid or nucleic acid sequence for optimal alignment). Further, non-homologous sequences may be disregarded for comparison purposes. The percent sequence identity referenced herein is calculated over the length of the reference sequence, unless indicated otherwise. Methods to determine sequence identity and similarity can be found in publicly available computer programs. Sequence alignments and percent identity calculations may be performed using a BLAST program (e.g., BLAST 2.0, BLASTP, BLASTN, or BLASTX). The mathematical algorithm used in the BLAST programs can be found in Altschul et al., *Nucleic Acids Res.* 25:3389-3402, 1997. Within the context of this disclosure, it will be understood that where sequence analysis software is used for analysis, the results of the analysis are based on the "default values" of the program referenced. "Default values" mean any set of values or parameters which originally load with the software when first initialized.

The term "isolated" means that the material is removed from its original environment (e.g., the natural environment if it is naturally occurring). For example, a naturally occurring nucleic acid or polypeptide present in a living animal is not isolated, but the same nucleic acid or polypeptide, separated from some or all of the co-existing materials in the natural system, is isolated. Such nucleic acid could be part of a vector and/or such nucleic acid or polypeptide could be part of a composition (e.g., a cell lysate), and still be isolated in that such vector or composition is not part of the natural environment for the nucleic acid or polypeptide.

The term "gene" means the segment of DNA or RNA involved in producing a polypeptide chain; it includes regions preceding and following the coding region (e.g., 5' untranslated region (UTR) and 3' UTR) as well as intervening sequences (introns) between individual coding segments (exons).

A "functional variant" refers to a polypeptide or polynucleotide that is structurally similar or substantially structurally similar to a parent or reference compound of this disclosure, but differs slightly in composition (e.g., one base, atom or functional group is different, added, or removed), such that the polypeptide or encoded polypeptide is capable of performing at least one function of the parent polypeptide with at least 50% efficiency, preferably at least 55%, 60%, 70%, 75%, 80%, 85%, 90%, 95%, 96%, 97%, 98%, 99%, 99.9%, or 100% level of activity of the parent polypeptide.

In other words, a functional variant of a polypeptide or encoded polypeptide of this disclosure has "similar binding," "similar affinity" or "similar activity" when the functional variant displays no more than a 50% reduction in performance in a selected assay as compared to the parent or reference polypeptide, such as an assay for measuring binding affinity (e.g., Biacore® or tetramer staining measuring an association (Ka) or a dissociation (KD) constant).

As used herein, a "functional portion" or "functional fragment" refers to a polypeptide or polynucleotide that comprises only a domain, portion or fragment of a parent or reference compound, and the polypeptide or encoded polypeptide retains at least 50% activity associated with the domain, portion or fragment of the parent or reference compound, preferably at least 55%, 60%, 70%, 75%, 80%, 85%, 90%, 95%, 96%, 97%, 98%, 99%, 99.9%, or 100% level of activity of the parent polypeptide, or provides a biological benefit (e.g., effector function). A "functional portion" or "functional fragment" of a polypeptide or encoded polypeptide of this disclosure has "similar binding" or "similar activity" when the functional portion or fragment displays no more than a 50% reduction in performance in a selected assay as compared to the parent or reference polypeptide (preferably no more than 20% or 10%, or no more than a log difference as compared to the parent or reference with regard to affinity).

As used herein, the term "engineered," "recombinant," or "non-natural" refers to an organism, microorganism, cell, nucleic acid molecule, or vector that includes at least one genetic alteration or has been modified by introduction of an exogenous or heterologous nucleic acid molecule, wherein such alterations or modifications are introduced by genetic engineering (i.e., human intervention). Genetic alterations include, for example, modifications introducing expressible nucleic acid molecules encoding functional RNA, proteins, fusion proteins or enzymes, or other nucleic acid molecule additions, deletions, substitutions, or other functional disruption of a cell's genetic material. Additional modifications include, for example, non-coding regulatory regions in which the modifications alter expression of a polynucleotide, gene, or operon.

As used herein, "heterologous" or "non-endogenous" or "exogenous" refers to any gene, protein, compound, nucleic acid molecule, or activity that is not native to a host cell or a subject, or any gene, protein, compound, nucleic acid molecule, or activity native to a host cell or a subject that has been altered. Heterologous, non-endogenous, or exogenous includes genes, proteins, compounds, or nucleic acid molecules that have been mutated or otherwise altered such that the structure, activity, or both is different as between the native and altered genes, proteins, compounds, or nucleic acid molecules. In certain embodiments, heterologous, non-endogenous, or exogenous genes, proteins, or nucleic acid molecules (e.g., receptors, ligands, etc.) may not be endogenous to a host cell or a subject, but instead nucleic acids encoding such genes, proteins, or nucleic acid molecules may have been added to a host cell by conjugation, transformation, transfection, electroporation, or the like, wherein the added nucleic acid molecule may integrate into a host cell genome or can exist as extra-chromosomal genetic material (e.g., as a plasmid or other self-replicating vector). The term "homologous" or "homolog" refers to a gene, protein, compound, nucleic acid molecule, or activity found in or derived from a host cell, species, or strain. For example, a heterologous or exogenous polynucleotide or gene encoding a polypeptide may be homologous to a native polynucleotide or gene and encode a homologous polypeptide or activity, but the polynucleotide or polypeptide may have an altered structure, sequence, expression level, or any combination thereof. A non-endogenous polynucleotide or gene, as well as the encoded polypeptide or activity, may be from the same species, a different species, or a combination thereof.

In certain embodiments, a nucleic acid molecule or portion thereof native to a host cell will be considered heterologous to the host cell if it has been altered or mutated, or a nucleic acid molecule native to a host cell may be considered heterologous if it has been altered with a heterologous expression control sequence or has been altered with an endogenous expression control sequence not normally associated with the nucleic acid molecule native to a host cell. In addition, the term "heterologous" can refer to a biological activity that is different, altered, or not endogenous to a host cell. As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When As used herein, the term "endogenous" or "native" refers to a polynucleotide, gene, protein, compound, molecule, or activity that is normally present in a host cell or a subject.

The term "expression", as used herein, refers to the process by which a polypeptide is produced based on the encoding sequence of a nucleic acid molecule, such as a gene. The process may include transcription, post-transcriptional control, post-transcriptional modification, translation, post-translational control, post-translational modification, or any combination thereof. An expressed nucleic acid molecule is typically operably linked to an expression control sequence (e.g., a promoter).

The term "operably linked" refers to the association of two or more nucleic acid molecules on a single nucleic acid fragment so that the function of one is affected by the other. For example, a promoter is operably linked with a coding sequence when it is capable of affecting the expression of that coding sequence (i.e., the coding sequence is under the transcriptional control of the promoter). "Unlinked" means that the associated genetic elements are not closely associated with one another and the function of one does not affect the other.

As described herein, more than one heterologous nucleic acid molecule can be introduced into a host cell as separate nucleic acid molecules, as a plurality of individually controlled genes, as a polycistronic nucleic acid molecule, as a single nucleic acid molecule encoding a fusion protein, or any combination thereof. When two or more heterologous nucleic acid molecules are introduced into a host cell, it is understood that the two or more heterologous nucleic acid molecules can be introduced as a single nucleic acid molecule (e.g., on a single vector), on separate vectors, integrated into the host chromosome at a single site or multiple sites, or any combination thereof. The number of referenced heterologous nucleic acid molecules or protein activities refers to the number of encoding nucleic acid molecules or the number of protein activities, not the number of separate nucleic acid molecules introduced into a host cell.

The term "construct" refers to any polynucleotide that contains a recombinant nucleic acid molecule (or, when the context clearly indicates, a fusion protein of the present disclosure). A (polynucleotide) construct may be present in a vector (e.g., a bacterial vector, a viral vector) or may be integrated into a genome. A "vector" is a nucleic acid molecule that is capable of transporting another nucleic acid molecule. Vectors may be, for example, plasmids, cosmids, viruses, a RNA vector or a linear or circular DNA or RNA molecule that may include chromosomal, non-chromosomal, semi-synthetic or synthetic nucleic acid molecules. Vectors of the present disclosure also include transposon systems (e.g., Sleeping Beauty, see, e.g., Geurts et al., *Mol. Ther.* 8:108, 2003: Mátés et al., *Nat. Genet.* 41:753, 2009). Exemplary vectors are those capable of autonomous replication (episomal vector), capable of delivering a polynucleotide to a cell genome (e.g., viral vector), or capable of expressing nucleic acid molecules to which they are linked (expression vectors).

As used herein, "expression vector" or "vector" refers to a DNA construct containing a nucleic acid molecule that is operably linked to a suitable control sequence capable of effecting the expression of the nucleic acid molecule in a suitable host. Such control sequences include a promoter to effect transcription, an optional operator sequence to control such transcription, a sequence encoding suitable mRNA ribosome binding sites, and sequences which control termination of transcription and translation. The vector may be a plasmid, a phage particle, a virus, or simply a potential genomic insert. Once transformed into a suitable host, the vector may replicate and function independently of the host genome, or may, in some instances, integrate into the genome itself or deliver the polynucleotide contained in the vector into the genome without the vector sequence. In the present specification, "plasmid," "expression plasmid," "virus," and "vector" are often used interchangeably.

The term "introduced" in the context of inserting a nucleic acid molecule into a cell, means "transfection", "transformation," or "transduction" and includes reference to the incorporation of a nucleic acid molecule into a eukaryotic or prokaryotic cell wherein the nucleic acid molecule may be incorporated into the genome of a cell (e.g., chromosome, plasmid, plastid, or mitochondrial DNA), converted into an autonomous replicon, or transiently expressed (e.g., transfected mRNA).

In certain embodiments, polynucleotides of the present disclosure may be operatively linked to certain elements of a vector. For example, polynucleotide sequences that are needed to effect the expression and processing of coding sequences to which they are ligated may be operatively linked. Expression control sequences may include appropriate transcription initiation, termination, promoter, and enhancer sequences; efficient RNA processing signals such as splicing and polyadenylation signals; sequences that stabilize cytoplasmic mRNA; sequences that enhance translation efficiency (i.e., Kozak consensus sequences); sequences that enhance protein stability; and possibly sequences that enhance protein secretion. Expression control sequences may be operatively linked if they are contiguous with the gene of interest and expression control sequences that act in trans or at a distance to control the gene of interest.

In certain embodiments, the vector comprises a plasmid vector or a viral vector (e.g., a lentiviral vector or a γ-retroviral vector). Viral vectors include retrovirus, adenovirus, parvovirus (e.g., adeno-associated viruses), coronavirus, negative strand RNA viruses such as ortho-myxovirus (e.g., influenza virus), rhabdovirus (e.g., rabies and vesicular stomatitis virus), paramyxovirus (e.g., measles and Sendai), positive strand RNA viruses such as picornavirus and alphavirus, and double-stranded DNA viruses including adenovirus, herpesvirus (e.g., Herpes Simplex virus types 1 and 2, Epstein-Barr virus, cytomegalovirus), and poxvirus (e.g., vaccinia, fowlpox, and canarypox). Other viruses include, for example, Norwalk virus, togavirus, flavivirus, reoviruses, papovavirus, hepadnavirus, and hepatitis virus. Examples of retroviruses include avian leukosis-sarcoma, mammalian C-type, B-type viruses, D type viruses, HTLV-BLV group, lentivirus, spumavirus (Coffin, J. M., Retroviridae: The viruses and their replication, In Fundamental Virology, Third Edition, B. N. Fields et al., Eds., Lippincott-Raven Publishers, Philadelphia, 1996).

"Retroviruses" are viruses having an RNA genome, which is reverse-transcribed into DNA using a reverse transcriptase enzyme, the reverse-transcribed DNA is then incorporated into the host cell genome. "Gammaretrovirus" refers to a genus of the retroviridae family. Examples of gammaretroviruses include mouse stem cell virus, murine leukemia virus, feline leukemia virus, feline sarcoma virus, and avian reticuloendotheliosis viruses.

"Lentiviral vectors" include HIV-based lentiviral vectors for gene delivery, which can be integrative or non-integrative, have relatively large packaging capacity, and can transduce a range of different cell types. Lentiviral vectors are usually generated following transient transfection of three (packaging, envelope, and transfer) or more plasmids into producer cells. Like HIV, lentiviral vectors enter the target cell through the interaction of viral surface glycoproteins with receptors on the cell surface. On entry, the viral RNA undergoes reverse transcription, which is mediated by the viral reverse transcriptase complex. The product of reverse transcription is a double-stranded linear viral DNA, which is the substrate for viral integration into the DNA of infected cells.

In certain embodiments, the viral vector can be a gammaretrovirus, e.g., Moloney murine leukemia virus (MLV)-derived vectors. In other embodiments, the viral vector can be a more complex retrovirus-derived vector, e.g., a lentivirus-derived vector. HIV-1-derived vectors belong to this category. Other examples include lentivirus vectors derived from HIV-2, FIV, equine infectious anemia virus, SIV, and Maedi-Visna virus (ovine lentivirus). Methods of using retroviral and lentiviral viral vectors and packaging cells for transducing mammalian host cells with viral particles containing transgenes are known in the art and have been previous described, for example, in: U.S. Pat. No. 8,119,772; Walchli et al., *PLoS One* 6:327930, 2011; Zhao et al., *J. Immunol.* 174:4415, 2005; Engels et al., *Hum. Gene Ther.* 14:1155, 2003; Frecha et al., *Mol. Ther.* 18:1748, 2010; and Verhoeyen et al., *Methods Mol. Biol.* 506:97, 2009. Retroviral and lentiviral vector constructs and expression systems are also commercially available. Other viral vectors also can be used for polynucleotide delivery including DNA viral vectors, including, for example adenovirus-based vectors and adeno-associated virus (AAV)-based vectors; vectors derived from herpes simplex viruses (HSVs), including amplicon vectors, replication-defective HSV and attenuated HSV (Krisky et al., *Gene Ther.* 5:1517, 1998).

Other vectors that can be used with the compositions and methods of this disclosure include those derived from baculoviruses and α-viruses. (Jolly, D J. 1999. Emerging Viral Vectors. pp 209-40 in Friedmann T. ed. The Development of Human Gene Therapy. New York: Cold Spring Harbor Lab), or plasmid vectors (such as sleeping beauty or other transposon vectors).

When a viral vector genome comprises a plurality of polynucleotides to be expressed in a host cell as separate transcripts, the viral vector may also comprise additional sequences between the two (or more) transcripts allowing for bicistronic or multicistronic expression. Examples of such sequences used in viral vectors include internal ribosome entry sites (IRES), furin cleavage sites, viral 2A peptide, or any combination thereof.

As used herein, the term "host" refers to a cell or microorganism targeted for genetic modification with a heterologous nucleic acid molecule to produce a polypeptide of interest (e.g., an antibody of the present disclosure).

A host cell may include any individual cell or cell culture which may receive a vector or the incorporation of nucleic acids or express proteins. The term also encompasses progeny of the host cell, whether genetically or phenotypically the same or different. Suitable host cells may depend on the vector and may include mammalian cells, animal cells, human cells, simian cells, insect cells, yeast cells, and bacterial cells. These cells may be induced to incorporate the vector or other material by use of a viral vector, transformation via calcium phosphate precipitation, DEAE-dextran, electroporation, microinjection, or other methods. See, for example, Sambrook et al., *Molecular Cloning: A Laboratory Manual* 2d ed. (Cold Spring Harbor Laboratory, 1989).

As used herein, "flagellar-capping protein", also referred to as "FliD", and "hook-associated protein 2 (HAP2)", is an approximately 70 kDa protein with high sequence conservation across the *C. jejuni* and *C. coli* species (Chintoan-Uta et al., *Vaccine,* 34:1739-1743 (2016)) (e.g., FIG. 12; SEQ ID NOs:43-95). Without wishing to be bound by theory, it is believed that *Campylobacter* FliD oligomers form a cap protein complex located at the tip of the flagellum, which controls the distal growth of the filament by regulating the assembly of the flagellin molecules. Due to its functional role in filament elongation, FliD-deficient mutants exhibit defects in bacterial motility (Song et al., *J. Mol. Biol.,* 429:847-857 (2017)). FliD has been proposed to be involved in cell adherence (Freitag et al., *Cell. Microbiol.,* (2017)) and immunogenicity in chickens during natural infection.

"Antigen" or "Ag", as used herein, refers to an immunogenic molecule that provokes an immune response. This immune response may involve antibody production, activation of specific immunologically-competent cells, activation of complement, antibody dependent cytotoxicicity, or any combination thereof. An antigen (immunogenic molecule) may be, for example, a peptide, glycopeptide, polypeptide, glycopolypeptide, polynucleotide, polysaccharide, lipid, or the like. It is readily apparent that an antigen can be synthesized, produced recombinantly, or derived from a biological sample. Exemplary biological samples that can contain one or more antigens include tissue samples, stool samples, cells, biological fluids, or combinations thereof. Antigens can be produced by cells that have been modified or genetically engineered to express an antigen. Antigens can also be present in a *Campylobacter*; e.g., a FliD protein or portion thereof.

The term "epitope" or "antigenic epitope" includes any molecule, structure, amino acid sequence, or protein determinant that is recognized and specifically bound by a cognate binding molecule, such as an immunoglobulin, or other binding molecule, domain, or protein. Epitopic determinants generally contain chemically active surface groupings of molecules, such as amino acids or sugar side chains, and can have specific three dimensional structural characteristics, as well as specific charge characteristics. Where an antigen is or comprises a peptide or protein, the epitope can be comprised of consecutive amino acids (e.g., a linear epitope), or can be comprised of amino acids from different parts or regions of the protein that are brought into proximity by protein folding (e.g., a discontinuous or conformational epitope), or non-contiguous amino acids that are in close proximity irrespective of protein folding.

Antibodies, Antigen-Binding Fragments, and Compositions

In one aspect, the present disclosure provides an isolated antibody, or an antigen-binding fragment thereof, that is specific for a *Campylobacter flagellum* capping protein (FliD) epitope. In certain embodiments, the epitope is a conformational epitope. In other embodiments, the epitope is a linear epitope.

An antibody or antigen-binding fragment of the present disclosure is "specific for" a FliD epitope or antigen, meaning that it associates with or unites with the epitope or antigen comprising the epitope, while not significantly associating or uniting with any other molecules or components in a sample. In certain embodiments, an antibody or antigen-binding fragment of the present disclosure associates with or unites (e.g., binds) to FliD, while not significantly associating with other molecules or components (e.g., other antigens or potential antigens, including other *Campylobacter* proteins) present in a sample. In certain embodiments, an antibody or antigen-binding fragment of the present disclosure that is specific for FliD is capable of binding to the FliD epitope with an EC50 of less than about 0.1 μg/mL, or less than about 0.05 μg/mL, or less than about 0.03 μg/mL, as measured by ELISA. In certain embodiments, the antibody or antigen-binding fragment is capable of binding to the FliD epitope with an EC50 of about 0.03 μg/mL, or about 0.025 μg/mL, or about 0.020 μg/mL.

In certain embodiments, an antibody or antigen-binding fragment of the present disclosure is capable of binding to the FliD epitope with an EC50 of less than about 0.1 μg/mL (i.e., less than about 0.1, 0.09, 0.08, 0.07, 0.06, 0.05, 0.04, 0.03, 0.025, or 0.02 μg/mL, or less), as measured by ELISA (e.g., with a readout of OD 450 nm). In certain embodiments, an antibody or antigen-binding fragment of the present disclosure is capable of binding to the FliD epitope with an EC50 of less than about 0.05 μg/mL, or less than about 0.03 μg/mL, as measured by ELISA (e.g., with a readout of OD 450 nm).

An exemplary assay for measuring EC50 of an antibody or antigen-binding fragment for FliD includes incubating the antibody or antigen-binding fragment for about 1 h at RT with FliD-pre-coated 96-well ELISA plates, and then performing detection using a biotinylated anti-Ig SC antibody followed by incubation with Streptavidin-AP.

As used herein, "specifically binds" refers to an association or union of an antibody or antigen-binding fragment to an antigen with an affinity or $K_a$ (i.e., an equilibrium association constant of a particular binding interaction with units of 1/M) equal to or greater than $10^5$ $M^{-1}$ (which equals the ratio of the on-rate [$K_{on}$] to the off rate [$K_{off}$] for this association reaction), while not significantly associating or uniting with any other molecules or components in a sample. Alternatively, affinity may be defined as an equilibrium dissociation constant ($K_d$) of a particular binding interaction with units of M (e.g., $10^{-5}$ M to $10^{-13}$ M). Antibodies may be classified as "high-affinity" antibodies or as "low-affinity" antibodies. "High-affinity" antibodies refer to those antibodies having a $K_a$ of at least $10^7 M^{-1}$, at least $10^8$ $M^{-1}$, at least $10^9$ $M^{-1}$, at least $10^{10}$ $M^{-1}$, at least $10^{11}$ $M^{-1}$, at least $10^{12} M^{-1}$, or at least $10^{13}$ $M^{-1}$. "Low-affinity" antibodies refer to those antibodies having a $K_a$ of up to $10^7 M^{-1}$, up to $10^6$ $M^{-1}$, up to $10^5 M^{-1}$. Alternatively, affinity may be defined as an equilibrium dissociation constant ($K_d$) of a particular binding interaction with units of M (e.g., $10^{-5}$ M to $10^{-13}$M).

A variety of assays are known for identifying antibodies of the present disclosure that bind a particular target, as well as determining binding domain or binding protein affinities, such as Western blot, ELISA, analytical ultracentrifugation, spectroscopy, and surface plasmon resonance (Biacore®) analysis (see, e.g., Scatchard et al., *Ann. N.Y. Acad. Sci.* 51:660, 1949; Wilson, *Science* 295:2103, 2002; Wolff et al., *Cancer Res.* 53:2560, 1993; and U.S. Pat. Nos. 5,283,173, 5,468,614, or the equivalent). Assays for assessing affinity or apparent affinity or relative affinity are also known. In certain examples, apparent affinity for an immunoglobulin binding protein is measured by assessing binding to various concentrations of tetramers, for example, by flow cytometry using labeled tetramers. In some examples, apparent $K_d$ of an immunoglobulin binding protein is measured using 2-fold dilutions of labeled tetramers at a range of concentrations, followed by determination of binding curves by non-linear regression, apparent $K_d$ being determined as the concentration of ligand that yielded half-maximal binding.

In certain embodiments, an antibody or antigen-binding fragment of the present disclosure is capable of reducing motility of the *Campylobacter* in an in vitro cell motility assay. An exemplary motility assay is illustrated schematically in FIG. 2; see also Riazi et al., *PLoS One* 8(12): e83928 (2013).

In certain embodiments, an antibody of the present disclosure is capable of neutralizing infection by one or more *Campylobacter* sp. As used herein, a "neutralizing antibody" is one that can neutralize, i.e., prevent, inhibit, reduce, impede, or interfere with, the ability of a pathogen to initiate and/or perpetuate an infection in a host. The terms "neutralizing antibody" and "an antibody that neutralizes" or "antibodies that neutralize" are used interchangeably herein.

In any of the presently disclosed embodiments, the *Campylobacter* comprises *Campylobacter jejuni, Campylobacter coli*, or both. In certain embodiments, the *Campylobacter* comprises *C. jejuni* 81-176, *C. coli* 10092/ATB, or both.

Terms understood by those in the art of antibody technology are each given the meaning acquired in the art, unless expressly defined differently herein. For example, the term "antibody" refers to an intact antibody comprising at least two heavy (H) chains and two light (L) chains inter-connected by disulfide bonds, as well as any antigen-binding portion or fragment of an intact antibody that has or retains the ability to bind to the antigen target molecule recognized by the intact antibody, such as an scFv, Fab, or Fab'2 fragment. Thus, the term "antibody" herein is used in the broadest sense and includes polyclonal and monoclonal antibodies, including intact antibodies and functional (antigen-binding) antibody fragments thereof, including fragment antigen binding (Fab) fragments, F(ab')2 fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific antibodies, diabodies, triabodies, tetrabodies, tandem di-scFv, and tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The terms "$V_L$" or "VL" and "$V_H$" or "VH" refer to the variable binding region from an antibody light and heavy chain, respectively. In certain embodiments, a VL is a kappa (κ) class (also "VK" herein). In certain embodiments, a VL is a lambda (λ) class. The variable binding regions are made up of discrete, well-defined sub-regions known as "complementarity determining regions" (CDRs) and "framework regions" (FRs). The terms "complementarity determining region," and "CDR," are synonymous with "hypervariable region" or "HVR," and refer to sequences of amino acids within antibody variable regions, which, in general, confer the antigen specificity and/or binding affinity of the antibody, and are separated from one another by a framework region. There are three CDRs in each variable region (HCDR1, HCDR2, HCDR3; LCDR1, LCDR2, LCDR3; also referred to as CDRHs and CDRLs, respectively). In certain embodiments, an antibody VH comprises four FRs and three CDRs as follows: FR1-HCDR1-FR2-HCDR2-FR3-HCDR3-FR4; and an antibody VL comprises four FRs and three CDRs as follows: FR1-LCDR1-FR2-LCDR2-FR3-LCDR3-FR4. In general, the VH and the VL together form the antigen-binding site through their respective CDRs.

As used herein, a "variant" of a CDR refers to a functional variant of a CDR sequence having up to 1-3 amino acid substitutions (e.g., conservative or non-conservative substitutions), deletions, or combinations thereof.

Numbering of CDR and framework regions may be according to any known method or scheme, such as the Kabat, Chothia, EU, IMGT, and AHo numbering schemes (see, e.g., Kabat et al., "Sequences of Proteins of Immunological Interest, US Dept. Health and Human Services, Public Health Service National Institutes of Health, 1991, $5^{th}$ ed.; Chothia and Lesk, *J. Mol. Biol.* 196:901-917 (1987)); Lefranc et al., *Dev. Comp. Immunol.* 27:55, 2003; Honegger and Plückthun, *J. Mol. Mo.* 309:657-670 (2001)). Equivalent residue positions can be annotated and for different molecules to be compared using Antigen receptor Numbering And Receptor Classification (ANARCI) software tool (2016, Bioinformatics 15:298-300).

In certain embodiments, an antibody or antigen-binding fragment of the present disclosure comprises HCDR1, HCDR2, HCDR3, LCDR1, LCDR2, and LCDR3 amino acid sequences according to: (i) SEQ ID NOs:9-14, respectively; or (ii) SEQ ID NOs:25-30, respectively.

The term "CL" refers to an "immunoglobulin light chain constant region" or a "light chain constant region," i.e., a constant region from an antibody light chain. The term "CH" refers to an "immunoglobulin heavy chain constant region" or a "heavy chain constant region," which is further divisible, depending on the antibody isotype into CH1, CH2, and CH3 (IgA, IgD, IgG), or CH1, CH2, CH3, and CH4 domains (IgE, IgM).

A "Fab" (fragment antigen binding) is the part of an antibody that binds to antigens and includes the variable region and CH1 of the heavy chain linked to the light chain via an inter-chain disulfide bond. Each Fab fragment is monovalent with respect to antigen binding, i.e., it has a single antigen-binding site. Pepsin treatment of an antibody yields a single large F(ab')2 fragment that roughly corresponds to two disulfide linked Fab fragments having divalent antigen-binding activity and is still capable of cross-linking antigen. Both the Fab and F(ab')2 are examples of "antigen-binding fragments." Fab' fragments differ from Fab fragments by having additional few residues at the carboxy terminus of the CH1 domain including one or more cysteines from the antibody hinge region. Fab'-SH is the designation herein for Fab' in which the cysteine residue(s) of the constant domains bear a free thiol group. F(ab')2 antibody fragments originally were produced as pairs of Fab' fragments that have hinge cysteines between them. Other chemical couplings of antibody fragments are also known.

"Fv" is the minimum antibody fragment that contains a complete antigen-recognition and antigen-binding site. This fragment consists of a dimer of one heavy- and one light-chain variable region domain in tight, non-covalent association. From the folding of these two domains emanate six hypervariable loops (three loops each from the H and L chain) that contribute the amino acid residues for antigen binding and confer antigen binding specificity to the antibody. However, even a single variable domain (or half of an Fv comprising only three CDRs specific for an antigen) has the ability to recognize and bind antigen, although typically at a lower affinity than the entire binding site.

"Single-chain Fv" also abbreviated as "sFv" or "scFv", are antibody fragments that comprise the $V_H$ and $V_L$ antibody domains connected into a single polypeptide chain. Preferably, the sFv polypeptide further comprises a polypeptide linker between the $V_H$ and $V_L$ domains that enables the sFv to form the desired structure for antigen binding. For a review of sFv, see Pluckthun in The Pharmacology of Monoclonal Antibodies, vol. 113, Rosenburg and Moore eds., Springer-Verlag, New York, pp. 269-315 (1994); Borrebaeck 1995, infra.

During antibody development, DNA in the germline variable (V), joining (J), and diversity (D) gene loci may be rearranged and insertions and/or deletions of nucleotides in the coding sequence may occur. Somatic mutations may be encoded by the resultant sequence, and can be identified by reference to a corresponding known germline sequence. In some contexts, somatic mutations that are not critical to a desired property of the antibody (e.g., specific binding to a *Campylobacter* sp.), or that confer an undesirable property upon the antibody (e.g., an increased risk of immunogenicity in a subject administered the antibody), or both, may be replaced by the corresponding germline-encoded amino acid, or by a different amino acid, so that a desirable property of the antibody is improved or maintained and the undesirable property of the antibody is reduced or abrogated. Thus, in some embodiments, the antibody or antigen-binding fragment of the present disclosure comprises at least one more germline-encoded amino acid in a variable region as compared to a parent antibody or antigen binding fragment, provided that the parent antibody or antigen binding fragment comprises one or more somatic mutations. Variable region amino acid sequences of exemplary anti-*Campylobacter* antibodies of the present disclosure are provided in Table 1 herein, wherein somatic mutations are shown by underlining.

Also provided herein are variant antibodies that comprise one or more amino acid alterations in a variable region (e.g., VH, VL, framework or CDR) as compared to a presently disclosed ("parent") antibody, wherein the variant antibody is capable of specifically binding to a *Campylobacter* FliD epitope with an affinity similar to or stronger than the parent antibody. For example, in some embodiments, an antibody or antigen-binding fragment of the present disclosure comprises a heavy chain variable domain (VH) having at least 70%, 75%, 80%, 85%, 90%, 91%, 92%, 93%, 94%, 95%, 96%, 97%, 98%, or at least 99% sequence identity to the amino acid sequence of SEQ ID NO:2 or 22, and a light chain variable domain (VL) having at least 70%, 75%, 80%, 85%, 90%, 91%, 92%, 93%, 94%, 95%, 96%, 97%, 98%, or at least 99% sequence identity to the amino acid sequence of SEQ ID NO:4 or 24, provided that the variant antibody or antigen-binding fragment specifically binds a *Campylobacter* FliD epitope with an affinity similar to or better than a parent antibody having a VH according to SEQ ID NO:2 or 22 and a VL according to SEQ ID NO:4 or 24, respectively.

In certain embodiments, the antibody or antigen-binding fragment can comprise: (i) VH having at least 85% (i.e., at least 85, 86, 87, 88, 89, 90, 91, 92, 93, 94, 95, 96, 97, 98, 99, or more) amino acid identity to SEQ ID NO:2, and a VL having at least 85% (i.e., at least 85, 86, 87, 88, 89, 90, 91, 92, 93, 94, 95, 96, 97, 98, 99, or more) amino acid identity to SEQ ID NO:4; or (ii) VH having at least 85% amino acid identity to SEQ ID NO:22, and a VL having at least 85% amino acid identity to SEQ ID NO:24.

In further embodiments, the antibody or antigen-binding fragment comprises: (i) a VH according to SEQ ID NO:2, and a VL according to SEQ ID NO:4; or (ii) a VH according to SEQ ID NO:22, and a VL according to SEQ ID NO:24.

In any of the presently disclosed embodiments, the antibody or antigen-binding fragment is multispecific; e.g., bispecific, trispecific, or the like.

In any of the presently disclosed embodiments, the antibody or antigen-binding fragment is an IgA, IgG, IgD, IgE, or IgM isotype.

In certain embodiments, the antibody or antigen-binding fragment is an IgA isotype. In humans, IgA antibodies are found in monomeric, dimeric, or tetrameric forms. IgA subclasses include IgA1 and IgA2. IgA1 has a longer hinge sequence (between the Fab arms and the Fc) than IgA2. See, e.g., Woof and Kerr, Immunology 113(2):175-177 (2004)).

Without wishing to be bound by theory, IgA dimers generally comprise two IgA monomers linked together by at least a joining chain ("J-chain") polypeptide formed in IgA-secreting cells. Soluble IgA dimers are generally capable of forming a complex with poly-Ig receptor ("pIgR") proteins found on the basolateral surface of epithelial cells. Following formation, the IgA dimer-pIgR complex is internalized into the epithelial cell and transported to the luminal surface for release into the lumen. Prior to secretion into the lumen, a portion of the pIgR is cleaved, while a portion known as the secretory component or "SC" remains bound to the IgA, forming secretory IgA (SIgA). Without wishing to be bound by theory, the SC is believed to improve stability of the IgA dimer in the vesicular and luminal environments, possibly by protecting proteolytically sensitive sites in the IgA dimer.

In certain embodiments, an antibody or antigen-binding fragment of the present disclosure is an IgA1 isotype or an IgA2 isotype.

In certain embodiments, an antibody or antigen-binding fragment of the present disclosure comprises an IgA dimer molecule.

In certain embodiments, an antibody or antigen-binding fragment of the present disclosure comprises a secretory IgA molecule.

The "Fc" fragment or Fc polypeptide comprises the carboxy-terminal portions (i.e., the CH2 and CH3 domains of IgG) of both antibody H chains held together by disulfides. The effector functions of antibodies are determined by sequences in the Fc region. The Fc domain is the portion of the antibody recognized by cell receptors, such as the FcRs, and to which the complement-activating protein, Clq, binds. As discussed herein, modifications (e.g., amino acid substitutions) may be made to an Fc domain in order to modify (e.g., improve, reduce, or ablate) one or more functionality of an Fc-containing polypeptide (e.g., an antibody of the present disclosure). In any of the presently disclosed embodiments, the antibody or antigen-binding fragment comprises a Fc polypeptide or a fragment thereof, including a CH2 (or a fragment thereof, a CH3 (or a fragment thereof), or a CH2 and a CH3, wherein the CH2, the CH3, or both can be of any isotype and may contain amino acid substitutions or other modifications as compared to a corresponding wild-type CH2 or CH3, respectively. In certain embodiments, a Fc polypeptide of the present disclosure comprises two CH2-CH3 polypeptides that associate to form a dimer.

In certain embodiments, the antibody or antigen-binding fragment of comprises a heavy chain constant region having at least 90% identity (i.e., at least 90%, 91%, 92%, 93%, 94%, 95%, 96%, 97%, 98%, or at least 99% sequence identity to any one of SEQ ID NOs:40-42.

In any of the presently disclosed embodiments, the antibody or antigen-binding fragment is monoclonal. The term "monoclonal antibody" (mAb) as used herein refers to an antibody obtained from a population of substantially homogeneous antibodies, i.e., individual antibodies comprising the population are identical except for possible naturally occurring mutations that may be present, in some cases in minor amounts. Monoclonal antibodies are highly specific, being directed against a single antigenic site. Furthermore, in contrast to polyclonal antibody preparations that include different antibodies directed against different epitopes, each monoclonal antibody is directed against a single epitope of the antigen. In addition to their specificity, the monoclonal antibodies are advantageous in that they may be synthesized uncontaminated by other antibodies. The term "monoclonal" is not to be construed as requiring production of the antibody by any particular method. For example, monoclonal antibodies useful in the present invention may be prepared by the hybridoma methodology first described by Kohler et al., *Nature* 256:495 (1975), or may be made using recombinant DNA methods in bacterial, eukaryotic animal, or plant cells (see, e.g., U.S. Pat. No. 4,816,567). Monoclonal antibodies may also be isolated from phage antibody libraries using the techniques described in Clackson et al., *Nature,* 352:624-628 (1991) and Marks et al., *J. Mol. Biol.,* 222:581-597 (1991), for example. Monoclonal antibodies may also be obtained using methods disclosed in PCT Publication No. WO 2004/076677A2.

Antibodies and antigen-binding fragments of the present disclosure include "chimeric antibodies" in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (see, U.S. Pat. Nos. 4,816,567; 5,530,101 and 7,498,415; and Morrison et al., Proc. Natl. Acad. Sci. USA, 81:6851-6855 (1984)). For example, chimeric antibodies may comprise human and non-human residues. Furthermore, chimeric antibodies may comprise residues that are not found in the recipient antibody or in the donor antibody. These modifications are made to further refine antibody performance. For further details, see Jones et al., *Nature* 321:522-525 (1986); Riechmann et al., *Nature* 332:323-329 (1988); and Presta, *Curr. Op. Struct. Biol.* 2:593-596 (1992). Chimeric antibodies also include primatized and humanized antibodies.

A "humanized antibody" is generally considered to be a human antibody that has one or more amino acid residues introduced into it from a source that is non-human. These non-human amino acid residues are typically taken from a variable domain. Humanization may be performed following the method of Winter and co-workers (Jones et al., *Nature,* 321:522-525 (1986); Reichmann et al., *Nature,* 332:323-327 (1988); Verhoeyen et al., *Science,* 239:1534-1536 (1988)), by substituting non-human variable sequences for the corresponding sequences of a human antibody. Accordingly, such "humanized" antibodies are chimeric antibodies (U.S. Pat. Nos. 4,816,567; 5,530,101 and 7,498,415) wherein substantially less than an intact human variable domain has been substituted by the corresponding sequence from a non-human species. In some instances, a "humanized" antibody is one which is produced by a non-human cell or animal and comprises human sequences, e.g., H domains.

A "human antibody" is an antibody containing only sequences that are present in an antibody that is produced by a human. However, as used herein, human antibodies may comprise residues or modifications not found in a naturally occurring human antibody (e.g., an antibody that is isolated from a human), including those modifications and variant sequences described herein. These are typically made to further refine or enhance antibody performance. In some instances, human antibodies are produced by transgenic animals. For example, see U.S. Pat. Nos. 5,770,429; 6,596,541 and 7,049,426.

In certain embodiments, an antibody or antigen-binding fragment of the present disclosure is chimeric, humanized, or human.

Also provided herein are compositions that comprise any antibody or antigen-binding fragment as disclosed herein, and a pharmaceutically acceptable carrier, excipient, or diluent. Pharmaceutically acceptable components for use in such compositions are discussed further herein.

In another aspect, the present disclosure provides kits, wherein a kit, comprises: (i) a first antibody or an antigen-binding fragment thereof, which is specific for a *Campylobacter flagellum* capping protein (FliD) linear epitope; and (ii) a second antibody or an antigen-binding fragment thereof, which is which is specific for a *Campylobacter flagellum* capping protein (FliD) conformational epitope.

In certain embodiments, (i) the first antibody or antigen-binding fragment comprises HCDR1, HCDR2, HCDR3, LCDR1, LCDR2, and LCDR3 sequences according to SEQ ID NOs:9-14, respectively; and (ii) the second antibody or antigen-binding fragment comprises HCDR1, HCDR2, HCDR3, LCDR1, LCDR2, and LCDR3 sequences according to SEQ ID NOs:25-30, respectively.

In certain embodiments, (i) the first antibody or antigen-binding fragment comprises a VH having at least 85% amino acid identity to SEQ ID NO:2, and a VL having at least 85% amino acid identity to SEQ ID NO:4; and (ii) the second antibody or antigen-binding fragment comprises a VH having at least 85% amino acid identity to SEQ ID NO:22, and a VL having at least 85% amino acid identity to SEQ ID NO:24. In further embodiments: (i) the first antibody or antigen-binding fragment comprises a VH according to SEQ ID NO:2, and a VL according to SEQ ID NO:4; and (ii) the second antibody or antigen-binding fragment comprises a VH according to SEQ ID NO:22, and a VL according to SEQ ID NO:24.

In certain embodiments, the first antibody or antigen-binding fragment and the second antibody or antigen-binding fragment of a kit are each a same isotype. In particular embodiments, the first antibody or antigen-binding fragment and the second antibody or antigen-binding fragment are each a secreted IgA.

In certain embodiments, a kit further comprises directions or instructions on using the first and second antibodies or antigen-binding fragments; e.g., to treat or diagnose a *Campylobacter* infection in a subject.

Polynucleotides, Vectors, and Host Cells

In another aspect, the present disclosure provides isolated polynucleotides that encode any of the presently disclosed antibodies or an antigen-binding fragment thereof. In certain embodiments, the polynucleotide is codon-optimized for expression in a host cell. Once a coding sequence is known or identified, codon optimization can be performed using known techniques and tools, e.g., using the GenScript® OptimiumGene™ tool; see also Scholten et al., *Clin. Immunol.* 119:135, 2006). Codon-optimized sequences include sequences that are partially codon-optimized (i.e., one or more codon is optimized for expression in the host cell) and those that are fully codon-optimized.

It will also be appreciated that polynucleotides encoding antibodies and antigen-binding fragments of the present disclosure may possess different nucleotide sequences while still encoding a same antibody or antigen-binding fragment due to, for example, the degeneracy of the genetic code, splicing, and the like.

In certain embodiments, an isolated polynucleotide encoding a FliD-specific antibody or antigen-binding fragment comprises: (i) a VH-encoding polynucleotide having at least 75% identity (i.e., at least 75%, 80%, 85%, 90%, 91%, 92%, 93%, 94%, 95%, 96%, 97%, 98%, or at least 99% sequence identity) to the nucleotide sequence set forth in any one of SEQ ID NOs:1, 5, 7, 8, 21, 37, or 38; (ii) a VL-encoding polynucleotide having at least 75% identity to the nucleotide sequence set forth in SEQ ID NO:3, 6, 23, or 39; and/or (iii) HCDR1-, HCDR2-, HCDR3-, LCDR1-, LCDR2-, and LCDR3-encoding sequences having at least 90% identity to the nucleotide sequences set forth in SEQ ID NOs:15-20, respectively, or in SEQ ID NOs:31-36, respectively.

Vectors are also provided, wherein the vectors comprise or contain a polynucleotide as disclosed herein (i.e., a polynucleotide that encodes a FliD-specific antibody or antigen-binding fragment). A vector can comprise any one or more of the vectors disclosed herein.

In a further aspect, the present disclosure also provides a host cell expressing an antibody or antigen-binding fragment according to the present disclosure; or comprising or containing a vector or polynucleotide according the present disclosure.

Examples of such cells include but are not limited to, eukaryotic cells, e.g., yeast cells, animal cells, insect cells, plant cells; and prokaryotic cells, including *E. coli*. In some embodiments, the cells are mammalian cells. In certain such embodiments, the cells are a mammalian cell line such as CHO cells (e.g., DHFR-CHO cells (Urlaub et al., *PNAS* 77:4216 (1980)), human embryonic kidney cells (e.g., HEK293T cells), PER.C6 cells, Y0 cells, Sp2/0 cells. NS0 cells, human liver cells, e.g. Hepa RG cells, myeloma cells or hybridoma cells. Other examples of mammalian host cell lines include mouse sertoli cells (e.g., TM4 cells); monkey kidney CV1 line transformed by SV40 (COS-7); baby hamster kidney cells (BHK); African green monkey kidney cells (VERO-76); monkey kidney cells (CV1); human cervical carcinoma cells (HELA); human lung cells (W138); human liver cells (Hep G2); canine kidney cells (MDCK; buffalo rat liver cells (BRL 3A); mouse mammary tumor (MMT 060562); TM cells; MRC 5 cells; and FS4 cells. Mammalian host cell lines suitable for antibody production also include those described in, for example, Yazaki and Wu, *Methods in Molecular Biology*, Vol. 248 (B. K. C. Lo, ed., Humana Press, Totowa, N.J.), pp. 255-268 (2003).

In certain embodiments, a host cell is a prokaryotic cell, such as an *E. coli*. The expression of peptides in prokaryotic cells such as *E. coli* is well established (see, e.g., Pluckthun, A. *Bio/Technology* 9:545-551 (1991). For example, antibodies may be produced in bacteria, in particular when glycosylation and Fc effector function are not needed. For expression of antibody fragments and polypeptides in bacteria, see, e.g., U.S. Pat. Nos. 5,648,237; 5,789,199; and 5,840,523.

In particular embodiments, the cell may be transfected with a vector according to the present description with an expression vector. The term "transfection" refers to the introduction of nucleic acid molecules, such as DNA or RNA (e.g. mRNA) molecules, into cells, such as into eukaryotic cells. In the context of the present description, the term "transfection" encompasses any method known to the skilled person for introducing nucleic acid molecules into cells, such as into eukaryotic cells, including into mammalian cells. Such methods encompass, for example, electroporation, lipofection, e.g., based on cationic lipids and/or liposomes, calcium phosphate precipitation, nanoparticle based transfection, virus based transfection, or transfection based on cationic polymers, such as DEAE-dextran or polyethylenimine, etc. In certain embodiments, the introduction is non-viral.

Moreover, host cells of the present disclosure may be transfected stably or transiently with a vector according to the present disclosure, e.g. for expressing an antibody, or an antigen-binding fragment thereof, according to the present disclosure. In such embodiments, the cells may be stably transfected with the vector as described herein. Alternatively, cells may be transiently transfected with a vector according to the present disclosure encoding an antibody or antigen-binding fragment as disclosed herein. In any of the presently disclosed embodiments, a polynucleotide may be heterologous to the host cell.

Accordingly, the present disclosure also provides recombinant host cells that heterologously express an antibody or antigen-binding fragment of the present disclosure. For example, the cell may be of a species that is different to the species from which the antibody was fully or partially obtained (e.g., CHO cells expressing a human antibody or an engineered human antibody). In some embodiments, the cell type of the host cell does not express the antibody or antigen-binding fragment in nature. Moreover, the host cell may impart a post-translational modification (PTM; e.g., glysocylation or fucosylation) on the antibody or antigen-binding fragment that is not present in a native state of the antibody or antigen-binding fragment (or in a native state of a parent antibody from which the antibody or antigen binding fragment was engineered or derived). Such a PTM may result in a functional difference (e.g., reduced immunogenicity). Accordingly, an antibody or antigen-binding fragment of the present disclosure that is produced by a host cell as disclosed herein may include one or more post-translational modification that is distinct from the antibody (or parent antibody) in its native state (e.g., a human antibody produced by a CHO cell can comprise a more post-translational modification that is distinct from the antibody when isolated from the human and/or produced by the native human B cell or plasma cell).

Insect cells useful expressing a binding protein of the present disclosure are known in the art and include, for example, *Spodoptera frugipera* Sf9 cells, *Trichoplusia ni* BTI-TN5B1-4 cells, and *Spodoptera frugipera* SfSWT01 "Mimic™" cells. See, e.g., Palmberger et al., *J. Biotechnol.* 153(3-4):160-166 (2011). Numerous baculoviral strains have been identified which may be used in conjunction with insect cells, particularly for transfection of *Spodoptera frugiperda* cells.

Eukaryotic microbes such as filamentous fungi or yeast are also suitable hosts for cloning or expressing protein-encoding vectors, and include fungi and yeast strains with "humanized" glycosylation pathways, resulting in the production of an antibody with a partially or fully human glycosylation pattern. See Gerngross, *Nat. Biotech.* 22:1409-1414 (2004); Li et al., *Nat. Biotech.* 24:210-215 (2006).

Plant cells can also be utilized as hosts for expressing a binding protein of the present disclosure. For example, PLANTIBODIES™ technology (described in, for example, U.S. Pat. Nos. 5,959,177; 6,040,498; 6,420,548; 7,125,978; and 6,417,429) employs transgenic plants to produce antibodies.

In certain embodiments, the host cell comprises a mammalian cell. In particular embodiments, the host cell is a CHO cell, a HEK293 cell, a PER.C6 cell, a Y0 cell, a Sp2/0 cell, a NS0 cell, a human liver cell, a myeloma cell, or a hybridoma cell. In a related aspect, the present disclosure provides methods for producing an antibody, antigen binding fragment, wherein the methods comprise culturing a host cell of the present disclosure under conditions and for a time sufficient to produce the antibody, or the antigen-binding fragment. Methods useful for isolating and purifying recombinantly produced antibodies, by way of example, may include obtaining supernatants from suitable host cell/vector systems that secrete the recombinant antibody into culture media and then concentrating the media using a commercially available filter. Following concentration, the concentrate may be applied to a single suitable purification matrix or to a series of suitable matrices, such as an affinity matrix or an ion exchange resin. One or more reverse phase HPLC steps may be employed to further purify a recombinant polypeptide. These purification methods may also be employed when isolating an immunogen from its natural environment. Methods for large scale production of one or more of the isolated/recombinant antibody described herein include batch cell culture, which is monitored and controlled to maintain appropriate culture conditions. Purification of soluble antibodies may be performed according to methods described herein and known in the art and that comport with laws and guidelines of domestic and foreign regulatory agencies.

Model of *Campylobacter* Infection

In yet another aspect, the present disclosure provides animal models for investigating *Campylobacter* infection and pathogenesis, as well as potential therapies and research reagents.

Briefly, existing animal models for studying *Campylobacter* pathogensis have numerous drawbacks, such as high cost and intensive care settings (e.g., gnotobiotic or germ-free animals), resistance to intestinal colonization by *Campylobacter* (e.g., laboratory mice), and unpredictable or deleterious effects of transgenic animals (e.g., SIGIRR or $IL10^{-}/^{-}$ mice). As described in the Examples, it was found that recently weaned animals (mice 21 days of age) that are no longer receiving maternal antibodies but do not possess a mature gastrointestinal immune system, and have a depleted intestinal flora, are surprisingly susceptible to infection by *Campylobacter*; thus, providing an improved model for studying *Campylobacter* pathogenesis and potential treatments thereof.

In certain embodiments, a non-human mammal is provided, wherein the non-human mammal comprises a weaned mammal that: (i) does not have a mature gastrointestinal immune system, and (ii) has a depleted intestinal flora, wherein the depletion is caused by an antibiotic agent. In certain embodiments, the non-human mammal further comprises a *Campylobacter* infection.

In certain embodiments, a non-human mammal of the present disclosure is or comprises a mouse (e.g., a C57BL/6 mouse), a rat, a pig, a rabbit, a dog, a cat, a guinea pig, a hamster, a non-human primate (e.g., cynomolgus), or the like. A non-human mammal that has been weaned is no longer receiving nutrients via milk from a mother mammal (i.e., the mother that gave birth to the non-human mammal, or a surrogate mother).

A mature gastrointestinal immune system according to the present disclosure is one that is capable of a functional endogenous immune activity (e.g., mucosal protection) against an antigen or pathogen. For example, a mature gastrointestinal immune system processes antigens from via microfold cells, dendritic cells, and macrophages for presentation to T cells in the gut-associated lymphoid tissue, and produces antigen-neutralizing IgA immunoglobulins by via B cells. See, e.g., Gutzeit et al., *Immunol. Rev.* 260(2): 76-85 (2014). In certain embodiments, a non-human mammal as disclosed herein does not endogenously produce IgA immunoglobulins, or produces a reduced amount of IgA immunoglobulins as compared to a reference healthy non-human mammal (i.e., of the same species) that is of an age and/or developmental stage at which the gastrointestinal immune system is considered to be mature and functional. A mature gastrointestinal immune system typically arises naturally with age in a healthy animal; e.g., healthy adult mice (56 days) have a mature gastrointestinal immune system.

It is understood that commensal bacteria (also referred collectively to as the "flora" or "microbiota") inhabit the intestine, conferring upon the host various defensive and metabolic capabilities (see Gutzeit et al., *Immunol. Rev.* 260(2):76-85 (2014)). The flora may prevent or inhibit colonization by pathogens, such as *Campylobacter*. A depleted intestinal flora is one that has a statistically significant reduction in one or more of the following: the overall number of bacteria; a growth rate of one or more of the bacteria; a metabolic function of the bacteria; a defensive function of the bacteria; and/or a diversity of bacteria, as compared to an intestinal flora of a healthy reference non-human mammal (i.e., of the same species and the same age, or of about the same age).

The age or developmental stage at which such a non-human mammal may be weaned by separation from the mother will be in accordance with the relevant animal care standards and the known biology of the organism. For example, mice may be weaned at about 15 days, about 16 days, about 17 days, about 18 days, about 19 days, about 20 days, about 21 days, about 22 days, about 23 days, about 24 days, about 25 days, about 26 days, about 27 days, about 28 days, about 29 days, or about 30 days after birth, or later. In certain embodiments, a weaned mouse is 18 days, 19 days, 20 days, 21 days, 22 days, 23 days, or 24 days old, or older. In certain embodiments, a non-human mammal is selected at an age or developmental stage that is less than the age, or is of an earlier developmental stage, respectively, than the age or developmental stage by which the non-human mammal will possess a mature gastrointestinal immune system. In other embodiments, a non-human mammal may be manipulated (e.g., genetically or otherwise) to delay or prevent development of a mature gastrointestinal immune system. It will be understood that a gastrointestinal immune system may mature over time; accordingly, in preferred embodiments, a non-human mammal is recently weaned. A recently weaned mammal is a mammal that has been weaned for from about 1 to about 10 days.

A non-human mammal according to the present disclosure has a depleted intestinal flora. Bacteria number, growth rate, metabolic function, defensive function, and diversity can be determined, and compared to a reference, using methods known to a person of ordinary skill in the art.

Intestinal flora can be depleted, for example, by administration of antibiotic agent. Exemplary antibiotic agents include vancomycin and other glycopeptide antibiotics, trimethoprim, ampicillin, metronidazole, and streptomycin, and analogs thereof, and combinations thereof. In preferred embodiments, the antibiotic agent is or comprises an agent to which *Campylobacter* have resistance; e.g., vancomycin or an analog thereof. Dosing and administration of an antibiotic agent to deplete an intestinal flora can be determined in accordance with known principles, accounting for, e.g., the age, size, and/or health of the non-human mammal, and the desired effect.

In further embodiments, the non-human mammal further comprises a *Camplyobacter* (e.g., a *Camplyobacter* of interest, such as a *C. jejuni*, a *C. coli*, or both). *Campylobacter* can be administered, for example, orally (e.g., via gavage), in an amount sufficient to form colonies in the intestine. For example, mice aged 12, 21, or 56 days are innoculated with $10^8$ to $10^9$ *Campylobacter*. In certain embodiments, the *Campylobacter* introduced to the non-human mammal comprises about $10^5$, about $5\times10^5$, about $10^6$, about $5\times10^6$, about $10^7$, about $5\times10^7$, about $10^8$, about $5\times10^8$, about $10^9$, about $5\times10^9$, about $10^{10}$, about $5\times10^5$, about $10^{11}$, about $5\times10^{11}$, or about $10^{12}$ *Campylobacter*, or more. Once administered, the number of *Campylobacter* may grow to a greater number in the non-human mammal host.

In a related aspect, methods are provided that comprise administering to or inoculating a weaned non-human mammal that (i) does not have a mature gastrointestinal immune system, and (ii) has a depleted intestinal flora with a *Camplyobacter* in an amount sufficient to cause an intestinal infection in the non-human mammal.

In another aspect, methods are provided that comprise administering to a non-human mammal that (i) is weaned, and (ii) does not have a mature gastrointestinal immune system, an agent that depletes an intestinal flora of the non-human mammal. In certain embodiments, the agent comprises an antibiotic agent as disclosed herein, such as, for example, vancomycin or an analog thereof. In certain embodiments, the method further comprises administering to the non-human mammal, or inoculating the non-human mammal with, a *Camplyobacter* in an amount sufficient to cause an intestinal infection comprising *Campylobacter* in the non-human mammal.

Methods and Uses

Also provided herein are methods of treating a subject using an antibody or antigen-binding fragment of the present disclosure, or a composition comprising the same, wherein the subject has, is believed to have, or is at risk for having an infection by a *Campylobacter* sp. "Treat," "treatment," or "ameliorate" refers to medical management of a disease, disorder, or condition of a subject (e.g., a human or non-human mammal, such as a primate, horse, cat, dog, goat, mouse, or rat). In general, an appropriate dose or treatment regimen comprising an antibody or composition of the present disclosure is administered in an amount sufficient to elicit a therapeutic or prophylactic benefit. Therapeutic or prophylactic/preventive benefit includes improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; prolonged survival; or any combination thereof.

A "therapeutically effective amount" or "effective amount" of an antibody, antigen-binding fragment, or composition of this disclosure refers to an amount of the composition or molecule sufficient to result in a therapeutic effect, including improved clinical outcome; lessening or alleviation of symptoms associated with a disease; decreased occurrence of symptoms; improved quality of life; longer disease-free status; diminishment of extent of disease, stabilization of disease state; delay of disease progression; remission; survival; or prolonged survival in a statistically significant manner. When referring to an individual active ingredient, administered alone, a therapeutically effective amount refers to the effects of that ingredient or cell expressing that ingredient alone. When referring to a combination, a therapeutically effective amount refers to the combined amounts of active ingredients or combined adjunctive active ingredient with a cell expressing an active ingredient that results in a therapeutic effect, whether administered serially, sequentially, or simultaneously. A combination may comprise, for example, two different antibodies that specifically bind a *Campylobacter* sp. epitope (e.g., a FliD epitope), which in certain embodiments, may be the same or different *Campylobacter* sp., and/or can comprise the same or different epitopes.

Accordingly, in certain embodiments, methods are provided for treating a *Campylobacter* infection in a subject, wherein the methods comprise administering to the subject an effective amount of an antibody, antigen-binding fragment, or composition as disclosed herein.

In certain embodiments, methods are provided for reducing (i.e., reducing or completely abrogating) intestinal inflammation in a subject having a *Campylobacter* infection, wherein the methods comprise administering to the subject an effective amount of an antibody, antigen-binding fragment, or composition as disclosed herein.

In certain embodiments, methods are provided for increasing intestinal shedding of a *Campylobacter* by a subject having a *Campylobacter* infection, wherein the methods comprise administering to the subject an effective amount of an antibody, antigen-binding fragment, or composition as disclosed herein.

In any of the presently disclosed embodiments, the antibody or antigen-binding fragment comprises a secretory IgA molecule.

Subjects that can be treated by the present disclosure are, in general, human and other primate subjects, such as monkeys and apes for veterinary medicine purposes. Other model organisms, such as mice and rats, may also be treated according to the present disclosure. In any of the aforementioned embodiments, the subject may be a human subject. The subjects can be male or female and can be any suitable age, including infant, juvenile, adolescent, adult, and geriatric subjects.

Typical routes of administering the presently disclosed compositions thus include, without limitation, oral, topical, transdermal, inhalation, parenteral, sublingual, buccal, rectal, vaginal, and intranasal. The term "parenteral", as used herein, includes subcutaneous injections, intravenous, intramuscular, intrasternal injection or infusion techniques. In certain embodiments, administering comprises administering by a route that is selected from oral, intravenous, parenteral, intragastric, intrapleural, intrapulmonary, intrarectal, intradermal, intraperitoneal, intratumoral, subcutaneous, topical, transdermal, intracisternal, intrathecal, intranasal, and intramuscular. In particular embodiments, a method comprises orally administering the antibody, antigen-binding fragment, or composition to the subject.

Pharmaceutical compositions according to certain embodiments of the present invention are formulated so as to allow the active ingredients contained therein to be bioavailable upon administration of the composition to a patient. Compositions that will be administered to a subject or patient may take the form of one or more dosage units, where for example, a tablet may be a single dosage unit, and a container of a herein described an antibody or antigen-binding in aerosol form may hold a plurality of dosage units. Actual methods of preparing such dosage forms are known, or will be apparent, to those skilled in this art; for example, see Remington: The Science and Practice of Pharmacy, 20th Edition (Philadelphia College of Pharmacy and Science, 2000). The composition to be administered will, in any event, contain an effective amount of an antibody or antigen-binding fragment thereof of the present disclosure, for treatment of a disease or condition of interest in accordance with teachings herein.

A composition may be in the form of a solid or liquid. In some embodiments, the carrier(s) are particulate, so that the compositions are, for example, in tablet or powder form. The carrier(s) may be liquid, with the compositions being, for example, an oral oil, injectable liquid or an aerosol, which is useful in, for example, inhalatory administration. When intended for oral administration, the pharmaceutical composition is preferably in either solid or liquid form, where semi solid, semi liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent. When the composition is in the form of a capsule, for example, a gelatin capsule, it may contain, in addition to materials of the above type, a liquid carrier such as polyethylene glycol or oil.

The composition may be in the form of a liquid, for example, an elixir, syrup, solution, emulsion or suspension. The liquid may be for oral administration or for delivery by injection, as two examples. When intended for oral administration, preferred compositions contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

Liquid pharmaceutical compositions, whether they be solutions, suspensions or other like form, may include one or more of the following adjuvants: sterile diluents such as water for injection, saline solution, preferably physiological saline, Ringer's solution, isotonic sodium chloride, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of an antibody or antigen-binding fragment as herein disclosed such that a suitable dosage will be obtained. Typically, this amount is at least 0.01% of the antibody or antigen-binding fragment in the composition. When intended for oral administration, this amount may be varied to be between 0.1 and about 70% of the weight of the composition. Certain oral pharmaceutical compositions contain between about 4% and about 75% of the antibody or antigen-binding fragment. In certain embodiments, pharmaceutical compositions and preparations according to the present invention are prepared so that a parenteral dosage unit contains between 0.01 to 10% by weight of antibody or antigen-binding fragment prior to dilution.

The composition may be intended for topical administration, in which case the carrier may suitably comprise a solution, emulsion, ointment or gel base. The base, for example, may comprise one or more of the following: petrolatum, lanolin, polyethylene glycols, bee wax, mineral oil, diluents such as water and alcohol, and emulsifiers and stabilizers. Thickening agents may be present in a composition for topical administration. If intended for transdermal administration, the composition may include a transdermal patch or iontophoresis device. The pharmaceutical composition may be intended for rectal administration, in the form, for example, of a suppository, which will melt in the rectum and release the drug. The composition for rectal administration may contain an oleaginous base as a suitable nonirritating excipient. Such bases include, without limitation, lanolin, cocoa butter and polyethylene glycol.

A composition may include various materials which modify the physical form of a solid or liquid dosage unit. For example, the composition may include materials that form a coating shell around the active ingredients. The materials that form the coating shell are typically inert, and may be selected from, for example, sugar, shellac, and other enteric coating agents. Alternatively, the active ingredients may be encased in a gelatin capsule. The composition in solid or liquid form may include an agent that binds to the antibody or antigen-binding fragment of the disclosure and thereby assists in the delivery of the compound. Suitable agents that may act in this capacity include monoclonal or polyclonal antibodies, one or more proteins or a liposome. The composition may consist essentially of dosage units that can be administered as an aerosol. The term aerosol is used to denote a variety of systems ranging from those of colloidal nature to systems consisting of pressurized packages. Delivery may be by a liquefied or compressed gas or by a suitable pump system that dispenses the active ingredients. Aerosols may be delivered in single phase, bi phasic, or tri phasic systems in order to deliver the active ingredient(s). Delivery of the aerosol includes the necessary container, activators, valves, subcontainers, and the like, which together may form a kit. One of ordinary skill in the art, without undue experimentation, may determine preferred aerosols.

The pharmaceutical compositions may be prepared by methodology well known in the pharmaceutical art. For example, a composition intended to be administered by injection can be prepared by combining a composition that comprises an antibody, antigen-binding fragment thereof, or antibody conjugate as described herein and optionally, one or more of salts, buffers and/or stabilizers, with sterile, distilled water so as to form a solution. A surfactant may be added to facilitate the formation of a homogeneous solution or suspension. Surfactants are compounds that non-covalently interact with the peptide composition so as to facilitate dissolution or homogeneous suspension of the antibody or antigen-binding fragment thereof in the aqueous delivery system.

In general, an appropriate dose and treatment regimen provide the composition(s) in an amount sufficient to provide therapeutic and/or prophylactic benefit (such as described herein, including an improved clinical outcome (e.g., a decrease in frequency, duration, or severity of diarrhea or associated dehydration, or inflammation, or longer disease-free and/or overall survival, or a lessening of symptom severity). For prophylactic use, a dose should be sufficient to prevent, delay the onset of, or diminish the severity of a disease associated with disease or disorder. Prophylactic benefit of the compositions administered according to the methods described herein can be determined by performing pre-clinical (including in vitro and in vivo animal studies) and clinical studies and analyzing data obtained therefrom by appropriate statistical, biological, and clinical methods and techniques, all of which can readily be practiced by a person skilled in the art.

Compositions are administered in an effective amount (e.g., to treat a *Campylobacter* infection), which will vary depending upon a variety of factors including the activity of the specific compound employed; the metabolic stability and length of action of the compound; the age, body weight, general health, sex, and diet of the subject; the mode and time of administration; the rate of excretion; the drug combination; the severity of the particular disorder or condition; and the subject undergoing therapy. In certain embodiments, following administration of therapies according to the formulations and methods of this disclosure, test subjects will exhibit about a 10% up to about a 99% reduction in one or more symptoms associated with the disease or disorder being treated as compared to placebo-treated or other suitable control subjects.

Generally, a therapeutically effective daily dose is (for a 70 kg mammal) from about 0.001 mg/kg (i.e., 0.07 mg) to about 100 mg/kg (i.e., 7.0 g); preferably a therapeutically effective dose is (for a 70 kg mammal) from about 0.01 mg/kg (i.e., 0.7 mg) to about 50 mg/kg (i.e., 3.5 g); more preferably a therapeutically effective dose is (for a 70 kg mammal) from about 1 mg/kg (i.e., 70 mg) to about 25 mg/kg (i.e., 1.75 g).

In certain embodiments, a method comprises administering the antibody, antigen-binding fragment, or composition to the subject at 2, 3, 4, 5, 6, 7, 8, 9, 10 times, or more.

In certain embodiments, a method comprises administering the antibody, antigen-binding fragment, or composition to the subject a plurality of times, wherein a second or successive administration is performed at about 6, about 7, about 8, about 9, about 10, about 11, about 12, about 24, about 48, about 74, about 96 hours, or more, following a first or prior administration, respectively.

In certain embodiments, a method comprises administering the antibody, antigen-binding fragment, or composition at least one time prior to the subject being infected by the *Campylobacter*.

In any of the presently disclosed methods, following the administering, a stool sample from the subject comprises an increased number of *Campylobacter* colony-forming units (CFUs) as compared to a stool sample from the subject prior to being administered an effective amount of the antibody, antigen-binding fragment, or composition.

Lipocalin-2 (LCN2) is a marker of intestinal inflammation and is linked to epithelial damage and neutrophil infiltration. In any of the presently disclosed methods, following the administering, a stool sample from the subject comprises a reduced amount of LCN2 as compared to a stool sample from the subject prior to being administered an effective amount of the antibody, antigen-binding fragment, or composition. LCN2 can be measured, for example, using anti-LCN2 antibody and performing an ELISA assay.

In any of the presently disclosed methods, following the administering, the subject comprises a reduced amount of polymorphonucleated (PMN) cell infiltrate in the subject's caecum as compared to the subject prior to being administered an effective amount of the antibody, antigen-binding fragment, or composition, wherein the PMN cells are $Gr1^+$ $CD11b^+$.

In any of the presently disclosed methods, following the administering, the subject has an improved caecum histology as compared to the subject prior to being administered an effective amount of the antibody, antigen-binding fragment, or composition. Standard histology analysis and scoring techniques may be employed to score a tissue (e.g., caecum) for damage, inflammation, or other indicia of a *Campylobacter* infection.

In any of the presently disclosed methods, following the administering, the antibody or antigen-binding fragment is present in the caecum and/or in feces of the subject for at least 4 hours or for at least 8 hours following the administration.

Compositions comprising an antibody or antigen-binding fragment of the present disclosure may also be administered simultaneously with, prior to, or after administration of one or more other therapeutic agents. Such combination therapy may include administration of a single pharmaceutical dosage formulation which contains a compound of the invention and one or more additional active agents, as well as administration of compositions comprising an antibody or antigen-binding fragment of the disclosure and each active agent in its own separate dosage formulation. For example, an antibody or antigen-binding fragment thereof as described herein and the other active agent can be administered to the patient together in a single oral dosage composition such as a tablet or capsule, or each agent administered in separate oral dosage formulations. Similarly, an antibody or antigen-binding fragment as described herein and the other active agent can be administered to the subject together in a single parenteral dosage composition such as in a saline solution or other physiologically acceptable solution, or each agent administered in separate parenteral dosage formulations. Where separate dosage formulations are used, the compositions comprising an antibody or antigen-binding fragment and one or more additional active agents can be administered at essentially the same time, i.e., concurrently, or at separately staggered times, i.e., sequentially and in any order; combination therapy is understood to include all these regimens.

In a related aspect, uses of the presently disclosed antibodies, antigen-binding fragments, and compositions are provided.

In certain embodiments, an antibody, antigen-binding fragment, or composition is provided for use in a method of: (a) treating a *Campylobacter* infection in a subject; (b) reducing intestinal inflammation in a subject having a *Campylobacter* infection; and/or (c) increasing intestinal shedding of a *Campylobacter* by a subject having a *Campylobacter* infection. It will be appreciated that treatment, reduction of inflammation, and increased intestinal shedding are as described herein.

In certain embodiments, an antibody, antigen-binding fragment, or composition is provided for use in a method of manufacturing or preparing a medicament for: (a) treating a *Campylobacter* infection in a subject; (b) reducing intestinal inflammation in a subject having a *Campylobacter* infection; and/or (c) increasing intestinal shedding of a *Campylobacter* by a subject having a *Campylobacter* infection. In certain embodiments, the medicament is formulated for oral administration.

EXAMPLES

Example 1

Experimental Methods

Immunoglobulins against select *Campylobacter* antigens associated with bacterial motility, adhesion, or mucosa invasion were isolated and tested for potency, selectivity, and breadth in vitro and ex-vivo. The corresponding recombinant SIgA (rSIgA) were expressed via co-transfection in mammalian cells and purified using affinity column chromatography.

rSIgA ability to curb *Campylobacter* motility was appraised in vitro by motility assay (Riazi et al., *PLoS One* 2013), whereas breadth and cross-reactivity of the rSIgA with the murine microbiota was evaluated by incubating the mAbs with the stools of infected or mock infected mice followed by FACS analysis of human IgA coated bacteria.

The prophylactic activity of orally administered rSIgA was tested in C57BL/6 mouse model for *Campylobacter* infection. In a first experiment, C57/BL6 mice were pre-treated 3 times via oral gavage with vancomycin 48 hours before mAbs administration. Next, after 1 hour the animals were infected with $10^9$ CFU of *Campylobacter jejuni* strain 81-176 (collection number ATCC BAA-2151) and then administered again twice with the antibodies at 6-hour intervals. In another experiment, C57BL/6 female mice (21 days old) were pre-treated with 10 mg of vancomycin (Sigma-Aldrich) in 200 μl PBS 48, 24 and 12 h prior to mAbs administration. Mice then received a single oral administration of 200 μg of FliD-reactive mAbs in 200 μl PBS 2 hours before being infected by oral gavage with $10^8$ CFU of *C. jejuni* 81-176 (collection number ATCC BAA-2151). This infection can also be done with other *Campylobacter* species, such as *Campylobacter coli* strain 10092/ATB (collection number NCTC 11437). Bacterial shedding in animal stools was monitored throughout the experiment. Lipocalin-2, a marker of intestinal inflammation, was measured by ELISA in stool samples and histological evaluation on the caecum was performed to investigate bacterial invasion and changes of the mucosal epithelium.

Example 2

Generation of a *Campylobacter*-Specific Monoclonal IgA Antibodies

*Campylobacter* flagellar capping protein (FliD) has not been assessed to-date as a potential target for therapeutic monoclonal antibodies. FliD was selected as antigen for mAb development. The frequencies of IgG+ and IgA+FliD-reactive memory B cells in 50 tonsillar samples of Swiss origin were evaluated using the Antigen-specific-Memory-B-cell-Repertoire-Analysis (AMBRA) (Pinna et al., *Eur. J. Immunol.,* 39:1260-1270 (2009)) (FIG. 13). IgG+ and IgA+ memory B cells from selected tonsils were then immortalized (Traggiai et al., *Nat. Med.,* 10:871-875 (2004)), and culture supernatants screened using a 384 well plate-based high-throughput platform to identify cell clones expressing FliD-reactive antibodies.

Memory B cell clones producing human monoclonal antibodies "CAA" and "CCG4" were isolated and selected based on their specificity and affinity for FliD antigen. CAA1 was isolated as an IgA1 encoded by $V_H$3-48/D2-15/$J_H$3 with a 21-amino acid HCDR3 and $V_K$1-39/$J_K$5. CCG4 was isolated as an IgG3 encoded by $V_H$3-9/D1-7/$J_H$1 bearing a shorter (11 amino acids) HCDR3 and $V_L$3-27/$J_L$3. Nucleic acid and amino acid sequences of variable regions from exemplary mAbs are provided in Table 1.

Humans present two IgA isotype subclasses that differ mainly in the length and glycosylation of the hinge region. IgA1 possesses a hinge that is 13 amino acids longer than that of IgA2 and contains up to five O-linked glycans at serine and threonine residues. The longer hinge of IgA1 is believed to confer greater flexibility and a longer Fab reach, but may also contribute to sensitivity of IgA1 to IgA1 proteases. IgA2 has a shorter hinge region that lacks proline-serine and/or proline-threonine peptide bonds, and is resistant to IgA1 proteases (Plaut, *Annu. Rev. Microbiol.,* 37:603-622 (1983)). In addition, the IgA2 isotype can undergo reverse transcytosis by contacting Dectin-I receptor on the surface of PPs M cells (Rochereau et al., *PLoS Biol.,* 11:e1001658 (2013)). IgG, IgM, and IgA1 isotypes are not believed to have this ability. Both the Cal region and the glycosylation pattern of IgA2 are thought to be important for interaction with Dectin-I receptor, which may boost adaptive immunity against pathogens (Rochereau et al., *Eur. J. Immunol.,* 45:773-779 (2015)).

The IgA2 scaffold was initially selected over IgA1 for further studies, and both CAA1 and CCG4 were produced as rSIgA2 before further in vitro characterization. For a control antibody non-reactive with the antigen, HGN194 mAb (Corti et al., *PLoS One,* 5:e8805 (2010)), which targets an HIV glycoprotein, was also expressed as rSIgA2. Antibodies were expressed as rSIgA2 via plasmid co-transfection in mammalian cells and purified using CaptureSelect IgA affinity columns.

Figure 1:
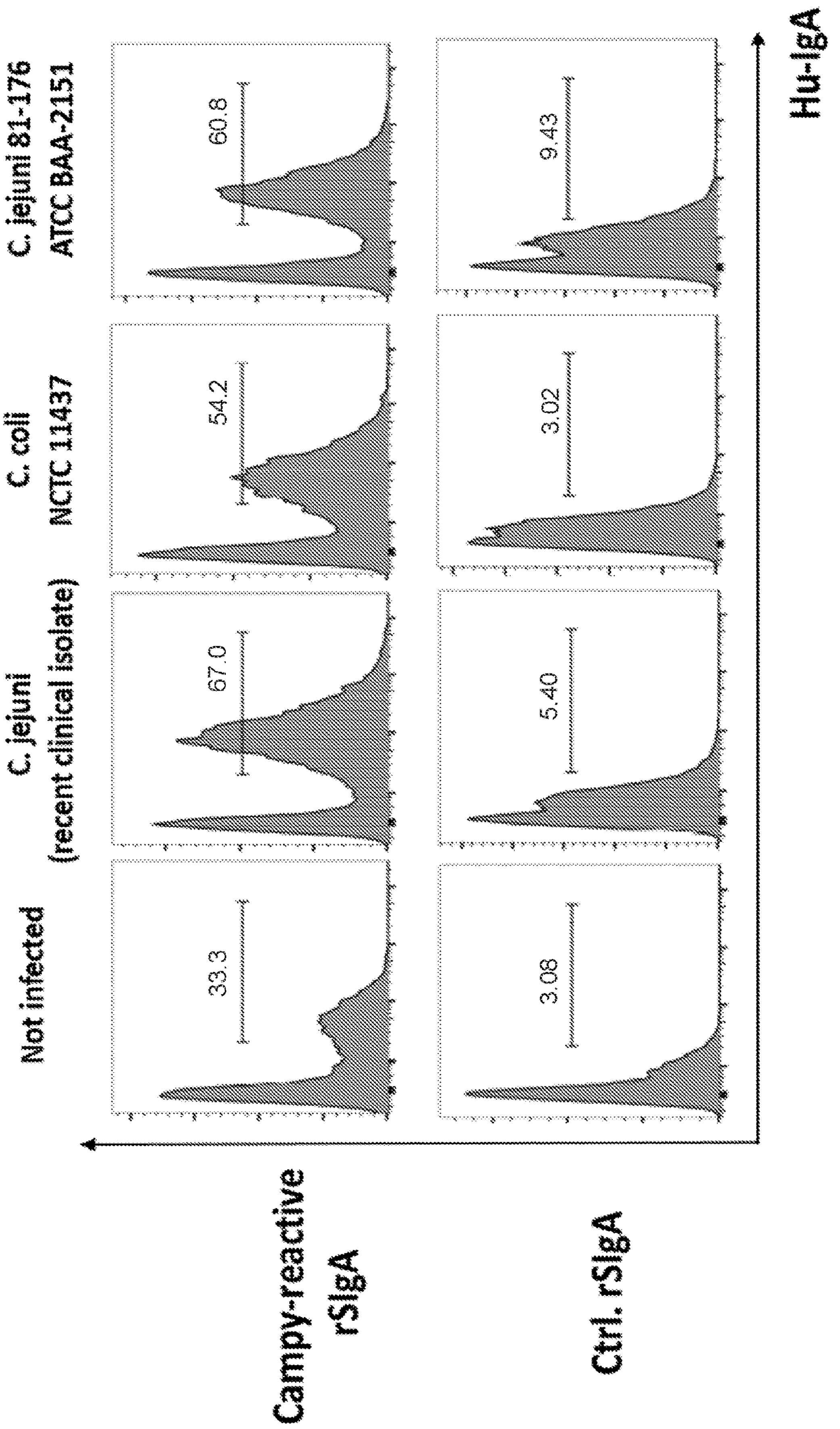
FIG. 1 shows cross-reactivity with murine microbiota and breadth of *Campylobacter* (“Campy”)-reactive rSIgA of the present disclosure.

Structural and functional characterization of purified rSIgA was performed using ELISA and UPLC analysis. *Campylobacter*-reactive rSIgA was able to recognize and bind the most common *Campylobacter* species associated with severe infections, including recent clinical isolates (FIG. 1), displaying limited cross-reactivity with the murine microbiota, which might be due to modest level of homology with similar antigens in the flagella of commensal species or to non-Fab mediated interactions.

Table 1 provides sequences of exemplary anti-FliD mAbs according to the present disclosure, as well as sequences of exemplary FliD proteins. Antibody CDR sequences (amino acid and nucleotide) are shown in bold. Antibody residues that arose from somatic mutation are underlined.

TABLE 1

| Sequences | | |
|---|---|---|
| Sequence Description | SEQ ID NO. | Sequence |
| CAA1<br>(VH, codon optimized<br>for IgA2m2) | 1 | gaagcacagctggtggagagcggcggcggcctgatcc<br>agccaggcggctctctgagactgagctgtgaggcctctg<br>gcttcagcctgagctcccacgagatgaactgggtgagac<br>aggcacctggcaagggactggagtggctgagctacatct<br>ccacctctggcatcacaatctactatgcagactccgtgcg<br>gggccggttcaccatcagcagggatacagccaagaact<br>ccctgtacctgcagatgaattctctgagggccgaggacac<br>cgccctgtatcactgtgcccgcgatctgggcggctactgc<br>tctggcggcctgtgctatcctcgcggcgccctggacctgt<br>ggggacagggaaccacagtgaccgtgtctagcg |
| CAA1<br>(VH) | 2 | EAQLVESGGGLIQPGGSLRLSCEAS**G**<br>**FSLSSHE**MNWVRQAPGKGLEWLSY**I**<br>**STSGITI**YYADSVRGRFTISRDTAKNS<br>LYLQMNSLRAEDTALYHC**ARDLGG**<br>**YCSGGLCYPRGALDL**WGQGTTVTV<br>SS |
| CAA1<br>(VK, codon<br>optimized) | 3 | gacatcctgatgacacagtctcctagctccctgtctgcctct<br>gtgggcgatagggtgaccatcacatgccgcgcctcccag<br>acaatccggacctacgtgaactggtatcagcagaagccc<br>ggcgagacacctaggctgctgatctacgcagcaaccatc<br>ctgcagcggggcgtgccatccagattctccggctctggc<br>agcggcacagactttaccctgacaatcacctctctgcagc<br>ccgaggatttcggcacctactattgtcagcagaattataag<br>acattcctgacctttggccagggcacccggctggagatca<br>agc |
| CAA1<br>(VK) | 4 | DILMTQSPSSLSASVGDRVTITCRAS**Q**<br>**TIRTY**VNWYQQKPGETPRLLIY**AAT**I<br>LQRGVPSRFSGSGSGTDFTLTITSLQP<br>EDFGTYYC**QQNYKTFLT**FGQGTRLE<br>IK |
| CAA1<br>(VH, native) | 5 | GAGGCGCAGCTGGTGGAGTCTGGG<br>GGAGGCCTGATACAGCCTGGAGGG<br>TCCCTGAGACTCTCCTGTGAAGCCT<br>CT**GGCTTCTCCCTCAGTTCTCATG**<br>**AA**ATGAATTGGGTCCGCCAGGCTC<br>CAGGGAAGGGGCTGGAGTGGCTTT<br>CATAT**ATTAGTACTAGTGGTATTA**<br>**CAATA**TATTACGCGGACTCTGTGA<br>GGGGCCGATTCACCATCTCCAGAG<br>ACACCGCCAAGAACTCACTGTATCT<br>GCAAATGAACAGCCTGAGAGCCGA<br>GGACACGGCTCTTTATCACTGT**GCG**<br>**AGAGATCTTGGCGGTTATTGTAG**<br>**TGGTGGTTTGTGCTACCCGAGGG**<br>**GTGCCTTGGATCTC**TGGGGCCAAG<br>GGACAACGGTCACCGTCTCGTCAG |
| CAA1<br>(VK, native) | 6 | GACATCCTGATGACCCAGTCTCCAT<br>CCTCCCTGTCTGCATCTGTCGGAGA<br>CAGAGTCACCATCACTTGCCGGGC<br>AAGT**CAGACCATTCGCACCTAT**GT<br>AAATTGGTATCAGCAGAAGCCAGG<br>GGAAACCCCAAGACTCCTTATCTAT<br>**GCTGCAACC**ATTTTGCAGAGAGGG<br>GTCCCATCAAGGTTCAGTGGCAGTG<br>GATCTGGGACAGATTTCACTCTCAC<br>CATTACCAGTCTGCAACCTGAAGAT<br>TTTGGAACTTACTACTGT**CAACAGA**<br>**ACTACAAAACCTTTCTCACC**TTCG<br>GCCAAGGGACACGACTGGAGATTA<br>AAG |
| CAA1<br>(VH, codon optimized<br>for IgA1 backbone) | 7 | GAAGCACAGCTGGTGGAGAGCGGC<br>GGCGGCCTGATCCAGCCAGGCGGC<br>TCTCTGAGACTGAGCTGTGAGGCAT<br>CTGGCTTCAGCCTGAGCTCCCACGA<br>GATGAACTGGGTGAGACAGGCACC<br>TGGCAAGGGCCTGGAGTGGCTGAG<br>CTACATCTCCACCTCTGGCATCACA<br>ATCTACTATGCAGACTCCGTGCGGG<br>GCCGGTTCACCATCAGCAGGGATA<br>CAGCCAAGAACTCCCTGTACCTGCA |

TABLE 1-continued

| Sequences | | |
|---|---|---|
| Sequence Description | SEQ ID NO. | Sequence |
| | | GATGAATTCTCTGAGGGCCGAGGA<br>CACCGCCCTGTATCACTGTGCCCGC<br>GATCTGGGCGGCTACTGCAGCGGC<br>GGCCTGTGCTATCCTCGCGGCGCCC<br>TGGACCTGTGGGGACAGGGAACCA<br>CAGTGACCGTGTCTAGCGCCTCCCC<br>AACATCTCCCAAGGTGTTCCCCCTG<br>AGCCTGTGCTCCACACAGCCTGATG<br>GCAACGTGGTCATCGCCTGTCTGGT<br>GCAGGGCTTCTTTCCTCAGGAGCCA<br>CTGTCTGTGACATGGTCTGAGTCTG<br>GACAGGGAGTGACAGCACGGAATT<br>TTCCCCCTTCCCAGGACGCCTCTGG<br>CGATCTGTAT |
| CAA1<br>(VH codon optimized<br>for IgG1 backbone) | 8 | GAGGCCCAGCTGGTGGAAAGCGGC<br>GGCGGCCTGATTCAGCCCGGCGGC<br>TCTCTGAGACTGAGCTGTGAGGCAT<br>CTGGCTTCTCCCTGAGCTCCCACGA<br>GATGAACTGGGTGAGACAGGCACC<br>TGGCAAGGGCCTGGAGTGGCTGTC<br>CTACATCTCCACCTCTGGCATCACA<br>ATCTACTATGCCGACTCTGTGCGGG<br>GCCGGTTCACCATCTCCAGGGATAC<br>AGCCAAGAACTCTCTGTACCTGCAG<br>ATGAATAGCCTGAGGGCCGAGGAC<br>ACCGCCCTGTATCACTGTGCACGCG<br>ATCTGGGCGGCTACTGCAGCGGCG<br>GCCTGTGCTATCCAAGAGGCGCCCT<br>GGACCTGTGGGGACAGGGAACCAC<br>AGTGACAGTGTCTAGC |
| CAA1<br>(HCDR1) | 9 | **GFSLSSHE** |
| CAA1<br>(HCDR2) | 10 | **ISTSGITI** |
| CAA1<br>(HCDR3) | 11 | **ARDLGGYCSGGLCYPRGALDL** |
| CAA1<br>(LCDR1) | 12 | **QTIRTY** |
| CAA1<br>(LCDR2) | 13 | **AAT** |
| CAA1<br>(LCDR3) | 14 | **QQNYKTFLT** |
| CAA1<br>(HCDR1; native) | 15 | GGCTTCTCCCTCAGTTCTCATGAA |
| CAA1<br>(HCDR2; native) | 16 | ATTAGTACTAGTGGTATTACAATA |
| CAA1<br>(HCDR3; native) | 17 | GCGAGAGATCTTGGCGGTTATTGTA<br>GTGGTGGTTTGTGCTACCCGAGGGG<br>TGCCTTGGATCTC |
| CAA1<br>(LCDR1; native) | 18 | CAGACCATTCGCACCTAT |
| CAA1<br>(LCDR2; native) | 19 | GCTGCAACC |
| CAA1<br>(LCDR3; native) | 20 | CAACAGAACTACAAAACCTTTCTCA<br>CC |
| CCG4<br>(VH, native) | 21 | GAAGTGCAGCTGGTGGAGTCTGGG<br>GGAGGCTTGGTACAGCCTGGCAGG<br>TCCCTGAGACTCTCCTGCGCAGCCT<br>CT**GGAATCACCTTTGATGAATATG**<br>**CC**ATGTACTGGGTCCGGCAAGCTC<br>CAGGGAAGGGCCTGGAGTGGGTCT<br>CAGGT**ATTAGTTGGAACAGTGCT** |

TABLE 1-continued

| Sequences | | |
|---|---|---|
| Sequence Description | SEQ ID NO. | Sequence |
| | | **AATATA**GGCTATGCGGACTCTGTG AAGGGCCGATTCACCATCTCCAGA GACAACGCCAAGAAGTCCCTCTAT CTGCAAATGAATAGTCTGAGAGCT GAAGACACGGCCTTGTATTACTGT**T** **CAGGTATAACTGGGACTACGGGG** **ATACAGTAC**TGGGGCCAGGGAACC CTGGTCACCGTCTCCTCAG |
| CCG4 (VH) | 22 | EVQLVESGGGLVQPGRSLRLSCAAS **GITFDEYA**MYWVRQAPGKGLEWVS G**ISWNSANI**GYADSVKGRFTISRDNA KKSLYLQMNSLRAEDTALYYC**SGIT** **GTTGIQY**WGQGTLVTVSS |
| CCG4 (VL, native) | 23 | TCCTATGAGCTGACACAGCCATCCT CAGTGTCAGTGTCTCCGGGACAGA CAGCCAGGATCACCTGCTCAGGAG AT**GTATTGGCAAATACATAT**GCTC GGTGGTTCCAGCAGAAGCCAGGCC AGGCCCCTGTACTGGTGATTTAT**AA** **AGACAGT**GAGCGGCCCTCAGGGAT CCCTGAGCGATTCTCCGGCTCCAGC TCAGGGACCACAGTCACCTTGATCA TCAGGGGGGCCCAGGTTGAGGATG AGGCTGACTATTACTGT**TACTCTG** **CGGCTGACAACAATCGGAGGGTG** TTCGGCGGAGGGACCAAGCTGACC GTCCTAG |
| CCG4 (VL) | 24 | SYELTQPSSVSVSPGQTARITCSGD**VL** **ANTY**ARWFQQKPGQAPVLVIY**KDSE** RPSGIPERFSGSSSGTTVTLIIRGAQVE DEADYYC**YSAADNNRRV**FGGGTKL TVL |
| CCG4 (HCDR1) | 25 | **GITFDEYA** |
| CCG4 (HCDR2) | 26 | **ISWNSANI** |
| CCG4 (HCDR3) | 27 | **SGITGTTGIQY** |
| CCG4 (LCDR1) | 28 | **VLANTY** |
| CCG4 (LCDR2) | 29 | **KDS** |
| CCG4 (LCDR3) | 30 | **YSAADNNRRV** |
| CCG4 (HCDR1; native) | 31 | **GGAATCACCTTTGATGAATATGC C** |
| CCG4 (HCDR2; native) | 32 | **ATTAGTTGGAACAGTGCTAATAT A** |
| CCG4 (HCDR3; native) | 33 | **TCAGGTATAACTGGGACTACGGG GATACAGTAC** |
| CCG4 (LCDR1; native) | 34 | **GTATTGGCAAATACATAT** |
| CCG4 (LCDR2; native) | 35 | **AAAGACAGT** |
| CCG4 (LCDR3; native) | 36 | **TACTCTGCGGCTGACAACAATCG GAGGGTG** |
| CCG4 (VH, codon optimized for IgA2M2 backbone) | 37 | gaggtgcagctggtggaaagcggcggcggcctggtgc agccaggccggtctctgagactgtcttgtgcagcatctgg aatcaccttcgacgagtatgcaatgtattgggtgcggcag gcaccaggcaagggactggagtgggtgtccggcatctct |

TABLE 1-continued

| Sequences | | |
|---|---|---|
| Sequence Description | SEQ ID NO. | Sequence |
| | | tggaacagcgccaatatcggctacgccgactccgtgaag<br>ggcaggtttacaatctcccgcgataacgccaagaagtctc<br>tgtatctgcagatgaatagcctgagggccgaggataccg<br>ccctgtactattgctctggcatcacaggcaccacaggcat<br>ccagtactggggccagggcaccctggtgacagtgagct<br>ccgcctccccaacctctcccaaggtgttccccctgagcct<br>ggactccacacctcaggatggcaacgtggtggtggcctg<br>tctggtgcagggcttctttcctcaggagccactgagcgtg<br>acctggtctgagagcggccagaacgtgacagcccggaa<br>ttttccccctctcaggacgccagcggcgatctgtatacc |
| CCG4<br>(VH, codon optimized<br>for IgG1 backbone) | 38 | gaggtgcagctggtggaaagcggcggcggcctggtgc<br>agcctggccggagcctgagactgtcttgtgcagcatctgg<br>aatcaccttcgacgagtacgccatgtattgggtgcggcag<br>gcacctggcaagggcctggagtgggtgtctggcatcagc<br>tggaactccgccaatatcggctacgccgactctgtgaagg<br>gcaggtttacaatctctcgcgataacgccaagaagagcct<br>gtatctgcagatgaattccctgagggccgaggataccgc<br>cctgtactattgtagcggcatcacaggcaccacaggcatc<br>cagtactggggccagggcaccctggtgacagtgagctc<br>c |
| CCG4<br>(VL, codon optimized) | 39 | agctacgagctgacccagcctagctccgtgtctgtgagcc<br>ctggacagacagcaagaatcacatgctctggcgacgtgc<br>tggccaacacatacgccaggtggtttcagcagaagcctg<br>gacaggcccccgtgctggtcatctacaaggattccgaga<br>ggccatctggcattcctgagcggttcagcggctctagctc<br>cggcaccacagtgaccctgatcattagaggcgcccaggt<br>ggaggatgaggcagattactattgttatagcgccgccgac<br>aacaatcggagagtgttcggcggcggaaccaagctgac<br>agtgctg |
| IgA1 - heavy chain<br>constant region | 40 | asptspkvfplslcstqpdgnvviaclvqgffpqeplsvt<br>wsesgqgvtarnfppsqdasgdlyttssqltlpatqclag<br>ksvtchvkhytnpsqdvtvpcpvpstpptpspstpptp<br>spscchprlslhrpaledlllgseanltctltglrdasgvtft<br>wtpssgksavqgpperdlcgcysvssvlpgcaepwnh<br>gktftctaaypesktpltatlsksgntfrpevhllpppseel<br>alnelvtltclargfspkdvlvrwlqgsqelprekyltwa<br>srqepsqgtttfavtsilrvaaedwkkgdtfscmvghea<br>lplaftqktidrlagkpthvnvsvvmaevdgtcy |
| IgA2(m1) - heavy<br>chain constant region | 41 | asptspkvfplsldstpqdgnvvvaclvqgffpqeplsv<br>twsesgqnvtarnfppsqdasgdlyttssqltlpatqcpd<br>gksvtchvkhytnpsqdvtvpcpvpppppcchprlsl<br>hrpaledlllgseanltctltglrdasgatftwtpssgksav<br>qgpperdlcgcysvssvlpgcaqpwnhgetftctaahp<br>elktpltanitksgntfrpevhllpppseelalnelvtltcla<br>rgfspkdvlvrwlqgsqelprekyltwasrqepsqgtttf<br>avtsilrvaaedwkkgdtfscmvghealplaftqktidrl<br>agkpthvnvsvvmaevdgtcy |
| IgA2(m2) - heavy<br>chain constant region | 42 | asptspkvfplsldstpqdgnvvvaclvqgffpqeplsv<br>twsesgqnvtarnfppsqdasgdlyttssqltlpatqcpd<br>gksvtchvkhytnssqdvtvpcrvpppppcchprlslh<br>rpaledlllgseanltctltglrdasgatftwtpssgksavq<br>gpperdlcgcysvssvlpgcaqpwnhgetftctaahpe<br>lktpltanitksgntfrpevhllpppseelalnelvtltclar<br>gfspkdvlvrwlqgsqelprekyltwasrqepsqgttty<br>avtsilrvaaedwkkgetfscmvghealplaftqktidr<br>magkpthinvsvvmaeadgtcy |
| Campylobacter jejuni<br>subsp. jejuni sero-<br>type<br>O:23/36 (strain 81-<br>176) Flagellar hook-<br>associated protein 2<br>(Uniprot<br>A0A0H3PIU8) | 43 | mafgslsslg fgsgvltqdt idklkeaeqk<br>aridpytkki eenttkqkdl teiktkllsf qtavsslada<br><br>tvfakrkvvg sisdnppasl tvnsgvalqs<br>mninvtqlaq kdvyqskgla ndsgfinanl<br>tgttdltffs ngkeytvtvd knttyrelad kineasggei<br>vakivntgek gtpyrltlts ketgedsais<br>fyagkkdsng kytsdseaet ifknlgweld<br>ttssidpakd kkgygikdas lhiqtaqnae<br>ftldgikmfr ssntvtdlgv gmtltinktg<br>einfdvqqdf egvtkamqdl vdayndlvtn<br>lnaatdynse tgtkgtlqgi sevnsirssi ladlfdsqvv<br>dgttedangn kvntkvmlsm qdfglslnda<br>gtlsfdsskf eqkvkedpds tesffsnitk |

TABLE 1-continued

| Sequence Description | SEQ ID NO. | Sequence |
|---|---|---|
| | | yedinhtgev ikqgslnqyl dssgtgnkgl dfkpgdftiv fnnqtydlsk nsdgtnfklt gkteeellqn lanhinskgi eglkvkvesy dqngvkgfkl nfsgdgssdf sikgnatilk elglsdvnit skpiegkgif sklkatlqem tgkdgsitky desltnniks lntskdstqa midtrydtma nqwlqyesil nklnqqlntv tnminaanns nn |
| Campylobacter jejuni subsp. jejuni sero-type O:2 (strain ATCC 700819/NCTC 11168) (Uniprot Q9PHW6) | 44 | mafgslsslg fgsgvltqdt idklkeaeqk aridpytkki eenttkqkdl teiktkllsf qtavsslada tvfakrkvvg sisdnppasl tvnsgvalqs mninvtqlaq kdvyqskgla ndggfvnaql ngtadltffs ngkeytvtvd knttyrdlad kineasggei vakivntgek gtpyrltlts ketgedsais fyagkkdsng kyqkdinaek ifddlgwgld vsasidpdkd kkgygikdas lhiqtaqnae ftldgikmfr ssntvtdlgv gmtltlnktg einfdvqqdf egvtkamqdl vdayndlvtn lnaatdynse tgtkgtlqgi sevnsirssi ladlfdsqvv dgttedangn kvntkvmlsm qdfglslnda gtlsfdsskf eqkvkedpds tesffsnitk yedinhtgev iktgslskyl nsnggntngl efkpgdftiv fnnqtydlsk nsdgtnfklt gkteeellqn lanhinskgi eglkvkvesy nqnnvtgfrl nfsgdgssdf sikgdanilk elglsdvnit skpiegkgif sklkatlqem tgkdgsitky desltndiks lntskdstqa midtrydtma nqwlqyesil nklnqqlntv tnminaanns nn |
| flagellar hook-associated protein 2 [Campylobacter jejuni subsp. jejuni NCTC 11168 = ATCC 700819] NCBI Reference Sequence: YP_002343979.1 | 45 | mafgslsslg fgsgvltqdt idklkeaeqk aridpytkki eenttkqkdl teiktkllsf qtavsslada tvfakrkvvg sisdnppasl tvnsgvalqs mninvtqlaq kdvyqskgla ndggfvnaql ngtadltffs ngkeytvtvd knttyrdlad kineasggei vakivntgek gtpyrltlts ketgedsais fyagkkdsng kyqkdinaek ifddlgwgld vsasidpdkd kkgygikdas lhiqtaqnae ftldgikmfr ssntvtdlgv gmtltlnktg einfdvqqdf egvtkamqdl vdayndlvtn lnaatdynse tgtkgtlqgi sevnsirssi ladlfdsqvv dgttedangn kvntkvmlsm qdfglslnda gtlsfdsskf eqkvkedpds tesffsnitk yedinhtgev iktgslskyl nsnggntngl efkpgdftiv fnnqtydlsk nsdgtnfklt gkteeellqn lanhinskgi eglkvkvesy nqnnvtgfrl nfsgdgssdf sikgdanilk elglsdvnit skpiegkgif sklkatlqem tgkdgsitky desltndiks lntskdstqa midtrydtma nqwlqyesil nklnqqlntv tnminaanns nn |
| flagellar filament capping protein FliD [Campylobacter jejuni] NCBI Reference Sequence: WP_038400380.1 | 46 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandsgfinanl agttdltffs ngkeytvtvd knttyrdlad kineasggei vakivntgekgtpyrltlts ketgedsais fyagkkdaqg qyksdleaek ifkslgweld ttssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl afkpgdftiv fnnqtydlsk nsdgtnfkltgkteeellqn lanhinskgi eglkvkvesy nqnnvtgfrl nfsgdgssdf sikgdgsilkelglsdvnit skpiegkgif sklkatlqem tgkdgsitky desltndiks lntskdstqamidtrydtma nqwlqyesil nklnqqlntv tnminaanns nn |

TABLE 1-continued

| Sequences | | |
|---|---|---|
| Sequence Description | SEQ ID NO. | Sequence |
| flagellar hook-associated protein FliD [Campylobacter jejuni subsp. jejuni 81-176] GenBank: EAQ73028.1 | 47 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd knttyrelad kineasggei vakivntgekgtpyrltlts ketgedsais fyagkkdsng kytsdseaet ifknlgweld ttssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev ikqgslnqyl dssgtgnkgl dfkpgdftiv fnnqtydlsk nsdgtnfkltgkteeellqn lanhinskgi eglkvkvesy dqngvkgfkl nfsgdgssdf sikgnatilkelglsdvnit skpiegkgif sklkatlqem tgkdgsitky desltnniks lntskdstqamidtrydtma nqwlqyesil nklnqqlntv tnminaanns nn |
| flagellar filament capping protein FliD [Campylobacter jejuni] NCBI Reference Sequence: WP_010790846.1 | 48 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld asasidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlnfdsskf eqkvkedpds aesffsnitkyedinhtgei iktgslskyl nsnggntngl dfkpgdftiv fnnqtydlsk nsdgtnfkltgkteeellqn lanhinskgi eglkvkvesy dqnnvkgfkl nfsgdgssdf sikgdasilkelglpdvnit skpiegkgif sklkatlqem tgkdgsitky desltndiks lntskdstqamidtrydtma nqwlqyesil nklnqqlntv tnminaanns nn |
| MULTISPECIES: flagellar filament capping protein FliD [Campylobacter] NCBI Reference Sequence: WP_004316510.1 | 49 | mafgslaslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnanl ngtadltffs ngkeytvtvd rnttyrdlad kineasggei vakivntgekgtpyrltlts ketgedsais fyagkkdang aykndpnaet ifknlgweld atssidlakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdginfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlstv tnminaanns nn |
| flagellar filament capping protein FliD [Campylobacter jejuni] NCBI Reference Sequence: WP_004306838.1 | 50 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnaql ngtadltffs ngkeytvtvd knttyrdlad kineasggei vakivntgekgtpyrltlts ketgedsais fyagkkdaqg qyksdleaek ifkslgweld ttssidpakdkkgygikdas lhiqtaqnae ftldgikmfr ssntvtdlgv gmtltlnktg einfdvqqdfegvtkamqdl vdayndlvtn |

TABLE 1-continued

| Sequences | | |
|---|---|---|
| Sequence Description | SEQ ID NO. | Sequence |
| | | lnaatdynse tgtkgtlqgi sevnsirssi ladlfdsqvvdgttedangn kvntkvmlsm qdfglslnda gtlsfdsskf ekkvkedpds aesffsnitkyedinhtgev iktgslskyl nsnggsangl dfkpgdftiv fnnqtydlsk nsdgtnfkltgkteeellqn lanhinskgi eglkvkvesy dqnnvkgfkl nfsgdgssdf sikgdanilkelglsdvnis skpiegkgif sklkatlqem tgkdgsitky desltndiks lntskdstq vmidtrydtma nqwlqyesil nklnqqlntv tnminaanns nn |
| flagellar filament capping protein FliD [Campylobacter jejuni] NCBI Reference Sequence: WP_002935293.1 | 51 | mafgslsslg fgsgvltqdt idklkeaeqk aridpytkki eenttkqkdl teiktkllsf qtavsslada tvfakrkvvg sisdnppasl tvnsgvalqs mninvtqlaq kdvyqskglandsgfvnaql ngtadltffs ngkeytvtvd knttyrdlad kineasggei vakivntgekgtpyrltlts ketgedsais fyagkkdsng kyqkdtnaek ifddlgweld vsasidpdkdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgyftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter jejuni] NCBI Reference Sequence: WP_002928464.1 | 52 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld asasidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlnfdsskf eqkvkedpds aesffsnitkyedinhtgei iktgslskyl nsnggntngl dfkpgdftiv fnnqtydlsk nsdgtnfkltgkteeellqn lanhinskgi eglkvkvesy dqnnvkgfkl nfsgdgssdf sikgdasilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter jejuni] NCBI Reference Sequence: WP_002924910.1 | 53 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnakl ngtadltffs ngkeytvtvd knttyrdlad kineasggei vakivntgekgtpyrltlts ketgedsais fyagkkdvqg qyksdseaek ifkslgweld ttssidpakdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks |

TABLE 1-continued

Sequences

| Sequence Description | SEQ ID NO. | Sequence |
|---|---|---|
| | | lntskdstqamidtrydtma nqwlqyesil<br>nklnqqlntv tnminaanns nn |
| flagellar filament capping protein FliD [Campylobacter jejuni] NCBI Reference Sequence: WP_002921586.1 | 54 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandsgfinanl<br>tgttdltffs ngkeytvtvd knttyrdlad<br>kineasggei vakivntgekdtpyrltlts ketgedsais<br>fyagkkdsng kytsdseaet ifknlgweld<br>ttssidpakd kkgygikdas lhiqtaqnae<br>ftldgikmfr ssntvtdlgv gmtltinktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev ikqgslnqyl<br>dssgtgnkgl dfkpgdftiv fnnqtydlsk<br>nsdgtnfkltgkteeellqn lanhinskgi<br>eglkvkvesy dqngvkgfkl nfsgdgssdf<br>sikgnatilqelglsdvnit skpiegkgif sklkatlqem<br>tgkdgsitky desltndiks<br>lntskdstqamidtrydtma nqwlqyesil<br>nklnqqlntv tnminaanns nn |
| flagellar filament capping protein FliD [Campylobacter jejuni] NCBI Reference Sequence: WP_002908989.1 | 55 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandggfvnaql<br>ngtadltffs ngkeytvtvd knttyrdlad<br>kineasggei vakivntgekgtpyrltlts ketgedsais<br>fyagkkdsng kyqkdtnaek ifddlgwgld<br>vsasidpdkdkkgy gikdas lhiqtaqnae<br>ftldgikmfr ssntvtdlgv gmtltlnktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev ikqgslnqyl<br>dssgtgnkgl dfkpgdftiv fnnqtydlsk<br>nsdgtnfkltgkteeellqn lanhinskgi<br>eglkvkvesy nqnnvtgfkl nfsgdgssdf<br>sikgnasilkelglsdvnit skpiegkgif<br>sklkatlqem tgkdgsitky desltndiks<br>lntskdstqamidtrydtma nqwlqyesil<br>nklnqqlntv tnminaanns nn |
| flagellar filament capping protein FliD [Campylobacter jejuni] NCBI Reference Sequence: WP_002901368.1 | 56 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandsgfinanl<br>tgttdltffs ngkeytvtvd knttyrdlad<br>kineasggei vakivntgekgtpyrltlts ketgedsais<br>fyagkkdsng kytsdleakt ifknlgweld<br>ttssidpakdkkgygikdas lhiqtaqnae<br>ftldgikmfr ssntvtdlgv gmtltinktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev ikqgslnqyl<br>dssgtgnkgl dfkpgdftiv fnnqtydlsk<br>nsdgtnfkltgkteeellqn lanhinskgi<br>eglkvkvesy nqnnvtgfrl nfsgdgssdf<br>sikgdanilkelglsdvnit skpiegkgif<br>sklkatlqem tgkdgsitky desltndiks<br>lntskdstqamidtrydtma nqwlqyesil<br>nklnqqlntv tnminaanns nn |
| MULTISPECIES: flagellar filament capping protein FliD [Campylobacter] NCBI Reference Sequence: WP_002892358.1 | 57 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandggfinanl<br>tgttdltffs ngkeytvtvd knttyrdlad<br>kineasggei vakivntgekgtpyrltlts ketgedsais<br>fyagkkdsng aykndpnaet ifknlgweld |

TABLE 1-continued

| Sequences | | |
|---|---|---|
| Sequence Description | SEQ ID NO. | Sequence |
| | | tttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg ldfkpgdfti vfnnqtydls knsdgtnfkltgkteeellq nlanhinskg ieglkvkves ydqngvkgfk lnfsgdgssd fsikgnatilqelglsdvni tskpiegkgi fsklkatlqe mtgkdgsitk ydesltndik slntskdstqamidtrydtm anqwlqyesi lnklnqqlnt vtnminaann snn |
| flagellar filament capping protein FliD [Campylobacter jejuni] NCBI Reference Sequence: WP_002874097.1 | 58 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnakl ngtadltffs ngkeytvtvd knttyrdlad kineasggei vakivntgekgtpyrltlts ketgedsais fyagkkdaqg qyksdseaek ifkslgweld ttssidpakdkkgysikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter jejuni] NCBI Reference Sequence: WP_002873395.1 | 59 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld vsasidpakdkkgygikdas lhiqtagnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar hook-associated protein FliD [Campylobacter jejuni subsp. jejuni 305] GenBank: EFV08769.1 | 60 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdinaek ifddlgwgld vsasidpdkdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf |

TABLE 1-continued

Sequences

| Sequence Description | SEQ ID NO. | Sequence |
|---|---|---|
| | | sikgdanilkelglsdvnit skpiegkgif sklkatlqem tgkdgsitky desltndiks lntskdstqamidtrydtma nqwlqyesil nklnqqlntv tnminaanns nn |
| flagellar hook-associated protein FliD [Campylobacter jejuni subsp. jejuni 327] GenBank: EFV10698.1 | 61 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfvnanl tgttdltffs ngkeytvtvd knttyrdlad kineasggei vakivntgekgtpyrltlts ketgedsais fyagkkdaqg qyqsdpeaen ifsnlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg ldfkpgdfti vfnnqtydls knsdgtnfkltgkteeellq nlanhinskg ieglkvkves ydqngvkgfk lnfsgdgssd fsikgnatilqelglsdvni tskpiegkgi fsklkatlqe mtgkdgsitk ydesltndik slntskdstqamidtrydtm anqwlqyesi lnklnqqlnt vtnminaann snn |
| flagellar hook-associated protein FliD [Campylobacter jejuni subsp. jejuni 84-25] | 62 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandsgfinanl agttdltffs ngkeytvtvd knttyrdlad kineasggei vakivntgekgtpyrltlts ketgedsais fyagkkdaqg qyqsdpeaek ifsnlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge viktgslsky lnsnggntng lefkpgdfti vfnnqtydls knsdgtnfkltgkteeellq nlanhinskg ieglkvkves ynqnnvtgfr lnfsgdgssd fsikgdanilkelglsdvni tskpiegkgi fsklkatlqe mtgkdgsitk ydesltndik slntskdstqamidtrydtm anqwlqyesi lnklnqqlnt vtnminaann snn |
| flagellar hook-associated protein FliD [Campylobacter jejuni subsp. jejuni HB93-13] GenBank: EAQ60315.1 | 63 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd ksttyrdlad kineasggei vakivntgekgtpyrltlts ketgedsais fyagkkdaqgqyksdseaekifsnlgweldkttqtidp akdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg lefkpggfti vfnnqtydls knsdgtnfkltgkteeellq nlanhinskg ieglkvkves ydqngvkgfk lnfsgdgssd fsikgdanilkelglsdvni tskpiegkgi fsklkatlge mtgkdgsitk ydesltndik slntskdstqamidtrydtm anqwlqyesi lnklnqqlnt vtnminaann snn |
| flagellar hook-associated protein FliD [Campylobacter jejuni subsp. jejuni 260.94] | 64 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad |

TABLE 1-continued

| Sequences | | |
|---|---|---|
| Sequence Description | SEQ ID NO. | Sequence |
| GenBank: EAQ58732.1 | | kineasggei vakivntgekgtpyrltlts ketgedsais fyagkkdsng kyqkdtnaek ifddlgwgld asasidpakdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlnfdsskf eqkvkedpds aesffsnitkyedinhtgei iktgnlskyl nsnggntngl dfkpgdftiv fnnqtydlsk nsdgtnfkltgkteeellqn lanhinskgi eglkvkvesy dqnnvkgfkl nfsgdgssdf sikgdasilkelglsdvnii skpiegkgif sklkatlqem tgkdgsitky desltndiks lntskdstqamidtrydtma nqwlqyesil nklnqqlntv tnminaanns nn |
| flagellar hook-associated protein FliD [Campylobacter jejuni subsp. jejuni CF93-6] GenBank: EAQ57731.1 | 65 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdinaek ifddlgwgld vsasidpdkdkkgy gikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| Flagellar hook-associated protein FliD [Campylobacter jejuni 4031] GenBank: CDH62398.1 | 66 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnakl ngtadltffs ngkeytvtvd knttyrdlad kineasggei vakivntgekgtpyrltlts ketgedsais fyagkkdaqg qyksdseaek ifkslgweld ttssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| Flagellar hook-associated protein 2 [Campylobacter jejuni subsp. jejuni M1] GenBank: ADN90737.1 | 67 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfvnanl tgttdltffs ngkeytvtvd knttyrdlad kineasggei vakivntgekgtpyrltlts ketgedsais fyagkkdaqg qyqsdpeaen ifsnlgweld kttqtidpakdkkgygikda slhiqtaqna eftldgikmf rssntvtdlg vgmtltinkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg ldfkpgdfti vfnnqtydls |

TABLE 1-continued

| Sequences | | |
|---|---|---|
| Sequence Description | SEQ ID NO. | Sequence |
| | | knsdgtnfkltgkteeellq nlanhinskg ieglkvkves ydqngvkgfk lnfsgdgssd fsikgnatilqelglsdvni tskpiegkgi fsklkatlqe mtgkdgsitk ydesltndik slntskdstqamidtrydtm anqwlqyesi lnklnqqlnt vtnminaann snn |
| flagellar fila-ment cap protein FliD [Campylobacter jejuni subsp. jejuni str. RM3420] GenBank: AOW96893.1 | 68 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd ksttyrdlad kineasggei vakivntgekgtpyrltlts ketgedsais fyagkkdaqg qyksdseaek ifsnlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg lefkpggfti vfnnqtydls knsdgtnfkltgkteeellq nlanhinskg ieglkvkves ydqngvkgfk lkfsgdgssd fsikgdanilkelglsdvni tskpiegkgi fsklkatlqe mtgkdgsitk ydesltndik slntskdstqamidtrydtm anqwlqyesi lnklnqqlnt vtnminaann snn |
| flagellar fila-ment cap protein FliD [Campylobacter jejuni subsp. jejuni] GenBank: AON66729.1 | 69 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnakl ngtadltffs ngkeytvtvd knttyrdlad kineasggei vakivntgekgtpyrltlts ketgedsais fyagkkdaqg qyksdpeaek ifkslgweld ttssidpakdkkgygikdas lhiqtaqnae ftldgikmfr ssntvtdlgv gmtltinktg einfdvqqdfegvtkamqdl vdayndlvtn lnaatdynse tgikgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar fila-ment cap protein FliD [Campylobacter jejuni subsp. jejuni] GenBank: AON65179.1 | 70 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandsgfinanl agttdltffs ngkeytvtvd knttyrdlad kineasggei vakivntgekgtpyrltlts ketgedsais fyagkkdaqg qyqsdpeaek ifsnlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge viktgslsky lnsnggntng lafkpgdfti vfnnqtydls knsdgtnfkltgkteeellq nlanhinskg ieglkvkves ynqnnvtgfr lnfsgdgssd fsikgdgsilkelglsdvni tskpiegkgi fsklkatlqe mtgkdgsitk ydesltndik slntskdstqamidtrydtm anqwlqyesi lnklnqqlnt vtnminaann snn |

TABLE 1-continued

Sequences

| Sequence Description | SEQ ID NO. | Sequence |
|---|---|---|
| flagellar fila-ment cap protein [Campylobacter jejuni subsp. jejuni] GenBank: AOH51565.1 | 71 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandggfvnaql<br>ngtadltffs ngkeytvtvd knttyrdlad<br>kineasggei vakivntgekgtpyrltlts ketgedsais<br>fyagkkdsng qyqsdseaen ifsnlgweld<br>ktssidpakdkkgygikdas lhiqtaqnae<br>ftldgikmfr ssntvtdlgv gmtltinktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev intgslskyl<br>npngldfkpg dftivfnnqt ydlsknsdgt<br>nfkltgkteeellqnlanhi nskgieglkv<br>kvesynqnnv tgfrlnfsgd gssdfsikgn<br>atilkelglsdvnitskpie gkgifsklka<br>tlqemtgkdg sitkydeslt ndikslntsk<br>dstqamidtrydtmanqwlq yesilnklnq<br>qlntvtnmin aannsnn |
| flagellar fila-ment cap protein FliD [Campylobacter jejuni subsp. jejuni] GenBank: ALF93210.1 | 72 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandggfvnaql<br>ngtadltffs ngkeytvtvd knttyrdlad<br>kineasggei vakivntgekgtpyrltlts ketgedsais<br>fyagkkdsng kyqkdtnaek ifddlgwgld<br>asasidpakdkkgygikdas lhiqtaqnae<br>ftldgikmfr ssntvtdlgv gmtltlnktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlnfdsskf eqkvkedpds<br>aesffsnitkyedinhtgei iktgnlskyl nsnggntngl<br>dfkpgdftiv fnnqtydlsk<br>nsdgtnfkltgkteeellqn lanhinskgi<br>eglkvkvesy dqnnvkgfkl nfsgdgssdf<br>sikgdasilkelglsdvnii skpiegkgif<br>sklkatlqem tgkdgsitky desltndiks<br>lntskdstqamidtrydtma nqwlqyesil<br>nklnqqlntv tnminaanns nn |
| Flagellar hook-associated protein 2 [Campylobacter jejuni subsp. jejuni] GenBank: AJP35034.1 | 73 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqsqglandggfvnaql<br>ngtadltffs ngkeytvtvd knttyrdlad<br>kineasggei vakivntgekgtpyrltlts ketgedsais<br>fyagkkdaqg qyesdseaek ifkslgweld<br>ttssinpakdkkgygikdas lhiqtaqnae<br>ftldgikmfr ssntvtdlgv gmtltinktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev iktgslskyl nsnggntngl<br>efqpgnftiv fnnqtydlsk<br>nsdgtnfkltgkteeellqn lanhinskgi<br>eglkvkvesy dqngvkgfrl nfsgdgssdf<br>sikgdanilkdlglsdvnit skpiegkgif<br>sklkatlqem tgkdgsitky desltndiks<br>lntskdstqamidtrydtma nqwlqyesil<br>nklnqqlntv tnminaanns nn |
| flagellar fila-ment cap protein [Campylobacter jejuni subsp. jejuni] GenBank: AOH51565.1 | 74 | mafgslsslg fgsgvltqdt idklkeaeqk<br>aridpytkki eenttkqkdl teiktkllsfqtavsslada<br>tvfakrkvvg sisdnppasl tvnsgvalqs<br>mninvtqlaq kdvyqskglandggfvnaql<br>ngtadltffs ngkeytvtvd knttyrdlad<br>kineasggei vakivntgekgtpyrltlts ketgedsais<br>fyagkkdsng qyqsdseaen ifsnlgweld |

TABLE 1-continued

| Sequences | | |
|---|---|---|
| Sequence Description | SEQ ID NO. | Sequence |
| | | ktssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev intgslskyl npngldfkpg dftivfnnqt ydlsknsdgt nfkltgkteeellqnlanhi nskgieglkv kvesynqnnv tgfrlnfsgd gssdfsikgn atilkelglsdvnitskpie gkgifsklka tlqemtgkdg sitkydeslt ndikslntsk dstqamidtrydtmanqwlq yesilnklnq qlntvtnmin aannsnn |
| flagellar capping protein [Campylobacter jejuni subsp. jejuni CG8421] GenBank: AHY39787.1 | 75 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandsgfinanl agttdltffs ngkeytvtvd knttyrdlad kineasggei vakivntgekgtpyrltlts ketgedsais fyagkkdaqg qyksdleaek ifkslgweld ttssidpakdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl afkpgdftiv fnnqtydlsk nsdgtnfkltgkteeellqn lanhinskgi eglkvkvesy nqnnvtgfrl nfsgdgssdf sikgdgsilkelglsdvnit skpiegkgif sklkatlqem tgkdgsitky desltndiks lntskdstqamidtrydtma nqwlqyesil nklnqqlntv tnminaanns nn |
| flagellar cap protein FliD [Campylobacter jejuni 32488] GenBank: AGQ95247.1 | 76 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqsqglandggfvnakl ngtadltffs ngkeytvtvd knttyrdlad kineasggei vakivntgekgtpyrltlts ketgedsais fyagkkdvqg qyksdseaek ifkslgweld ttssidpakd kkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar capping protein [Campylobacter jejuni subsp. jejuni IA3902] GenBank: ADC28162.1 | 77 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdinaek ifddlgwgld vsasidpdkdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf |

TABLE 1-continued

| Sequences | | |
|---|---|---|
| Sequence Description | SEQ ID NO. | Sequence |
| | | sikgdanilkelglsdvnit skpiegkgif sklkatlqem tgkdgsitky desltndiks lntskdstqamidtrydtma nqwlqyesil nklnqqlntv tnminaanns nn |
| flagellar hook-associated protein FliD [Campylobacter jejuni subsp. jejuni 81116] GenBank: ABV52108.1 | 78 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfvnanl tgttdltffs ngkeytvtvd knttyrdlad kineasggei vakivntgekgtpyrltlts ketgedsais fyagkkdaqg qyqsdpeaen ifsnlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge vikqgslnqy ldssgtgnkg ldfkpgdfti vfnnqtydls knsdgtnfkltgkteeellq nlanhinskg ieglkvkves ydqngvkgfk lnfsgdgssd fsikgnatilqelglsdvni tskpiegkgi fsklkatlqe mtgkdgsitk ydesltndik slntskdstqamidtrydtm anqwlqyesi lnklnqqlnt vtnminaann snn |
| flagellar hook-associated protein FliD [Campylobacter jejuni RM1221] GenBank: AAW35835.1 | 79 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd knttyrdlad kineasggei vakivntgekgtpyrltlts ketgedsais fyagkkdaqg qyksdseaee ifkslgweld tassidpakd kkgygikdps lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl tnglefkpgd ftivfnnqty dlsknsdgtn fkltgkteeellqnlanhin skgieglkvk vesynqnnvt gfrlnfsgdg ssdfsikgna silkelglsdvnitskpieg kgifsklkat lqemtgkdgs itkydesltn dikslntskd stqamidtrydtmanqwlqy esilnklnqq lntvtnmina annsnn |
| flagellar cap protein FliD [Campylobacter coli RM5611] GenBank: AHK75426.1 | 80 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd knttyrdlad kineasggei vakivntgekgtpyrltlts ketgedsais fyagkkdsng qyqsdseaen ifsnlgweld ktssidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgnasilkelglsdvnit skpiegkgif sklkatlqem tgkdgsitky desltndiks lntskdstqamidtrydtma nqwlqyesil nklnqqlntv tnminaanns nn |
| flagellar cap protein FliD [Campylobacter coli RM4661] GenBank: AHK76446.1 | 81 | mafgslsslg fgsgvltqdt idklkeaeqk arinpytkki eenttkqkdl teiktkllsfqtavsslada tvfakrkvvg sisdnppasl tvnsgvalqn mninvtqlaq kdvyqskglandsgfvnaql ngtadltffs ngkeytvtvd knttyrdlad kineasggei vakivntgekgapyrltlts |

TABLE 1-continued

| Sequence Description | SEQ ID NO. | Sequence |
| --- | --- | --- |
| | | ketgedsais fyagkkdssg kytsdsnaet ifknlgweld ttssidpdkdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedvngn kvntkvmlsm qdfglslnda gtlsfdsskf eqkvkedpds tesffsnitkyedinhtgev intgslskyl npngldfkqg dftivfnnqt ydlsknsdgt nfkltgkteeellqnlanhi nskgieglkv kvesynqngv kgfklnfsgd gssdfsikgn asilkelglsdvnitskpie gkgifsklka tlqemtgkdg sitkydeslt ndikslntsk dstqamidtr ydtmanqwlq yesilnklnq qlntvtnmin aannssn |
| Flagellar hook-associated protein FliD [Campylobacter coli 15-537360] GenBank: AGZ21001.1 | 82 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng qyqsdseaen ifsnlgweld ktssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter coli] NCBI Reference Sequence: WP_004284951.1 | 83 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglvndggfvnaql ngtadltffs ngkeytvtvd knttyrdlad kineasggei vakivntgekgtpyrltlts ketgedsais fyagkkdsng kyqkdtnaek ifddlgwgld vsasidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfnsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnitskpie gkgifsklka tlqemtgkdg sitkydeslt ndikslntsk dstqamidtr ydtmanqwlq yesilnklnq qlntvtnmin aannsnn |
| Flagellar hook-associated protein 2 [Campylobacter coli] GenBank: AJW57994.1 | 84 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld vsasidpakdkkgygikdts lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfnsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnitskpie gkgifsklka |

TABLE 1-continued

| Sequences | | |
|---|---|---|
| Sequence Description | SEQ ID NO. | Sequence |
| | | tlqemtgkdg sitkydeslt ndikslntsk dstqamidtrydtmanqwlq yesilnklnq qlntvtnmin aannsnn |
| Flagellar hook-associated protein 2 [Campylobacter coli] GenBank: ALV00075.1 | 85 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kytsdseaet ifknlgweld kttqtidpakdkkgygikda slhiqtaqna eftldgikmf rssntvtdlg vgmtltlnkt geinfdvqqdfegvtkamqd lvdayndlvt nlnaatdyns etgtkgtlqg isevnsirss iladlfdsqvvdgttedang nkvntkvmls mqdfglslnd agtlsfdssk feqkvkedpd stesffsnitkyedinhtge viktgslsky lnsnglefkp gdftivfnnq tydlsknsdg tnfkltgkteeellqnlanh inskgieglk vkvesynqnn vtgfrlnfsg dgssdfsikg nasilkelglsdvnitskpi egkgifsklk atlqemtgkd gsitkydesltndikslntskdstqamidtry dtmanqw l qyesilnkln qqlntvtnmi naannsnn |
| Flagellar hook-associated protein FliD [Campylobacter coli IPSID-1] GenBank: CDL88777.1 | 86 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd knttyrdlad kineasggei vakivntgekgtpyrltlts ketgedsais fyagkkdsng kytsdseaetifknlgweldttssidpakdkkgygikda s lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev ikqgslnqyl dssgtgnkgl dfkpgdftiv fnnqtydlsk nsdgtnfkltgkteeellqn lanhinskgi eglkvkvesy dqngvkgfkl nfsgdgssdf sikgnatilkelglsdvnit skpiegkgif sklkatlqem tgkdgsitky desltndiks lntskdstqamidtry dtma nqwlqyesil nklnqqlntv tnminaanns nn |
| flagellar hook-associated protein 2 (fliD), putative [Campylobacter coli RM2228] GenBank: EAL57379.1 | 87 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld vsasidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfnsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnitskpie gkgifsklka tlqemtgkdg sitkydeslt ndikslntsk dstqamidtrydtmanqwlq yesilnklnq qlntvtnmin aannsnn |
| flagellar filament capping protein FliD [Campylobacter coli] NCBI Reference Sequence: WP_002842748.1 | 88 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng kyqkdtnaek ifddlgwgld |

TABLE 1-continued

| Sequences | | |
|---|---|---|
| Sequence Description | SEQ ID NO. | Sequence |
| | | vsasidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnisskpie gkgifsklka tlqemtgkdg sitkydeslt ndikslntsk dstqamidtrydtmanqwlq yesilnklnq qlntvtnmin aannsnn |
| flagellar filament capping protein FliD [Campylobacter coli] NCBI Reference Sequence: WP_002833936.1 | 89 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng qyqsdseaen ifsnlgweld ktssidpakdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfnsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnitskpie gkgifsklka tlqemtgkdg sitkydeslt ndikslntsk dstqamidtrydtmanqwlq yesilnklnq qlntvtnmin aannsnn |
| flagellar hook-associated protein 2 [Campylobacter coli JV20] GenBank: EFM36457.1 | 90 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglvndggfvnaql ngtadltffs ngkeytvtvd knttyrdlad kineasggei vakivntgekgtpyrltlts ketgedsais fyagkkdsng kyqkdtnaek ifddlgwgld vsasidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfnsskf eqkvkedpds tesffsnitkyedinhtgev iktgslskyl nsnglefkpg dftivfnnqt ydlsknsdgt nfkltgkteeellqnlanhi nskgieglkv kvesynqnnv tgfrlnfsgd gssdfsikgn asilkelglsdvnitskpie gkgifsklka tlqemtgkdg sitkydeslt ndikslntsk dstqamidtrydtmanqwlq yesilnklnq qlntvtnmin aannsnn |
| flagellar filament capping protein FliD [Campylobacter coli] NCBI Reference Sequence: WP_002832776.1 | 91 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandggfvnaql ngtadltffs ngkeytvtvd knttyrdlad kineasggei vakivntgekgtpyrltlts ketgedsais fyagkkdsng qyqsdsgaen ifsnlgweld ktssidpakdkkgygikdas lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgnlskyl nsnggntngl efkpgdftiv fnnqtydlsk nsdgtnfkltgkteeellqn lanhinskgi eglkvkvesy nqnnvtgfrl nfsgdgssdf sikgdanilkelglsdvnit skpiegkgif sklkatlqem tgkdgsitky desltndiks |

TABLE 1-continued

Sequences

| Sequence Description | SEQ ID NO. | Sequence |
|---|---|---|
| | | lntskdstqamidtrydtma nqwlqyesil nklnqqlntv tnminaanns nn |
| flagellar filament capping protein FliD [Campylobacter coli] NCBI Reference Sequence: WP_002825071.1 | 92 | mafgslsslg fgsgvltqdt idklkeaeqk arinpytkki eenttkqkdl teiktkllsfqtavsslada tvfakrkvvg sisdnppasl tvnsgvalqs mninvtqlaq kdvyqskglandsgfinanl tgttdltffs ngkeytvtvd ksttyrdlad kineasggei vakivntgekgtpyrltlts ketgedsais fyagkkdssg kytsdsnaet ifknlgweld ttssidpdkdkkgygikdas lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedvngn kvntkvmlsm qdfglslnda gtlsfdsskf eqkvkedpds tesffsnitkyedinhtgev intgslskyl nsnggntngl efkpgdftiv fnnqtydlsk nsdgtnfkltgkteeellqn lanhinskgi eglkvkvesy nqnnvtgfrl nfsgdgssdf sikgnasilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter coli] NCBI Reference Sequence: WP 002804771.1 | 93 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfinanl tgttdltffs ngkeytvtvd knttyrdlad kineasggei vakivntgekgtpyrltlts ketgedsais fyagkkdsng qyqsdseaen ifsnlgweld ktssidpakdkkgygikdts lhiqtaqnae ftldgikmfr ssntvtdlgv gmtltlnktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgnasilkelglsdvnit skpiegkgif sklkatlqem tgkdgsitky desltndiks lntskdstqamidtrydtma nqwlqyesil nklnqqlntv tnminaanns nn |
| flagellar filament capping protein FliD [Campylobacter coli] NCBI Reference Sequence: WP_002793506.1 | 94 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfvnanl tgttdltffs ngkeytvtvd knttyrdlad kineasggei vakivntgekgtpyrltlts ketgedsais fyagkkdsng qyqsdseaen ifsnlgweld ktssidpakdkkgygikdts lhiqtaqnae ftldgikmfr ssntvtdlgv gmtltinktg einfdvqqdfegvtkamqdl vdayndlvtn lnaatdynse tgtkgtlqgi sevnsirssi ladlfdsqvvdgttedangn kvntkvmlsm qdfglslnda gtlsfdsskf eqkvkedpds tesffsnitkyedinhtgev iktgslskyl nsnggntngl efkpgdftiv fnnqtydlsk nsdgtnfkltgkteeellqn lanhinskgi eglkvkvesy nqnnvtgfrl nfsgdgssdf sikgdasilkelglsdvnis skpiegkgif sklkatlqem tgkdgsitky desltndiks lntskdstqamidtrydtma nqwlqyesil nklnqqlntv tnminaanns nn |
| flagellar filament capping protein FliD [Campylobacter coli] NCBI Reference Sequence: WP_002791831.1 | 95 | mafgslsslg fgsgvltqdt idklkeaeqk aridpytkki eenttkqkdl teiktkllsfqtavsslada tvfakrkvvg sisdnppasl tvnsgvalqs mninvtqlaq kdvyqskglandsgfvsanl tgttdltffs ngkeytvtvd knttyrdlad kineasggei vakivntgekgtpyrltlts ketgedsais fyagkkdssg kytsdsnaet ifknlgweld |

TABLE 1-continued

| Sequences | | |
|---|---|---|
| Sequence Description | SEQ ID NO. | Sequence |
| | | ktssidpakdkkgygikdts lhiqtaqnae<br>ftldgikmfr ssntvtdlgv gmtltlnktg<br>einfdvqqdfegvtkamqdl vdayndlvtn<br>lnaatdynse tgtkgtlqgi sevnsirssi<br>ladlfdsqvvdgttedangn kvntkvmlsm<br>qdfglslnda gtlsfdsskf eqkvkedpds<br>tesffsnitkyedinhtgev iktgslskyl nsnggntngl<br>efkpgdftiv fnnqtydlsk<br>nsdgtnfkltgkteeellqn lanhinskgi<br>eglkvkvesy nqnnvtgfrl nfsgdgssdf<br>sikgdasilkelglsdvnis skpiegkgif<br>sklkatlqem tgkdgsitky desltndiks<br>lntskdstqamidtrydtma nqwlqyesil<br>nklnqqlntv tnminaanns nn |

Example 3

Campylobacter-Specific Antibodies in rSIgA2 Bind to FliD

Figure 7A:
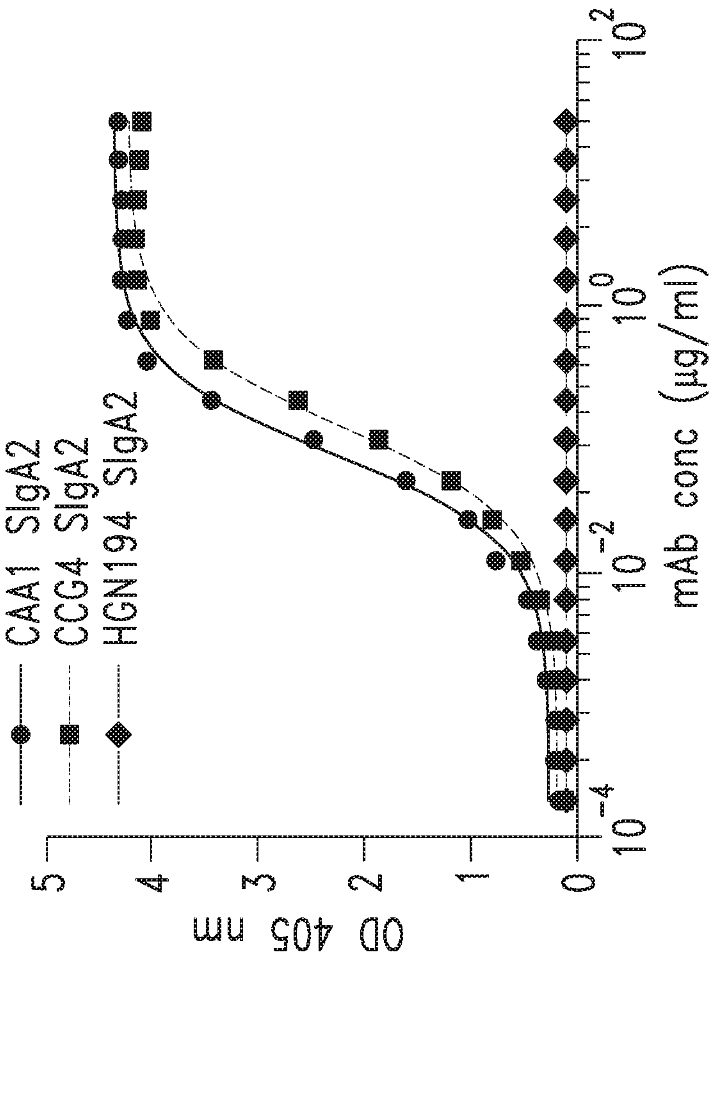
FIGS. 7A-7E show in vitro characterization of exemplary antibodies CAA1 and CCG4 of the present disclosure (expressed as rSIgA) binding to FliD. (A) Binding of CAA1, CCG4 and HGN194 rSIgA to coated recombinant FliD as measured by ELISA. Serial dilutions of the three mAbs were incubated for 1 h at RT with FliD pre-coated 96 well ELISA plates. Detection was performed using a biotinylated anti-human SC antibody followed by incubation with Streptavidin-AP. (B) Cross-competition studies performed by bio-layer interferometry (BLI). FliD antigen was immobilized on APS sensors and then incubated with CAA1 prior to association with CGG4, CAA1 or PBS with 1% BSA. (C) Western blot analysis of CAA1, CCG4 and HGN194 rSIgA binding to FliD antigen (70 KDa) under reducing and denaturing conditions. (D) Representative histograms of the in vitro binding of the indicated mAbs against pure culture of *C. jejuni* and *C. coli*. One representative experiment out of three is shown. (E) Binding of CAA1, CCG4 and HGN194 rSIgA2 to *C. jejuni* as observed in confocal microscopy. Bacteria were stained using Syto BC, whereas the mAbs were detected using anti-human IgA AF647 conjugated.
Figure 7B:
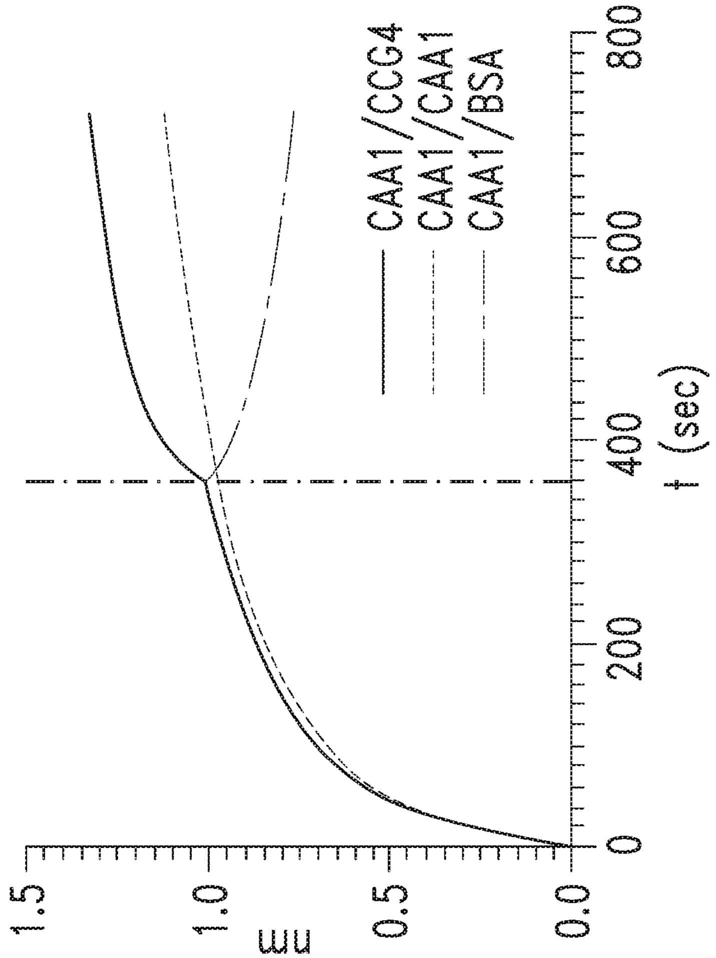
Figure 7C:
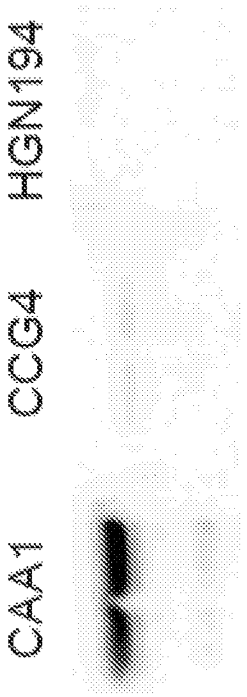
Figure 7D:
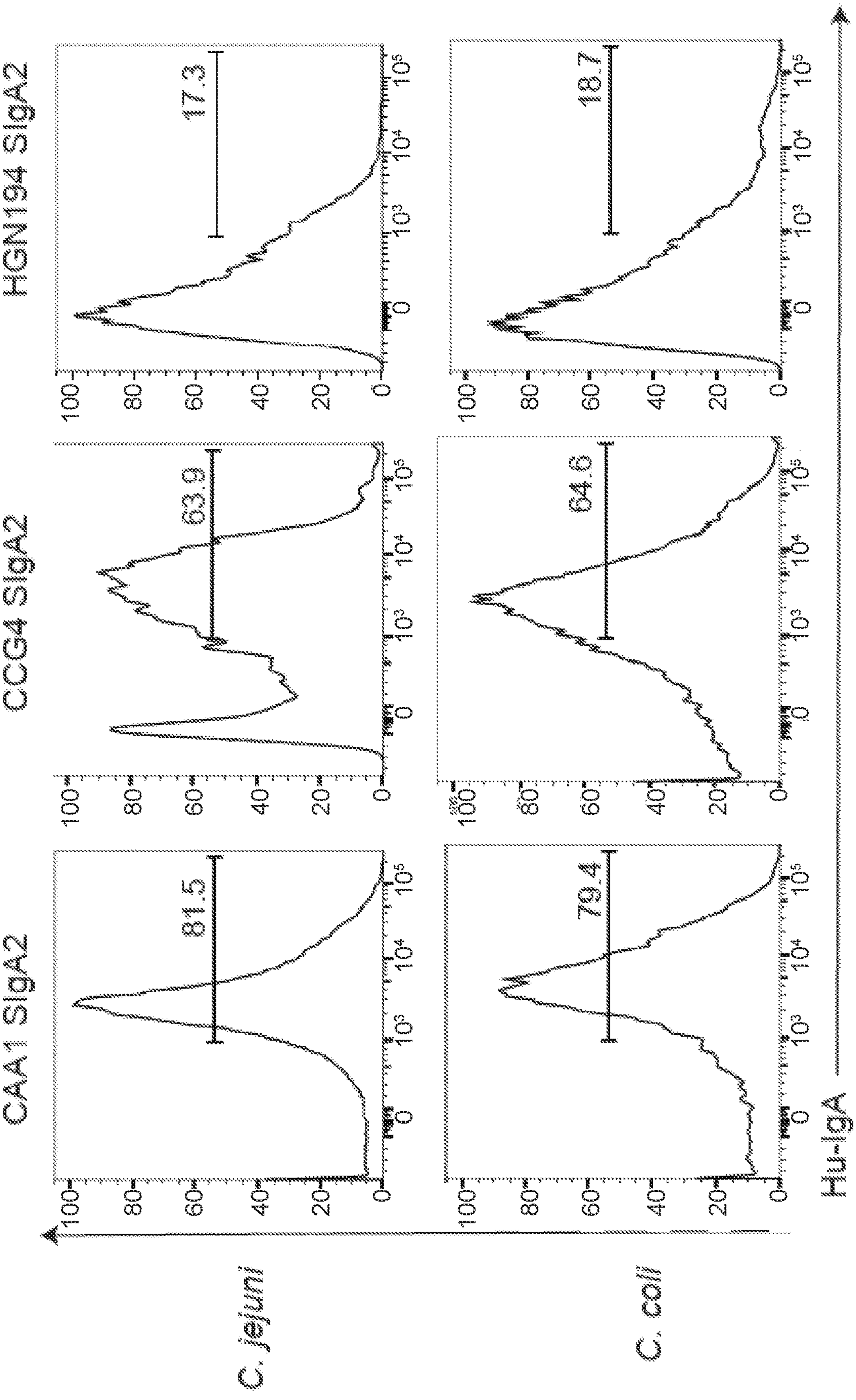
Figure 7E:
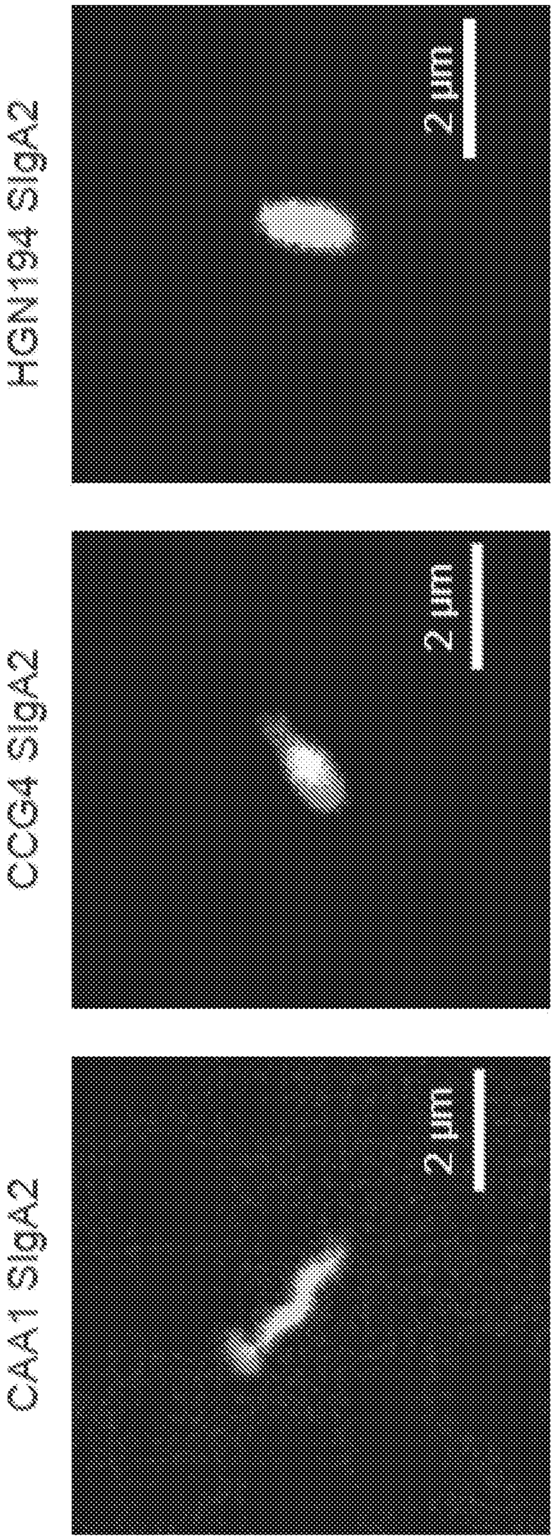

In the SIgA2 format, CAA1 and CCG4 maintained the original FliD binding activity, displaying similar EC50 for the flagellar protein (FIG. 7A). The EC50 of CAA1 SIgA2 was 0.02372, and the EC50 of CCG4 SIgA2 was 0.02954. Epitope binning showed that the binding of one antibody to the antigen did not prevent the binding of the other mAb (FIG. 7B), thus indicating the recognition of two different epitopes. Western blot analysis in denaturing reducing conditions indicated that the two mAbs bind structurally different antigenic determinants, with CAA1 targeting a linear epitope and CCG4 a conformational one (FIG. 7C). The accessibility of the antibodies to these epitopes in the flagella of *C. jejuni* and *C. coli* historical isolates was confirmed by flow cytometry and by confocal imaging (FIGS. 7D, 7E).

Example 4 rSIgA Inhibits Motility of *Campylobacter* In Vitro

Figure 2:
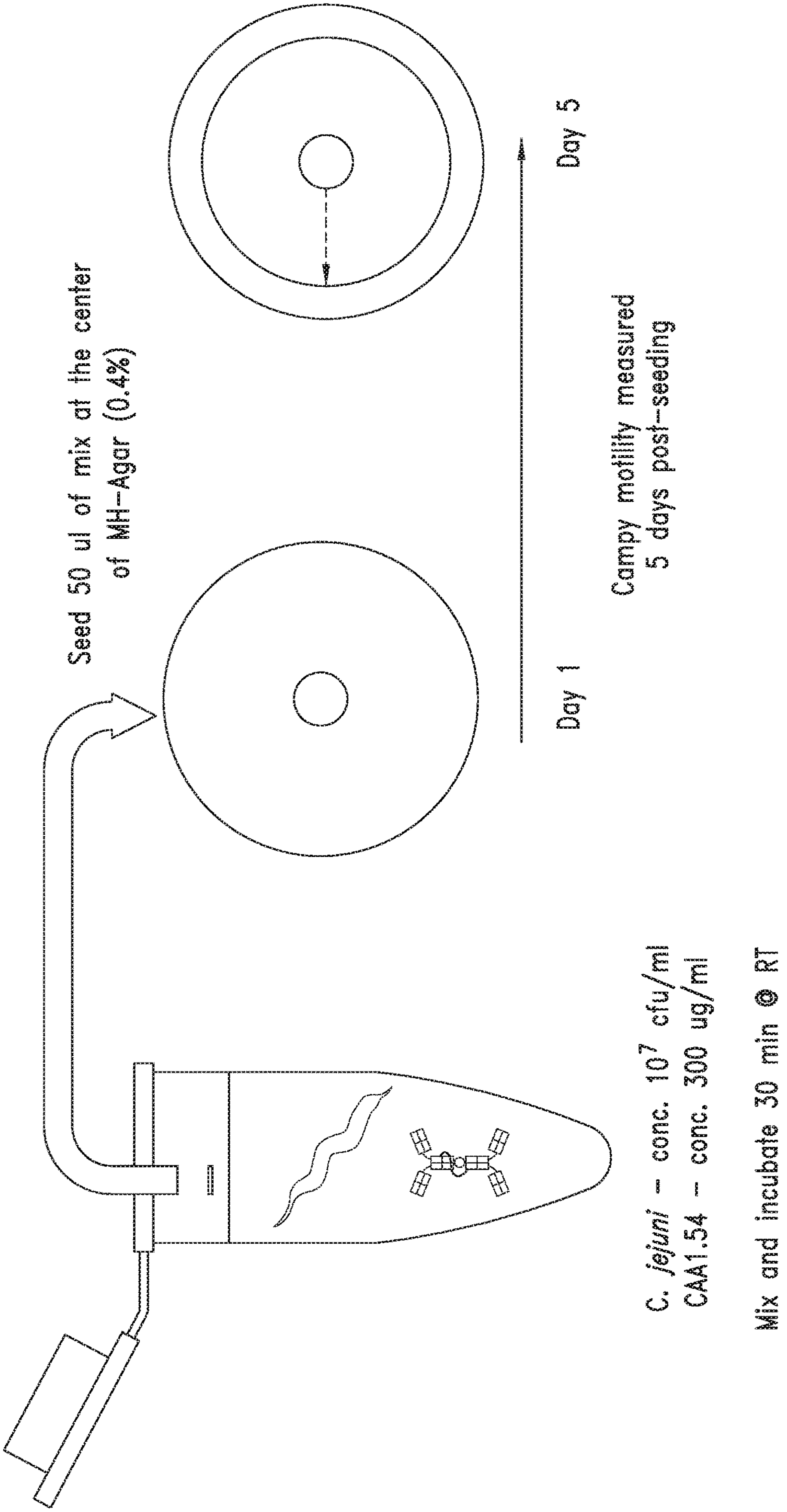
FIG. 2 shows the design of a bacterial motility assay examining the ability of Campy-reactive rSIgA of the present disclosure to limit bacteria motility.
Figure 3:
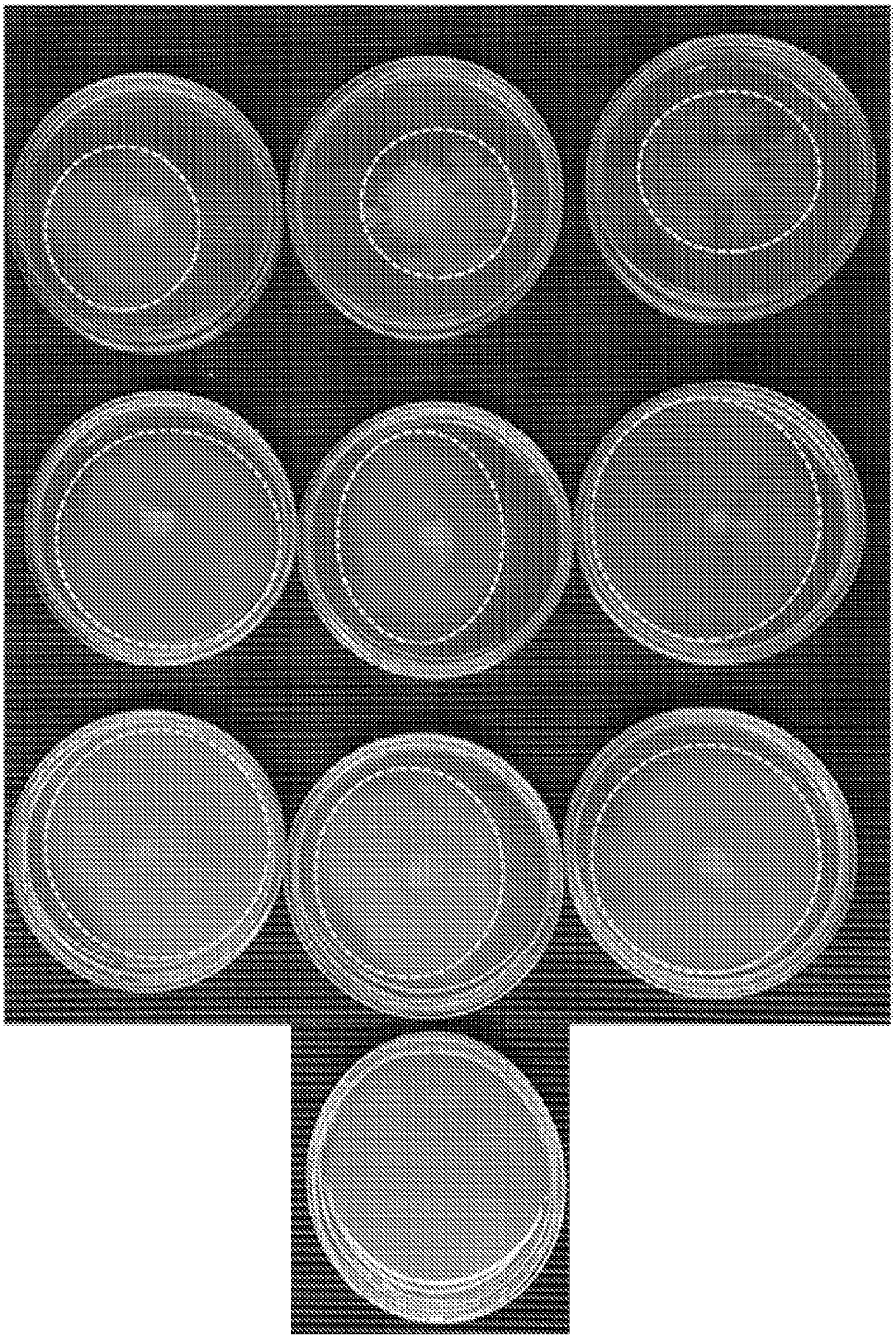
FIG. 3 shows results from the experiment shown in FIG. 2. Culture plates were as follows: (left to right)=mock infected; no mAb; ctrl rSIgA; Campy-reactive rSIgA.
Figure 4A:
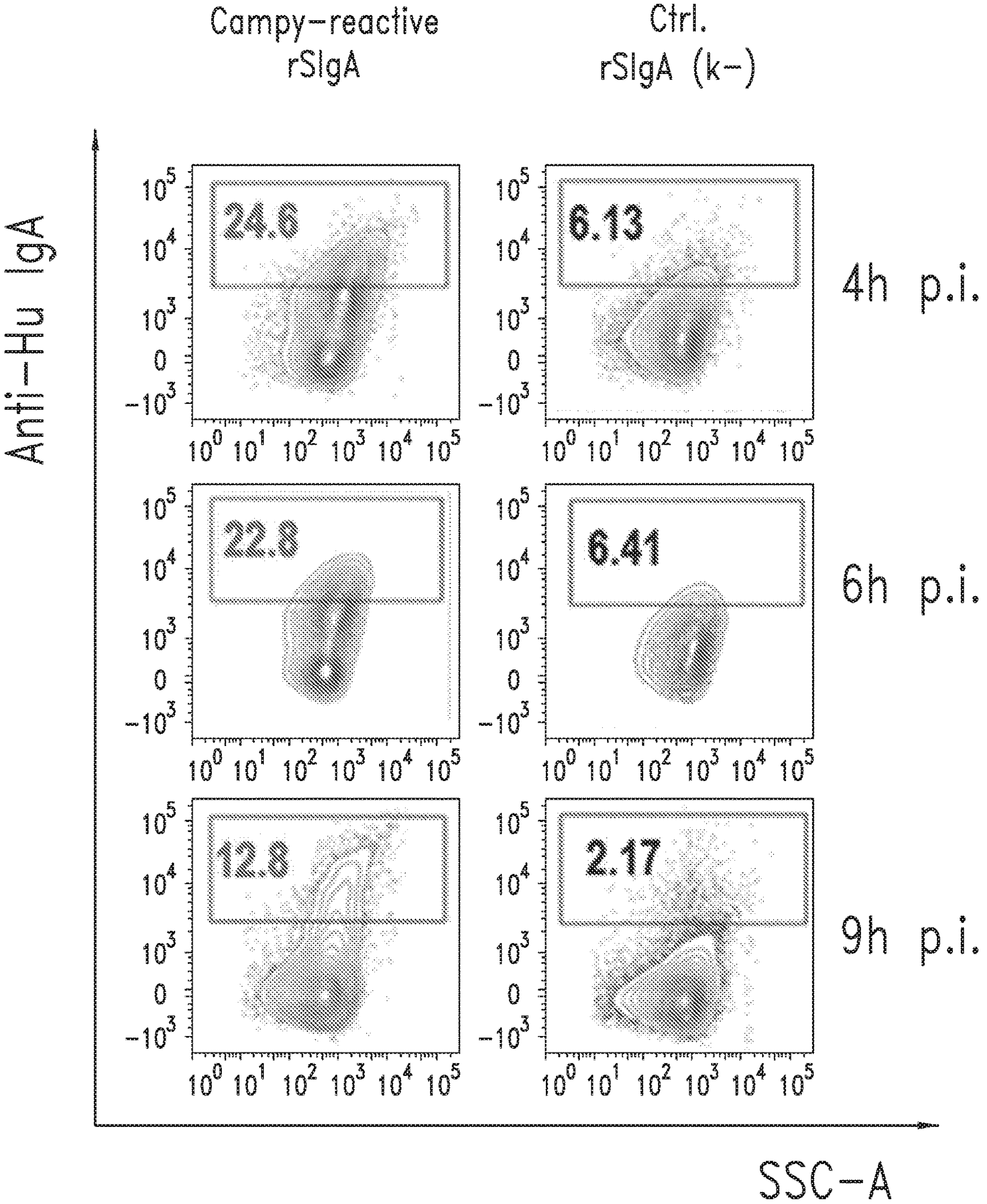
FIG. 4A shows FACS analysis of human IgA-coated bacteria in the stools of C57BL/6 mice that received a prophylactic dose of Campy-reactive rSIgA 1 h prior to infection with $10^9$ CFU of *Campylobacter jejuni* strain 81-176, followed by a second dose of rSIgA at 6 h p.i. Stool samples were taken at 4 h, 6 h, and 9 h p.i., as indicated.
Figure 4B:
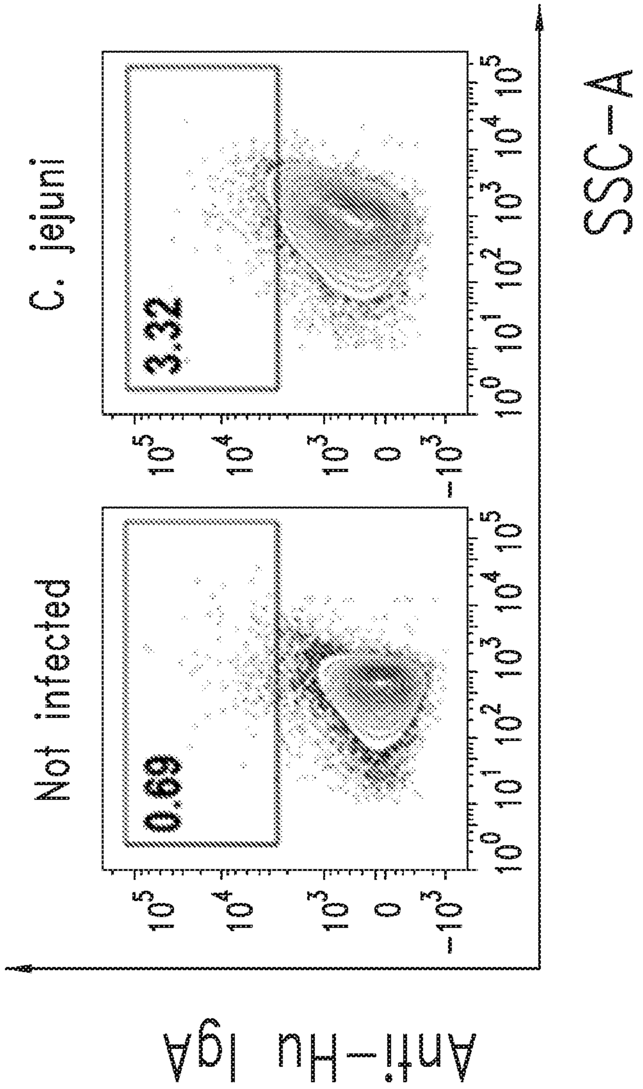
FIG. 4B shows anti-HuIgA-coated bacteria in the stools of uninfected (L) versus infected (R) mice.

A motility assay is shown schematically in Figure. 2. Results are provided in FIG. 3. Binding of CAA1 (rSIgA2) to the *Campylobacter* flagella reduced bacteria motility, a condition required to maximize infection and invasiveness. The control rSIgA2 HGN194, directed against HIV-1 gp120, was unable to curb bacteria diffusion in the motility assay, indicating that that the inhibition of bacterial motility was not resulting from "innate" cross-reactivity of the highly glycosylated structure of SIgA.

Example 5

Mouse Model of *Campylobacter* Infection

Genetically manipulated animals characterized by an exacerbated inflammatory responses to bacteria, such as SIGIRR or $IL10^{-}/^{-}$ mice, have been proposed as models to study *Campylobacter* pathogenesis (Heimesaat et al., *Front. Cell. Infect. Microbiol.,* 4:77 (2014); Stahl et al., *PLoS Pathog.,* 10:e1004264 (2014)). However, these mutations dramatically alter the murine immune system to an extent that even the presence of commensal microbes can potentially result in spontaneous enterocolitis (Mansfield et al., *Infect. Immun.,* 75:1099-1115 (2007)).

Moreover, the murine intestine has been shown to be highly resistant to *Campylobacter* due to colonization resistance and a certain level of tolerance, which limits inflammation (Bereswill et al., *PLoS One,* 6:e20953 (2011); Chang and Miller, *Infect. Immun.,* 74:5261-5271 (2006); Masanta et al., *Clin. Dev. Immunol.,* 2013:526860 (2013)). To overcome the potential effects of the resident microbiota, pretreatment via oral gavage with vancomycin, for which *Campylobacter* species are inherently resistant (Taylor and Courvalin, *Antimicrob. Agents Chemother.,* 32:1107-1112 (1988)), was adopted. Although the pretreatment allows robust bacterial colonization in the caecum, it does not appear to enhance the pathology in adult wild type mice, as minimal signs of inflammation were observed (Stahl et al., *PLoS Pathog.,* 10:e1004264 (2014)).

Figure 8A:
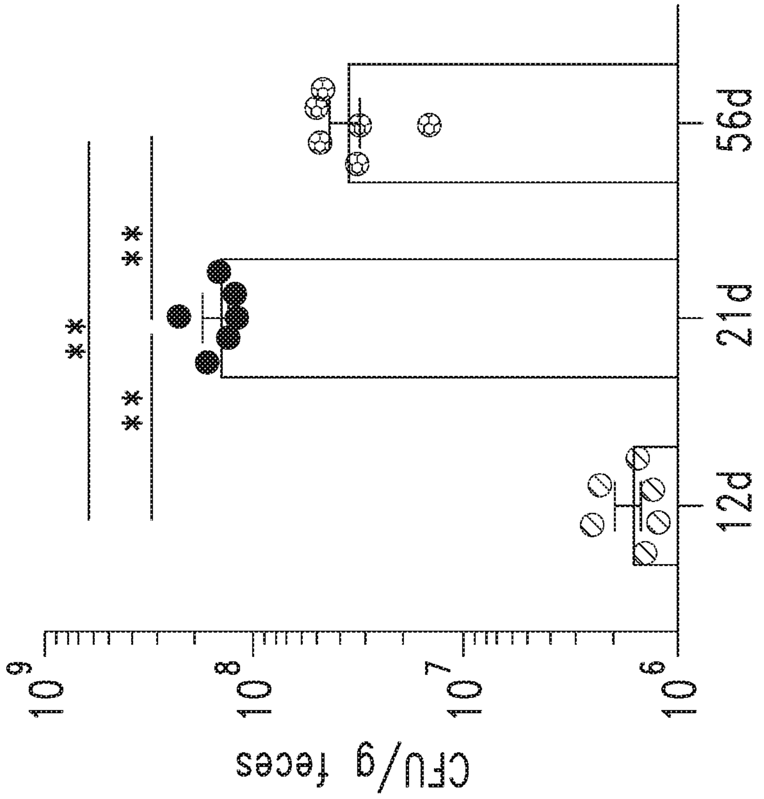
FIGS. 8A-8D show that C57BL/6 just-weaned mice are highly sensitive to *C. jejuni* infection. (A-C) C57BL/6 mice at 12, 21 and 56 days of age were orally infected with $10^8$ CFU of *C. jejuni*. (A) Bacteria loads (CFU), and (B) Lipocalin 2 (LCN2) in the stools of infected animals were determined at 6 days post-infection. (C) Representative H&E sections of the caecum from infected mice and statistical analysis of histopathological scores at 6 days post-infection. White arrows: submucosal inflammation; white asterisk: crypt hyperplasia with decreased number of goblet cells; black asterisk: epithelial desquamation; black arrows: mucosal inflammation. Scale bar: 200 (D) Quantification of fecal IgA concentrations in C57BL/6 mice at 12, 21 and 56 days of age. Dots represent individual mice and results are shown as ±SEM. Mann-Whitney test (A-D) was used. *$p<0.05$, **$p<0.01$. One representative experiment out of two is shown.
Figure 8B:
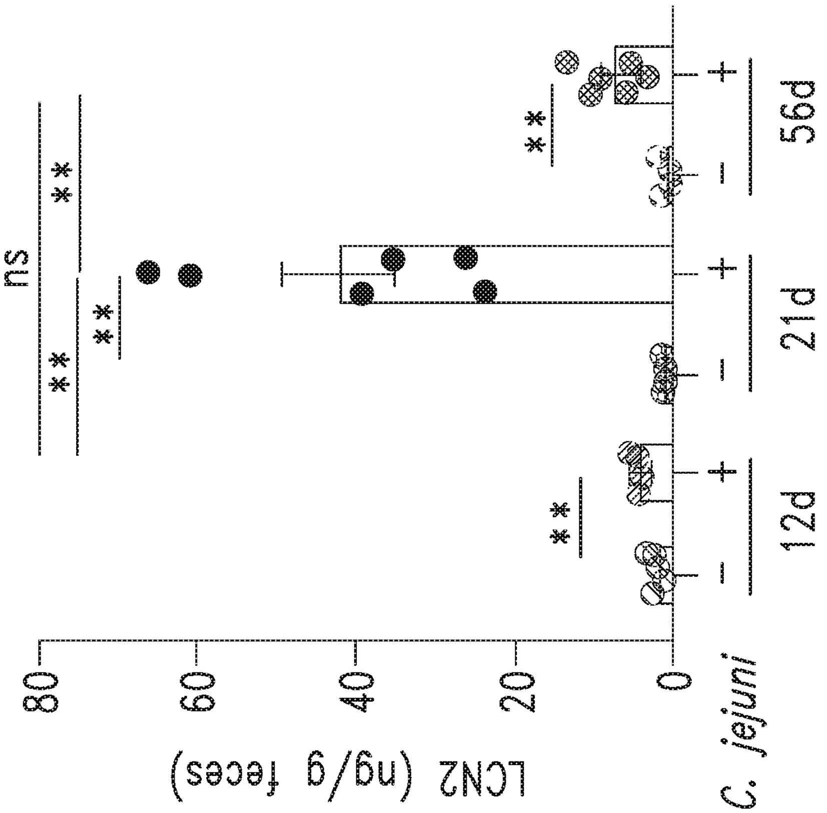
Figure 8C:
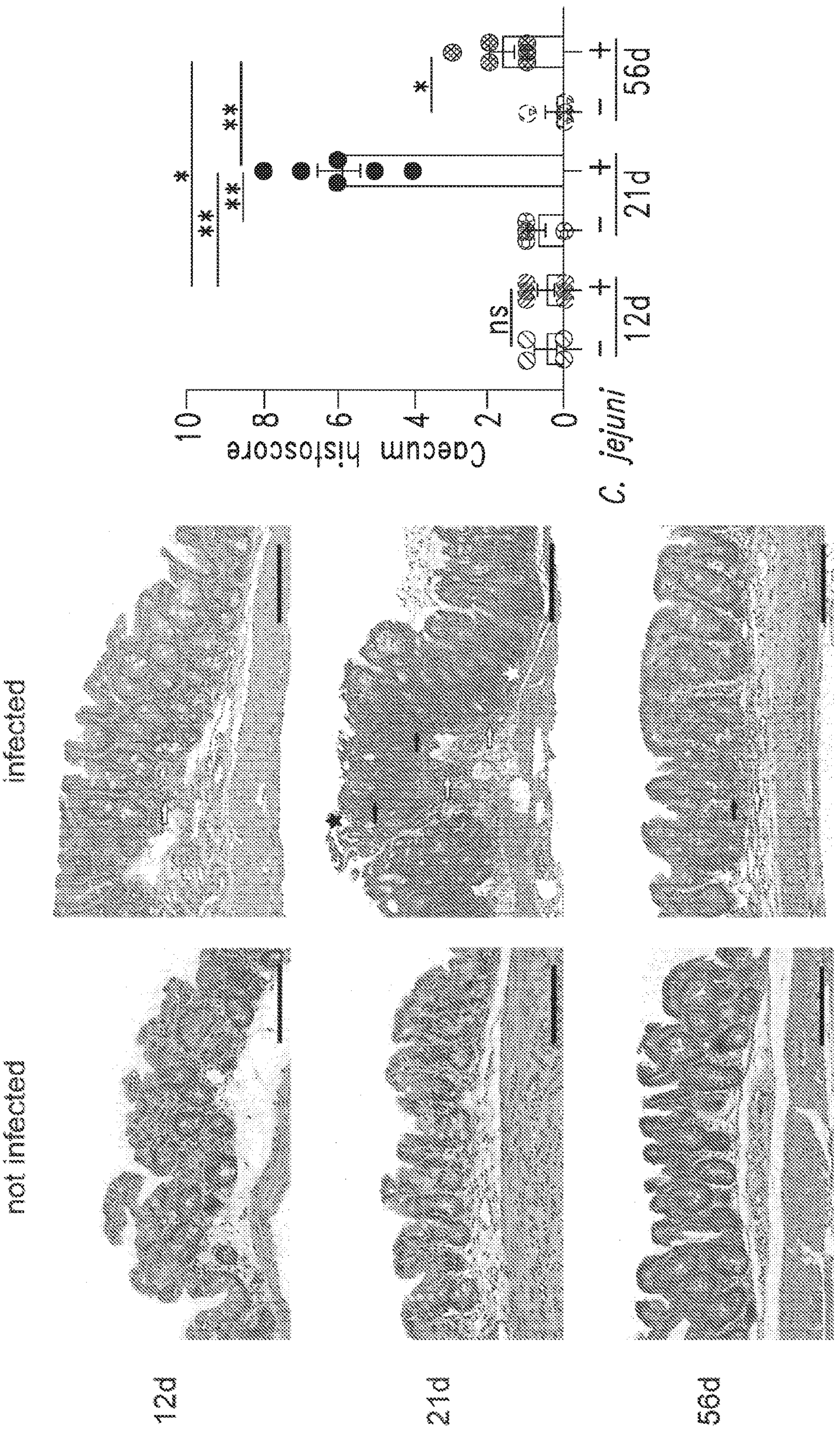

Higher susceptibility to *C. jejuni* infection of infant wild type mice in comparison to adult animals has been previously reported and linked to significant differences in the microbiota composition (Haag et al., *Eur. J. Microbiol. Immunol.* (Bp), 2:2-11 (2012)). To set up a model that could recapitulate the disease in newborn and infants under immunocompetent conditions, the sensitivity to *C. jejuni* 81-176 infection of was evaluated in pups (12 day-old), just-weaned (21 day-old) and adult (56 day-old) C57BL/6 mice. Animals were pre-treated with vancomycin via oral gavage to deplete the murine microbiota before being infected with *C. jejuni* 81-176 at $10^9$ CFU/mouse. *Campylobacter* isolation from stools at 6 days post-infection revealed almost 2-log-higher shedding from 21-day-old animals than from 12 and 56-day-old mice (FIG. 8A). In-line with these results, just-weaned mice displayed significantly higher intestinal inflammation as measured by the levels of lipocalin-2 in the stools and histological score values in the caecum in comparison to pups and adult mice (FIGS. 8B-8C).

Figure 8D:
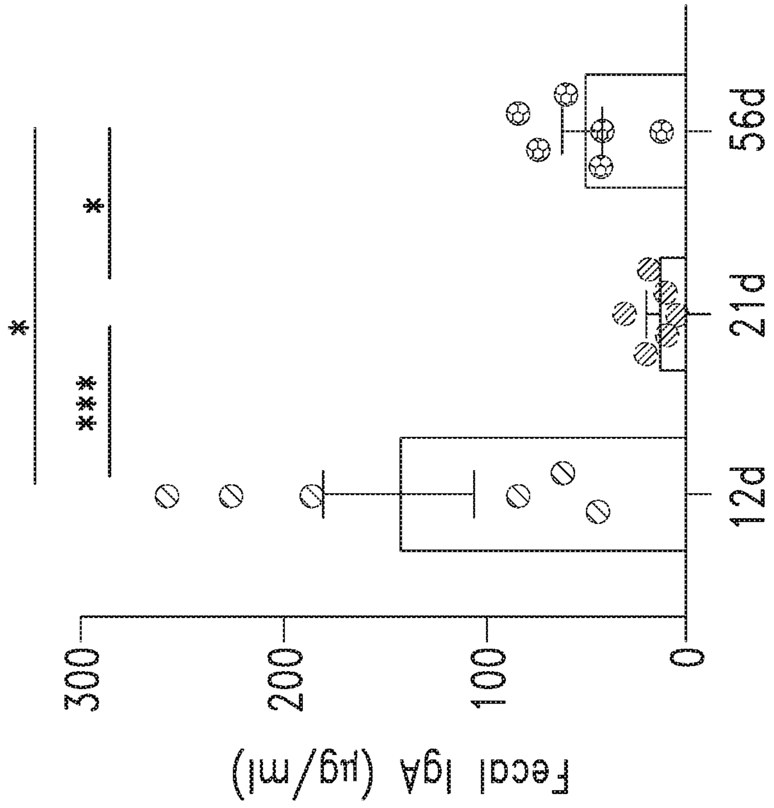

Since the antibiotic pre-treatment is expected to provide comparable ecological niches for infection in the different animals, other factors could account for the different sensitivity to *C. jejuni* infection displayed by the three groups of mice. Analysis of murine IgA in the stools of 12, 21 and 56-day-old mice revealed different concentrations among the groups (FIG. 8D). Notably, just-weaned mice presented negligible levels of IgA in the stools in comparison to both pups and adult mice. Without wishing to be bound by theory, this observation may be consistent with the transition between the exogenous supply of maternal antibodies provided with milk (12 days-old mice) and the beginning of the endogenous production that is established in adult animals (56 days-old mice). Therefore, a factor in the susceptibility of just-weaned mice to *C. jejuni* infection may be a lower concentration of secretory IgA due to the relative immaturity of intestinal immune system and the depletion of maternal antibodies in these animals. Based on these data, just-weaned mice were selected as an immune competent mouse model to study the prophylactic activity of FliD-reactive mAbs.

Off-target binding by CAA1 and CCG4 to the murine microbiota could result in reduced mAb availability and thus, reduced activity against pathogens in a prophylactic setting. To investigate this, potential cross-reactivity of the rSIgAs with the microbiota of just-weaned mice was evaluated. Stools from animals orally infected with *C. jejuni, C. coli* or PBS (mock infected) were collected 24 hours post-infection and incubated with the two FliD-reactive mAbs and the control rSIgA HGN194. Analysis of human-IgA coated bacteria from stools of mock and infected animals revealed that both *Campylobacter*-reactive rSIgA were able to recognize and bind the most common species associated with severe infections, displaying limited cross-reactivity with the murine microbiota (FIG. 14A).

To set-up the conditions for testing the prophylactic efficacy of the antibodies, the pharmacokinetics of orally administered SIgA in different gastrointestinal tracts of just weaned mice were evaluated. The *Campylobacter*-irrelevant HGN194 rSIgA2, which displayed no cross-reactivity with the murine microbiota (FIG. 14A), was administered as a single oral gavage of 150 ug in PBS (≈15 mg/Kg) and its concentration in the different intestinal sub-compartments was measured at 2, 4 and 8 h post-administration (FIG. 14B). HGN194 rSIgA concentration in the caecum was maintained almost constant within the first 4 hours post-administration and then tended to dramatically decrease by 8 hours (FIG. 14B). The human antibody was not detectable at 12- or 24-hours post-administration (data not shown).

Example 6

Prophylactic Effect of Orally Administered rSIgA

Figure 5A:
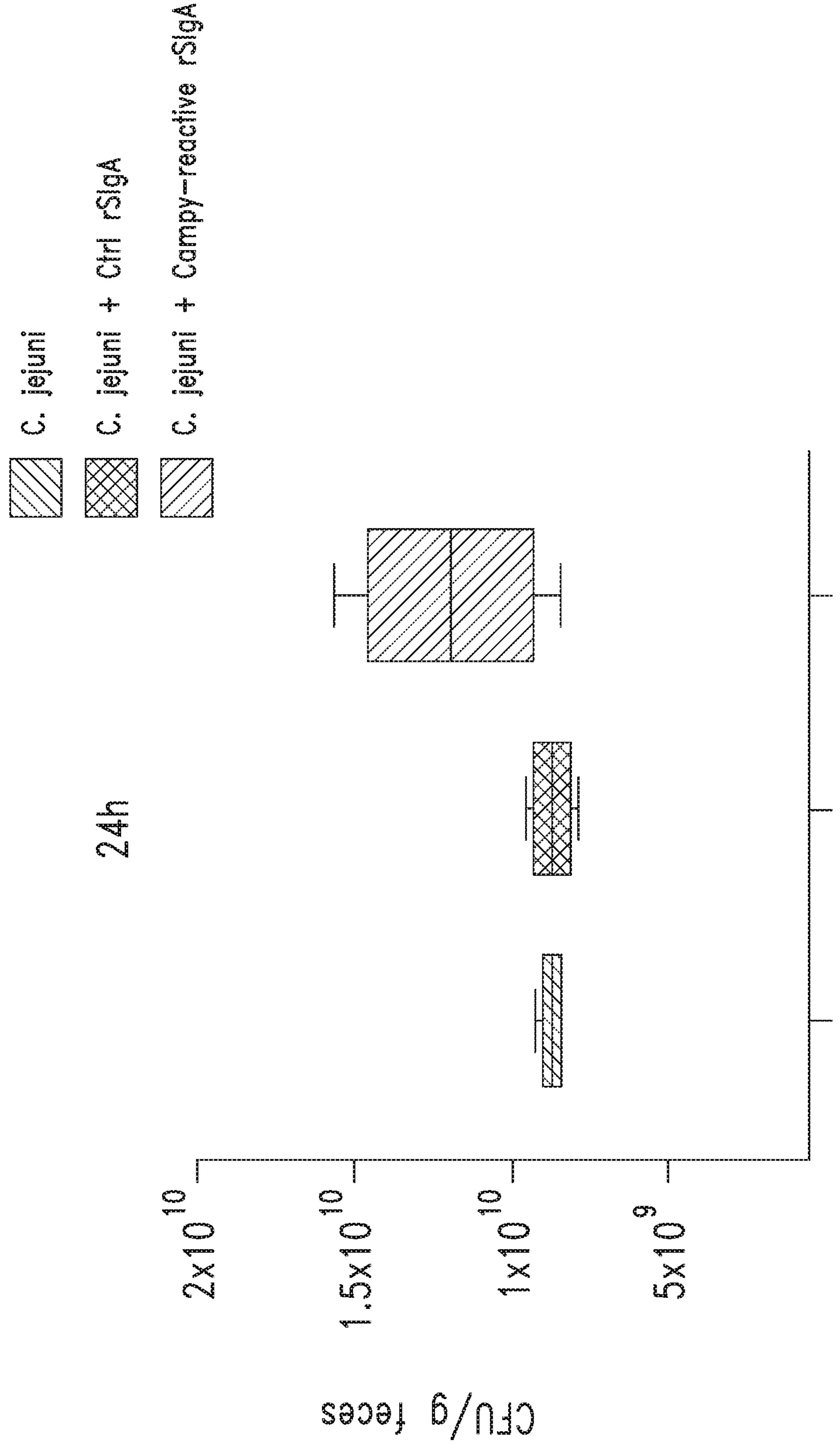
FIGS. 5A and 5B show *Campylobacter* shedding in treated and untreated animals at (A) 24 hours and (B) 72 hours post-infection.
Figure 5B:
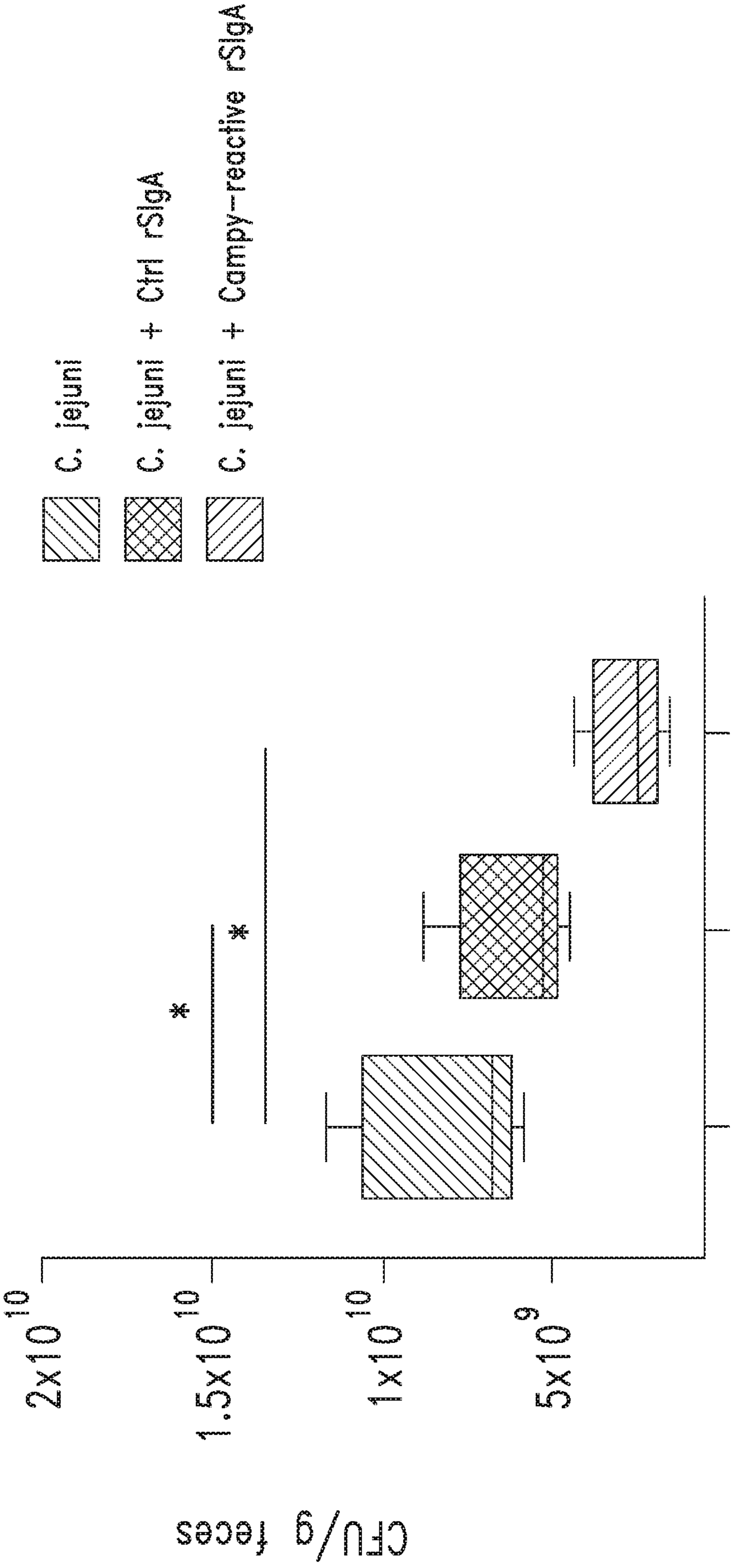
Figure 9A:
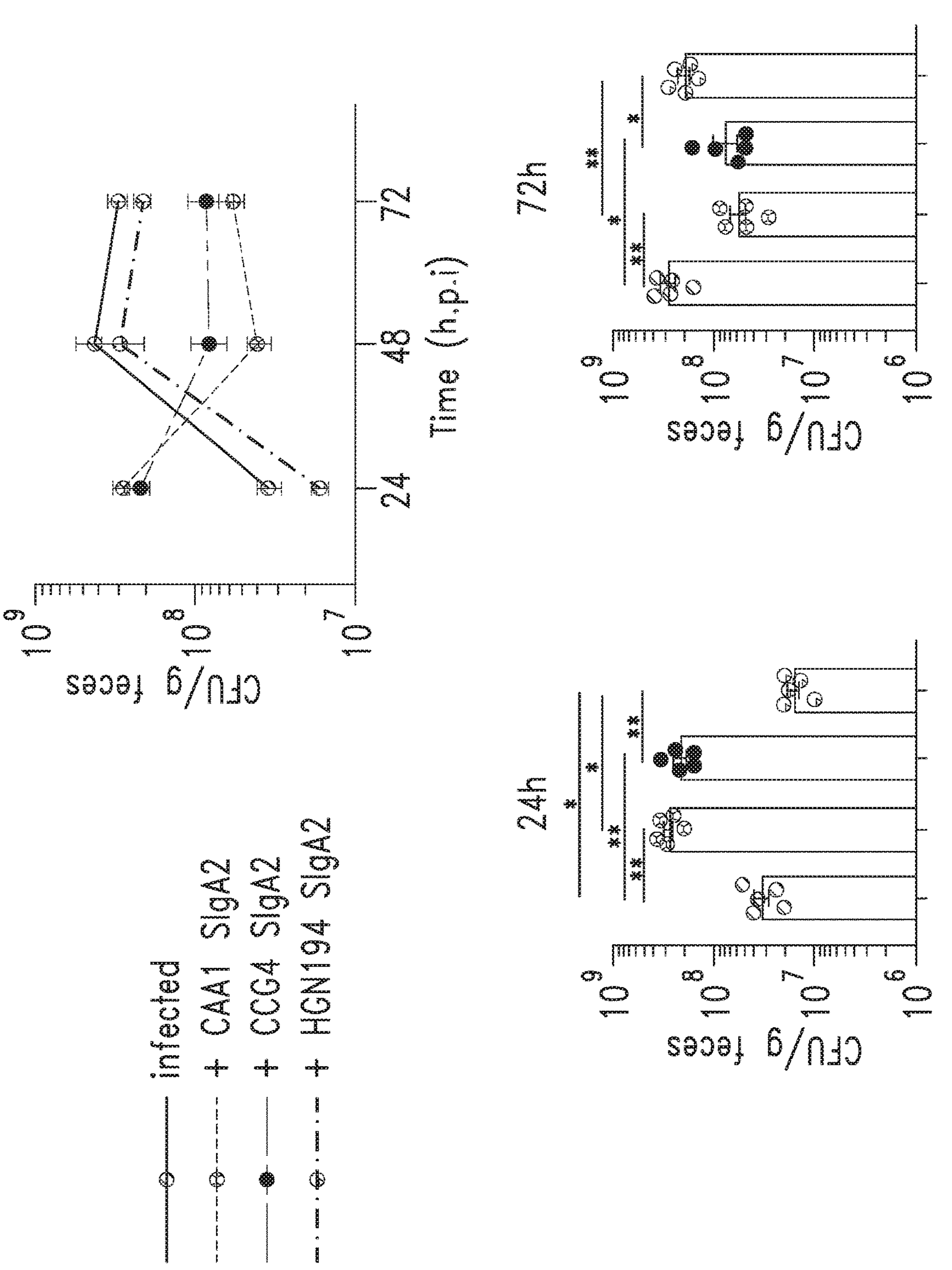
FIGS. 9A-9D show prophylactic activity of orally administered CAA1 and CCG4 rSIgA2 against *C. jejuni* infection in just-weaned mice. (A-D) Two hours prior to infection with $10^8$ cfu of *C. jejuni,* 21-day-old C57BL/6 mice were orally administered by gavage with 200 μg of the indicated mAbs in PBS. (A) Fecal bacterial loads (CFU) at 24 h, 48 h and 72 h post *C. jejuni* infection were determined. (B) Lipocalin-2 (LCN) levels in the stools, (C) statistical analysis of polymorphonucleated (PMN) cell infiltrates gated as $Gr1^+CD11b^+$, and (D) histopathological score in the caecum were determined at 72 h post infection in the different treatment conditions. Dots represent individual mice and results are shown as ±SEM. Mann-Whitney test (A-D) was used. *$p<0.05$, $p<0.01$, *$p<0.001$. One representative experiment out of at least two is shown.

Just-weaned animals (21d) were treated with vanocmycin and then administered a single oral gavage of 200 μg/mouse of rSIgA2 CAA1, CCG4, HGN194 or PBS two hours before oral infection with $10^8$ CFU/mouse of *C. jejuni* 81-176. Treated animals and the corresponding control groups were monitored for 72 hours, during which the severity of infection and degree of inflammation were recorded. Analysis of the stools from treated mice revealed a trend characterized by higher *Campylobacter* shedding at 24 hours post-infection followed by a significant decrease over time. Conversely, untreated and HGN194-treated groups presented lower shedding at early time points followed by a consistent CFU increase at 48 hours post-infection (FIG. 9A). FIGS. 5A and 5B show data from a separate experiment in which mice were administered 200 μg mAb once before infection, and twice after infection, with $10^9$ CFU/mouse of *C. jejuni* 81-176.

Figure 6:
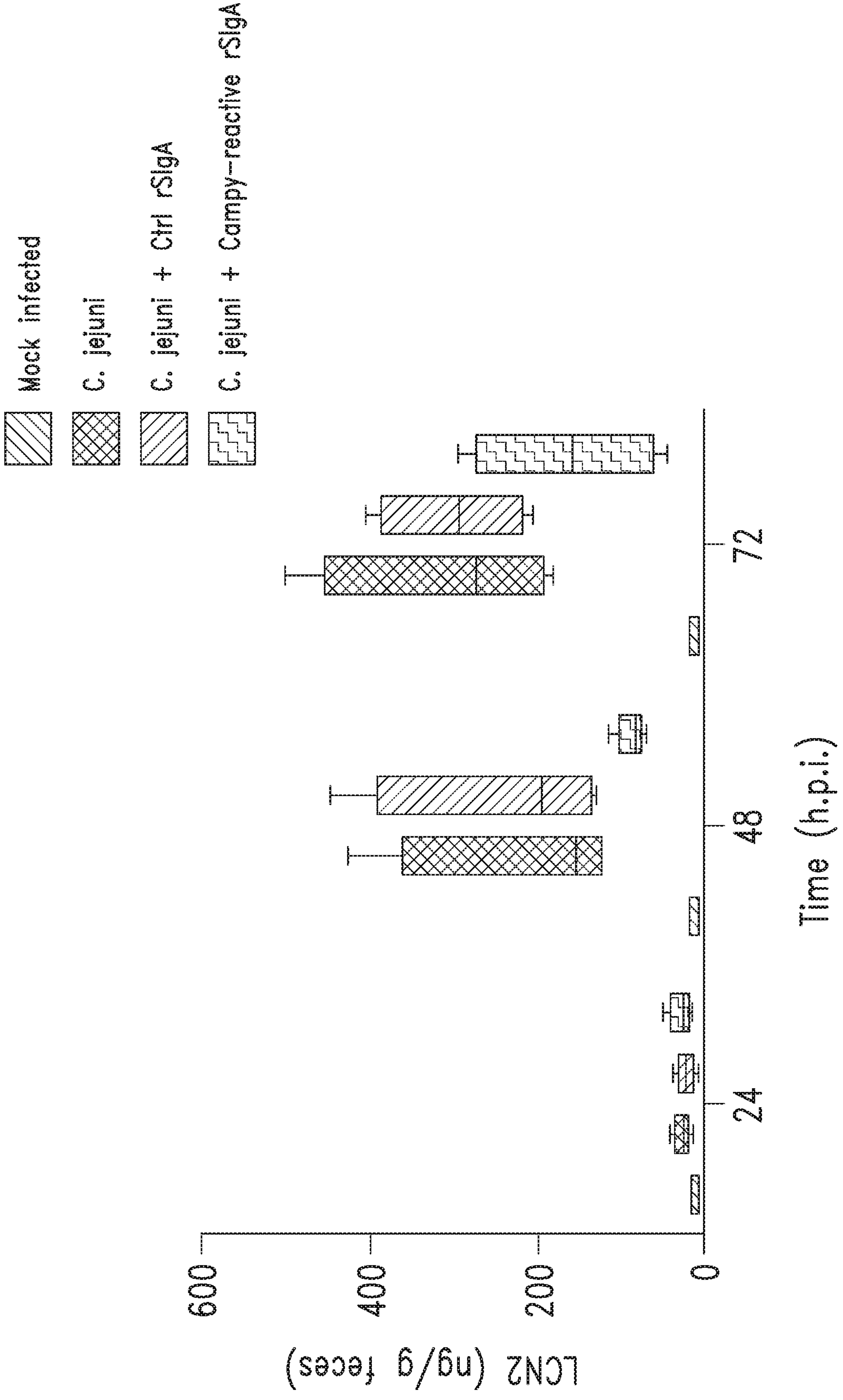
FIG. 6 shows ELISA quantification of Lipocalin-2 at 24, 48 and 72 hours post-infection in animal stools.
Figure 9B:
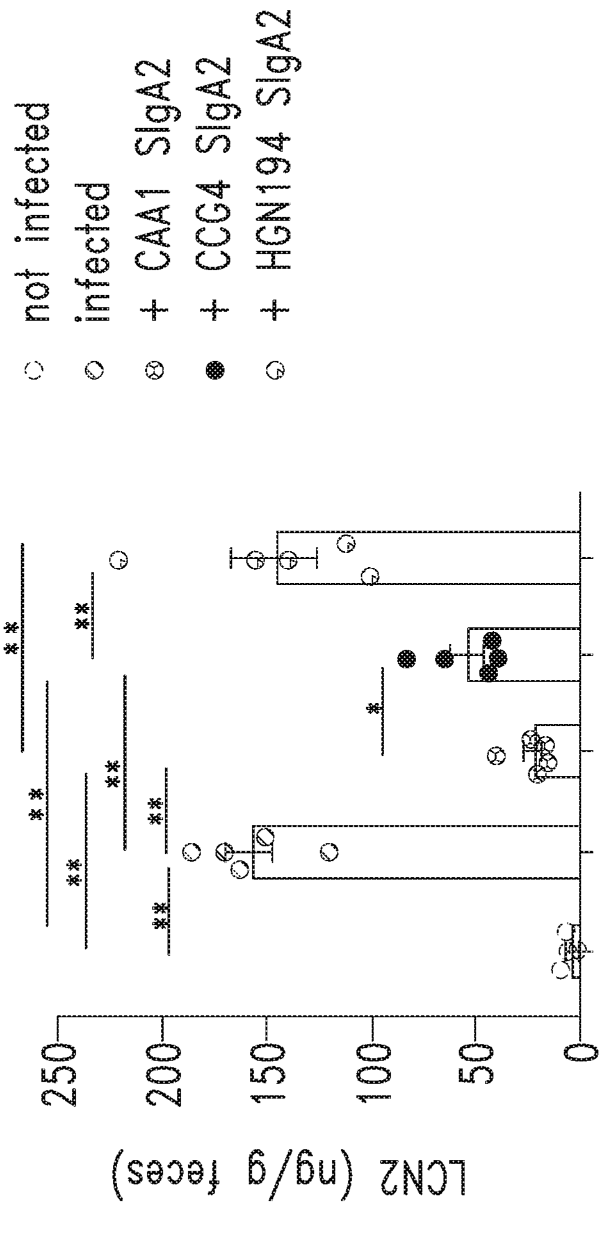

These results suggest that CAA1 and CCG4 may prevent or reduce the ability of the pathogen to adhere to the surface of the mucosal epithelium, thus facilitating the clearance of bacteria via peristalsis or mucocilliary activity at early stages post-infection. This hypothesis was further supported by significantly lower levels of lipocalin-2, a marker of intestinal inflammation linked to epithelial damage and neutrophil infiltration, recorded at 72 hours post-infection in the stools of CAA1 and CCG4 treated animals in comparison to the control groups (infected/non-treated and infected/HGN194 treated groups) (FIG. 9B). FIG. 6 shows data from a separate experiment in which mice were administered 200 μg mAb once before infection, and twice after infection, with $10^9$ CFU/mouse of *C. jejuni* 81-176.

Figure 9C:
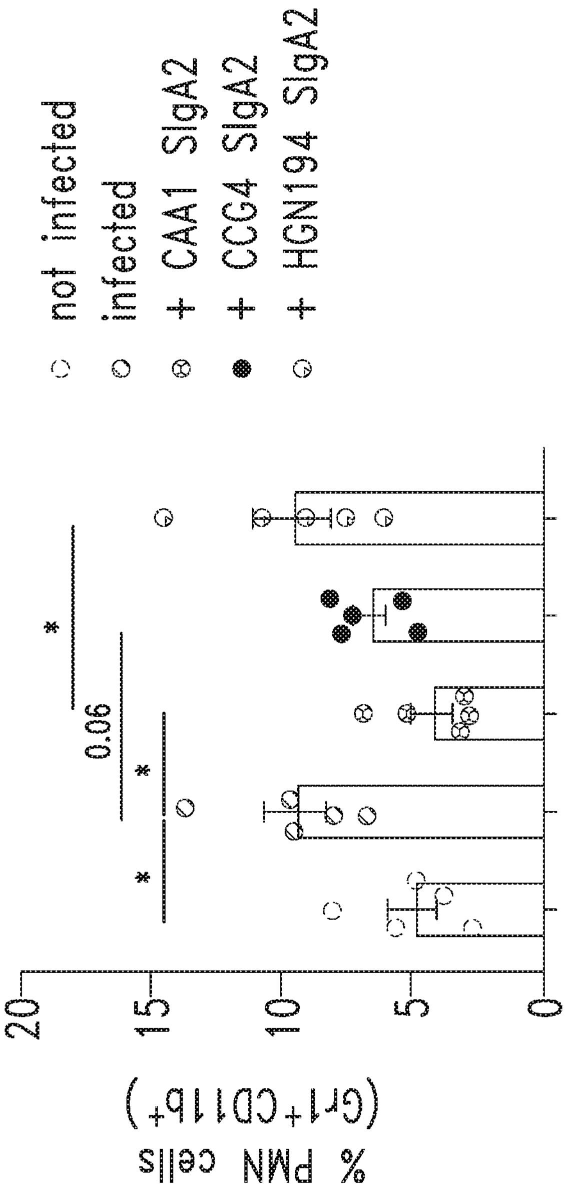
Figure 9D:
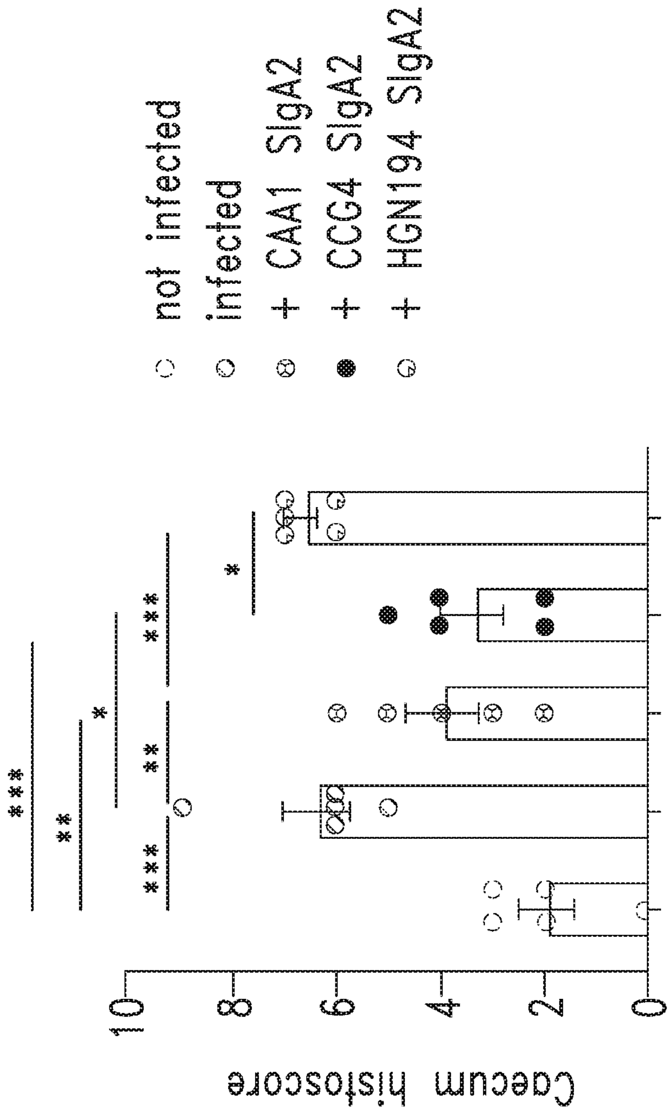
Figure 15A:
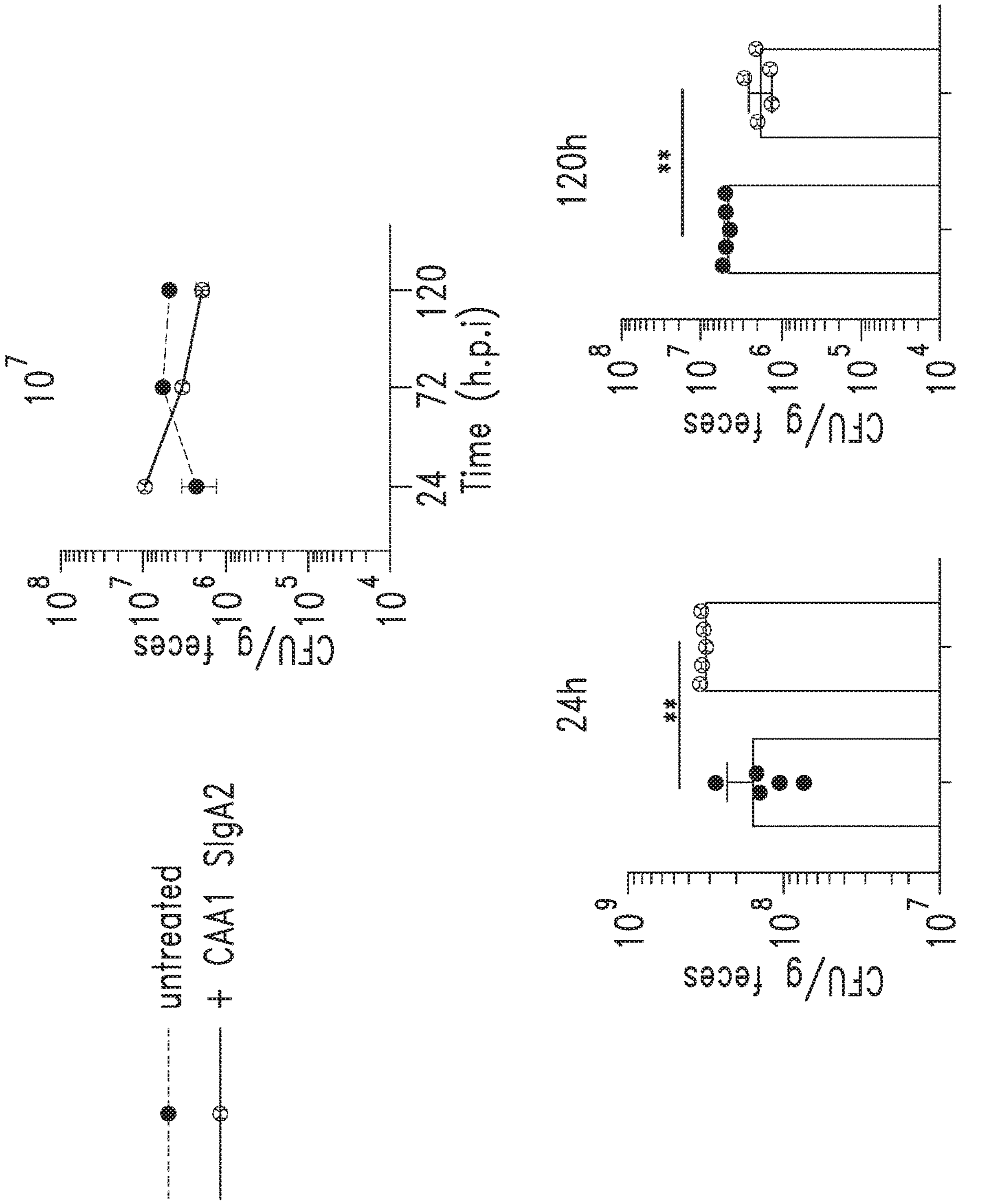
Figure 15B:
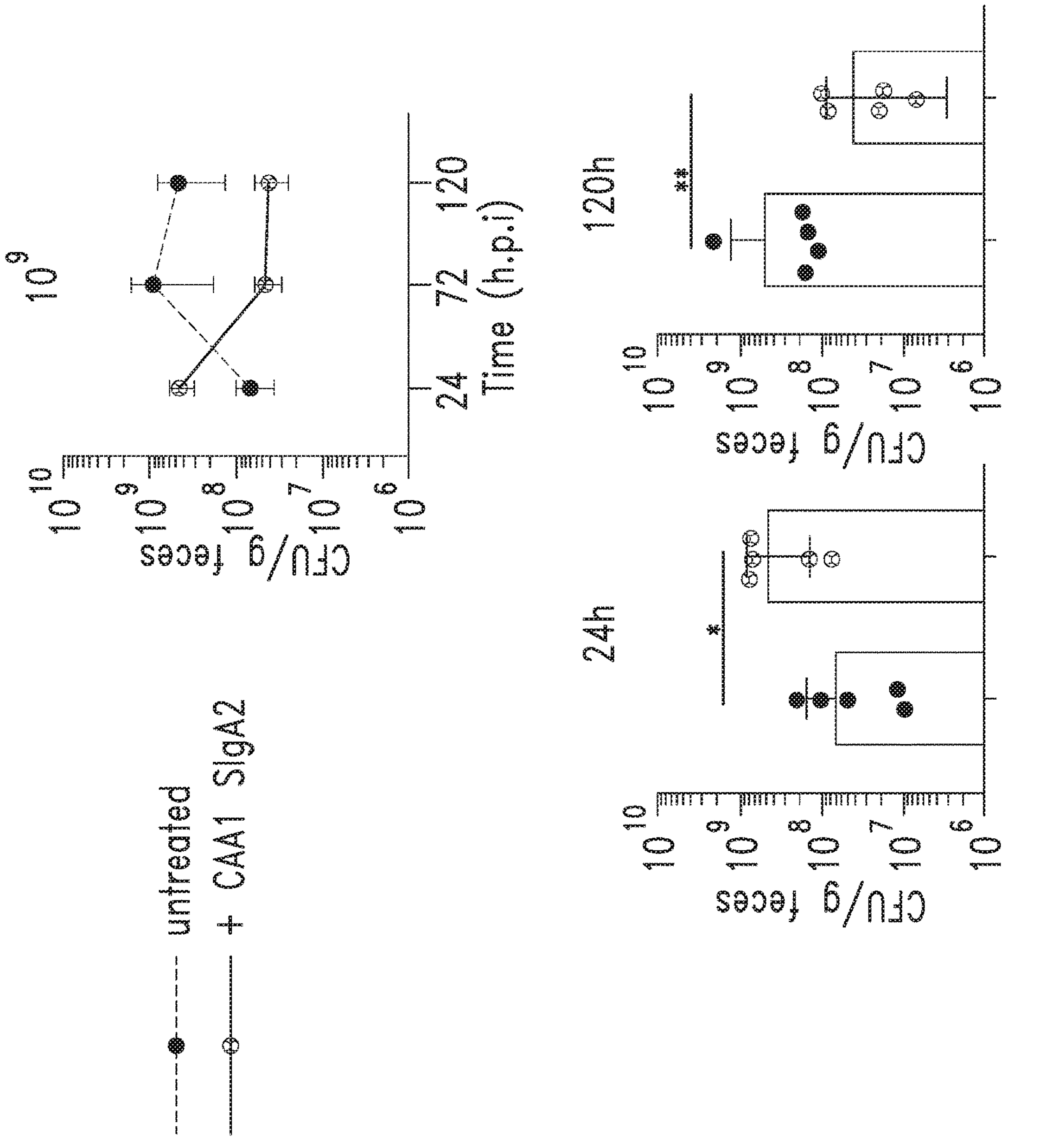
Figure 15C:
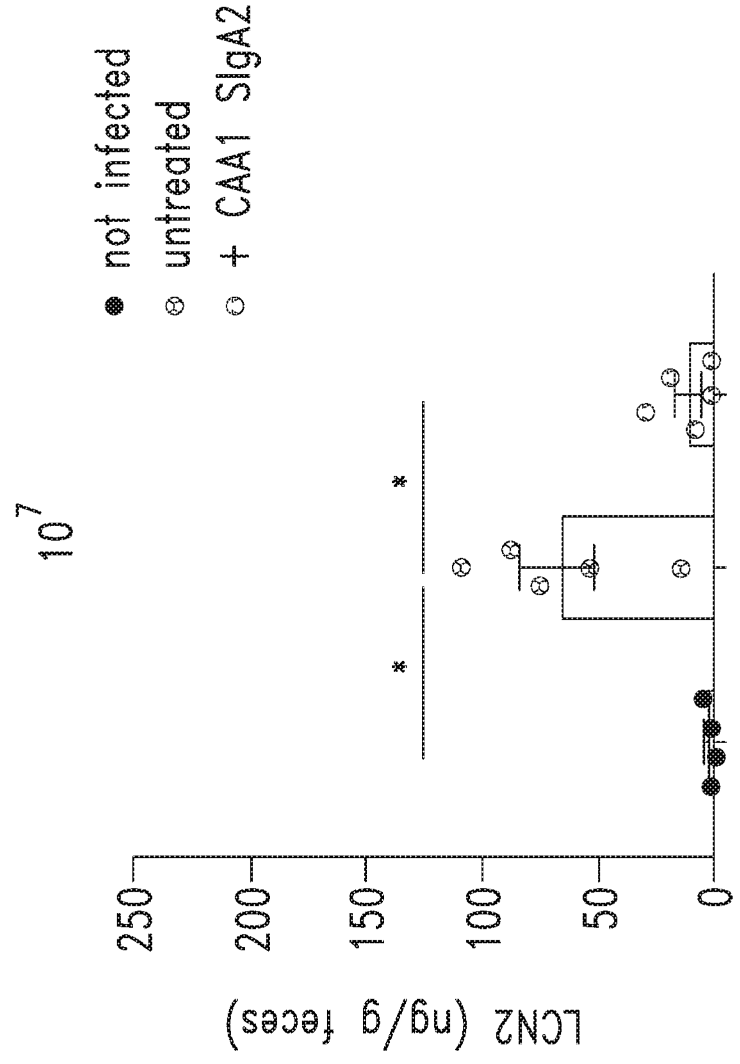
Figure 15D:
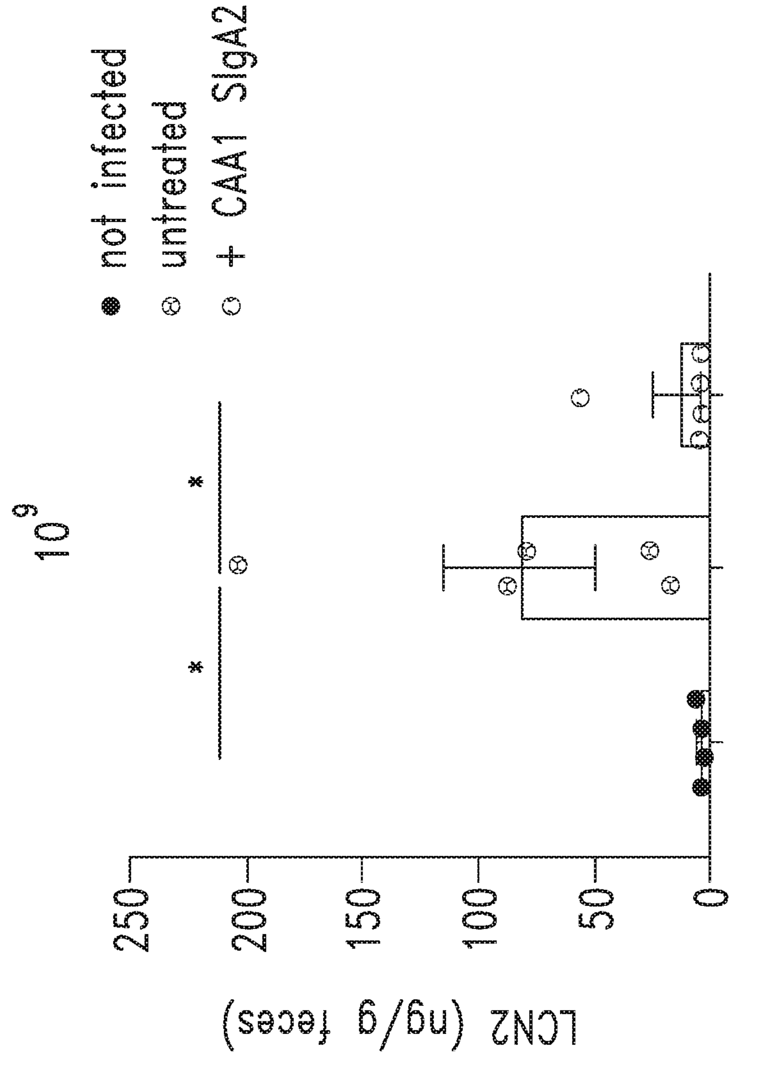

Similar findings were observed in animals administered with higher or lower *Campylobacter* inoculum ($10^7$ or $10^9$ CFU/mouse; FIGS. 15A, 15B). In addition, animals treated with a single administration of FliD-reactive mAbs presented levels of PMN cells infiltration and histological score values in the caecum that were comparable with non-infected mice and significantly lower than the HGN194-treated group, hence supporting in vivo efficacy that is not driven by the “innate activity” (Kaetzel, *Immunol. Rev.,* 206:83-99 (2005); Phalipon et al., *Immunity,* 17:107-115 (2002)), associated with the highly glycosylated SIgA (FIGS. 9C, 9D).

These results indicate that FliD-specific antibodies of the present disclosure in rSIgA2 format protect against *Campylobacter* infection and inflammation following oral delivery by accelerating bacterial clearance at early stages after infection.

Example 7

IgA Isotype Switch does not Affect CAA1 Prophylactic Activity

Since IgA1 and IgA2 can have differences in Fab reach, flexibility, and glycosylation that might affect the cross-linking ability and/or persistence of the polymeric Ig in the intestine, the following experiments were performed to determine whether the two IgA isotypes may exert different prophylactic activities in the herein-described immunocompetent mouse model of *Campylobacter* infection.

Figure 16A:
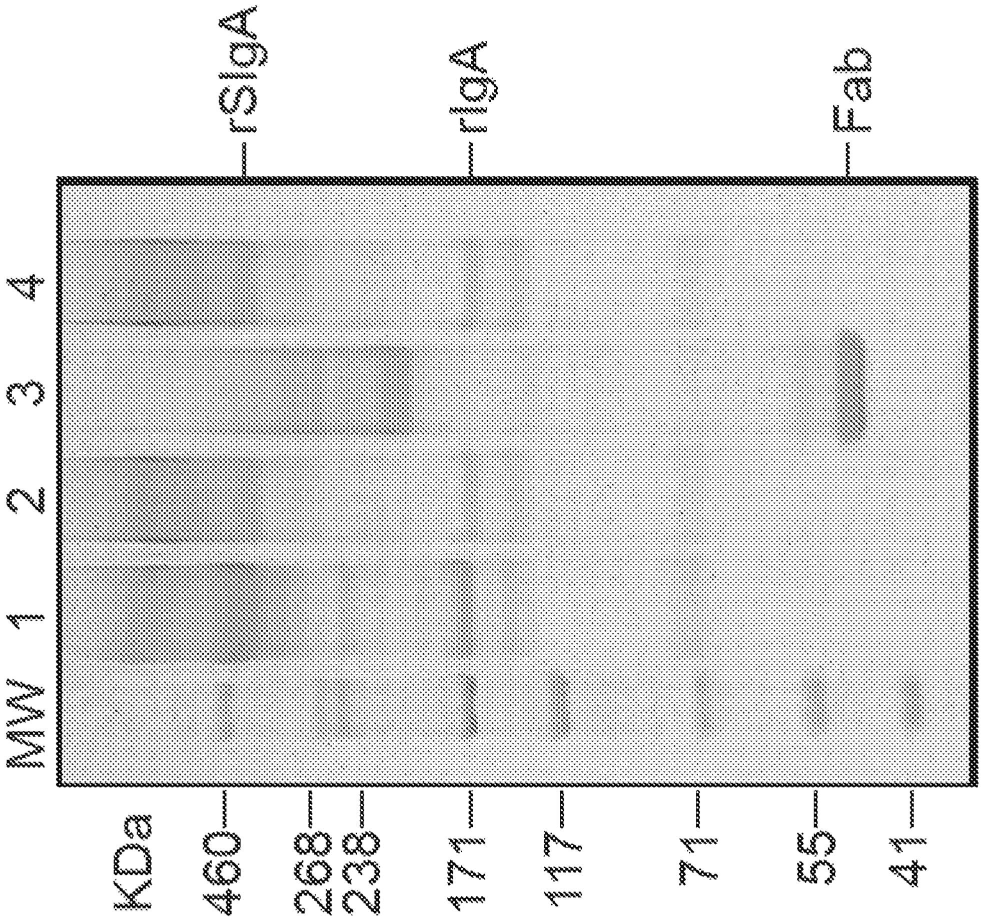
Figure 16B:
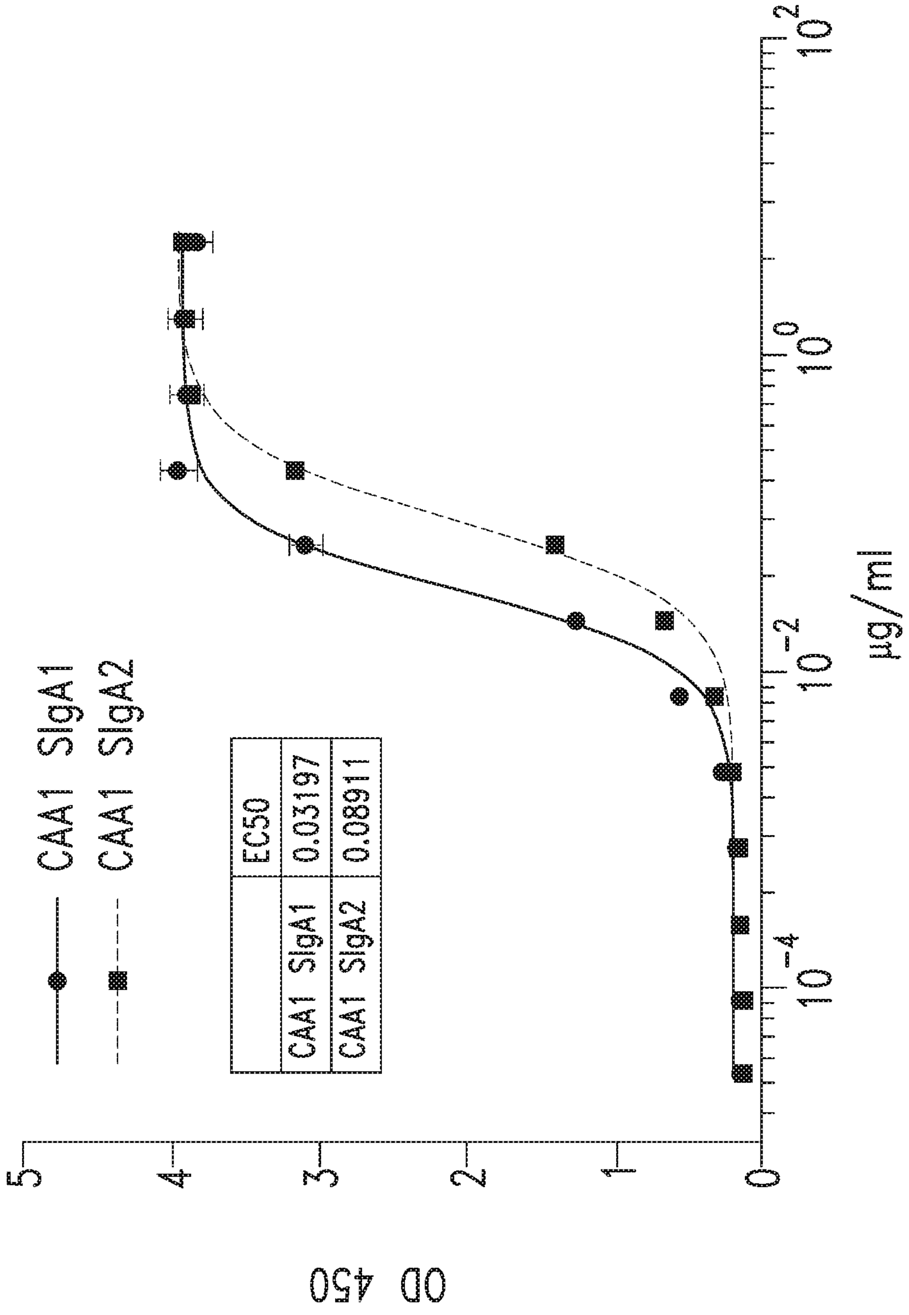
Figure 16C:
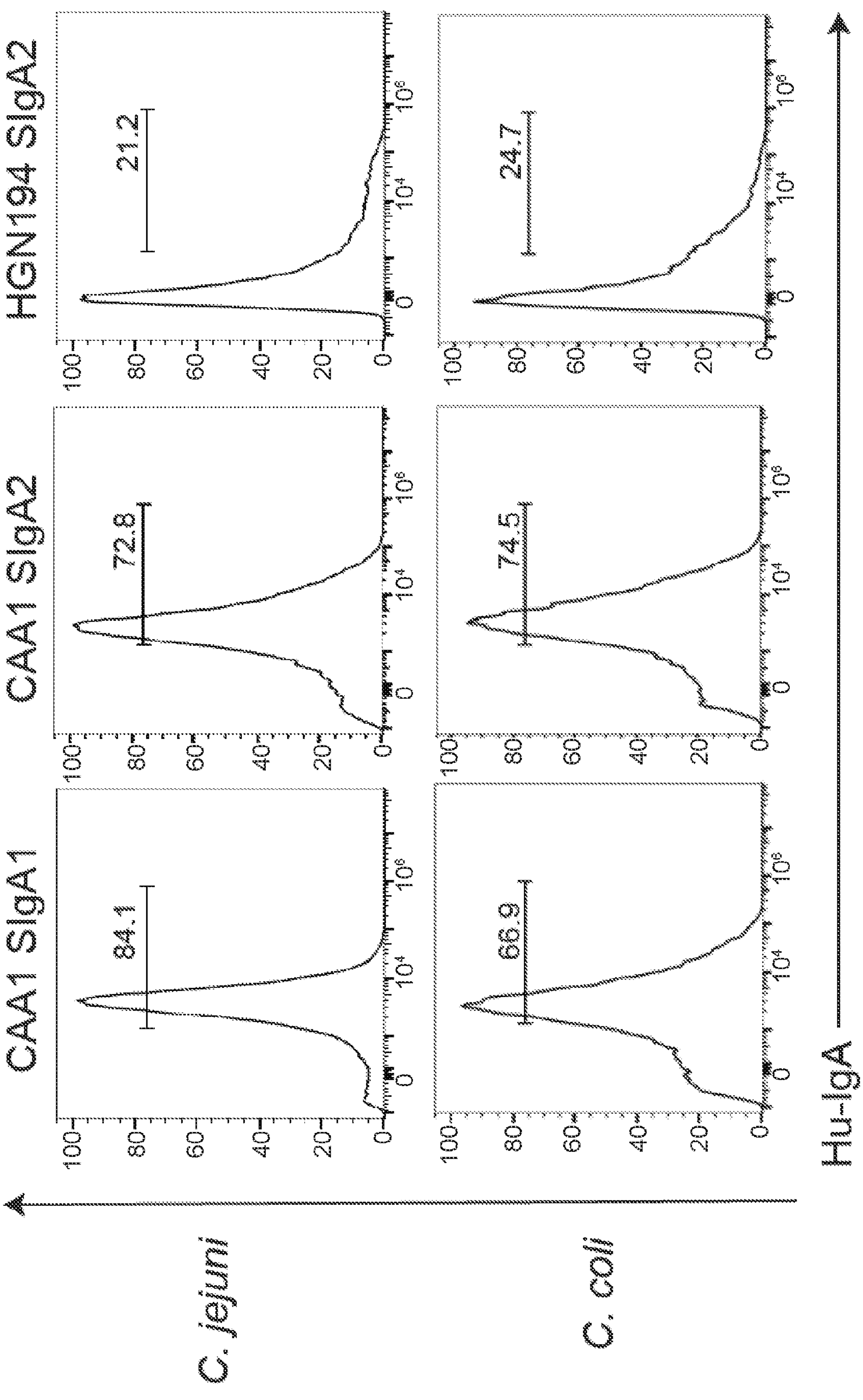
Figure 16D:
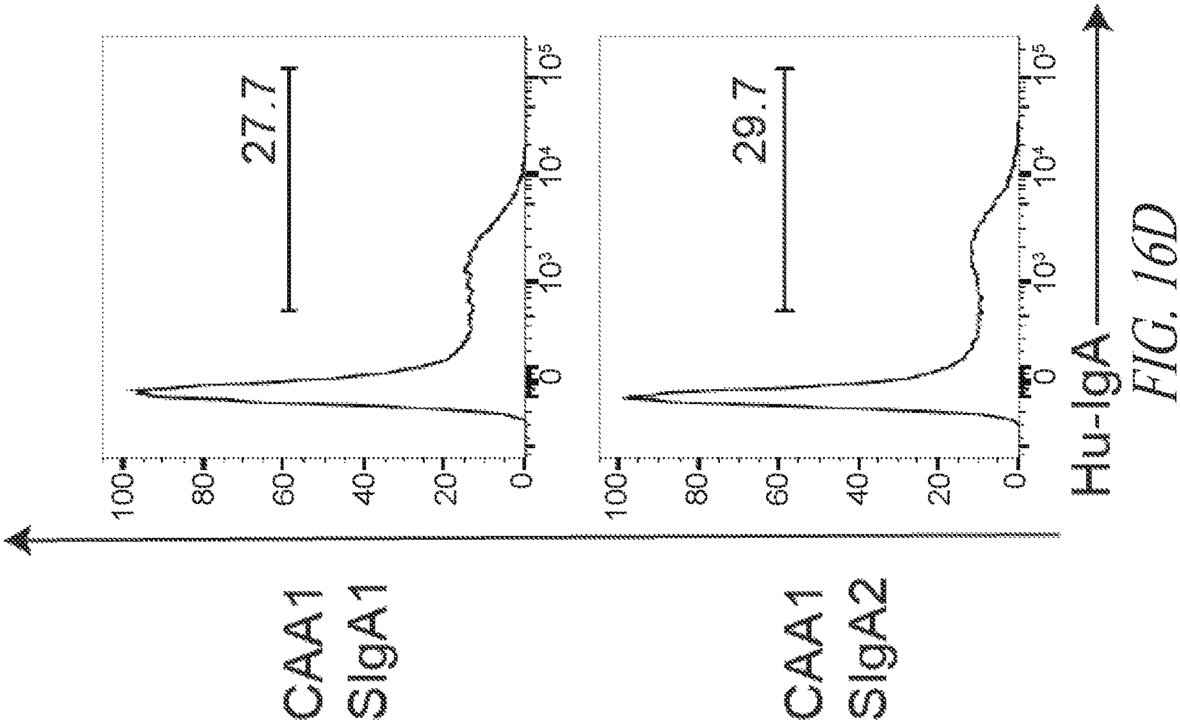

FliD-reactive CAA1 was recombinantly produced as SIgA1 and SIgA2. Proper assembly of the two subclasses was confirmed by analytical methods and by digestion with IgA1 proteases from *Neisseria* gonhorrehoeae (FIG. 16A). CAA1 SIgA1 and SIgA2 displayed comparable binding to FliD (FIG. 16B) and no significant differences in reactivity to *Campylobacter* species in vitro or with murine microbiota ex vivo were observed between the two formats (FIGS. 16C, 16D).

Figure 10A:
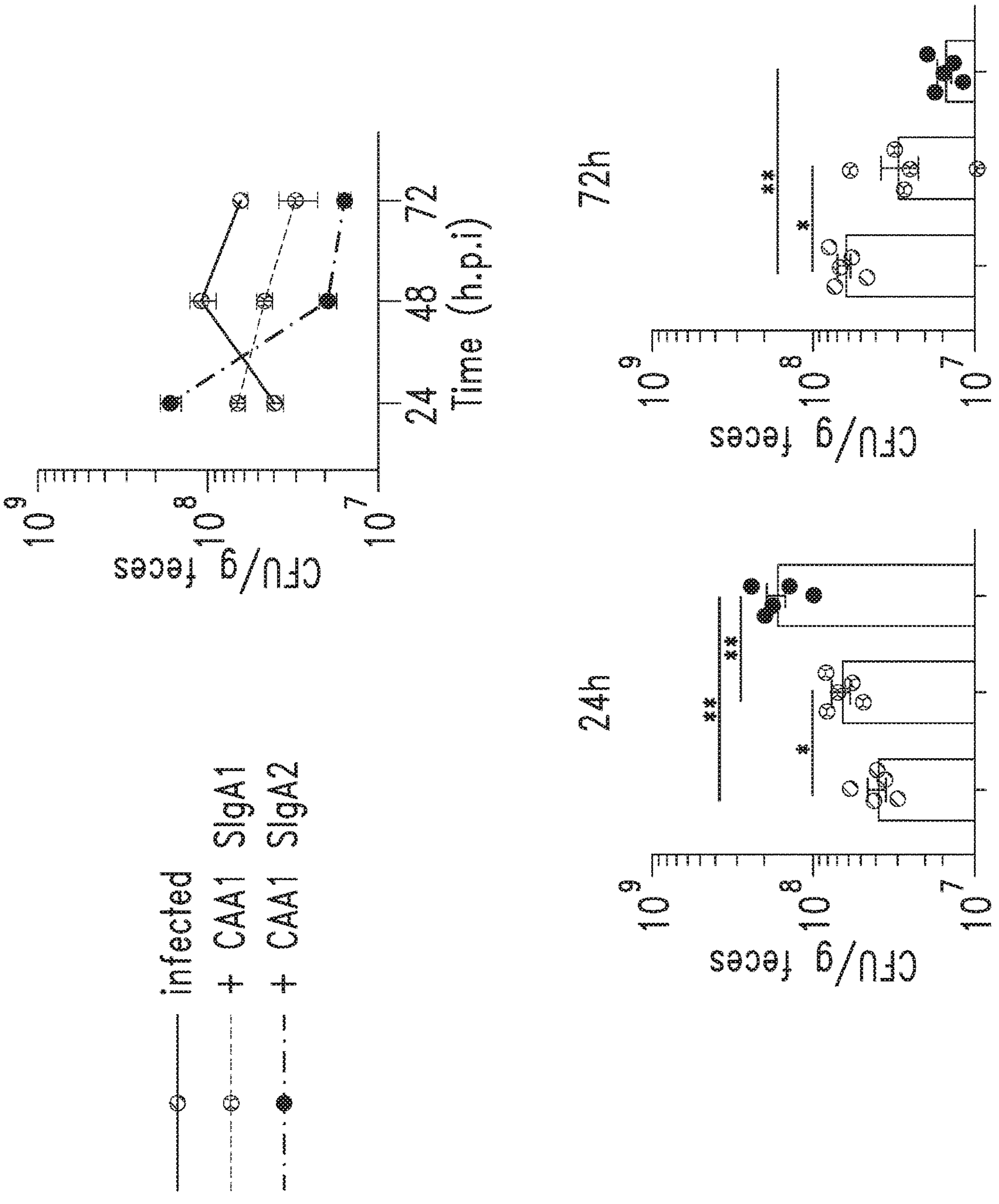
FIGS. 10A-10D show that CAA1 SIgA1 and SIgA2 have similar prophylactic activity against *C. jejuni* infection. (A-D) Two hours prior to infection with $10^8$ CFU of *C. jejuni,* 21-day-old C57BL/6 mice were orally administered via gavage with 200 of CAA1 as rSIgA1 or rSIgA2. (A) Quantification of the bacterial load (CFU) in the stools of the animals at 24 h, 48 h and 72 h post-infection. (B) Representative dot plot and relative quantification of polymorphonucleated cells infiltrated in the caecum gated as $Gr1^+$ $CD11b^+$. (C) Quantification of Lipocalin-2 (LCN) in the stools, and (D) statistical analysis of histopathological score in the caecum at 72 h post infection in the different treatment conditions. Dots represent individual mice and results are shown as ±SEM. Mann-Whitney test (A-D) was used. *$p<0.05$, **$p<0.01$. One representative experiment out of at least two is shown.
Figure 10B:
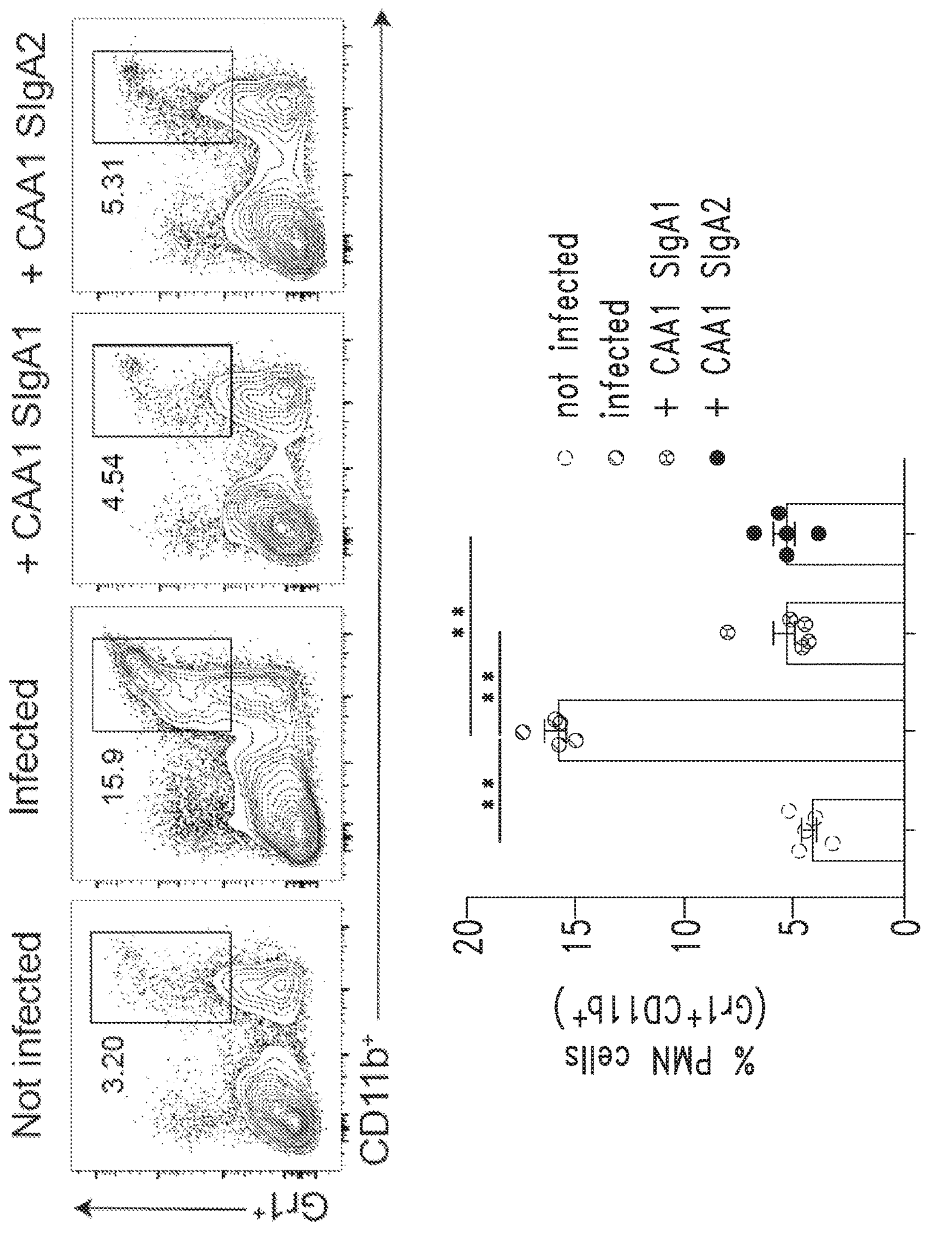
Figure 10C:
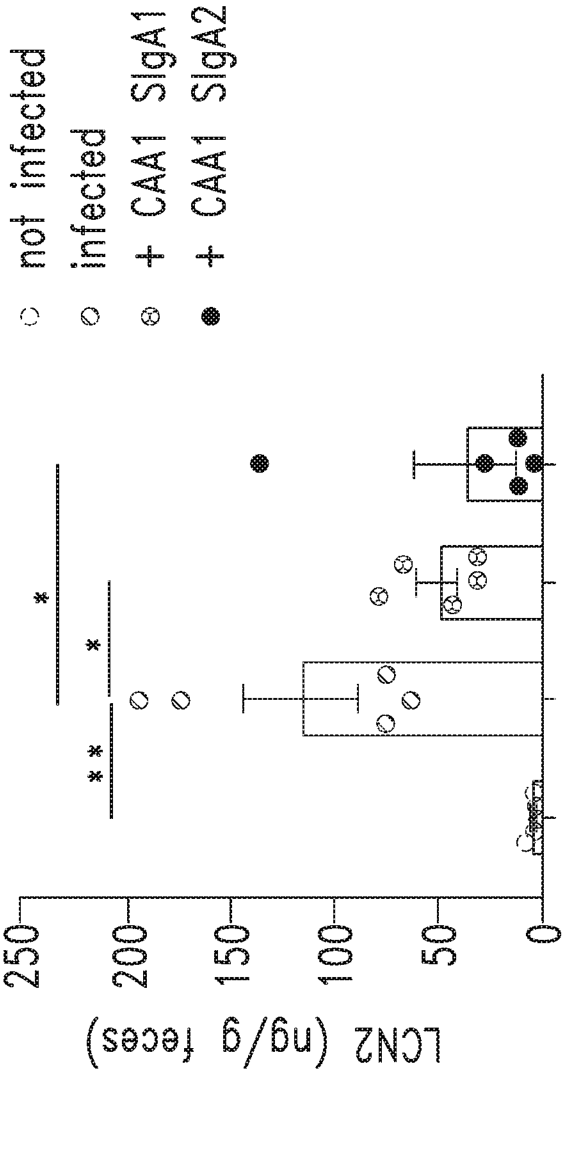
Figure 10D:
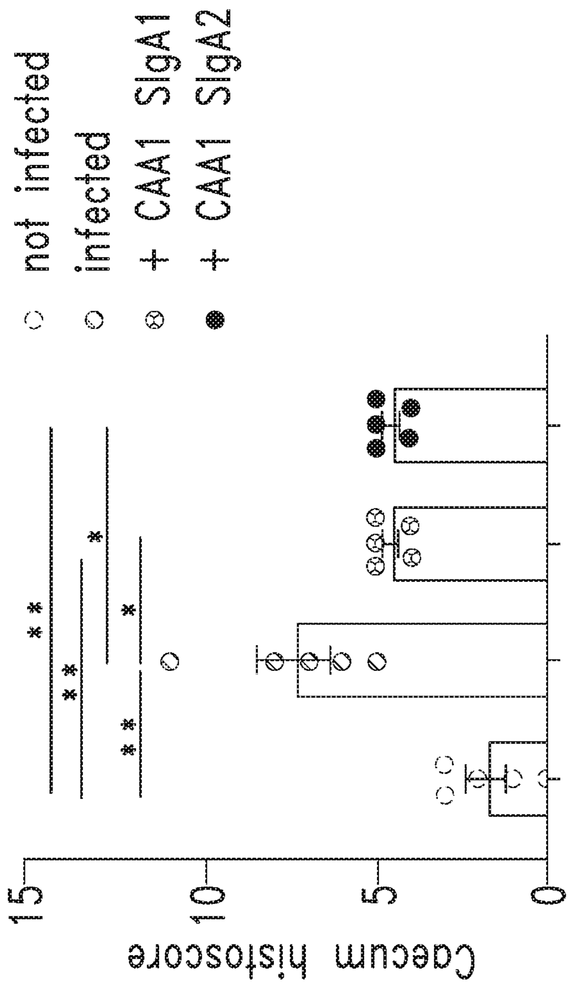

The prophylactic activity of the two subclasses was then tested in the murine model of *Campylobacter* infection. In line with previous findings, animals administered the FliD-reactive mAbs displayed higher *Campylobacter* shedding at early timepoints post-infection followed by a decrease over time, while infected non-treated animals produced an opposite trend (FIG. 10A). Although CAA1 rSIgA2 accelerated shedding faster than rSIgA1, both subclasses were equally capable of limiting inflammation in infected animals, as shown by the levels of lipocalin-2 in the stools, the PMN infiltration and the corresponding histological score in the caecum at 72 hours post-infection (FIGS. 10B-10D).

These results indicate that structural differences between IgA1 and IgA2 do not result in differences in prophylactic activity exerted by these two CAA1 formats in the in-vivo model.

Example 8 mAbs CAA1 and CCG4 have Reduced Oral Prophylactic Activity when Expressed as IgG Although SIgAs are thought to be the most abundant antibodies expressed in association with the intestinal mucosa and may be the first line of defense against enteric pathogens, they are characterized by a complex protein structure and their development as drugs may present challenges in comparison to IgG-based monoclonal antibodies. Since the activity of the *Campylobacter*-reactive mAbs was shown to be dependent on specificity for FliD, CAA1, CCG4 and the *Campylobacter*-irrelevant antibody HGN194 were generated as rIgG1 and evaluated for prophylactic activity in comparison to their corresponding SIgA2 counterparts.

Since glycosylation might affect the ability of mAbs to interact with mucin on the mucosal surface, the localization and persistence of control mAb HGN194 as rIgG1 in the murine intestinal tract was appraised by administering the antibody be a single oral gavage to 21-day old mice and then by measuring its concentration in the different intestinal sub-compartments after 2, 4 and 8 h (FIG. 14C). As with HGN194 rSIgA2, at every time-point, the highest concentration of the rIgG1 was detected in the caecum; however, in this intestinal sub-compartment the rIgG1 concentration tended to decrease faster than rSIgA2, with a significant reduction observed by 4 hours post-administration (FIGS. 14B, 14C).

Figure 11A:
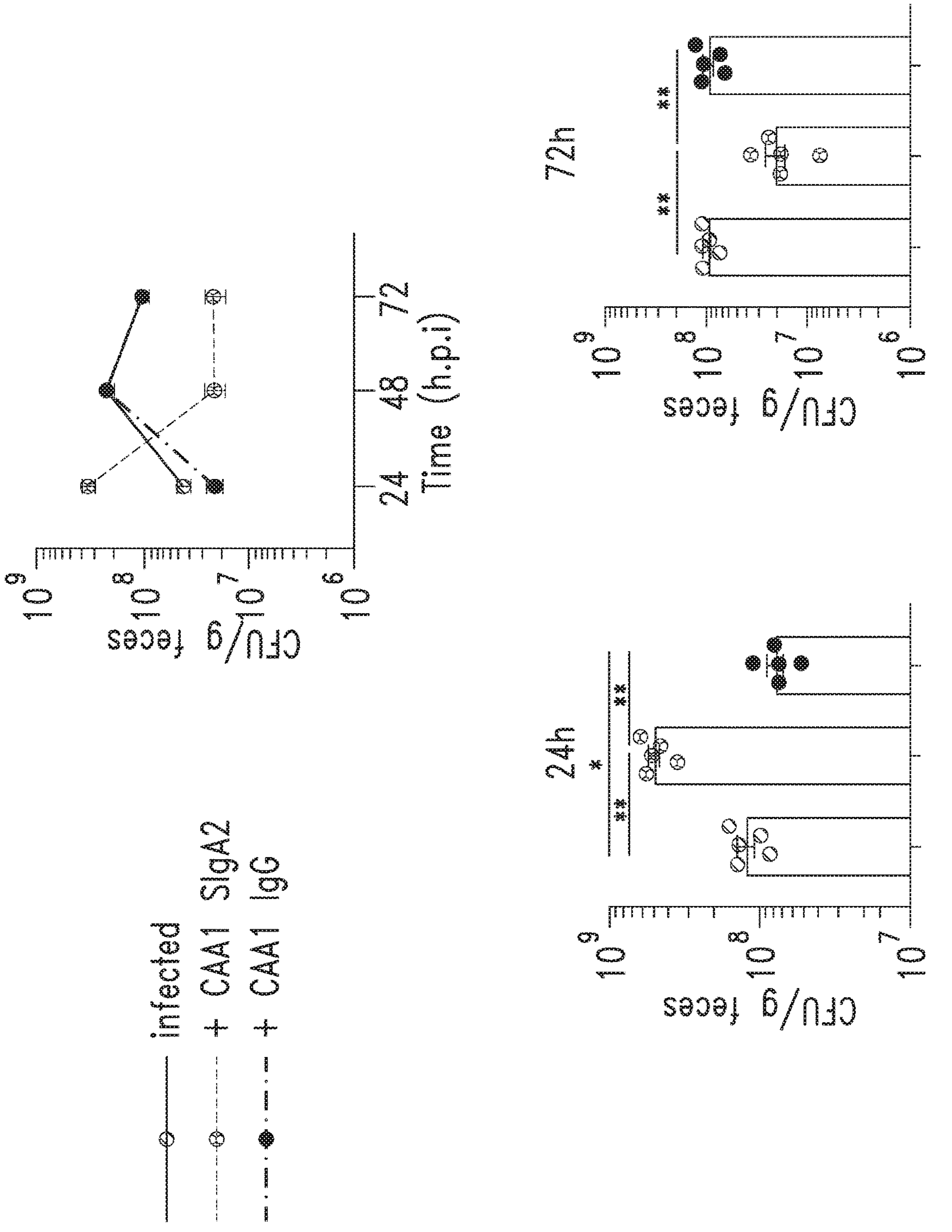
FIGS. 11A-11D show that conversion to IgG reduces oral CAA1 prophylactic activity against *C. jejuni* infection. (A-D) 2 h prior to infection with $10^8$ CFU of *C. jejuni,*
Figure 11B:
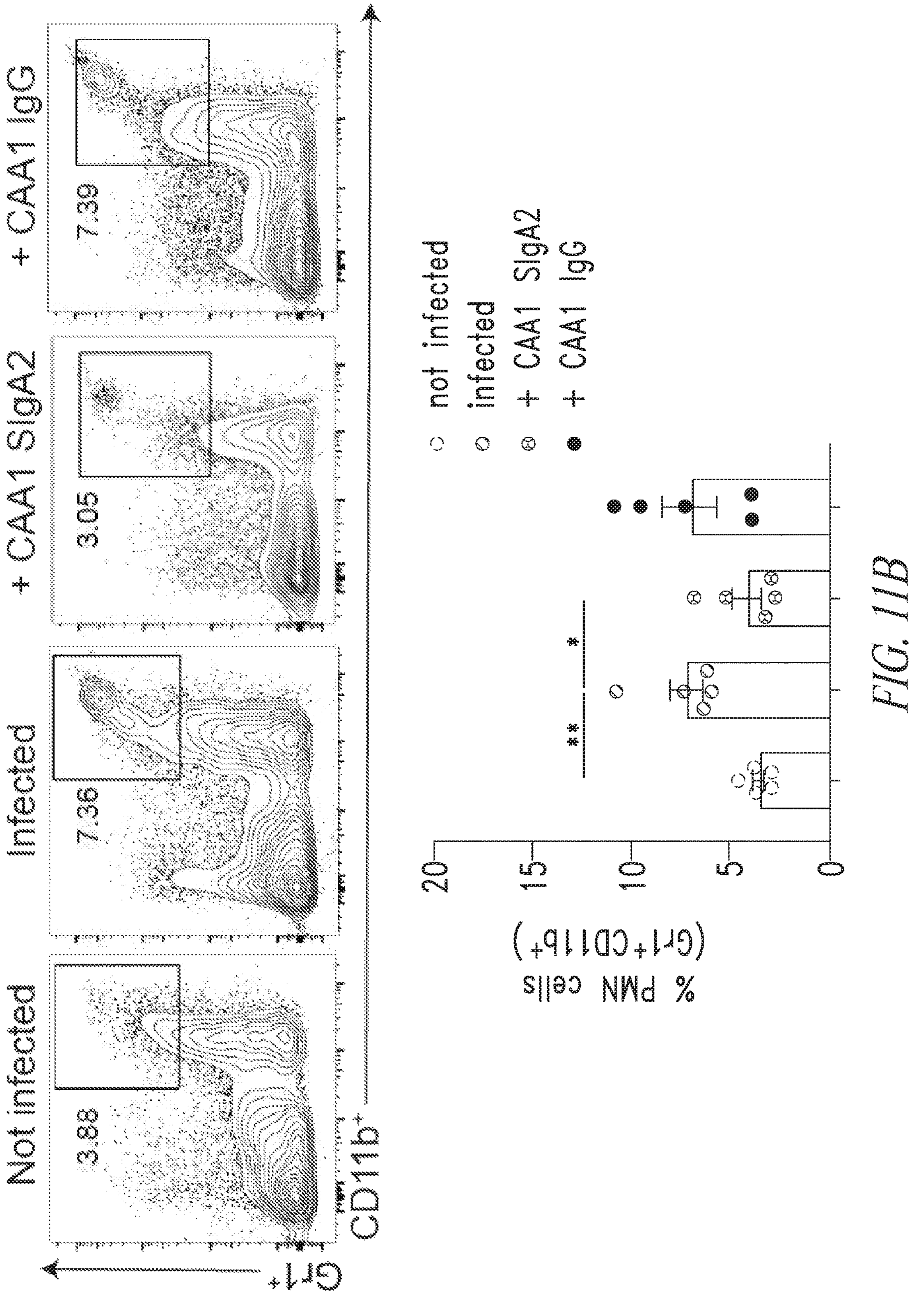
Figure 11C:
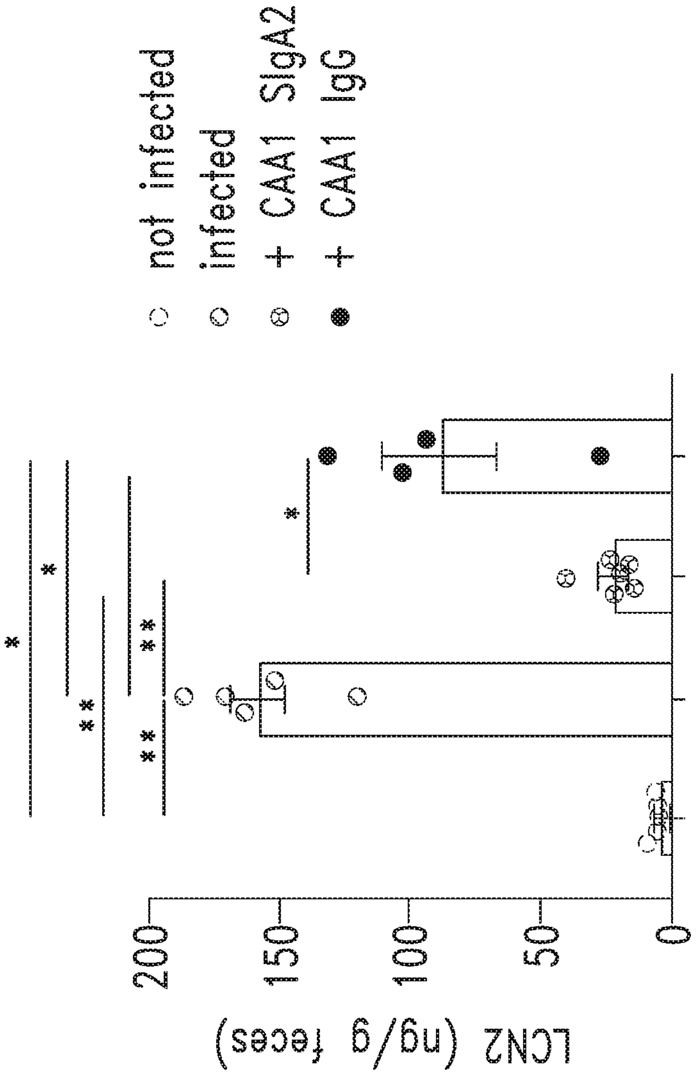
Figure 11D:
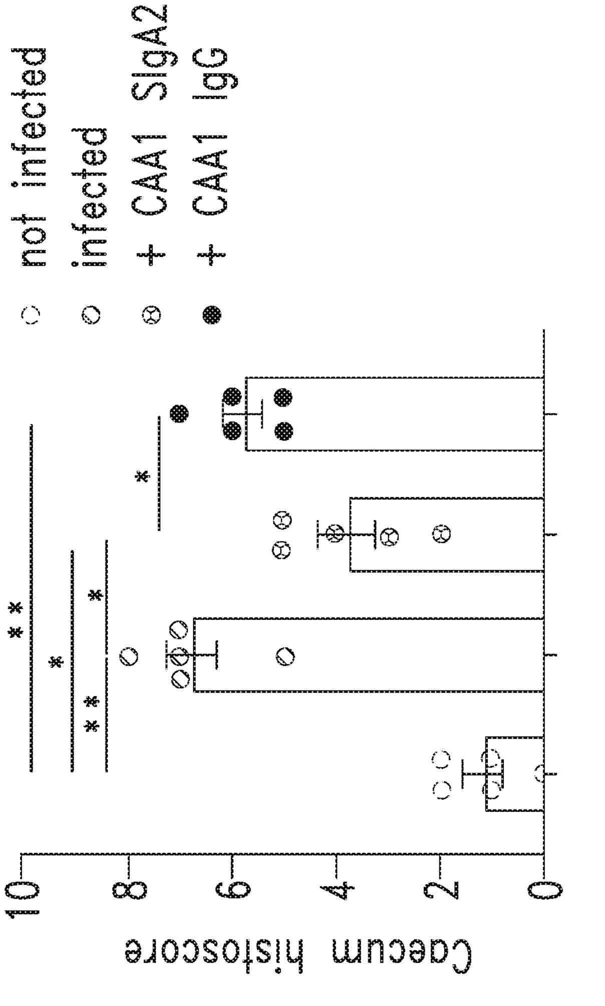
Figure 17A:
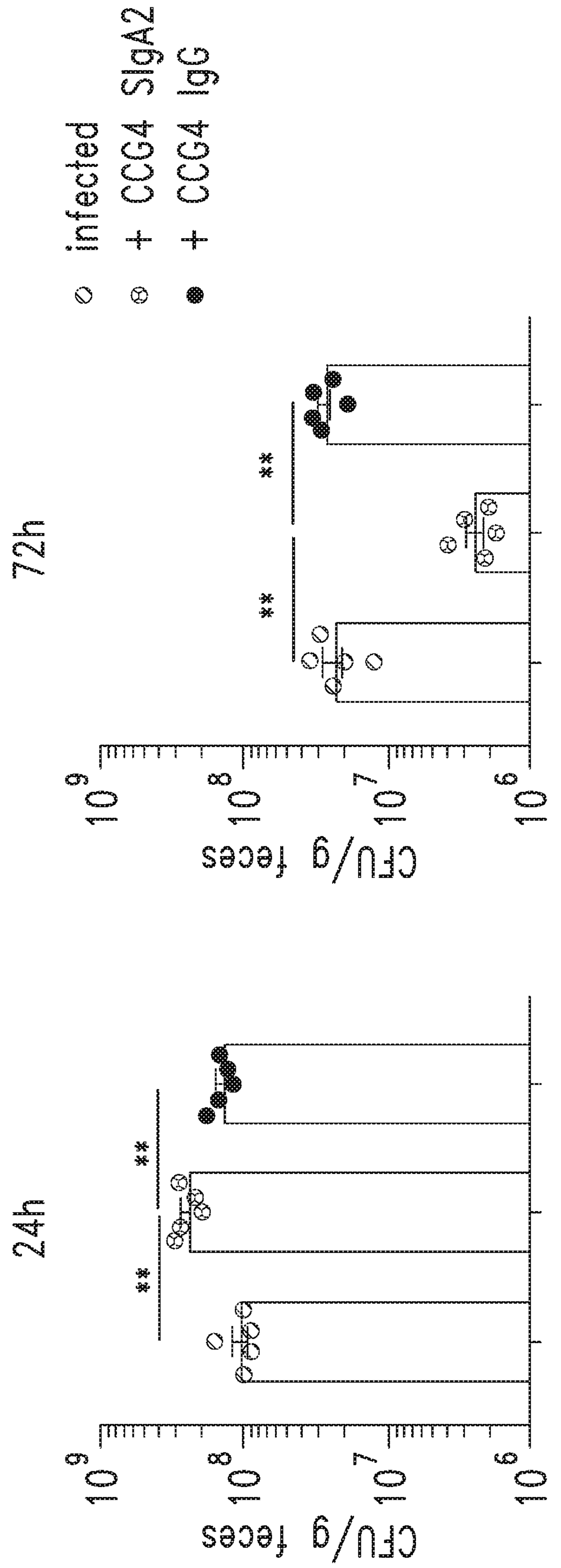
Figure 17B:
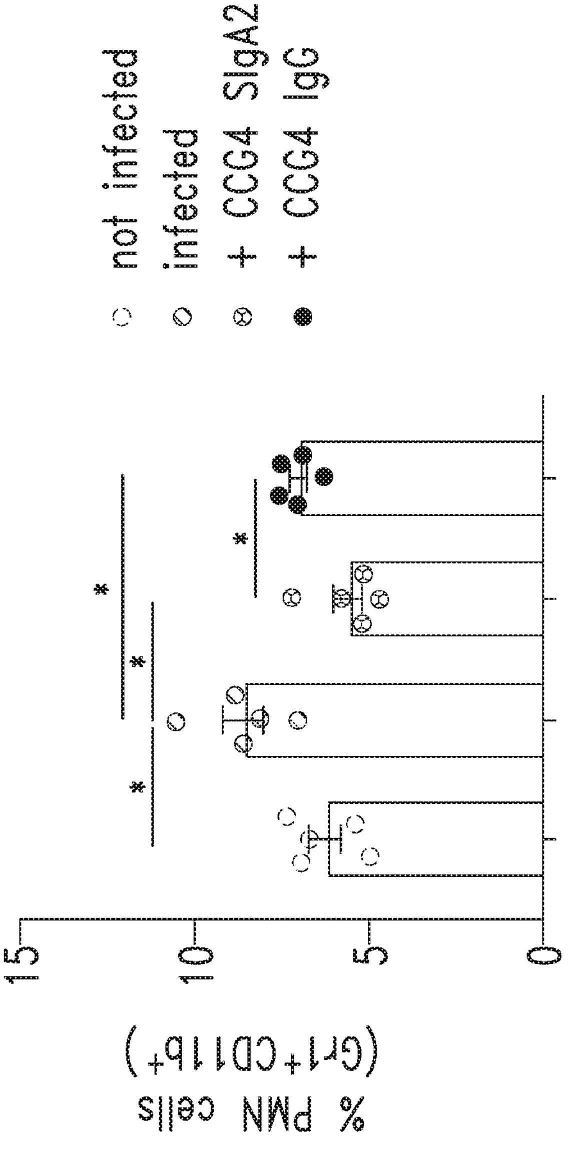
Figure 17C:
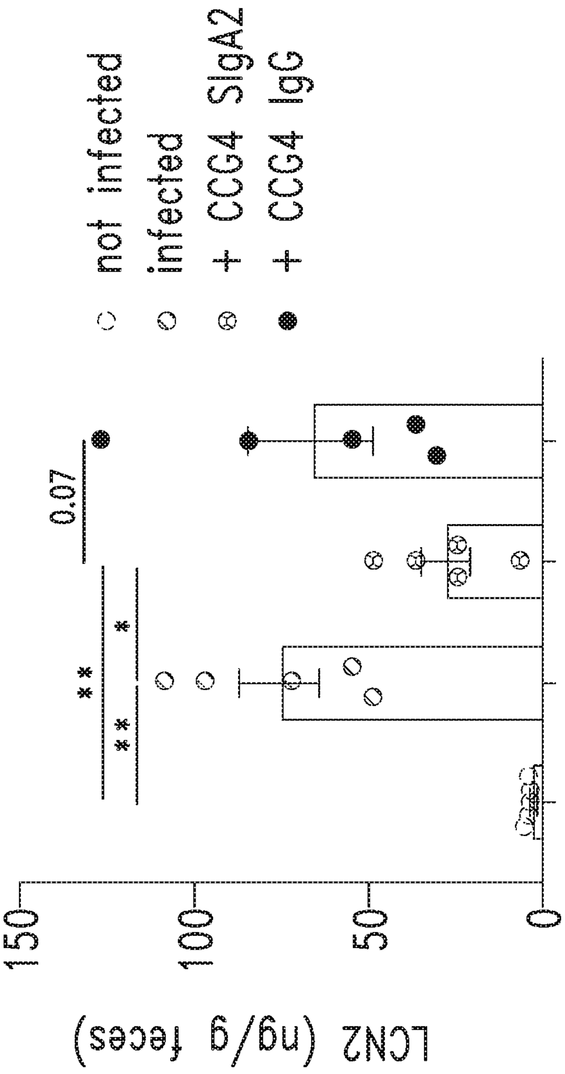
Figure 17D:
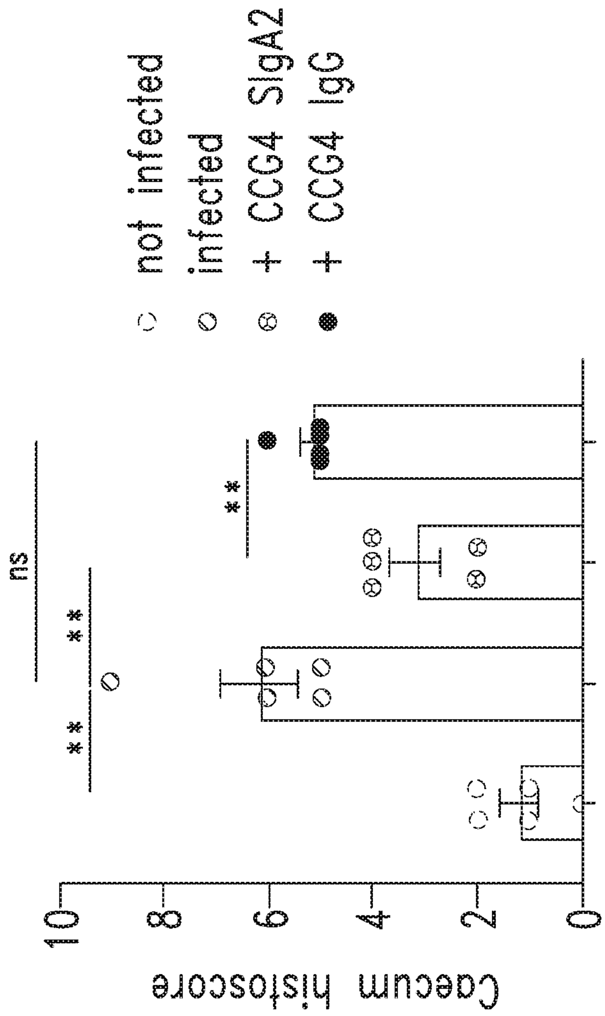

The prophylactic activity of the FliD-reactive mAbs CAA1 and CCG4 as rIgG1 or SIgA2 was also evaluated. MAbs were administered orally to just-weaned mice 2 hours before infection with *C. jejuni* 81-176. Interestingly, while animals treated with SIgA2 antibodies displayed the previously observed pattern characterized by higher shedding at 24 hours post-infection followed by a significant decrease at 48 and 72 h, the groups treated with the IgG version of the same antibodies revealed trends similar to the non-treated groups (FIGS. 11A and 17A). The importance of the SIgA format for in vivo efficacy was further confirmed by the lower ability of CAA1 and CCG4 IgG to limit inflammation in comparison to their polymeric counterparts, as shown by PMN cells infiltration in the caecum and lipocalin-2 levels in the stools of the infected animals at 72 post-infection (FIGS. 11B, C and 17B, 17C). Overall, no significant differences in the histological scores were observed between the mice treated with the FliD-reactive IgG antibodies and the non-treated animals. Conversely, the SIgA versions of the antibodies were able to replicate the beneficial effect previously observed, maintaining the histological score in the caecum to values significantly lower than both non-treated and IgG treated mice (FIGS. 11D and 17D).

These data indicate that CAA1 and CCG4 IgGs have limited prophylactic activity when orally administered prior to *Campylobacter* infection, as compared to the same antibodies expressed as SIgA. Without wishing to be bound by theory, the lack of activity of orally administered CAA1 and CCG4 IgGs might rely both on a lower persistence in the gastrointestinal tract and on different cross-linking properties associated with the SIgA format.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet, including U.S. Provisional Patent Application No. 62/699,573, filed Jul. 17, 2018, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

What is claimed is:

1. An isolated antibody, or an antigen-binding fragment thereof, that is specific for a *Campylobacter flagellum* capping protein (FliD) epitope, wherein:

(i) the antibody or antigen-binding fragment thereof comprises HCDR1, HCDR2, HCDR3, LCDR1, LCDR2, and LCDR3 sequences according to SEQ ID NOs: 9-14, respectively, and is an IgA2, IgG, IgD, IgE, or IgM isotype; or (ii) the antibody or antigen-binding fragment thereof comprises HCDR1, HCDR2, HCDR3, LCDR1, LCDR2, and LCDR3 sequences according to SEQ ID NOs: 25-30, respectively, and is an IgA, IgD, IgE, IgG1, or IgM isotype.

2. The antibody or antigen-binding fragment of claim 1, wherein the antibody or antigen-binding fragment is capable of binding to the FliD epitope with an EC50 of less than about 0.1 μg/mL, or less than about 0.05 μg/mL, or less than about 0.03 μg/mL, as measured by ELISA.

3. The antibody or antigen-binding fragment of claim 1, wherein the *Campylobacter* comprises *Campylobacter jejuni, Campylobacter coli*, or both.

4. The antibody or antigen-binding fragment of claim 1, wherein the antibody or antigen-binding fragment comprises:

(i) VH having at least 85% amino acid identity to SEQ ID NO:2, and a VL having at least 85% amino acid identity to SEQ ID NO:4; or (ii) VH having at least 85% amino acid identity to SEQ ID NO:22, and a VL having at least 85% amino acid identity to SEQ ID NO:24.

5. The antibody or antigen-binding fragment of claim 4, wherein the antibody or antigen-binding fragment comprises:

(i) a VH according to SEQ ID NO:2, and a VL according to SEQ ID NO:4; or (ii) a VH according to SEQ ID NO:22, and a VL according to SEQ ID NO:24.

6. The antibody or antigen-binding fragment of claim 1, wherein the antibody or antigen-binding fragment comprises HCDR1, HCDR2, HCDR3, LCDR1, LCDR2, and LCDR3 sequences according to SEQ ID NOs: 9-14, respectively and is an IgA2 isotype.

7. The antibody or antigen-binding fragment of claim 6, comprising a heavy chain constant region having at least 90% identity to SEQ ID NO:41 or SEQ ID NO:42.

8. The antibody or antigen-binding fragment of claim 1, wherein the antibody or antigen-binding fragment comprises HCDR1, HCDR2, HCDR3, LCDR1, LCDR2, and LCDR3 sequences according to SEQ ID NOs: 25-30, respectively, is an IgA2 isotype.

9. The antibody or antigen-binding fragment of claim 8, comprising a heavy chain constant region having at least 90% to SEQ ID NO:41 or SEQ ID NO:42.

10. The antibody or antigen-binding fragment of claim 8, comprising a heavy chain constant region according to SEQ ID NO:41 or SEQ ID NO:42.

11. The antibody or antigen-binding fragment claim 1, wherein the antibody or antigen-binding fragment comprises a Fc polypeptide or a fragment thereof.

12. The antibody or antigen-binding fragment of claim 11, comprising a VH according to SEQ ID NO:2, a VL according to SEQ ID NO:4, and a heavy chain constant region according to SEQ ID NO:41 or SEQ ID NO:42.

13. The antibody or antigen-binding fragment of claim 11, comprising a VH according to SEQ ID NO:22, a VL according to SEQ ID NO:24, and a heavy chain constant region according to SEQ ID NO:41 or SEQ ID NO:42.

14. The antibody or antigen-binding fragment of claim 1, wherein the antibody or antigen-binding fragment comprises an IgA2 dimer molecule and/or a secretory IgA2 molecule.

15. The antibody or antigen-binding fragment of claim 1, wherein the antibody or antigen binding fragment is (i) monoclonal and/or (ii) chimeric, humanized, or human.

16. A composition, comprising the antibody or antigen-binding fragment of claim 1, and a pharmaceutically acceptable carrier, excipient, or diluent.

17. The antibody or antigen-binding fragment of claim 1, wherein the antibody or antigen-binding fragment comprises HCDR1, HCDR2, HCDR3, LCDR1, LCDR2, and LCDR3 sequences according to SEQ ID NOs: 9-14, respectively and is an IgG1 isotype.

18. The antibody or antigen-binding fragment of claim 1, wherein the antibody or antigen-binding fragment comprises HCDR1, HCDR2, HCDR3, LCDR1, LCDR2, and LCDR3 sequences according to SEQ ID NOs: 25-30, respectively, is an IgG1 isotype.

19. The antibody or antigen-binding fragment thereof of claim 1, wherein the antibody or antigen-binding fragment comprises HCDR1, HCDR2, HCDR3, LCDR1, LCDR2, and LCDR3 sequences according to SEQ ID NOs: 25-30, respectively, and is an IgA1 isotype.

20. The antibody or antigen-binding fragment of claim 19, comprising a heavy chain constant region having at least 90% identity to SEQ ID NO:40.

21. The antibody or antigen-binding fragment of claim 19, comprising a heavy chain constant region according to SEQ ID NO:40.

22. The antibody or antigen-binding fragment of claim 19, wherein the antibody or antigen-binding fragment comprises an IgA1 dimer molecule and/or a secretory IgA1 molecule.

23. A kit, comprising:

(i) a first antibody or an antigen-binding fragment thereof comprising HCDR1, HCDR2, HCDR3, LCDR1, LCDR2, and LCDR3 sequences according to SEQ ID NOs: 9-14, respectively, and is an IgA2, IgG, IgD, IgE, or IgM isotype, and (ii) a second antibody or an antigen-binding fragment thereof comprising HCDR1, HCDR2, HCDR3, LCDR1, LCDR2, and LCDR3 sequences according to SEQ ID NOs: 25-30, respectively, and is an IgA, IgD, IgE, IgG1, or IgM isotype.

24. The kit of claim 23, wherein:

(i) the first antibody or antigen-binding fragment comprises a VH having at least 85% amino acid identity to SEQ ID NO:2, and a VL having at least 85% amino acid identity to SEQ ID NO:4; and (ii) the second antibody or antigen-binding fragment comprises a VH having at least 85% amino acid identity to SEQ ID NO:22, and a VL having at least 85% amino acid identity to SEQ ID NO:24.

25. The kit of claim 24, wherein the first antibody or antigen-binding fragment and the second antibody or antigen-binding fragment are each a secretory IgA2 molecule.

26. The kit of claim 24, wherein:

(i) the first antibody or antigen-binding fragment comprises a VH according to SEQ ID NO: 2, and a VL according to SEQ ID NO:4; and (ii) the second antibody or antigen-binding fragment comprises a VH according to SEQ ID NO:22, and a VL according to SEQ ID NO:24.

27. An isolated polynucleotide encoding the antibody or antigen-binding fragment of claim 1.

28. A vector comprising the polynucleotide of claim 27.

29. The isolated polynucleotide of claim 27, wherein the polynucleotide is codon-optimized for expression in a host cell.

30. A recombinant host cell comprising the isolated polynucleotide claim 27, or the vector of claim 28.

31. A method for treating a *Campylobacter* infection in a subject, the method comprising administering to the subject an effective amount of the antibody or antigen-binding fragment of claim 1.

32. The method of claim 31, further comprising reducing intestinal inflammation and/or increasing intestinal shedding in a subject having a *Campylobacter* infection.

33. The method of claim 31, wherein the administering comprises oral administration of the antibody or antigen-binding fragment.

34. The method of claim 31, wherein following the administering:

(i) a stool sample from the subject comprises an increased number of *Campylobacter* colony-forming units (CFUs) as compared to a stool sample from the subject prior to being administered an effective amount of the antibody or antigen-binding fragment;

(ii) a stool sample from the subject comprises a reduced amount of lipocalin-2 (LCN2) as compared to a stool sample from the subject prior to being administered an effective amount of the antibody or antigen-binding fragment;

(iii) the subject comprises a reduced amount of polymorphonucleated (PMN) cell infiltrate in a caecum as compared to the subject prior to being administered an effective amount of the antibody or antigen-binding fragment, wherein the PMN cells are $Gr1^+CD11b^+$;

(iv) the subject has an improved caecum histology as compared to the subject prior to being administered an effective amount of the antibody or antigen-binding fragment; and/or (v) the antibody or antigen-binding fragment is present in the caecum and/or in feces of the subject for at least 4 hours or for at least 8 hours following the administration.

35. A method for treating a *Campylobacter* infection in a subject, the method comprising administering to the subject an effective amount of the antibody or antigen-binding fragment of claim 5.

36. A method for treating a *Campylobacter* infection in a subject, the method comprising administering to the subject an effective amount of the antibody or antigen-binding fragment of claim 12.

37. A method for treating a *Campylobacter* infection in a subject, the method comprising administering to the subject an effective amount of the antibody or antigen-binding fragment of claim 13.

38. The antibody or antigen-binding fragment of claim 6, comprising a heavy chain constant region according to SEQ ID NO:41 or SEQ ID NO:42.

* * * * *